United States Patent
Larsen et al.

(10) Patent No.: US 10,662,183 B2
(45) Date of Patent: May 26, 2020

(54) INHIBITORS OF MYOCARDIN-RELATED TRANSCRIPTION FACTOR AND SERUM RESPONSE FACTOR (MRTF/SRF)-MEDIATED GENE TRANSCRIPTION AND METHODS FOR USE OF THE SAME

(71) Applicants: THE REGENTS OF THE UNIVERSITY OF MICHIGAN, Ann Arbor, MI (US); BOARD OF TRUSTEES OF MICHIGAN STATE UNIVERSITY, East Lansing, MI (US)

(72) Inventors: Scott D. Larsen, South Lyon, MI (US); Richard Neubig, East Lansing, MI (US); Andrew Haak, Rochester, MN (US); Kim Hutchings, Dexter, MI (US); Walajapet Rajeswaran, Canton, MI (US); Dinesh Khanna, Ann Arbor, MI (US); Erika Mathes Lisabeth, Howell, MI (US)

(73) Assignees: THE REGENTS OF THE UNIVERSITY OF MICHIGAN, Ann Arbor, MI (US); BOARD OF TRUSTEES OF MICHIGAN STATE UNIVERSITY, East Lansing, MI (US)

(*) Notice: Subject to any disclaimer, the term of this patent is extended or adjusted under 35 U.S.C. 154(b) by 198 days.

(21) Appl. No.: 14/934,769

(22) Filed: Nov. 6, 2015

(65) Prior Publication Data
US 2016/0145251 A1 May 26, 2016

Related U.S. Application Data

(60) Provisional application No. 62/076,735, filed on Nov. 7, 2014.

(51) Int. Cl.
| | | |
|---|---|---|
| C07D 211/06 | (2006.01) |
| C07D 211/60 | (2006.01) |
| C07D 417/14 | (2006.01) |
| C07D 405/10 | (2006.01) |
| C07D 409/10 | (2006.01) |
| C07D 405/14 | (2006.01) |
| C07D 401/10 | (2006.01) |
| C07D 401/06 | (2006.01) |
| C07D 417/06 | (2006.01) |
| C07D 413/14 | (2006.01) |

(Continued)

(52) U.S. Cl.
CPC .......... *C07D 417/14* (2013.01); *C07D 211/60* (2013.01); *C07D 401/06* (2013.01); *C07D 401/10* (2013.01); *C07D 405/06* (2013.01); *C07D 405/10* (2013.01); *C07D 405/14* (2013.01); *C07D 409/10* (2013.01); *C07D 413/06* (2013.01); *C07D 413/14* (2013.01); *C07D 417/06* (2013.01); *C07D 417/10* (2013.01)

(58) Field of Classification Search
CPC . C07D 211/06; C07D 295/104; C07D 295/10
See application file for complete search history.

(56) References Cited

U.S. PATENT DOCUMENTS

2004/0167224 A1 8/2004 Ozaki et al.
2009/0286778 A1 11/2009 Combs et al.
(Continued)

FOREIGN PATENT DOCUMENTS

JP 53-031669 3/1978
JP 2005-112804 A 4/2005
(Continued)

OTHER PUBLICATIONS

STN entries for CAS Reg. Nos. 929863-05-8 and 929969-31-3 (entry date Apr. 13, 2007).*
Nogrady et al. Medicinal Chemistry: A Molecular and Biochemical Approach, 3rd Ed. (2005), Ch. 1, pp. 9-66.*
STN entries for CAS Reg. Nos. 67691-52-5 (1984) and 853325-72-1 (2005) (accessed on Oct. 20, 2017).*
(Continued)

*Primary Examiner* — Soren Harward
*Assistant Examiner* — Chris E Simmons
(74) *Attorney, Agent, or Firm* — Marshall, Gerstein & Borun LLP

(57) ABSTRACT

Disclosed herein are inhibitors of gene transcription mediated by myocardin-related transcription factor and serum response factor, or both myocardin-related transcription factor and serum response factor ("MRTF/SRF"), and methods for their use in treating or preventing cancer and fibrosis. In particular, disclosed herein are compounds of Formula (I) and Formula (II), and pharmaceutically acceptable salts thereof:

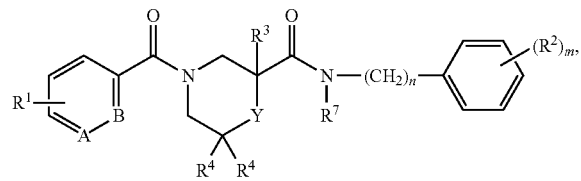

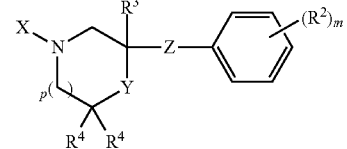

wherein the substituents are as described.

12 Claims, 1 Drawing Sheet

(51) Int. Cl.
C07D 417/10 (2006.01)
C07D 413/06 (2006.01)
C07D 405/06 (2006.01)

(56) References Cited

U.S. PATENT DOCUMENTS

| | | | |
|---|---|---|---|
| 2012/0022080 | A1 | 1/2012 | Miyata et al. |
| 2012/0252792 | A1 | 10/2012 | Neubig et al. |
| 2012/0252807 | A1 | 10/2012 | Larsen et al. |
| 2013/0158020 | A1 | 6/2013 | Deng et al. |
| 2014/0031347 | A1 | 1/2014 | Rodriguez De Fonseca et al. |

FOREIGN PATENT DOCUMENTS

| | | |
|---|---|---|
| JP | 2005-537224 A | 12/2005 |
| JP | 2006-519232 A | 8/2006 |
| JP | 2011-519849 A | 7/2011 |
| WO | WO-2002/034718 A1 | 5/2002 |
| WO | WO-2003/084948 A1 | 10/2003 |
| WO | WO-2003/086398 A1 | 10/2003 |
| WO | WO-2004/071390 A2 | 8/2004 |
| WO | WO-2004/076412 A2 | 9/2004 |
| WO | WO-2008/011131 A2 | 1/2008 |
| WO | WO-2008/049919 A2 | 5/2008 |
| WO | WO-2009/133522 A1 | 11/2009 |
| WO | WO-2010/057141 A2 | 5/2010 |
| WO | WO-2011/035143 A2 | 3/2011 |

OTHER PUBLICATIONS

Shay ("The role of fluorine in medicinal chemistry." Journal of Enzyme Inhibition and Medicinal Chemistry, Oct. 2007; 22(5): 527-540). (Year: 2007).*
Patani (Chemical Reviews, 1996, vol. 96, No. 8). (Year: 1996).*
Bartolome et al., Stromal cell-derived factor-1alpha promotes melanoma cell invasion across basement membranes involving stimulation of membrane-type 1 matrix metalloproteinase and Rho GTPase activities. *Cancer Res.* 64: 2534-43 (2004).
Bell et al., Optimization of novel nipecotic bis(amide) inhibitors of the Rho/MKL1/SRF transcriptional pathway as potential anti-metastasis agents. *Bioorg. Med. Chem. Lett.* 23: 3826-32 (2013).
Benbow et al., The AP-1 site and MMP gene regulation: what is all the fuss about? *Matrix Biol.* 15: 519-26 (1997).
Beyer et al., Animal models of systemic sclerosis: prospects and limitations. *Arthritis Rheum.* 62: 2831-44 (2010).
Beyer et al., Innovative antifibrotic therapies in systemic sclerosis. *Curr. Opin. Rheumatol.* 24: 274-80 (2012).
Boukhalfa et al., Relationship between alpha-smooth muscle actin expression and fibrotic changes in human kidney. *Exp. Nephrol.* 4: 241-7 (1996).
Buhl et al., G alpha 12 and G alpha 13 stimulate Rho-dependent stress fiber formation and focal adhesion assembly. *J. Biol. Chem.* 270: 24631-4 (1995).
Burridge et al., Rho and Rac take center stage. *Cell*, 116: 167-79 (2004).
Cen et al., Megakaryoblastic leukemia 1, a potent transcriptional coactivator for serum response factor (SRF), is required for serum induction of SRF target genes. *Mol. Cell Biol.* 23: 6597-608 (2003).
Chaqour et al., Mechanical regulation of the Cyr61/CCN1 and CTGF/CCN2 proteins. *FEBS J.* 273: 3639-49 (2006).
Charles et al., Systemic sclerosis: hypothesis-driven treatment strategies. *Lancet*, 367: 1683-91 (2006).
Clark et al., Genomic analysis of metastasis reveals an essential role for RhoC. *Nature*, 406: 532-5 (2000).
Evelyn et al., Design, synthesis and prostate cancer cell-based studies of analogs of the Rho/MKL1 transcriptional pathway inhibitor, CCF-1423. *Bioorg. Med. Chem. Lett.* 20: 665-72 (2010).
Haak et al, Targeting the myofibroblast genetic switch: inhibitors of myocardin-related transcription factor/serum response factor-regulated gene transcription prevent fibrosis in a murine model of skin injury. *J. Pharmacol. Exp. Ther.* 349: 480-6 (2014).

Hakem et al., RhoC is dispensable for embryogenesis and tumor initiation but essential for metastasis. *Genes Dev.* 19: 1974-9 (2005).
Ikoma et al., A definitive role of RhoC in metastasis of orthotopic lung cancer in mice. *Clin. Cancer Res.* 10: 1192-200 (2004).
Iwahara et al., CrkII induces serum response factor activation and cellular transformation through its function in Rho activation. *Oncogene*, 22: 5946-57 (2003).
Johnson et al., Novel Rho/MRTF/SRF inhibitors block matrix-stiffness and TGF-β-induced fibrogenesis in human colonic myofibroblasts. *Inflamm. Bowel Dis.* 20: 154-65 (2014).
Luchsinger et al., Myocardin-related transcription factor-A complexes activate type I collagen expression in lung fibroblasts. *J. Biol. Chem.* 286: 44116-25 (2011).
Matsui et al., Rho-kinase phosphorylates COOH-terminal threonines of ezrin/radixin/moesin (ERM) proteins and regulates their head-to-tail association. *J. Cell Biol.* 140: 647-57 (1998).
Medjkane et al., Myocardin-related transcription factors and SRF are required for cytoskeletal dynamics and experimental metastasis. *Nat. Cell Biol.* 11: 257-68 (2009).
Mercher et al., Recurrence of OTT-MAL fusion in t(1;22) of infant AML-M7. *Genes Chromosomes Cancer*, 33: 22-8 (2002).
Miralles et al., Actin dynamics control SRF activity by regulation of its coactivator MAL. *Cell*, 113: 329-42 (2003).
Norman et al., Isolation and properties of cDNA clones encoding SRF, a transcription factor that binds to the c-fos serum response element. *Cell*, 55: 989-1003 (1988).
Psichari et al., High activity of serum response factor in the mesenchymal transition of epithelial tumor cells is regulated by RhoA signaling. *J. Biol. Chem.* 277: 29490-5 (2002).
PubChem, Substance Record for SID 174522780, available date Apr. 3, 2014 <<https://pubchem.ncbi.nlm.nih.gov/substance/174522780/version/1#section=Top?>> [retrieved on Dec. 9, 2015].
Sah et al., The role of Rho in G protein-coupled receptor signal transduction. *Annu. Rev. Pharmacol. Toxicol.* 40: 459-89 (2000).
Sahai et al., Differing modes of tumour cell invasion have distinct requirements for Rho/ROCK signalling and extracellular proteolysis. *Nat. Cell Biol.* 5: 711-9 (2003).
Sahai et al., RHO-GTPases and cancer. *Nat.Rev.Cancer*,2: 133-42 (2002).
Sandbo et al., Critical role of serum response factor in pulmonary myofibroblast differentiation induced by TGF-beta. *Am. J. Respir. Cell Mol. Biol.* 41: 332-8 (2009).
Sasazuki et al., Identification of a novel transcriptional activator, BSAC, by a functional cloning to inhibit tumor necrosis factor-induced cell death. *J. Biol. Chem.* 277: 28853-60 (2002).
Sawyer, Cancer metastasis therapeutic targets and drug discovery: emerging small-molecule protein kinase inhibitors. *Expert Opin. Investig. Drugs*. 13: 1-9 (2004).
Schmidt et al., Guanine nucleotide exchange factors for Rho GTPases: turning on the switch. *Genes Dev.* 16: 1587-609 (2002).
Selvaraj et al., Megakaryoblastic leukemia-1/2, a transcriptional co-activator of serum response factor, is required for skeletal myogenic differentiation. *J. Biol. Chem.* 278: 41977-87 (2003).
Shaposhnikov, Myocardin related transcription factors are required for coordinated cell cycle progression. *Cell Cycle*, 12: 1762-72 (2013).
Shaw et al., The Nf2 tumor suppressor, merlin, functions in Rac-dependent signaling. *Dev Cell*, 1: 63-72 (2001).
Shikada et al., Higher expression of RhoC is related to invasiveness in non-small cell lung carcinoma. *Clin. Cancer Res.* 9: 5282-6 (2003).
Whitehead et al., Rho GTPase-dependent transformation by G protein-coupled receptors. *Oncogene*, 20: 1547-55 (2001).
Worthylake et al., RhoA is required for monocyte tail retraction during transendothelial migration. *J. Cell Biol.* 154: 147-60 (2001).
Wu et al., RhoC induces differential expression of genes involved in invasion and metastasis in MCF10A breast cells. *Breast Cancer Res. Treat.* 84: 3-12 (2004).
Wynn et al., Mechanisms of fibrosis: therapeutic translation for fibrotic disease. *Nat. Med.* 18: 1028-40 (2012).

(56) References Cited

OTHER PUBLICATIONS

Anilkumar, et al., I. Novel HCV NS5B polymerase inhibitors: Discovery of indole 2-carboxylic acids with C3-heterocycles, *Bioorganic & Medicinal Chemistry Letters*, 21(18):5336-5341 (2011).

Coleman et al., Discovery of [(2R,5R)-5-{[(5-fluoropyridin-2-yl)oxy]methyl}-2-methylpiperidin-1-yl][5-methyl-2-(pyrimidin-2-yl)phenyl]methanone (MK-6096): a dual orexin receptor antagonist with potent sleep-promoting properties, *ChemMedChem*. 7:415-24 (2012).

Database: Registry, RN 1316547-21-3 Registryed Entered STN: Aug. 12, 2011.

Database: Registry, RN 1008348-83-1 Registryed Entered STN: JMar. 16, 2008.

Database: Registry, RN 1010199-82-2 Registryed Entered STN: Mar. 26, 2008.

Database: Registry, RN 1031141-01-1 Registryed Entered STN: Jun. 27, 2008.

Database: Registry, RN 1203252-93-0 Registryed Entered STN: Jan. 24, 2010.

Database: Registry, RN 1316607-13-2 Registryed Entered STN: Aug. 12, 2011.

Database: Registry, RN 1320976-13-3 Registryed Entered STN: Aug. 21, 2011.

Database: Registry, RN 929819-62-5 Registryed Entered STN: Apr. 13, 2007.

Database: Registry, RN 929822-31-1 Registryed Entered STN: Apr. 13, 2007.

Database: Registry, RN 929845-46-5 Registryed Entered STN: Apr. 13, 2007.

Database: Registry, RN 929969-31-3 Registryed Entered STN: Apr. 13, 2007.

Database: Registry, RN 941400-27-7 Registryed Entered STN: Jul. 6, 2007.

Edmondson, et al., Potent and selective proline derived dipeptidyl peptidase IV inhibitors, *Bioorganic & Medicinal Chemistry Letters*, 14(20):5151-5155 (2004).

Ettorre, et al., hNK2 receptor antagonists. The use of intramolecular hydrogen bonding to increase solubility and membrane permeability, *Bioorganic & Medicinal Chemistry Letters*, 21(6):1807-1809 (2011).

Fournie-Zaluski, et al., New dual inhibitors of neutral endopeptidase and angiotensin-converting enzyme: rational design, bioavailability, and pharmacological responses in experimental hypertension, *J. Med. Chem.*, 37(8):1070-1083 (1994).

Gillis, et al., Applications of Fluorine in Medicinal Chemistry, *J. Med. Chem.*, 58(21):8315-8359 (2015).

Goldstein, et al., Discovery of 6-(2,4-Difluorophenoxy)-2-[3-hydroxy-1-(2-hydroxyethyl)propylamino]-8-methyl-8H-pyrido[2,3-d]pyrimidin-7-one (Pamapimod) and 6-(2,4-Difluorophenoxy)-8-methyl-2-(tetrahydro-2H-pyran-4-ylamino)pyrido[2,3-d]pyrimidin-7(8H)-one (R1487) as Orally Bioavailable and Highly Selective Inhibitors of p38α Mitogen-Activated Protein Kinase, *J. Med. Chem.*, 54(7):2255-2265 (2011).

Hameed, et al., Novel N-linked aminopiperidine-based gyrase inhibitors with improved hERG and in vivo efficacy. against *Mycobacterium tuberculosis*, *J. Med. Chem.*, 57(11):4889-4905 (2014).

Hof, et al., A weak attractive interaction between organic fluorine and an amide group. *Angewandte Chemie International Edition*, 43(38):5056-5059 (2004).

Humphrey, J.M.,. Medicinal Chemistry of Selective Neurokinin-1 Antagonists, *Current Topics in Medicinal Chemistry*, 3(12):1423-1435 (2003).

Ilyin et al., Synthesis of heterocyclic compounds possessing the 4H-thieno[3,2-b]pyrrole moiety, *J. Comb. Chem.* 9:96-106 (2007).

Kim, et al., (2R)-4-Oxo-4-[3-(trifluoromethyl)-5,6-dihydro[1,2,4] triazolo[4,3-a]pyrazin-7(8H)-yl]-1-(2,4,5-trifluorophenyl)butan-2-amine: A Potent, Orally Active Dipeptidyl Peptidase IV Inhibitor for the Treatment of Type 2 Diabetes, *J. Med. Chem.*, 48(1):141-151 (2005).

McDonald, et al., Discovery of a novel series of quinolone α7 nicotinic acetylcholine receptor agonists, *Bioorganic & Medicinal Chemistry Letters*, 23(6):1684-1688 (2013).

Miao, et al., A New Strategy to Improve the Metabolic Stability of Lactone: Discovery of (20 S, 21 S)-21-fluorocamptothecins as Novel, Hydrolytically Stable Topoisomerase I Inhibitors, *J. Med. Chem.*, 56(20):7902-7910 (2013).

Mukherjee et al., N-Benzyl-3-sulfonamidopyrrolidines as novel inhibitors of cell division in *E. coli*, *Bioorg. Med. Chem. Lett.* 17:6651-5 (2007).

Olsen, et al., A Fluorine Scan of Thrombin Inhibitors to Map the Fluorophilicity/Fluorophobicity of an Enzyme Active Site: Evidence for C—F•••C=O Interactions, *Angewandte Chemie International Edition*, 42(22):2507-2511 (2003).

Olsen, et al., Fluorine Interactions at the Thrombin Active Site: Protein Backbone Fragments H-CαC=O Comprise a Favorable C—F Environment and Interactions of C—F with Electrophiles, *ChemBioChem*, 5(5):666-675 (2004).

Reck, et al., Novel N-linked aminopiperidine inhibitors of bacterial topoisomerase type II with reduced p K a: antibacterial agents with an improved safety profile, *J. Med. Chem.*, 55(15):6916-6933 (2012).

Reck, et al., Novel N-linked aminopiperidine inhibitors of bacterial topoisomerase type II: broad-spectrum antibacterial agents with reduced hERG activity, *J. Med. Chem.*, 54(22):7834-7847 (2011).

Schweizer, et al., Multipolar interactions in the D pocket of thrombin: large differences between tricyclic imide and lactam inhibitors, *Organic & Biomolecular Chemistry*, 4(12):2364-2375 (2006).

Thornberry, et al., Discovery of JANUVIA™(Sitagliptin), a Selective Dipeptidyl Peptidase IV Inhibitor for the Treatment of Type2 Diabetes, *Current Topics in Medicinal Chemistry*, 7(6):557-568 (2007).

van Niel, et al., Fluorination of 3-(3-(piperidin-1-yl) propyl) indoles and 3-(3-(piperazin-1-yl) propyl) indoles gives selective human 5-HT1 D receptor ligands with improved pharmacokinetic profiles, *J. Med. Chem.*, 42(12):2087-2104 (1999).

Zhu, et al., Phenylcyclobutyl triazoles as selective inhibitors of 11β-hydroxysteroid dehydrogenase type I, *Bioorganic & Medicinal Chemistry Letters*, 18(11):3412-3416 (2008).

\* cited by examiner

INHIBITORS OF MYOCARDIN-RELATED TRANSCRIPTION FACTOR AND SERUM RESPONSE FACTOR (MRTF/SRF)-MEDIATED GENE TRANSCRIPTION AND METHODS FOR USE OF THE SAME

CROSS-REFERENCE TO RELATED APPLICATION

The benefit under 35 U.S.C. § 119(e) of U.S. Provisional Patent Application Ser. No. 62/076,735 filed Nov. 7, 2014, is hereby claimed, and the disclosure thereof is hereby incorporated herein by reference.

STATEMENT OF GOVERNMENT SUPPORT

This invention was made with government support under grant number R01 AR066049-01 awarded by the National Institutes of Health. The Government has certain rights in the invention.

BACKGROUND

Technical Field

The present disclosure relates to novel, small molecule inhibitors of gene transcription mediated by myocardin-related transcription factor and/or serum response factor ("MRTF/SRF"), and methods of using the small molecules to inhibit MRTF/SRF-mediated gene transcription and to treat diseases.

Description of Related Technology

Cell growth, proliferation, migration, and invasion are dependent on many growth factors, mitogens, and chemotactic agents. The medium for growing cells in tissue culture generally contains serum (e.g., fetal bovine serum) and serum also stimulates migration and invasion of cancer cells and fibroblasts. Treatment of cells with serum results in robust activation of gene transcription via the serum response factor ("SRF") (see Norman et al., Cell 55:989-1003 (1988)). SRF is associated with cellular transformation and epithelial-mesenchymal transformation (see Iwahara et al., Oncogene 22:5946-5957 (2003); Psichari et al., J Biol Chem 277:29490-29495 (2002)).

One key mechanism of activation of SRF by serum involves activation of the Rho GTPases (especially rhoA and rhoC) through G protein-coupled receptors and possibly other mechanisms. Activation of rhoA and rhoC induces actin polymerization and release of the transcriptional coactivator, myocardin-related transcription factor ("MRTF") (see Cen et al., Mol Cell Biol 23:6597-6608 (2003); Miralles et al., Cell 113:329-342 (2003); Selvaraj and Prywes, J Biol Chem 278:41977-41987 (2003)). MRTF, which is also known as MKL, was first identified as a site of gene translocation in leukemia (megakaryoblastic leukemia), like the leukemia-associated rhoGEF ("LARG", see Mercher et al., Genes Chromosomes Cancer 33:22-28 (2002)). The protein product of the translocated gene is hyperactive compared to the wild-type protein. MRTF and MKL have also been called modified in acute leukemia ("MAL") and BSAC (see Miralles et al., Cell 113:329-342 (2003); Sasazuki et al., J Biol Chem 277:28853-28860 (2002)). There are two MRTF genes (MRTF-A and MRTF-B or MKL1 and MKL2, respectively). Their actions are largely redundant where both proteins are expressed (see Shaposhnikov, Cell Cycle 12:1762-72 (2013)). MRTF was identified in an antiapoptosis screen for genes that abrogate tumor necrosis factor-induced cell death (see Sasazuki et al., J Biol Chem 277:28853-28860 (2002)). As a consequence of rho signaling, MRTF translocates to the nucleus and binds SRF leading to the expression of c-fos which, along with c-jun, forms the transcription factor AP-1. The AP-1 transcription factor promotes the activity of various MMPs and other cell motility genes (see Benbow and Brinckerhoff, Matrix Biol 15:519-526 (1997)). Expression of these genes leads to cancer cell invasion and metastasis. Thus, there is a link between Rho/MRTF-controlled biological processes and cancer metastasis. Similarly, both LARG and MKL are important players in these processes.

Rho GTPase signaling and MRTF-regulated gene transcription have also been implicated in tissue fibrosis in lung (see Sandbo et al, Am J Respir Cell Mol Biol. 41:332-8 (2009); Luchsinger J Biol Chem. 286:44116-25 (2011)), skin (see Haak et al, J Pharmacol Exp Ther. 349:480-6 (2014)), and intestine (see Johnson et al, Inflamm Bowel Dis. 20:154-65 (2014)). Many genes involved in fibrosis (alpha-smooth muscle actin, CTGF, and collagen itself) are activated by Rho-regulated MRTF/SRF mechanisms (see Haak et al, J Pharmacol Exp Ther. 349:480-6, (2014)).

Cancer metastasis is a significant medical problem in the United States, where it is estimated that over 500,000 cancer-related deaths in 2003 resulted from metastatic tumors rather than primary tumors (approximately 90% of cancer deaths). Cancer metastasis requires malfunction in several tightly regulated cellular processes controlling cell movement from a primary site to a secondary site. These cellular processes include cell survival, adhesion, migration, and proteolysis resulting in extracellular matrix remodeling, immune escape, angiogenesis and lymphangiogenesis, and target 'homing' Most existing cancer treatments focus on killing tumor cells; however, such chemotherapeutic intervention leads to substantial toxicity to healthy cells and tissue. Since spread, or metastasis, of cancers is the primary cause of cancer-related mortalities, there is a need for agents that can specifically inhibit or prevent signals that trigger metastasis.

Rho proteins are overexpressed in various tumors, including colon, breast, lung, testicular germ cell, and head and neck squamous-cell carcinoma (see Sawyer, Expert Opin. Investig. Drugs., 13: 1-9 (2004)). The rho family of small GTP binding proteins plays important roles in many normal biological processes and in cancer (see Schmidt and Hall, Genes Dev., 16:1587-1609 (2002); Burridge and Wennerberg, Cell, 116:167-179 (2004)). This family includes three main groups: rho, rac, and cdc42. Rho is activated by numerous external stimuli including growth factor receptors, immune receptors, cell adhesion, and G protein coupled receptors (GPCRs) (see Schmidt and Hall, Genes Dev., 16:1587-1609 (2002), Sah et al., Annu. Rev. Pharmacol. Toxicol., 40:459-489 (2000)).

RhoA and rhoC play roles in metastasis (see Clark et al., Nature 406:532-535 (2000); Ikoma et al., Clin Cancer Res 10:1192-1200 (2004); Shikada et al., Clin Cancer Res 9:5282-5286 (2003); Wu et al., Breast Cancer Res Treat 84:3-12 (2004); Hakem et al, Genes Dev 19:1974-9 (2005). Both rhoA and rac1 can regulate the function of the extracellular matrix (ECM) proteins, ezrin, moesin, and radixin, by the phosphorylation of ezrin via the rhoA pathway and the phosphorylation of the ezrin antagonist, neurofibromatosis 2, by the rac1 pathway (see Shaw et al., Dev Cell 1:63-72 (2001); Matsui et al., J Cell Biol 140:647-657 (1998)). These ECM proteins promote cell movement by utilizing the ECM receptor, CD44, to link the actin cytoskeleton with the plasma membrane. In addition, rhoA and racl regulate ECM remodeling by controlling the levels of matrix metalloproteinases (MMPs) or their antagonists, tissue inhibitors of metalloproteinases (TIMPs) (see Bartolome et al., Cancer Res 64:2534-2543 (2004)). RhoA is also required for monocyte tail retraction during transendothelial migration, indicating a role in extravasation, which is a key process in metastasis (see Worthylake et al., J Cell Biol 154:147-160 (2001).

The relative contributions of rho and rac proteins in the metastatic phenotype has been studied (see Sahai and Marshall, Nat Rev Cancer 2:133-142 (2002); Whitehead et al., Oncogene 20:1547-1555 (2001)). Sahai and Marshall (see Nat Cell Biol 5:711-719 (2003)) showed that different tumor cell lines exhibit different mechanisms of motility and invasion. In particular, 375 m2 melanoma and LS174T colon carcinoma cell lines showed striking "rounded" and "blebbed" morphology during invasion into Matrigel matrices. This invasion was entirely rho-dependent and was blocked by C3 exotoxin, the N17rho dominant negative protein, and a ROCK kinase inhibitor. In contrast, two other cell lines were blocked instead by a rac dominant negative mutation, but not rho or ROCK inhibitors. These latter two cell lines (BE colon carcinoma and SW962 squamous cell carcinoma) had elongated morphologies. A third line showed a mixed morphology and was blocked partially by both rho and rac inhibitors. Additionally, mice lacking rhoC have greatly reduced metastasis of virally-induced breast tumors to lung (see Hakem et al, Genes Dev 19:1974-9 (2005)). Also, knock-down of SRF or its transcriptional co-activator MKL reduced lung metastases from breast or melanoma xenografts (see Medjkane et al, Nat Cell Biol. 11:257-68 (2009)). Thus, there is important heterogeneity in mechanisms of tumor cell behavior that contributes to metastasis. It is widely recognized that cell growth and apoptosis mechanisms vary greatly among tumors, necessitating customized therapeutic approaches.

Nearly 40% of chronic diseases such as cirrhosis, heart failure, and diabetic nephropathy are characterized by fibrosis or excess deposition of extracellular matrix, including collagen. The poor clinical outcome of several orphan diseases (scleroderma or systemic sclerosis ("SSc"), idiopathic pulmonary fibrosis ("IPF") etc.) is primarily determined by tissue fibrosis; there are absolutely no effective treatments despite their rapid and lethal clinical course.

Systemic sclerosis is an orphan, multisystem autoimmune disorder that can cause fibrosis of the skin and internal organ systems (lungs, heart, kidneys, and gastrointestinal system). It has the highest case fatality rate of any rheumatic disease. SSc predominately affects women (see Beyer et al., Arthritis Rheum 62: 2831-2844 (2010); Boukhalfa G, et al., Exp Nephrol 4: 241-247 (1996); Buhl A M, et al., J Biol Chem 270: 24631-24634 (1995); Chaqour et al., FEBS J 273: 3639-3649 (2006); Charles et al., Lancet 367: 1683-1691 (2006) and increases with age. The precise pathogenesis of SSc is yet to be defined but the major clinical features of SSc—collagen production, vascular damage and inflammation/autoimmunity—require environmental triggers and genetic effects which interact with the three cardinal features of the disease at several points (see Charles et al., Lancet 367: 1683-1691 (2006)). Generally, there is initial inflammation but fibrosis persists even after the inflammation has resolved or has been suppressed by medications (see Beyer et al., Curr Opin Rheumatol 24: 274-280 (2012); Wynn T A, and Ramalingam T R. Nat Med 18: 1028-1040 (2012)).

Therefore, there is a need for new compounds and methods for targeted therapy that can treat and manage cancer and fibrosis.

SUMMARY

One aspect of the disclosure provides a compound of Formula (II), or a pharmaceutically acceptable salt thereof:

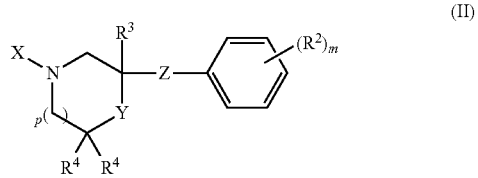

wherein:

X is

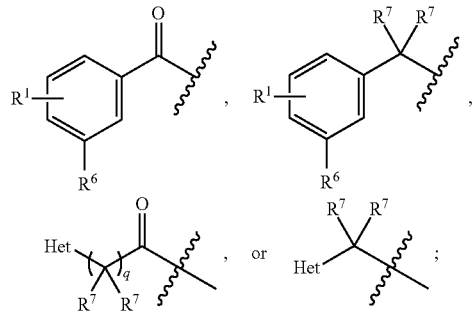

Het is heteroaryl;
Y is $CH_2$, C=O, CHOH, CHF, $CF_2$, $NR^5$, $NCONHR^5$, $NCOR^5$, $NCO_2R^5$, $NSO_2R^5$, $S(O)_2$, or S;
Z is

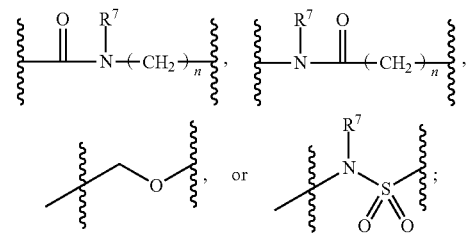

m is 0, 1, or 2;
n is 0, 1, or 2;
p is 0 or 1;
q is 0, 1, or 2;
$R^1$ is heteroaryl;
each $R^2$ independently is halo, $C_{1-6}$ alkyl, $OC_1$-$C_6$ alkyl, $OC_{0-6}$ alkylene-aryl, $OC_{0-6}$ alkylene-heteroaryl, $SO_2NR^5_2$, CN, or $SO_2C_{1-3}$alkyl.
$R^3$ is H, halo, OH, $C_{1-3}$ alkyl, or $OC_{1-3}$ alkyl;
each $R^4$ independently is H, F, $C_{1-3}$ alkyl, $OR^5$, $NR^5_2$, $NR^5CONHR^5$, $NR^5COR^5$, $NR^5CO_2R^5$, $NR^5SO_2R^5$, or both $R^4$ together with the carbon to which they are attached form C=O, C=$CH_2$, or $C_{3-7}$ cycloalkyl;
each $R^5$ independently is H, $C_{1-6}$ alkyl, $C_{3-7}$ cycloalkyl, $C_{2-6}$ alkenyl, $C_{3-6}$ alkylene-ether, $C_{0-6}$ alkylene-aryl, $C_{0-6}$ alkylene-heteroaryl, or two $R^5$ together with a nitrogen to which they are attached form a 3-7 atom heterocyclic ring;

$R^6$ is H, halo, $C_{1-3}$ haloalkyl, or $OC_{1-3}$ haloalkyl; and
$R^7$ is H or $C_{1-3}$ alkyl;
with the proviso that when:
(a) X is

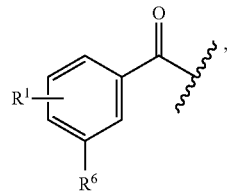

Y is $CH_2$, Z is

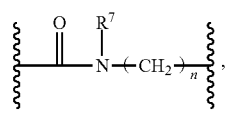

m is 1, n is 0, p is 1, $R^2$ is chloro, $R^3$ is H, each $R^4$ is H, and $R^6$ is H, then $R^1$ is other than furanyl, thiophenyl, thiazolyl, oxazolyl, or oxadiazolyl; or
(b) $R^1$ is unsubstituted furanyl, unsubstituted thiophenyl, unsubstituted thiazolyl, unsubstituted oxazolyl, or unsubstituted oxadiazolyl, then:
(i) X is other than

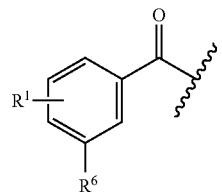

and $R^6$ is other than H; or
(ii) Y is other than $CH_2$; or
(iii) Z is other than

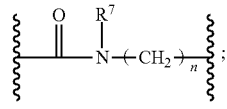

or
(iv) $R^2$ is other than Cl; or
(v) $R^3$ is other than H; or
(vi) at least one $R^4$ is other than H; or
(vi) p is other than 1.
In some embodiments, p is 1.
In some cases, X is

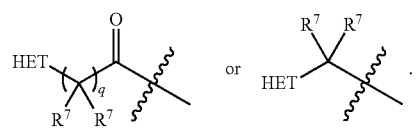

HET can be pyridyl, pyrazolyl, oxazolyl, isoxazolyl, thiazolyl, indolyl, indazolyl, benzofuranyl, benzothiazolyl, benzoimidazolyl, pyrazinyl, pyrimidinyl, pyrrolyl, imidazolyl, or furanyl. In various cases, HET is pyridyl, pyrazolyl, oxazolyl, isoxazolyl, thiazolyl, indolyl, indazolyl, benzofuranyl, benzothiazolyl, benzoimidazolyl, or pyrimidinyl. For example, HET can be selected from the group consisting of:

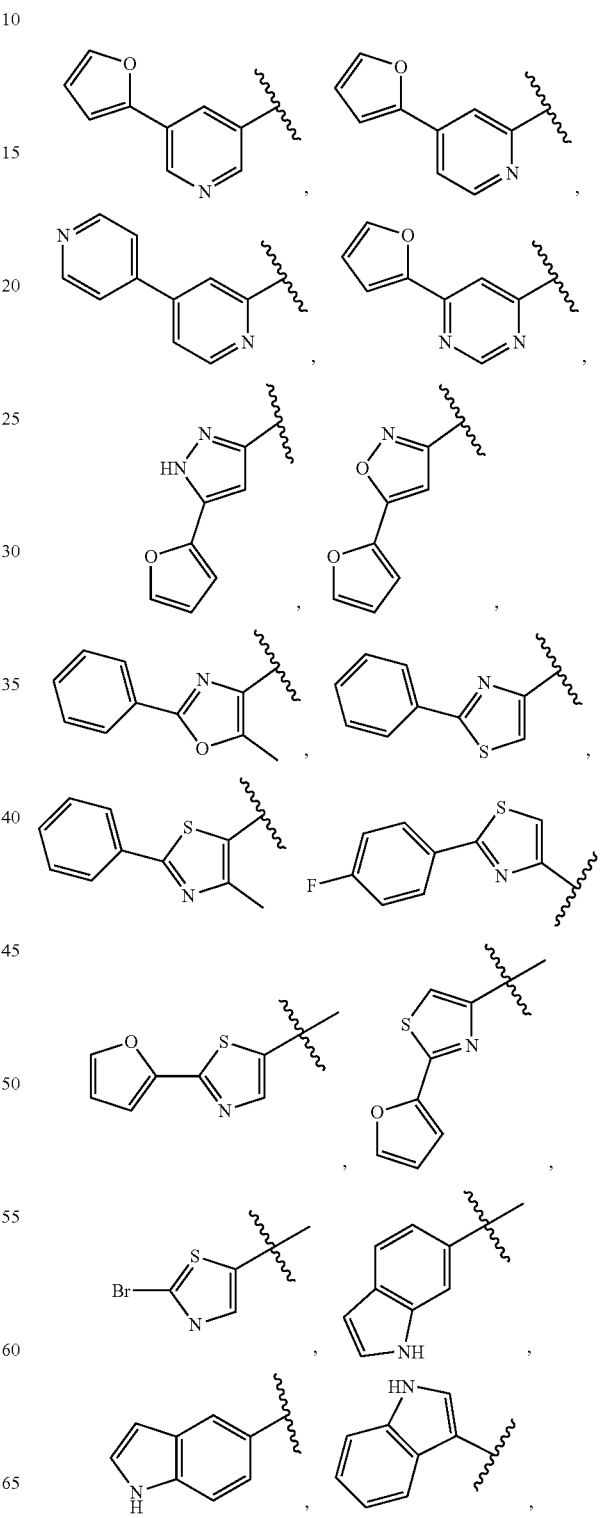

-continued

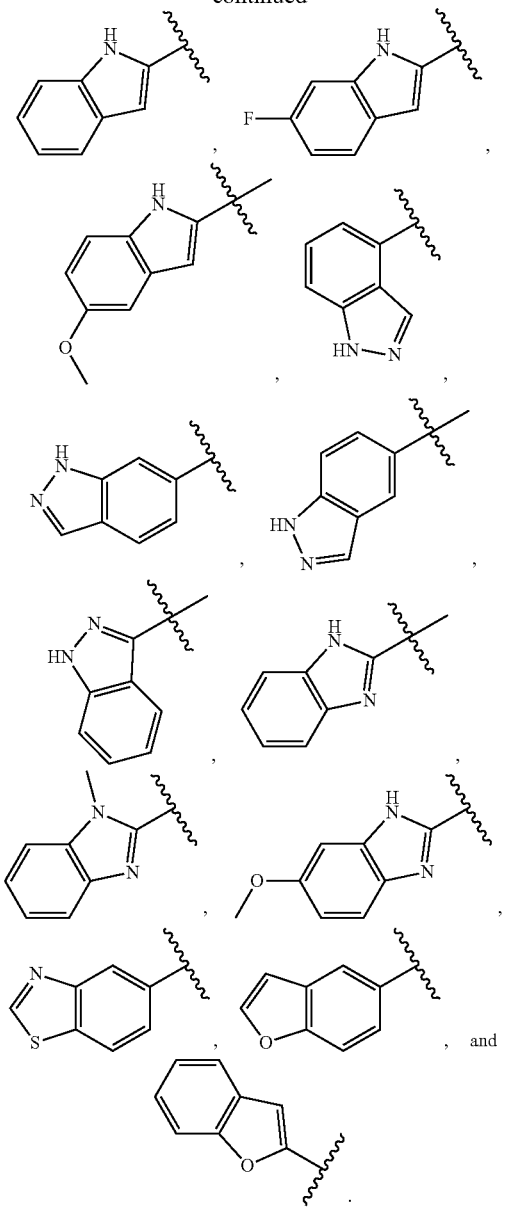

In various cases, q is 0. In some embodiments, each $R^7$ independently is H or $CH_3$.

In various cases, X is

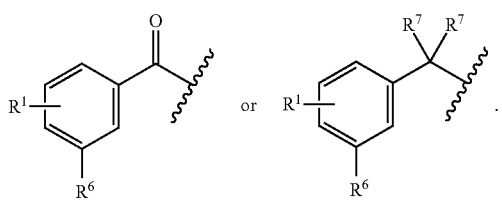

In some embodiments, $R^1$ is selected from the group consisting of pyrrolyl, pyrazolyl, imidazolyl, triazolyl, furanyl, thiophenyl, oxazolyl, isooxazolyl, oxadiazolyl, thiazolyl, pyridyl, pyridazinyl, pyrimidinyl, pyrazinyl, tetrazolyl, and thiadiazolyl. In various embodiments, $R^1$ is pyrrolyl, pyrazolyl, imidazolyl, furanyl, thiophenyl, oxazolyl, isooxazolyl, oxadiazolyl, or thiazolyl. For example, $R^1$ is selected from the group consisting of

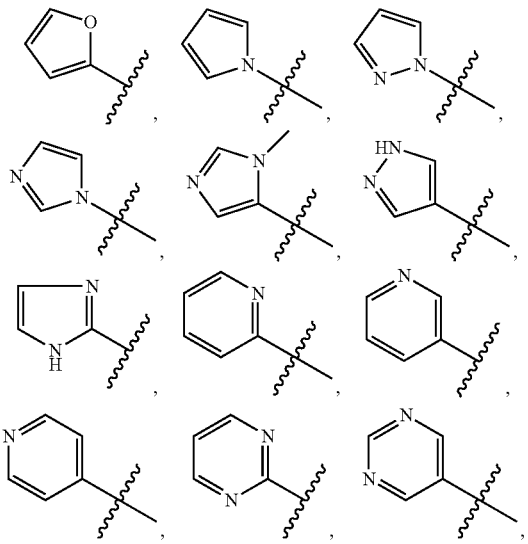

and $NHCH_2CH_3$. In some cases, $R^6$ is H or halo.

For example, X can be selected from the group consisting of:

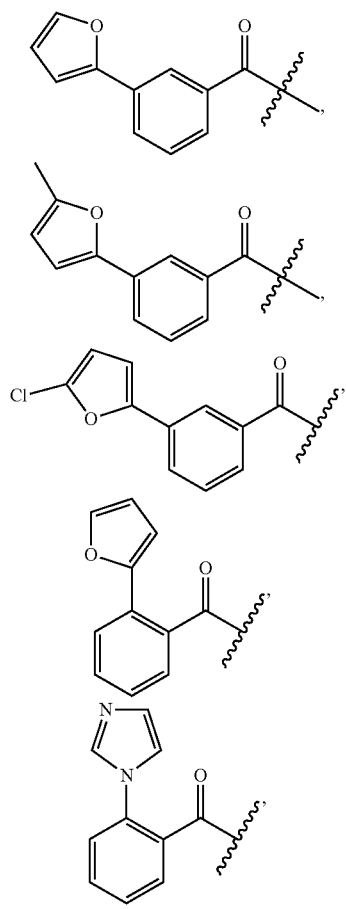

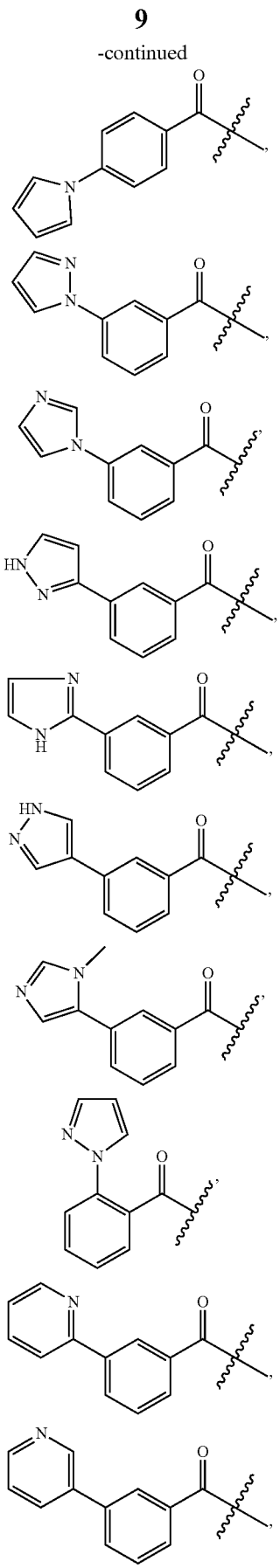
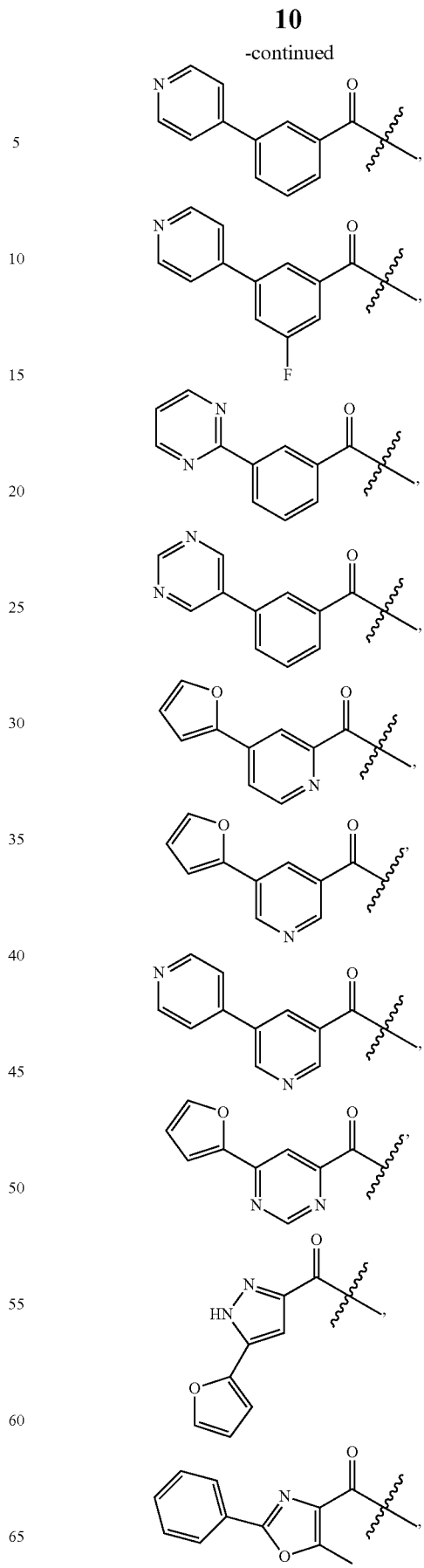

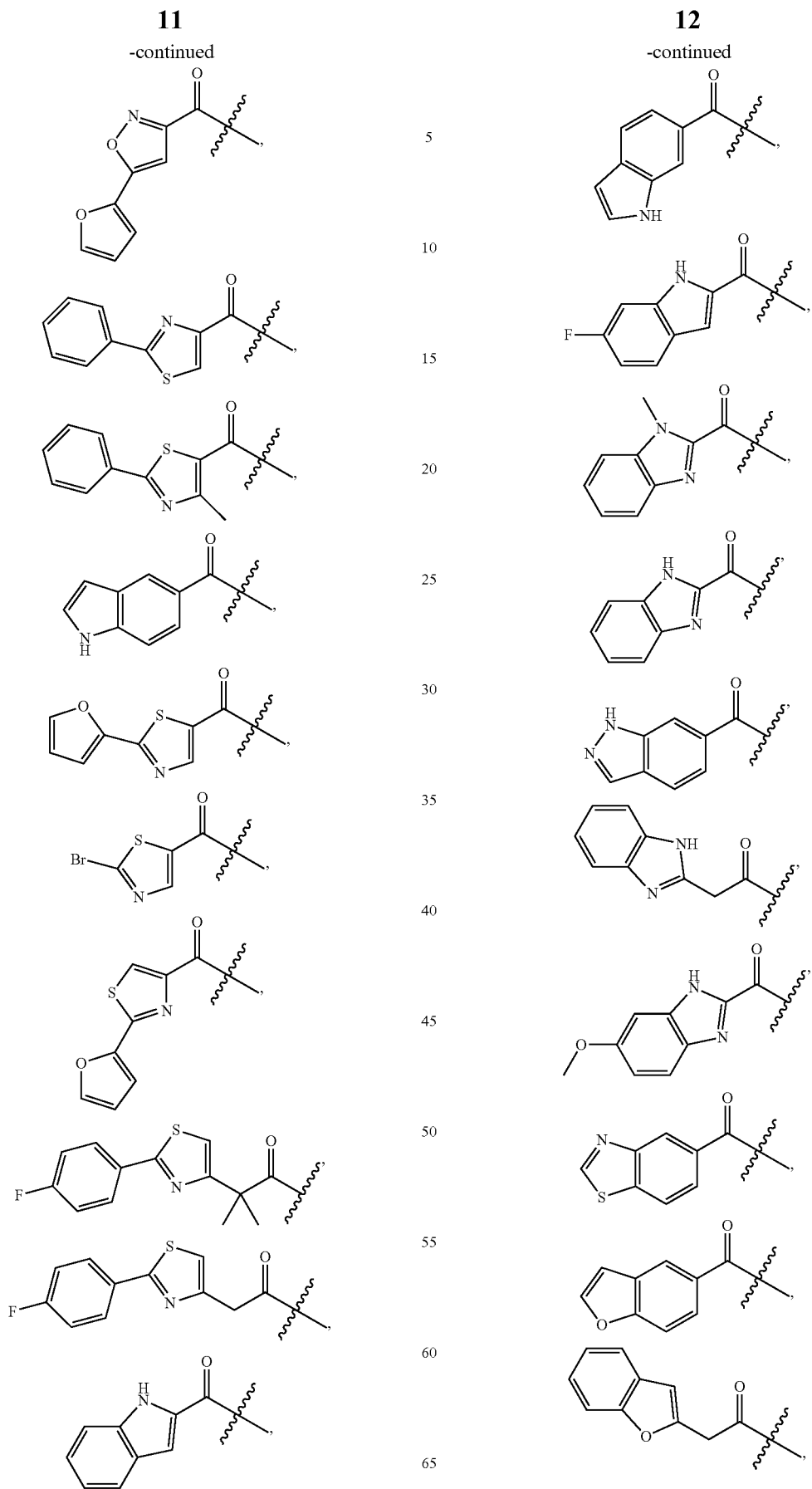

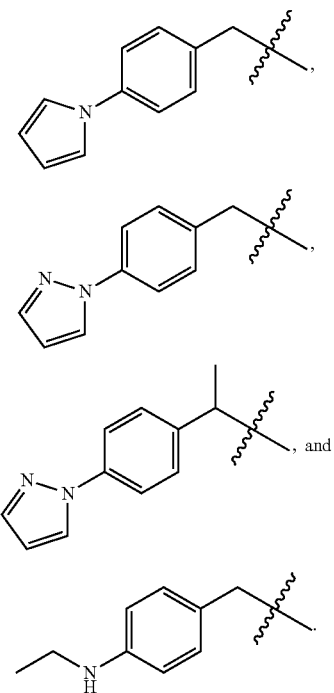

In some cases, X is

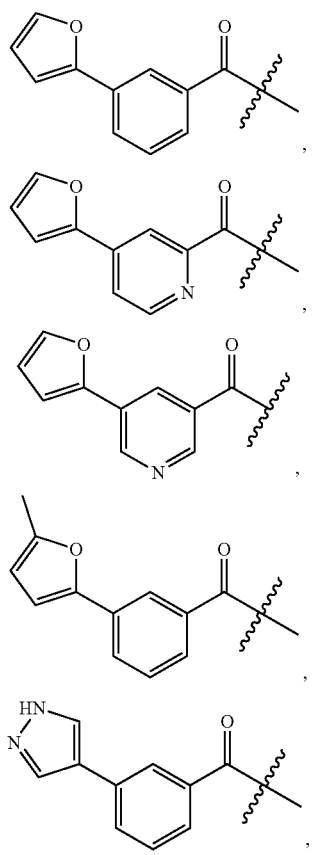

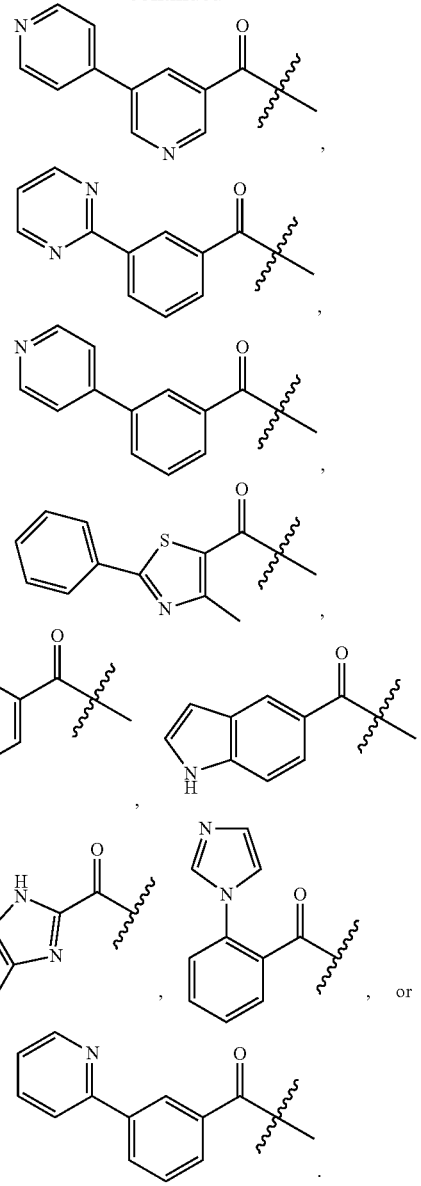

In some embodiments, Z is

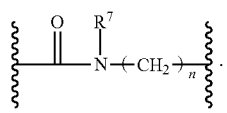

In various cases, $R^7$ is H or $CH_3$ and n is 0.

In various embodiments, Y is $CH_2$, $NR^5$, $NCONHR^5$, $NCOR^5$, $NCO_2R^5$, $S(O)_2$, or S, and $R^5$ is $C_{1-6}$ alkyl, $C_{3-7}$ cycloalkyl, $C_{2-6}$ alkenyl, $C_{3-6}$ alkylene-ether, or $C_{0-6}$ alkylene-aryl. For example, Y can be $CH_2$, NMe, $NCH_2Ph$, NCONHiPr, NCONHPh, NCONH-cyclopentyl, $NCONHCH_2CH=CH_2$, NCOMe, NCOEt, NCOiPr, NCO(para-methoxyphenyl), $NCO_2Et$, $NCO_2Pr$, $NCO_2Ph$, $NCO_2CH_2Ph$, $NCO_2CH_2CH_2OMe$, $S(O)_2$, or S. In some embodiments, Y is $CH_2$.

In various cases, $R^3$ is H, F, or Me. For example $R^3$ can be H.

In some embodiments, each $R^4$ is H. In various embodiments, each $R^4$ is F. In some cases, one $R^4$ is H and the other is OH, OMe, $NR^5_2$, $NR^5COR^5$, or $NR^5CO_2R^5$. In various cases, each $R^4$ is F or OMe. In some embodiments, both $R^4$ together with the carbon to which they are attached form C=O or C=CH$_2$. For example, one $R^4$ can be selected from the group consisting of NH$_2$, NHMe, NMe$_2$, NHCH$_2$Ph, N(Me)CH$_2$Ph, NHC(O)Et, NHC(O)Ph, NHCO$_2$Me, NHCO$_2$Et, and NHCO$_2$Ph.

In some embodiments, m is 1 and $R^2$ is halo. For example, $R^2$ can be Cl. In various embodiments, Cl is para to Z. In some cases, at least one $R^2$ is F, CN, SO$_2$Me, or Me.

Another aspect of the disclosure provides a compound selected from the group consisting of E-001, E-003 to E-033, E-035, E-037 to E-073, and E-075 to E-115. In some cases, the disclosure provides a compound selected from the group consisting of E-019, E-023, E-024, E-029, E-031, E-042, E-050, E-068, E-072, E-086, E-087, E-089, E-090, and E-100.

Yet another aspect of the disclosure provides a compound of Formula (I), or a pharmaceutically acceptable salt thereof:

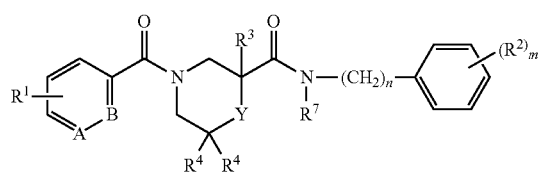

(I)

wherein:
m is 0, 1, or 2;
n is 0, 1, or 2;
one of A and B is $CR^6$ and the other is $CR^6$ or N;
Y is CH$_2$, C=O, CHOH, CHF, CF$_2$, $NR^5$, NCONHR$^5$, NCOR$^5$, NCO$_2R^5$, or NSO$_2R^5$;
$R^1$ is heteroaryl;
each $R^2$ independently is halo, $C_{1-6}$ alkyl, $OC_1$-$C_6$ alkyl, $OC_{0-6}$ alkylene-aryl, $OC_{0-6}$ alkylene-heteroaryl, or SO$_2NR^5_2$;
$R^3$ is H, halo, OH, $C_{1-3}$ alkyl, or $OC_{1-3}$ alkyl;
each $R^4$ independently is H, F, $C_{1-3}$ alkyl, OR$^5$, $NR^5_2$, NR$^5$CONHR$^5$, NR$^5$COR$^5$, NR$^5$CO$_2R^5$, NR$^5$SO$_2R^5$, or both $R^4$ together with the carbon to which they are attached form C=O, C=CH$_2$, or $C_{3-7}$ cycloalkyl;
each $R^5$ independently is H, $C_{1-6}$ alkyl, $C_{3-7}$ cycloalkyl, $C_{2-6}$ alkenyl, $C_{3-6}$ alkylene-ether, $C_{0-6}$ alkylene-aryl, $C_{0-6}$ alkylene-heteroaryl, or two $R^5$ together with a nitrogen to which they are attached form a 3-7 atom heterocyclic ring;
each $R^6$ independently is H, halo, $C_{1-3}$ haloalkyl, or $OC_{1-3}$ haloalkyl; and
$R^7$ is H or $C_{1-3}$ alkyl;
with the proviso that when n is 0, m is 1, A and B are each CH, $R^2$ is halo (e.g., chloro), each $R^4$ is H, and Y is CH$_2$, then $R^1$ is other than unsubstituted furanyl, unsubstituted thiophenyl, unsubstituted thiazolyl, unsubstituted oxazolyl, or unsubstituted oxadiazolyl.

In some embodiments, $R^1$ is ortho. In various embodiments, $R^1$ is meta. In some cases, $R^1$ is para. In some embodiments, the compound comprises Formula (IA):

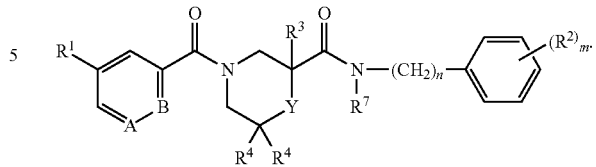

(IA)

In various embodiments for compounds of Formula (IA), n is 0.

In some cases, A and B are each CH. In various cases, one of A or B is CH and the other is N.

In some embodiments, Y is CH$_2$, $NR^5$, NCONHR$^5$, NCOR$^5$, or NCO$_2R^5$; and $R^5$ is $C_{1-6}$ alkyl, $C_{3-7}$ cycloalkyl, $C_{2-6}$ alkenyl, $C_{3-6}$ alkylene-ether, or $C_{0-6}$ alkylene-aryl. In various embodiments, Y is CH$_2$, NMe, NCH$_2$Ph, NCON-HiPr, NCONHPh, NCONH-cyclopentyl, NCONHCH$_2$CH=CH$_2$, NCOMe, NCOEt, NCOiPr, NCO(para-methoxyphenyl), NCO$_2$Et, NCO$_2$Pr, NCO$_2$Ph, NCO$_2$CH$_2$Ph, or NCO$_2$CH$_2$CH$_2$OMe. In some cases, Y is CH$_2$.

In some cases, $R^1$ is pyrrolyl, pyrazolyl, imidazolyl, triazolyl, furanyl, thiophenyl, oxazolyl, isooxazolyl, oxadiazolyl, thiazolyl, pyridinyl, pyridazinyl, pyrimidinyl, or pyrazinyl. In various cases, $R^1$ is pyrrolyl, pyrazolyl, imidazolyl, furanyl, thiophenyl, oxazolyl, isooxazolyl, oxadiazolyl, or thiazolyl.

In some embodiments, m is 1 and $R^2$ is halo. In various embodiments, at least one $R^2$ is halo. In some cases, $R^2$ is Cl. In some embodiments, the compound of Formula (I) comprises Formula (IB):

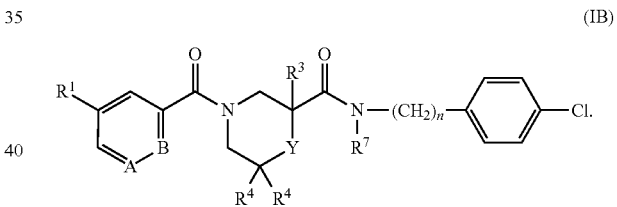

(IB)

In some cases for compounds of Formula (IB), n is 0.

In some cases, $R^3$ is H, F or Me. In various cases, $R^3$ is H. In some embodiments, $R^3$ is OH, $C_{1-3}$ alkyl (e.g., Me, Et, n-Pr, or iPr), or $OC_{1-3}$ alkyl (e.g., OMe, OEt, O-n-Pr, or O-iPr).

In some embodiments, each $R^4$ is H. In various embodiments, one $R^4$ is OH or OMe, and the other is H, OH, or OMe, or both $R^4$ together with the carbon to which they are attached form C=O or C=CH$_2$. In some cases, each $R^4$ is F.

In some cases, $R^7$ is $C_{1-3}$ alkyl. In various cases, $R^7$ is H.

In various embodiments, the compound of Formula (I) comprises Formula (IC):

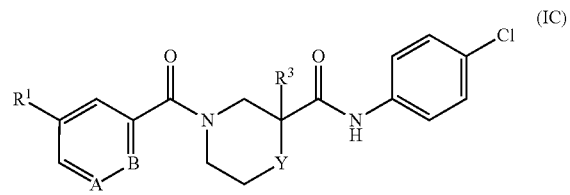

(IC)

wherein:

each of A and B are CH, or one of A and B is CH and the other is N;

Y is $CH_2$, NMe, $NCH_2Ph$, NCONHiPr, NCONHPh, NCONH-cyclopentyl, $NCONHCH_2CH=CH_2$, NCOMe, NCOEt, NCOiPr, NCO(para-methoxypenyl), $NCO_2Et$, $NCO_2Pr$, $NCO_2Ph$, $NCO_2CH_2Ph$, or $NCO_2CH_2CH_2OMe$;

$R^1$ is pyrrolyl, pyrazolyl, imidazolyl, furanyl, thiophenyl, oxazolyl, isooxazolyl, oxadiazolyl, or thiazolyl; and $R^3$ is H, F, or methyl;

with the proviso that when A and B are each CH, and Y is $CH_2$, then $R^1$ is other than unsubstituted furanyl, unsubstituted thiophenyl, unsubstituted thiazolyl, unsubstituted oxazolyl, and unsubstituted oxadiazolyl.

In some embodiments, the compound Formula (I) comprises Formula (ID):

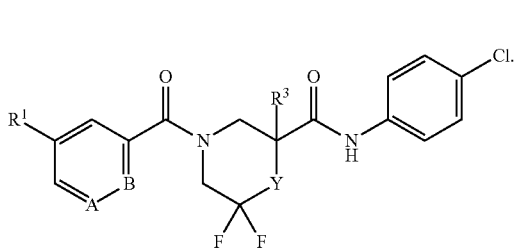

(ID)

For example, the compound of Formula (I) can be selected from the group consisting of E-001 to E-0032.

Another aspect of the disclosure relates to a pharmaceutical formulation comprising a compound of Formula (I) (e.g., Formula (IA), (IB), (IC), or (ID)) or Formula (II) and a pharmaceutically acceptable excipient. In some cases, the pharmaceutical formulation comprises a compound E-001, E-003 to E-033, E-035, E-037 to E-073, E-075 to E-115, or combinations thereof, and a pharmaceutically acceptable excipient.

Still another aspect of the disclosure relates to a kit comprising the pharmaceutical formulation disclosed herein and instructions for administering the pharmaceutical formulation to a patient.

Still another aspect of the disclosure relates to a method of inhibiting MRTF/SRF-mediated gene transcription in a cell, comprising contacting the cell with a compound of Formula (I) (e.g., Formula (IA), (IB), (IC), or (ID)) and/or a compound of Formula (II) in an amount to inhibit the gene transcription. In some cases, the compound of Formula (I) is E-001, E-003 to E-033, E-035, E-037 to E-073, E-075 to E-115, or combinations thereof. In some embodiments, the contacting occurs in vivo. In various embodiments, the contacting comprises administering to a patient in need thereof. In some cases, the patient suffers from a disease associated with dysfunction of MRTF/SRF-mediated gene transcription.

Yet another aspect of the disclosure relates to a method of treating a disease associated with dysfunction of MRTF/SRF-mediated gene transcription in a patient comprising administering to the patient a therapeutically effective amount of the pharmaceutical formulation disclosed herein. In some embodiments, the disease is selected from the group consisting of cancer, fibrotic disease, diabetes, insulin sensitivity, hyperactive platelets, metabolic disease, inflammation, inflammatory disease, pulmonary arterial hypertension, axon regeneration following nerve damage, Raynaud's phenomenon, cerebral vascular disease, cardiovascular disease, erectile dysfunction, and combinations thereof.

In some cases, the cancer is selected from the group consisting of fibrosarcoma, myxosarcoma, liposarcoma, chondrosarcoma, osteogenic sarcoma, chordoma, angiosarcoma, endotheliosarcoma, lymphangiosarcoma, Ewing's tumor, lymphangioendotheliosarcoma, synovioma, mesothelioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, glioblastoma, leukemia, megakaryoblastic leukemia, polycythemia vera, lymphoma, multiple myeloma, Waldenstrom's macroglobulinemia, heavy chain disease, and combinations thereof. For example, the cancer can be megakaryoblastic leukemia, melanoma, breast cancer, prostate cancer, glioblastoma, or combinations thereof.

In some cases, the fibrotic disease is systemic sclerosis, pulmonary fibrosis, cardiac fibrosis, liver fibrosis, liver cirrhosis, renal fibrosis, chronic renal failure, lung fibrosis, nephrogenic systemic fibrosis, graft versus host disease, Dupuytren's contracture, inflammatory bowel disease, Crohn's disease, ocular fibrosis, diabetic retinopathy, age-related macular degeneration, postoperative adhesions, reactive fibrosis, chronic heart failure, glaucoma, post-trabeculectomy fibrosis, corneal fibrosis, pterygia, Grauves opthmalopathy, or combinations thereof. For example, the fibrotic disease can be systemic sclerosis or idiopathic pulmonary fibrosis.

In some cases, the metabolic disease is obesity, diabetes (e.g., type II diabetes), insulin resistance, or combinations thereof.

Further aspects and advantages will be apparent to those of ordinary skill in the art from a review of the following detailed description, taken in conjunction with the drawings. The description hereafter includes specific embodiments with the understanding that the disclosure is illustrative, and is not intended to limit the invention to the specific embodiments described herein.

DETAILED DESCRIPTION

Figure 1:
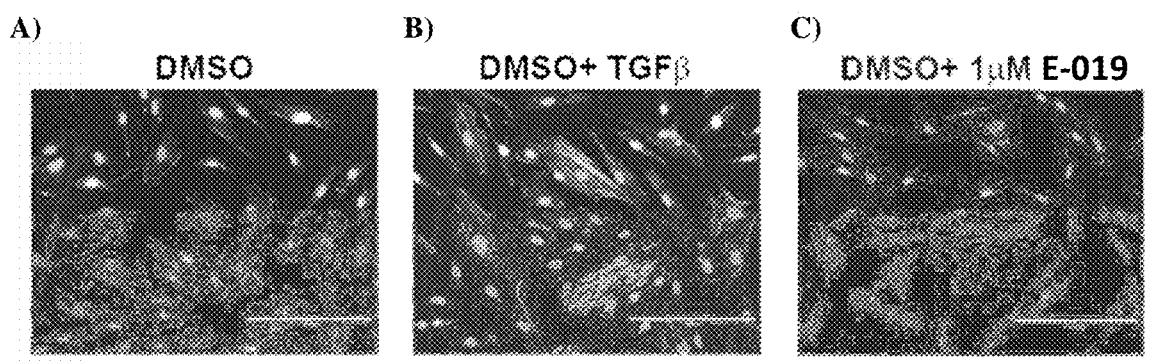
FIG. 1 depicts an optical micrograph of dermal fibroblasts that were treated with (A) 0.1% DMSO, (B) 0.1% DMSO and 10 ng/mL of TGF β1, and (C) 1 μM of E-019 in 0.1% DMSO.

Disclosed herein are compounds that can inhibit gene transcription mediated by myocardin-related transcription factor and/or serum response factor, which demonstrate potency over other small molecule inhibitors (e.g., about 100 times more potent than pirfenidone at inhibiting myofibroblast markers in SSc dermal fibroblasts in vitro). The inhibitors disclosed herein can be used to treat or prevent diseases, such as cancer or fibrotic disease, improving the quality of life for afflicted individuals.

The inhibitors disclosed herein have a structure of Formula (I) or Formula (II), wherein the substituents are described in detail below.

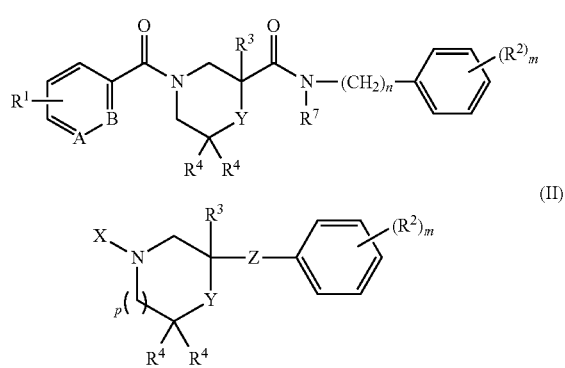

In various cases, the compounds of Formula (I) and Formula (II) inhibit the serum response element (SRE) with an $IC_{50}$ up to about 75 µM, or up to about 50 µM, or up to about 25 µM, or up to about 15 µM, or up to about 10 µM, or up to about 5 µM, or up to about 1 µM. In some embodiments, the compounds of Formula (I) have an $IC_{50}$ value for SRE of less than about 50 µM, or less than about 25 µM, or less than about 20 µM, or less than about 15 µM, or less than about 10 µM, or less than about 5 µM, or less than about 4 µM, or less than about 3 µM, or less than about 2 µM, or less than about 1 µM, or less than about 0.8 µM, or less than about 0.6 µM, or less than about 0.4 µM, or less than about 0.3 µM, or less than about 0.2 µM, or less than about 0.1 µM, or less than about 0.05 µM. In various cases, the $IC_{50}$ value of the compound of Formula (I) is about 0.05 µM to about 50 µM, 0.3 µM to about 50 µM, or about 0.4 µM to about 2.0 µM, or about 0.4 µM to about 1 µM.

Definitions

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_1$-$C_7$ alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl(2-methylpropyl), t-butyl(1,1-dimethylethyl), 3,3-dimethylpentyl, and 2-ethylhexyl. Unless otherwise indicated, an alkyl group can be an unsubstituted alkyl group or a substituted alkyl group.

As used herein, the term "alkenyl" is defined identically as "alkyl" except for containing at least one carbon-carbon double bond, and having two to thirty carbon atoms, for example, two to twenty carbon atoms, or two to ten carbon atoms. The term $C_n$ means the alkenyl group has "n" carbon atoms. For example, $C_4$ alkenyl refers to an alkenyl group that has 4 carbon atoms. $C_2$-$C_7$ alkenyl refers to an alkenyl group having a number of carbon atoms encompassing the entire range (i.e., 2 to 7 carbon atoms), as well as all subgroups (e.g., 2-6, 2-5, 3-6, 2, 3, 4, 5, 6, and 7 carbon atoms). Specifically contemplated alkenyl groups include ethenyl, 1-propenyl, 2-propenyl, and butenyl. Unless otherwise indicated, an alkenyl group can be an unsubstituted alkenyl group or a substituted alkenyl group.

As used herein, the term "alkylene" refers to an alkyl group having a substituent. For example, the term "alkylenearyl" refers to an alkyl group substituted with an aryl group. The term $C_n$ means the alkylene group has "n" carbon atoms. For example, $C_{1-6}$alkylene refers to an alkylene group having a number of carbon atoms encompassing the entire range, as well as all subgroups, as previously described for "alkyl" groups.

As used herein, the term "cycloalkyl" refers to an aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_5$-$C_8$ cycloalkyl refers to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group. The cycloalkyl groups described herein can be isolated, share a carbon atom with another cycloalkyl or heterocycloalkyl group, or fused to another cycloalkyl group, a heterocycloalkyl group, an aryl group and/or a heteroaryl group. Cycloalkyl groups can be saturated or partially unsaturated ring systems optionally substituted with, for example, one to three groups, independently selected alkyl, alkylene-OH, $C(O)NH_2$, $NH_2$, oxo (=O), aryl, haloalkyl, halo, and OH.

As used herein, the term "heterocycloalkyl" or "heterocyclic" is defined similarly as cycloalkyl, except the ring contains one to three heteroatoms independently selected from oxygen, nitrogen, or sulfur. Nonlimiting examples of heterocycloalkyl groups include piperdine, tetrahydrofuran, tetrahydropyran, dihydrofuran, morpholine, and the like. Heterocycloalkyl groups can be saturated or partially unsaturated ring systems optionally substituted with, for example, one to three groups, independently selected alkyl, alkyleneOH, $C(O)NH_2$, $NH_2$, oxo (=O), aryl, haloalkyl, halo, and OH. Heterocycloalkyl groups optionally can be further N-substituted with alkyl, hydroxyalkyl, alkylene-aryl, and alkylene-heteroaryl. The heterocycloalkyl groups described herein can be isolated, share a carbon atom with another cycloalkyl or heterocycloalkyl group, or fused to another heterocycloalkyl group, a cycloalkyl group, an aryl group and/or a heteroaryl group.

As used herein, the term "aryl" refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, and fluorenyl. Unless otherwise indicated, an aryl group can be an unsubstituted aryl group or a substituted aryl group.

As used herein, the term "heteroaryl" refers to monocyclic or polycyclic (e.g., fused bicyclic and fused tricyclic) aromatic ring systems, wherein one to four-ring atoms are selected from oxygen, nitrogen, or sulfur, and the remaining ring atoms are carbon, said ring system being joined to the remainder of the molecule by any of the ring atoms. Non-limiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, thiophenyl, quinolinyl, isoquinolinyl, benzoxazolyl, benzimidazolyl, and benzothiazolyl. Unless otherwise indicated, a heteroaryl group can be an unsubstituted heteroaryl group or a substituted heteroaryl group.

As used herein, the term "halo" refers to a fluoro, chloro, bromo, or iodo group. the term "haloalkyl" refers to an alkyl group that is substituted with at least one halogen.

As used herein, the term "ether" refers to a "alkyl-O-alkyl" group. The ether group can be unsubstituted or substituted.

A used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, thioether, polythioether, aryl, heteroaryl, hydroxyl, oxy, alkoxy, heteroalkoxy, aryloxy, heteroaryloxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms. A substituted chemical functional group can itself include one or more substituents.

As used herein, the term "therapeutically effective amount" means an amount of a compound or combination of therapeutically active compounds that ameliorates, attenuates or eliminates one or more symptoms of a particular disease or condition, or prevents or delays the onset of one of more symptoms of a particular disease or condition.

As used herein, the terms "patient" and "subject" may be used interchangeably and mean animals, such as dogs, cats, cows, horses, and sheep (i.e., non-human animals) and humans. Particular patients or subjects are mammals (e.g., humans). The terms patient and subject includes males and females.

As used herein, the term "pharmaceutically acceptable" means that the referenced substance, such as a compound of the present disclosure, or a formulation containing the compound, or a particular excipient, are safe and suitable for administration to a patient or subject. The term "pharmaceutically acceptable carrier" refers to a medium that does not interfere with the effectiveness of the biological activity of the active ingredient(s) and is not toxic to the host to which it is administered.

As used herein the terms "treating", "treat" or "treatment" and the like include preventative (e.g., prophylactic) and palliative treatment. In some cases, the treating refers to treating a symptom of a disorder or disease as disclosed herein.

As used herein, the term "excipient" means any pharmaceutically acceptable additive, carrier, diluent, adjuvant, or other ingredient, other than the active pharmaceutical ingredient (API).

As used herein the term "rho" or "rho protein" refers to the rho subfamily that includes rhoA, rhoB, rhoC, and others, and is described in Sahai and Marshall Nat. Rev. Cancer 2:133-142 (2002).

As used herein, the "MRTF/SRF-mediated gene transcription" refers to gene transcription that is mediated by myocardin-related transcription factor, serum response factor, or both myocardin-related transcription factor and serum response factor.

As used herein, the term "dysfunction of MRTF/SRF-mediated gene transcription" relates to an abnormality or impairment gene transcription that is mediated by MRTF, SRF, or both MRTF and SRF.

As used herein, the term "fibrotic disease" relates to diseases involving fibrosis, which may, e.g., be due to chronic inflammation or repair and reorganization of tissues. Fibrosis may involve any organ of the human body (e.g. the skin, lung, pancreas, liver or kidney). Therefore, the disclosure also relates to treatment and/or prevention of fibrotic diseases such as systemic sclerosis, pulmonary fibrosis, cardiac fibrosis, liver fibrosis, liver cirrhosis, renal fibrosis, chronic renal failure, lung fibrosis, nephrogenic systemic fibrosis, graft versus host disease, Dupuytren's contracture, inflammatory bowel disease, Crohn's disease, ocular fibrosis, diabetic retinopathy, age-related macular degeneration, keloid and other scarring/wound healing abnormalities, postoperative adhesions, reactive fibrosis, chronic heart failure (e.g., after myocardial infarction), or combinations thereof.

Small Molecule Inhibitors of MRTF/SRF-Mediated Gene Transcription

Provided herein are compounds of Formula (II), or pharmaceutically acceptable salts thereof:

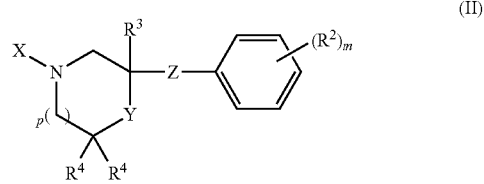

wherein:

X is

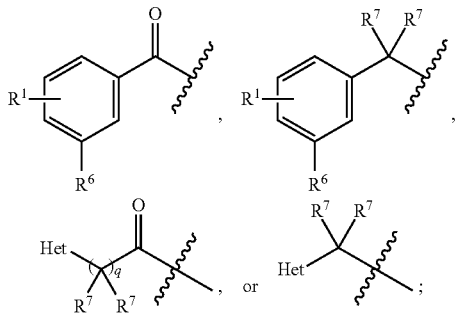

Het is heteroaryl;
Y is $CH_2$, $C=O$, CHOH, CHF, $CF_2$, $NR^5$, $NCONHR^5$, $NCOR^5$, $NCO_2R^5$, $NSO_2R^5$, $S(O)_2$, or S;
Z is

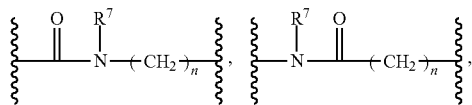

-continued

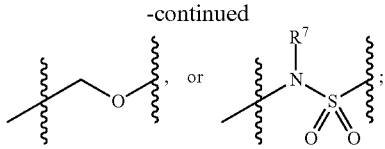

m is 0, 1, or 2;
n is 0, 1, or 2;
p is 0 or 1;
q is 0, 1, or 2;
$R^1$ is heteroaryl;
each $R^2$ independently is halo, $C_{1-6}$ alkyl, $OC_1\text{-}C_6$ alkyl, $OC_{0-6}$ alkylene-aryl, $OC_{0-6}$ alkylene-heteroaryl, $SO_2NR^5_2$, CN, or $SO_2C_{1-3}$alkyl;
$R^3$ is H, halo, OH, $C_{1-3}$ alkyl, or $OC_{1-3}$ alkyl;
each $R^4$ independently is H, F, $C_{1-3}$ alkyl, $OR^5$, $NR^5_2$, $NR^5CONHR^5$, $NR^5COR^5$, $NR^5CO_2R^5$, $NR^5SO_2R^5$, or both $R^4$ together with the carbon to which they are attached form C=O, C=CH$_2$, or $C_{3-7}$ cycloalkyl;
each $R^5$ independently is H, $C_{1-6}$ alkyl, $C_{3-7}$ cycloalkyl, $C_{2-6}$ alkenyl, $C_{3-6}$ alkylene-ether, $C_{0-6}$ alkylene-aryl, $C_{0-6}$ alkylene-heteroaryl, or two $R^5$ together with a nitrogen to which they are attached form a 3-7 atom heterocyclic ring;
$R^6$ is H, halo, $C_{1-3}$ haloalkyl, or $OC_{1-3}$ haloalkyl; and
$R^7$ is H or $C_{1-3}$ alkyl;
with the proviso that when:
(a) X is

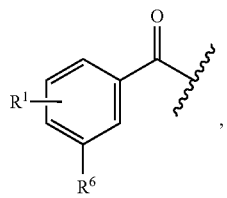

Y is CH$_2$, Z is

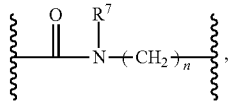

m is 1, n is 0, p is 1, $R^2$ is chloro, $R^3$ is H, each $R^4$ is H, and $R^6$ is H, then $R^1$ is other than furanyl, thiophenyl, thiazolyl, oxazolyl, or oxadiazolyl; or
(b) $R^1$ is unsubstituted furanyl, unsubstituted thiophenyl, unsubstituted thiazolyl, unsubstituted oxazolyl, or unsubstituted oxadiazolyl, then:
(i) X is other than

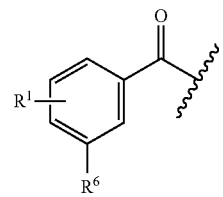

and $R^6$ is other than H; or
(ii) Y is other than CH$_2$; or
(iii) Z is other than

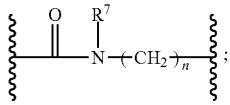

or
(iv) $R^2$ is other than Cl; or
(v) $R^3$ is other than H; or
(vi) at least one $R^4$ is other than H; or
(vi) p is other than 1.

In some embodiments, p is 0. In various embodiments, p is 1.

In some cases, X is

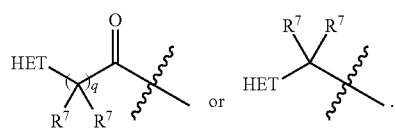

In some embodiments, HET is pyridyl, pyrazolyl, oxazolyl, isoxazolyl, thiazolyl, indolyl, indazolyl, benzofuranyl, benzothiazolyl, benzoimidazolyl, pyrazinyl, pyrimidinyl, pyrrolyl, imidazolyl, or furanyl. In some cases, HET can be pyridyl, pyrazolyl, oxazolyl, isoxazolyl, thiazolyl, indolyl, indazolyl, benzofuranyl, benzothiazolyl, benzoimidazolyl, or pyrimidinyl. In some embodiments, HET is substituted with halo, $C_{1-3}$alkyl (e.g., CH$_3$, CF$_3$, Et, Pr, iPr), or $OC_{1-3}$alkyl (e.g., OCH$_3$, OCF$_3$, OEt, OPr, OiPr). For example, HET can include

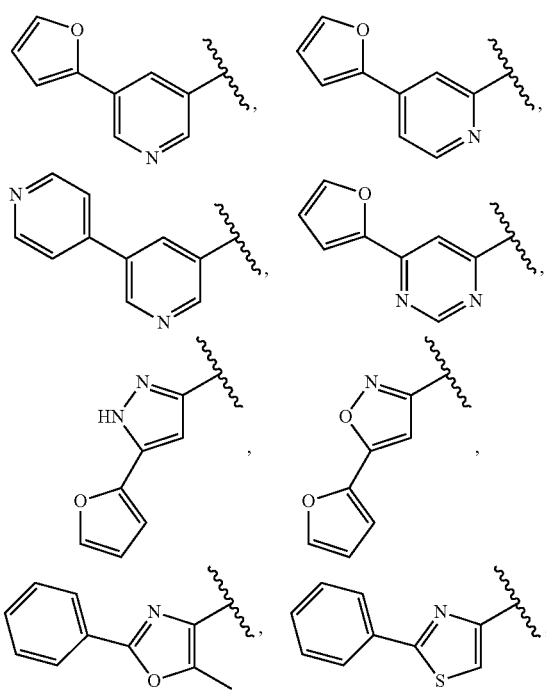

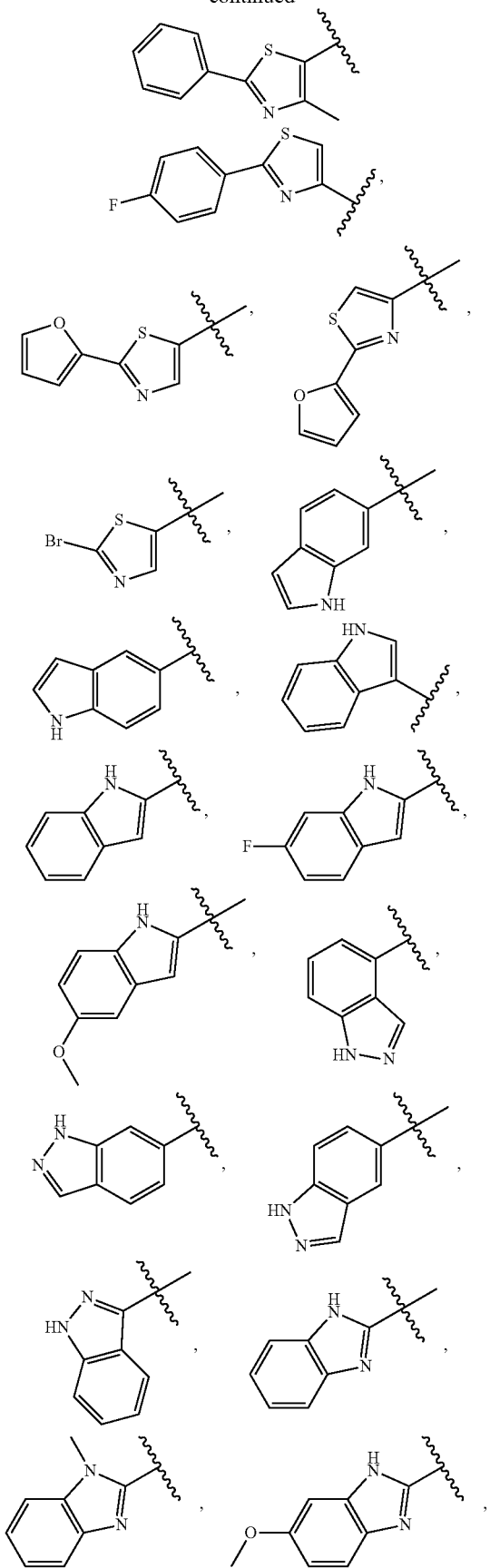

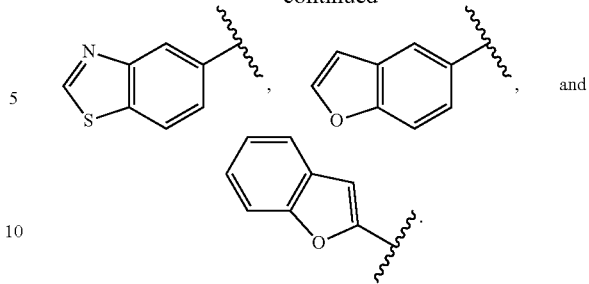

In some embodiments, q is 0. In various cases, q is 1. In some embodiments, q is 2. In various embodiments, each $R^7$ is H. In some embodiments, $R^7$ is methyl, ethyl, propyl, or isopropyl. In some cases, each $R^7$ independently is H or $CH_3$. In some embodiments, one $R^7$ is H and one $R^7$ is $CH_3$.

In some embodiments, X is

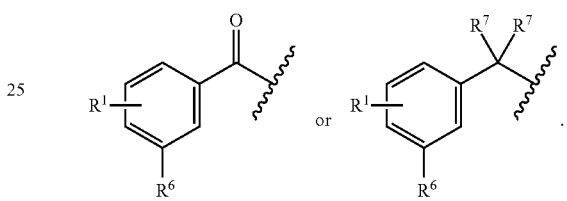

In various embodiments, $R^1$ is selected from the group consisting of pyrrolyl, pyrazolyl, imidazolyl, triazolyl, furanyl, thiophenyl, oxazolyl, isooxazolyl, oxadiazolyl, thiazolyl, pyridyl, pyridazinyl, pyrimidinyl, pyrazinyl, tetrazolyl, and thiadiazolyl. In some cases, $R^1$ is pyrrolyl, pyrazolyl, imidazolyl, furanyl, thiophenyl, oxazolyl, isooxazolyl, oxadiazolyl, or thiazolyl. For example, $R^1$ can be selected from the group consisting of

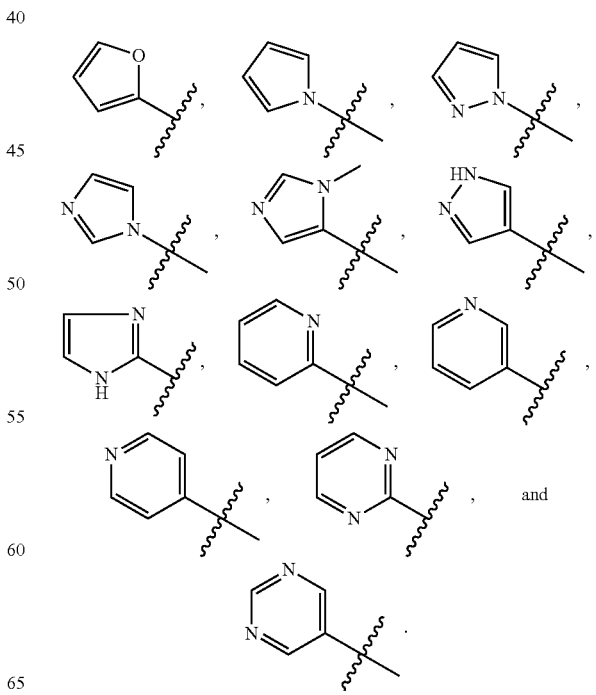

In some embodiments, R¹ is ortho to the carbonyl and the substituent with R⁷. In various embodiments, R¹ is meta to the carbonyl and the substituent with R⁷. In some cases, R¹ is para to the carbonyl and the substituent with R⁷. In various embodiments, R⁶ is H or halo (e.g., F, Cl Br, or I). In some embodiments, R⁶ is F. In some embodiments, R⁶ is H. In some cases, R⁶ is $C_{1-3}$ haloalkyl (e.g., $CF_3$), or $OC_{1-3}$ haloalkyl (e.g., $OCF_3$).

For example, X can be selected from the group consisting of

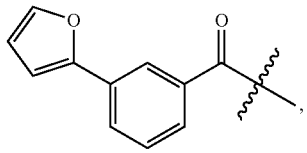

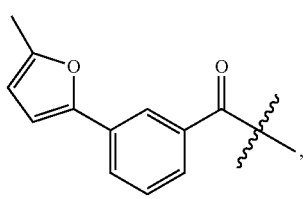

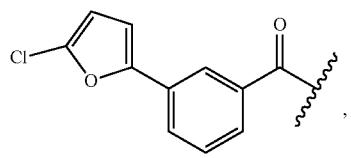

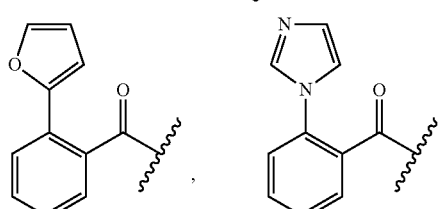

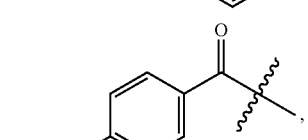

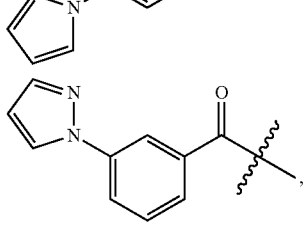

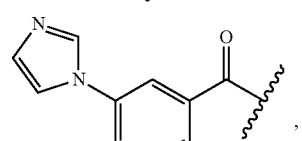

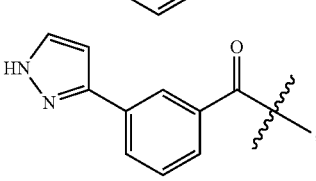

-continued

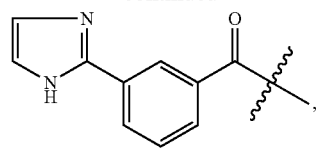

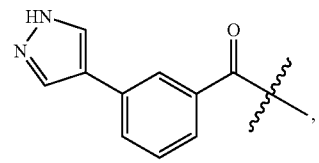

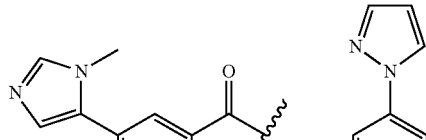

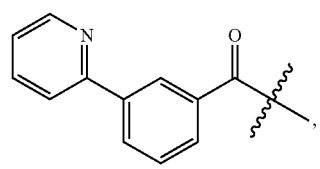

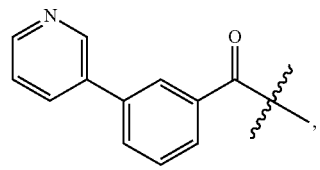

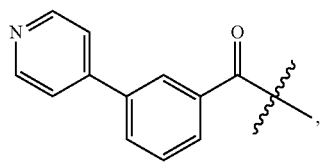

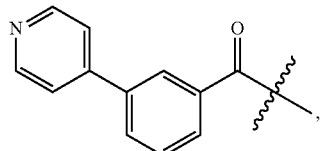

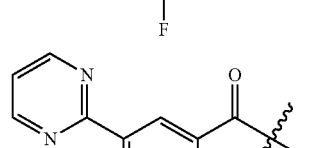

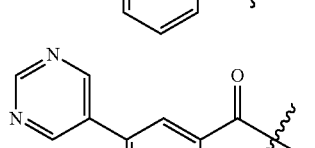

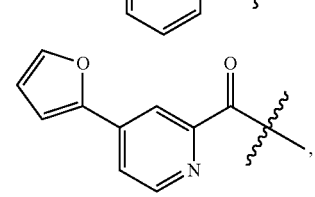

-continued
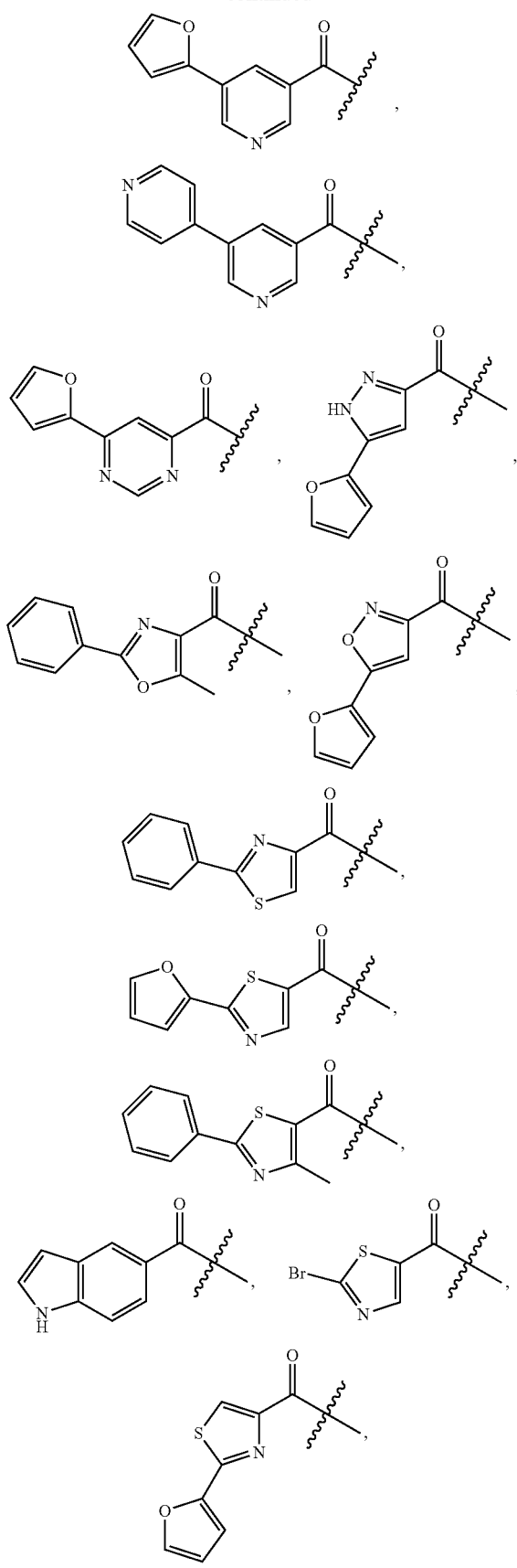
-continued
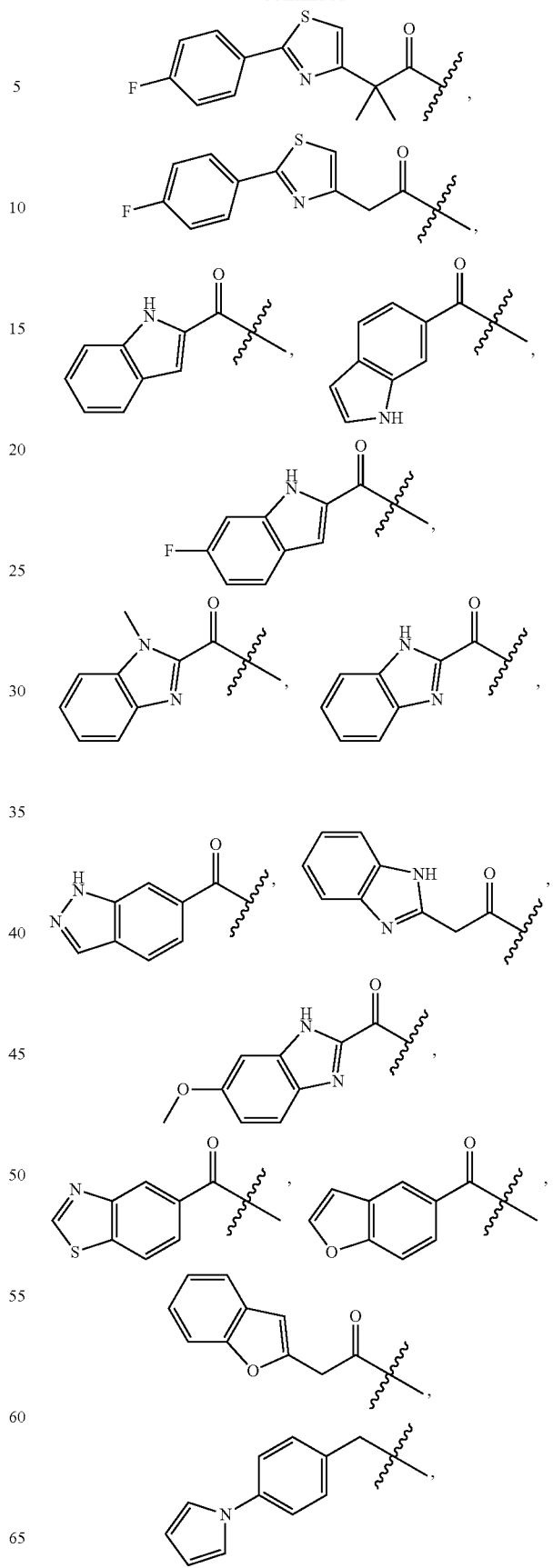

-continued

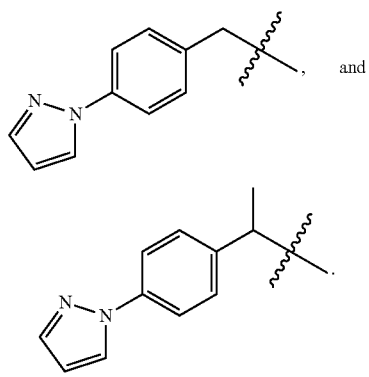, and

In some embodiments, X is

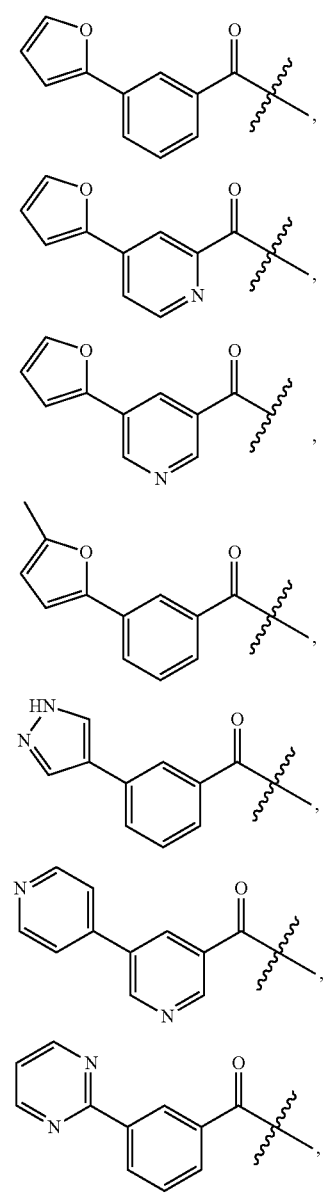

-continued

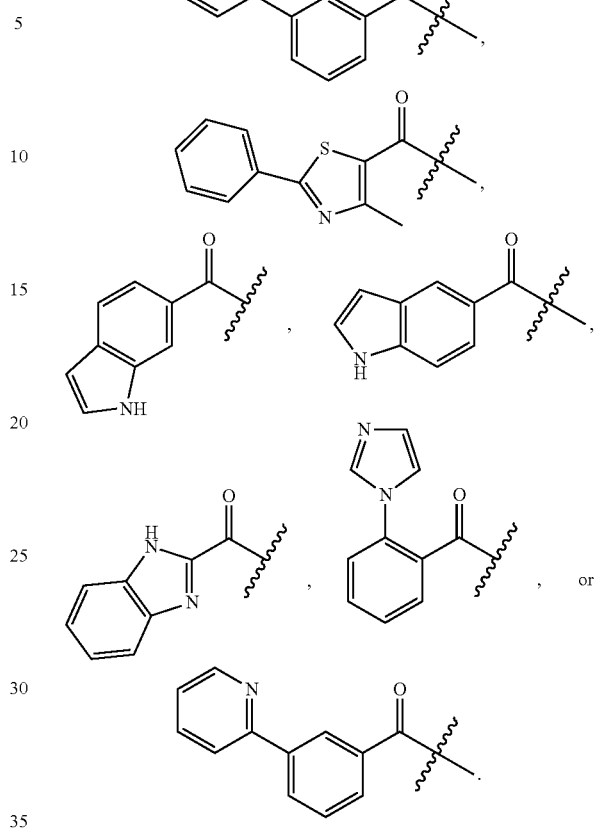, or

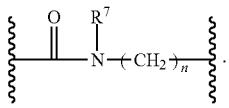.

In some cases, Y is $CH_2$, C=O, CHOH, CHF, $CF_2$, $NR^5$, $NCONHR^5$, $NCOR^5$, $NCO_2R^5$, or $NSO_2R^5$. In some of these cases, $R^5$ is H. In various cases, $R^5$ is $C_{1-6}$ alkyl (e.g., methyl, ethyl, propyl, isopropyl, n-butyl, sec-butyl, or ten-butyl). In some of these embodiments, $R^5$ is $C_{3-7}$ cycloalkyl (e.g., cyclopropyl, cyclobutyl, cyclopentyl, or cyclohexyl). In some embodiments, $R^5$ is $C_{2-6}$ alkenyl (e.g., 1-propenyl, 2-propenyl, 1-butenyl, 2-butenyl, or 3-butenyl). In various embodiments, $R^5$ is $C_{3-6}$ alkylene-ether (e.g., $CH_2CH_2OCH_3$ or $CH_2OCH_3$). In some cases, $R^5$ is $C_{0-6}$ alkylene-aryl (e.g., unsubstituted phenyl, substituted phenyl, or $CH_2$-phenyl). In some cases, $R^5$ is $C_{0-6}$ alkylene-heteroaryl). In some embodiments, two $R^5$ together with a nitrogen to which they are attached form a 3-7 atom heterocyclic ring (e.g., a pyrroline ring or a piperidine ring). For example, Y can be selected from $CH_2$, NMe, $NCH_2Ph$, NCONHiPr, NCONHPh, NCONH-cyclopentyl, $NCONHCH_2CH=CH_2$, NCOMe, NCOEt, NCOiPr, NCO(para-methoxyphenyl), $NCO_2Et$, $NCO_2Pr$, $NCO_2Ph$, $NCO_2CH_2Ph$, $NCO_2CH_2CH_2OMe$, $S(O)_2$, and S. For example, Y can be $CH_2$.

In some cases, Z is

In various cases, Z is

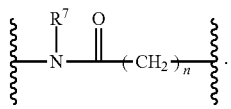

In some embodiments, Z is

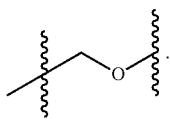

In various embodiments, Z is

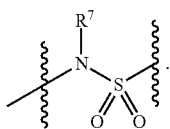

In some embodiments, n is 0. In various embodiments, n is 1. In some cases, n is 2. In some embodiments, $R^7$ is H. In some cases, $R^7$ is $C_{1-3}$ alkyl (e.g., methyl, ethyl, propyl, or isopropyl). In some embodiments, $R^7$ is H or $CH_3$, and n is 0. In some cases, $R^7$ is H and n is 0.

In some cases, m is 0.

In various cases, m is 1. In some of these cases, $R^2$ is ortho to Z. In some embodiments, $R^2$ is meta to Z. In various cases, $R^2$ is para to Z. In any of these embodiments, $R^2$ can be halo (e.g., F, Cl, Br, or I). In some embodiments, $R^2$ is $C_{1-6}$ alkyl (e.g., methyl, ethyl, propyl, isopropyl, n-butyl, sec-butyl, tert-butyl, pentyl, or hexyl). In some cases, $R^2$ is $OC_{1-6}$ alkyl (e.g., O-methyl, O-ethyl, O-propyl, O-isopropyl, O-n-butyl, O-sec-butyl, O-tert-butyl, pentyl, or hexyl). In various embodiments, $R^2$ is $OC_{0-6}$ alkylene-aryl (e.g., $CH_2$-phenyl or phenyl) or $OC_{0-6}$ alkylene-heteroaryl. In some cases, $R^2$ is $SO_2NR^5_2$ (e.g., $SO_2NH_2$, $SO_2NHCH_3$, or $SO_2N(CH_3)_2$). In some cases, $R^2$ is CN. In various embodiments, $R^2$ is $SO_2C_{1-3}$alkyl (e.g., $SO_2Me$). In some embodiments, m is 1 and $R^2$ is halo (e.g., Cl). In various embodiments, at least one $R^2$ is F, CN, $SO_2Me$, or Me.

In some embodiments, m is 2. In some of these cases, the $R^2$ moieties are ortho and meta, in relation to Z. In various cases, the $R^2$ moieties are ortho and para to Z. In some embodiments, the $R^2$ moieties are meta and para to Z. In some cases, each $R^2$ is ortho to Z. In various cases, each $R^2$ is meta to Z. In any of these embodiments, one or each $R^2$ is halo (e.g., F, Cl, Br, or I). In some embodiments, one or each $R^2$ is $C_{1-6}$ alkyl (e.g., methyl, ethyl, propyl, isopropyl, n-butyl, sec-butyl, tert-butyl, pentyl, or hexyl). In some cases, one or each $R^2$ is $OC_{1-6}$ alkyl (e.g., O-methyl, O-ethyl, O-propyl, O-isopropyl, O-n-butyl, O-sec-butyl, O-tert-butyl, pentyl, or hexyl). In various embodiments, one or each $R^2$ is $OC_{0-6}$ alkylene-aryl (e.g., $CH_2$-phenyl or phenyl) or $OC_{0-6}$ alkylene-heteroaryl. In some cases, one or each $R^2$ is $SO_2NR^5_2$ (e.g., $SO_2NH_2$, $SO_2NHCH_3$, or $SO_2N(CH_3)_2$).

In various embodiments, $R^3$ is H. In some cases, $R^3$ is halo (e.g., F, Cl, Br). In some embodiments, $R^3$ is $C_{1-3}$alkyl (e.g., methyl, ethyl, propyl, or isopropyl). In various cases, $R^3$ is $OC_{1-3}$alkyl (e.g., OMe, OEt, OPr, or OiPr). For example, $R^3$ can be H, F or Me.

In some cases, each $R^4$ is H. In various embodiments, each $R^4$ is F. In various cases, at least one $R^4$ is $C_{1-3}$ alkyl (e.g., methyl, ethyl, propyl, or isopropyl). In some cases, at least one $R^4$ is $OR^5$ (e.g., OH, OMe, OEt, OPr, or OiPr). In some cases, each $R^4$ is $OR^5$ (e.g., OH, OMe, OEt, OPr, or OiPr). In some cases, at least one $R^4$ is $NR^5_2$, $NR^5CONHR^5$, $NR^5COR^5$, $NR^5CO_2R^5$, $NR^5SO_2R^5$. In various cases, one $R^4$ is H and the other is OH, OMe, $NR^5_2$, $NR^5COR^5$, or $NR^5CO_2R^5$. In some embodiments, each $R^4$ is F or OMe. In some cases, both $R^4$ together with the carbon to which they are attached form C=O, C=$CH_2$, or $C_{3-7}$ cycloalkyl. For example, at least one $R^4$ is selected from the group consisting of $NH_2$, NHMe, $NMe_2$, $NHCH_2Ph$, $N(Me)CH_2Ph$, NHC(O)Et, NHC(O)Ph, $NHCO_2Me$, $NHCO_2Et$, and $NHCO_2Ph$.

In some embodiments, disclosed herein is a compound selected from the group consisting of E-001 to E-0115, such as a compound selected from the group consisting of E-001, E-003 to E033, E035, E037 to E073, and E075 to E115. In some cases, the disclosure provides a compound selected from the group consisting of E-019, E-023, E-024, E-029, E-031, E-042, E-050, E-068, E-072, E-086, E-087, E-089, E-090, and E-100.

Also provided herein are compounds of Formula (I), and pharmaceutically acceptable salts thereof:

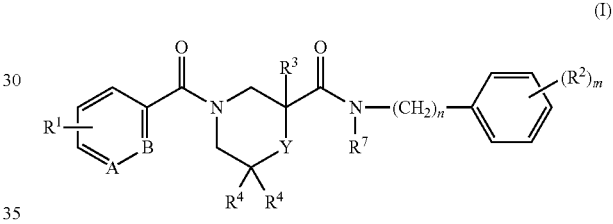

(I)

wherein:
m is 0, 1, or 2;
n is 0, 1, or 2;
one of A and B is $CR^6$ and the other is $CR^6$ or N;
Y is $CH_2$, C=O, CHOH, CHF, $CF_2$, $NR^5$, $NCONHR^5$, $NCOR^5$, $NCO_2R^5$, or $NSO_2R^5$;
$R^1$ is heteroaryl;
each $R^2$ independently is halo, $C_{1-6}$ alkyl, $OC_{1-6}$ alkyl, $OC_{0-6}$ alkylene-aryl, $OC_{0-6}$ alkylene-heteroaryl, or $SO_2NR^5_2$;
$R^3$ is H, halo, OH, $C_{1-3}$ alkyl, or $OC_{1-3}$ alkyl;
each $R^4$ independently is H, F, $C_{1-3}$ alkyl, $OR^5$, $NR^5_2$, $NR^5CONHR^5$, $NR^5COR^5$, $NR^5CO_2R^5$, $NR^5SO_2R^5$, or both $R^4$ together with the carbon to which they are attached form C=O, C=$CH_2$, or $C_{3-7}$ cycloalkyl;
each $R^5$ independently is H, $C_{1-6}$ alkyl, $C_{3-7}$ cycloalkyl, $C_{2-6}$ alkenyl, $C_{3-6}$ alkylene-ether, $C_{0-6}$ alkylene-aryl, $C_{0-6}$ alkylene-heteroaryl, or two $R^5$ together with a nitrogen to which they are attached form a 3-7 atom heterocyclic ring;
each $R^6$ independently is H, halo, $C_{1-3}$ haloalkyl, or $OC_{1-3}$ haloalkyl; and
$R^7$ is H or $C_{1-3}$ alkyl;
with the proviso that when n is 0, m is 1, A and B are each CH, $R^2$ is halo (e.g., chloro), each $R^4$ is H, and Y is $CH_2$, then $R^1$ is other than unsubstituted furanyl, unsubstituted thiophenyl, unsubstituted thiazolyl, unsubstituted oxazolyl, and unsubstituted oxadiazolyl.

In some embodiments, n is 0. In various embodiments, n is 1. In some cases, n is 2.

In some embodiments, A and B are each $CR^6$. In various cases, at least one $R^6$ is H, and in some cases, both $R^6$ are H.

In some embodiments, at least one $R^6$ is F, Cl, Br or I (e.g., $R^6$ is F), and in various embodiments, both $R^6$ are F, Cl, Br or I (e.g., both $R^6$ are F) In some embodiments, at least one $R^6$ is $C_{1-3}$ fluoroalkyl (e.g., $R^6$ is $CF_3$) or $OC_{1-3}$ fluoroalkyl (e.g., $R^6$ is $OCF_3$), and in some cases, both $R^6$ are $C_{1-3}$ fluoroalkyl (e.g., both $R^6$ are $CF_3$) or $OC_{1-3}$ fluoroalkyl (e.g., both $R^6$ are $OCF_3$). For example, at least one of A or B is CH, or both A and B are CH.

In some embodiments, one of A and B is $CR^6$, and the other is N. In various cases, A is $CR^6$ and B is N. In some cases, A is N and B is $CR^6$. In various embodiments $R^6$ is H. In some cases, $R^6$ is F, Cl, Br or I (e.g., $R^6$ is F). In various embodiments, $R^6$ is $C_{1-3}$ fluoroalkyl (e.g., $R^6$ is $CF_3$) or $OC_{1-3}$ fluoroalkyl (e.g., $R^6$ is $OCF_3$. For example, A is CH and B is N, or A is N and B is CH.

In some cases, Y is $CH_2$, C=O, CHOH, CHF, $CF_2$, $NR^5$, $NCONHR^5$, $NCOR^5$, $NCO_2R^5$, or $NSO_2R^5$. In some of these cases, $R^5$ is H. In various cases, $R^5$ is $C_{1-6}$ alkyl (e.g., methyl, ethyl, propyl, isopropyl, n-butyl, sec-butyl, or tenbutyl). In some of these embodiments, $R^5$ is $C_{3-7}$ cycloalkyl (e.g., cyclopropyl, cyclobutyl, cyclopentyl, or cyclohexyl). In some embodiments, $R^5$ is $C_{2-6}$ alkenyl (e.g., 1-propenyl, 2-propenyl, 1-butenyl, 2-butenyl, or 3-butenyl). In various embodiments, $R^5$ is $C_{3-6}$ alkylene-ether (e.g., $CH_2CH_2OCH_3$ or $CH_2OCH_3$). In some cases, $R^5$ is $C_{0-6}$ alkylene-aryl (e.g., unsubstituted phenyl, substituted phenyl, or $CH_2$-phenyl). In some cases, $R^5$ is $C_{0-6}$ alkylene-heteroaryl). In some embodiments, two $R^5$ together with a nitrogen to which they are attached form a 3-7 atom heterocyclic ring (e.g., a pyrroline ring or a piperidine ring). For example, Y can be selected from $CH_2$, NMe, $NCH_2Ph$, NCONHiPr, NCONHPh, NCONH-cyclopentyl, $NCONHCH_2CH=CH_2$, NCOMe, NCOEt, NCOiPr, NCO(para-methoxyphenyl), $NCO_2Et$, $NCO_2Pr$, $NCO_2Ph$, $NCO_2CH_2Ph$, or $NCO_2CH_2CH_2OMe$. In some embodiments, Y is $CH_2$.

In some embodiments, $R^1$ is pyrrolyl, pyrazolyl, imidazolyl, triazolyl, furanyl, thiophenyl, oxazolyl, isooxazolyl, oxadiazolyl, thiazolyl, pyridinyl, pyridazinyl, pyrimidinyl, or pyrazinyl. In some cases, $R^1$ is pyrrolyl, pyrazolyl, imidazolyl, furanyl, thiophenyl, oxazolyl, isooxazolyl, oxadiazolyl, or thiazolyl. For example, $R^1$ can be furanyl (e.g., 2-furanyl), thiophenyl (e.g., 2-thiophenyl), thiazolyl (e.g., 2-thiazolyl, 2-methyl-4-thiazolyl), oxazolyl (e.g., 5-oxazolyl), or oxadiazolyl (e.g., 5-methyl-1,2,4-oxadiazol-3-yl).

In some embodiments, $R^1$ is ortho. In various embodiments, $R^1$ is meta. In some cases, $R^1$ is para. In some embodiments, the compound of Formula (I) comprises a compound of Formula (IA):

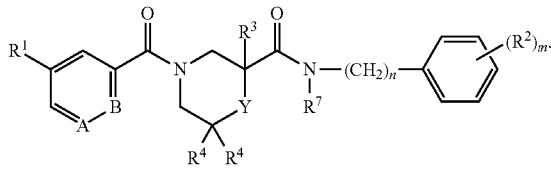

(IA)

In some cases for compounds of Formula (IA), n is 0.
In some cases, m is 0.
In various cases, m is 1. In some of these cases, $R^2$ is ortho, in relation to the $—N(R^7)—(CH_2)_n—$ moiety on the phenyl ring. In some embodiments, $R^2$ is meta, in relation to the $—N(R^7)—(CH_2)_n—$ moiety on the phenyl ring. In various cases, $R^2$ is para, in relation to the $—N(R^7)—(CH_2)_n—$ moiety on the phenyl ring. In any of these embodiments, $R^2$ can be halo (e.g., F, Cl, Br, or I). In some embodiments, $R^2$ is $C_{1-6}$ alkyl (e.g., methyl, ethyl, propyl, isopropyl, n-butyl, sec-butyl, tert-butyl, pentyl, or hexyl). In some cases, $R^2$ is $OC_{1-6}$ alkyl (e.g., O-methyl, O-ethyl, O-propyl, O-isopropyl, O-n-butyl, O-sec-butyl, O-tert-butyl, pentyl, or hexyl). In various embodiments, $R^2$ is $OC_{0-6}$ alkylene-aryl (e.g., $CH_2$-phenyl or phenyl) or $OC_{0-6}$ alkylene-heteroaryl. In some cases, $R^2$ is $SO_2NR^5_2$ (e.g., $SO_2NH_2$, $SO_2NHCH_3$, or $SO_2N(CH_3)_2$).

In some embodiments, m is 2. In some of these cases, the $R^2$ moieties are ortho and meta, in relation to the $—N(R^7)—(CH_2)_n—$ moiety on the phenyl ring. In various cases, the $R^2$ moieties are ortho and para, in relation to the $—N(R^7)—(CH_2)_n—$ moiety on the phenyl ring. In some embodiments, the $R^2$ moieties are meta and para, in relation to the $—N(R^7)—(CH_2)_n$-moiety on the phenyl ring. In some cases, each $R^2$ is ortho, in relation to the $—N(R^7)—(CH_2)_n$-moiety on the phenyl ring. In various cases, each $R^2$ is meta, in relation to the $—N(R^7)—(CH_2)_n—$ moiety on the phenyl ring. In any of these embodiments, one or each $R^2$ is halo (e.g., F, Cl, Br, or I). In some embodiments, one or each $R^2$ is $C_{1-6}$ alkyl (e.g., methyl, ethyl, propyl, isopropyl, n-butyl, sec-butyl, tert-butyl, pentyl, or hexyl). In some cases, one or each $R^2$ is $OC_{1-6}$ alkyl (e.g., O-methyl, O-ethyl, O-propyl, O-isopropyl, O-n-butyl, O-sec-butyl, O-tert-butyl, pentyl, or hexyl). In various embodiments, one or each $R^2$ is $OC_{0-6}$ alkylene-aryl (e.g., $CH_2$-phenyl or phenyl) or $OC_{0-6}$ alkylene-heteroaryl. In some cases, one or each $R^2$ is $SO_2NR^5_2$ (e.g., $SO_2NH_2$, $SO_2NHCH_3$, or $SO_2N(CH_3)_2$).

In some embodiments, m is 1 and $R^2$ is Cl. In various embodiments, the compound of Formula (I) comprises a compound of Formula (IB):

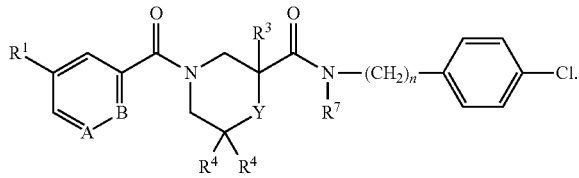

(IB)

In some cases for compounds of Formula (IB), n is 0.

In some embodiments, $R^3$ is H. In some cases, $R^3$ is halo (e.g., F, Cl, or Br). In some embodiments, one $R^4$ is H and the other $R^4$ is F. In various embodiments, $R^3$ is $C_{1-3}$ alkyl (e.g., methyl, ethyl, propyl, or isopropyl). For example $R^3$ can be H, F, or methyl. In some embodiments, $R^3$ is OH. In various embodiments, $R^3$ is $OC_{1-3}$ alkyl. For example, $R^3$ can be OMe, OEt, O-n-Pr, or O-iPr.

In some cases, each $R^4$ is H. In various cases, each $R^4$ is F. In some embodiments, one or each $R^4$ is $C_{1-3}$ alkyl (e.g. methyl, ethyl, propyl, or isopropyl). In some cases one or each $R^4$ is $OR^5$ (e.g., OH, OMe, OEt, OPr, or OiPr). In some embodiments, one or each $R^4$ is $NR^5_2$ (e.g. $NH_2$, $NHCH_3$, or $N(CH_3)_2$). In various embodiments, one or each $R^4$ is selected from $NR^5CONHR^5$, $NR^5COR^5$, $NR^5CO_2R^5$, $NR^5SO_2R^5$ (e.g., NHCONHiPr, NHCONHPh, NHCONH-cyclopentyl, $NHCONHCH_2CH=CH_2$, NHCOMe, NHCOEt, NHCOiPr, NHCO(para-methoxyphenyl), $NHCO_2Et$, $NHCO_2Pr$, $NHCO_2Ph$, $NHCO_2CH_2Ph$, or $NHCO_2CH_2CH_2OMe$).

In various cases, both R⁴ together with the carbon to which they are attached form C=O, C=CH$_2$, or C$_{3-7}$ cycloalkyl (e.g., cyclopropyl, cyclobutyl, or cyclpentyl).

In some embodiments, each R⁴ independently is selected from H, F, OH, OMe, or both R⁴ together with the carbon to which they are attached form C=O or C=CH$_2$.

In some embodiments, R⁷ is H. In various embodiments, R⁷ is C$_{1-3}$ alkyl (e.g., methyl, ethyl, propyl, or isopropyl). For example R⁷ can be H or methyl.

In various embodiments, the compound of Formula (I) comprises Formula (IC):

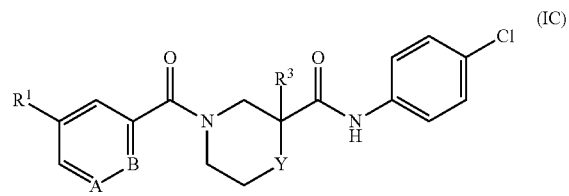

wherein:
each of A and B are CH, or one of A and B is CH and the other is N;
Y is CH$_2$, NMe, NCH$_2$Ph, NCONHiPr, NCONHPh, NCONH-cyclopentyl, NCONHCH$_2$CH=CH$_2$, NCOMe, NCOEt, NCOiPr, NCO(para-methoxypenyl), NCO$_2$Et, NCO$_2$Pr, NCO$_2$Ph, NCO$_2$CH$_2$Ph, or NCO$_2$CH$_2$CH$_2$OMe;
R¹ is pyrrolyl, pyrazolyl, imidazolyl, furanyl, thiophenyl, oxazolyl, isooxazolyl, oxadiazolyl, or thiazolyl; and
R³ is H, F, or methyl;
with the proviso that when A and B are each CH, and Y is CH$_2$, then R¹ is other than unsubstituted furanyl, unsubstituted thiophenyl, unsubstituted thiazolyl, unsubstituted oxazolyl, and unsubstituted oxadiazolyl.

In some embodiments, the compound of Formula (I) comprises Formula (ID):

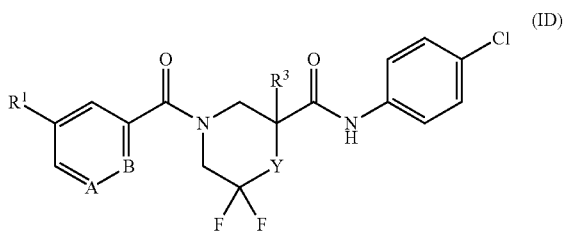

each of A and B are CH, or one of A and B is CH and the other is N;
Y is CH$_2$, NMe, NCH$_2$Ph, NCONHiPr, NCONHPh, NCONH-cyclopentyl, NCONHCH$_2$CH=CH$_2$, NCOMe, NCOEt, NCOiPr, NCO(para-methoxypenyl), NCO$_2$Et, NCO$_2$Pr, NCO$_2$Ph, NCO$_2$CH$_2$Ph, or NCO$_2$CH$_2$CH$_2$OMe;
R¹ is pyrrolyl, pyrazolyl, imidazolyl, furanyl, thiophenyl, oxazolyl, isooxazolyl, oxadiazolyl, or thiazolyl; and
R³ is H, F, or methyl.

In some embodiments, disclosed herein is a compound selected from the group consisting of E-001 to E-032.

Synthesis of Inhibitors of MRTF/SRF-Mediated Gene Transcription

The inhibitors described herein are can be synthesized by any method known to one skilled in the art. For example, an amine-protected piperidine-3-carboxylic acid can undergo an amide coupling reaction with an amino-substituted phenyl group (Scheme 1, step a) to form an intermediate. The intermediate can then be deprotected (Scheme 1, step b), and coupled with a benzoic or heterocycylic acid derivative to form the desired inhibitor (Scheme 1, step c).

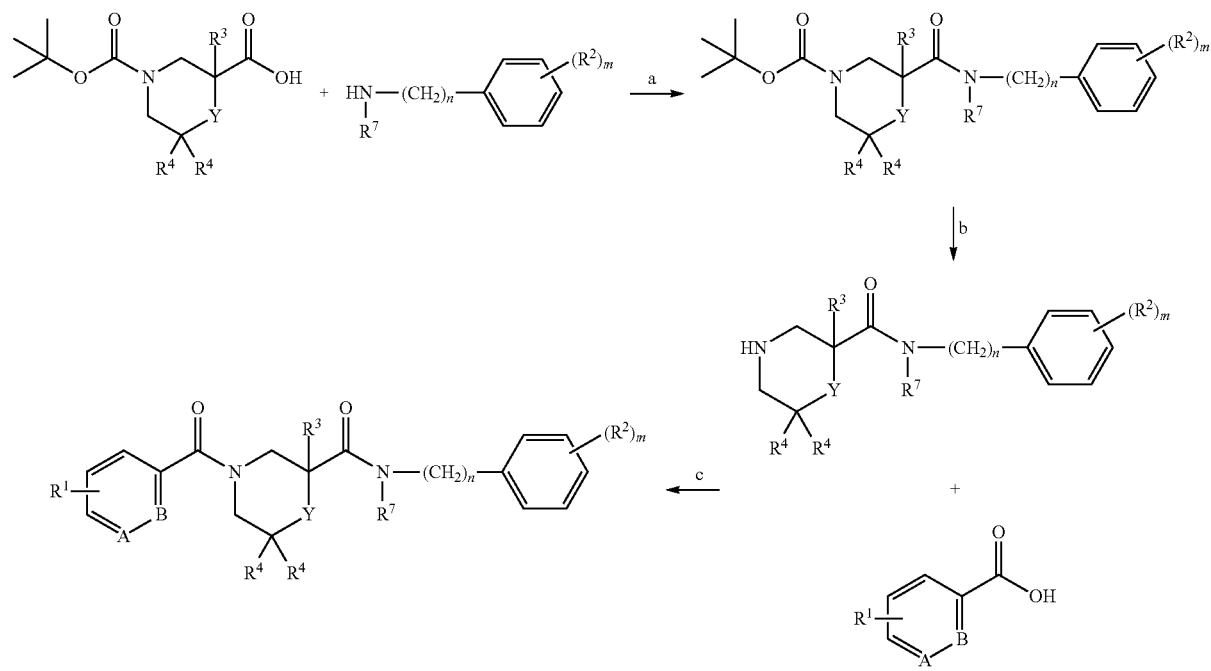

Scheme 1

Additional synthetic procedures for preparing the inhibitors disclosed herein can be found in the Examples section.

Methods

The compounds disclosed herein can inhibit MRTF/SRF-mediated gene transcription, which is useful in preventing or treating diseases related to a dysfunction in MRTF/SRF-mediated gene transcription.

The rho family of GTPases regulates many aspects of intracellular actin dynamics Rho signaling causes MRTF to translocate to the cell nucleus and bind to SRF. The binding of MRTF to SRF leads to expression of c-fos, which along with c-jun, forms the transcription factor AP-1. The AP-1 transcription factor promotes the activity of various matrix metalloproteinases ("MMPs") and other cell motility genes, the overexpression of which leads to cancer cell invasion and metastasis. Thus, dysfunction of MRTF/SRF-mediated gene transcription has been implicated in cancer metastasis.

Dysfunction of MRTF/SRF-mediated gene transcription also has been implicated in fibrosis. The hallmark of fibrotic disease is the transition of normal fibroblasts into myofibroblasts, which are characterized by the expression of alpha smooth muscle actin ("α-SMA") and the production of extracellular matrix ("ECM"). Fibroblast activation to myofibroblasts results from gene transcription stimulated by a common Rho-mediated signaling pathway that originates from divergent extracellular profibrotic stimuli. Specifically, rho mediates the conversion of G-actin to F-actin, which releases G-actin-bound MRTF. The release of G-actin-bound MRTF results in accumulation of MRTF in the nucleus, where it binds to SRF on the serum response element ("SRE") promoter. Thus, MRTF serves as a regulator of the fibrotic process used in wound healing, and dysregulation and/or overstimulation of it can lead to fibrosis.

As such, further provided are methods of treating or preventing a disease related to dysfunction of MRTF/SRF-mediated gene transcription using a compound as disclosed herein, such as a compound of Formula (I) and/or Formula (II).

Thus, one aspect of the disclosure relates to a method of inhibiting MRTF/SRF-mediated gene transcription in a cell, comprising contacting the cell with a compound disclosed herein in an amount effective to inhibit gene transcription. For example, MRTF/SRF-mediated gene transcription can be inhibited in a cell by contacting the cell with a compound disclosed herein, such as a compound of Formula (I) and/or Formula (II). The contacting of the cell can occur in vitro or in vivo. In some cases, contacting of the cell occurs in vitro. In other cases, contacting of the cell occurs in vivo. A compound disclosed herein, such as a compound of Formula (I) (e.g., a compound of Formula (IA), (IB), (IC), or (ID)) and/or Formula (II), can contact a cell in vivo by administering the compound to a subject in need of inhibition of MRTF/SRF-mediated gene transcription. Therefore, the disclosure includes administering one or more of the compounds disclosed herein, such a compound of Formula (I) (e.g., a compound of Formula (IA), (IB), (IC), or (ID)) and/or Formula (II), to a subject, such as a human, in need thereof. In some embodiments, the subject suffers from a disease associated with dysfunction of MRTF/SRF-mediated gene transcription (e.g., cancer, fibrotic disease, diabetes, insulin sensitivity, hyperactive platelets, metabolic disease, inflammation, inflammatory disease, pulmonary arterial hypertension, axon regeneration following nerve damage, Raynaud's phenomenon, cerebral vascular disease, cardiovascular disease, erectile dysfunction, and combinations thereof).

In various cases, the subject suffers from a cancer. In some embodiments, the cancer is selected from the group consisting of fibrosarcoma, myxosarcoma, liposarcoma, chondrosarcoma, osteogenic sarcoma, chordoma, angiosarcoma, endotheliosarcoma, lymphangiosarcoma, Ewing's tumor, lymphangioendotheliosarcoma, synovioma, mesothelioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, glioblastoma, leukemia, megakaryoblastic leukemia, polycythemia vera, lymphoma, multiple myeloma, Waldenstrom's macroglobulinemia, heavy chain disease, and combinations thereof. In some cases, the subject suffers from a cancer selected from the group consisting of megakaryoblastic leukemia, melanoma, breast cancer, prostate cancer, glioblastoma, and combinations thereof.

In some cases, the subject suffers from a fibrotic disorder. In some cases, the fibrotic disease is systemic sclerosis, pulmonary fibrosis, cardiac fibrosis, liver fibrosis, liver cirrhosis, renal fibrosis, chronic renal failure, lung fibrosis, nephrogenic systemic fibrosis, graft versus host disease, Dupuytren's contracture, inflammatory bowel disease, Crohn's disease, ocular fibrosis, glaucoma, post-trabeculectomy fibrosis, corneal fibrosis, pterygia, Grauves opthmalopathy, diabetic retinopathy, age-related macular degeneration, postoperative adhesions, reactive fibrosis, chronic heart failure, or combinations thereof. In some cases, the subject suffers from systemic sclerosis or idiopathic pulmonary fibrosis.

In some embodiments, the subject suffers from a metabolic disease. In some cases, the metabolic disease is obesity, diabetes, insulin resistance, or combinations thereof. In some cases, the metabolic disease is diabetes, such as type II diabetes.

Use of a compound disclosed herein, such as a compound of Formula (I) and/or Formula (II), to treat a condition resulting from dysfunction of MRTF/SRF-mediated gene transcription in a subject, as well as use of the compound in the preparation of a medicament for treating the condition, also are contemplated.

Further guidance for using compounds disclosed herein for inhibiting MRTF/SRF-mediated gene transcription, such as a compound of Formula (I) and/or Formula (II), can be found in the Examples section, below.

Pharmaceutical Formulations

Also provided herein are pharmaceutical formulations that include a compound of Formula (I) and/or Formula (II), as previously described herein, and one or more pharmaceutically acceptable excipients.

The inhibitors described herein can be administered to a subject in a therapeutically effective amount. A inhibitor can be administered alone or as part of a pharmaceutically acceptable composition or formulation. In addition, an inhibitor can be administered all at once, multiple times, or delivered substantially uniformly over a period of time. It is also noted that the dose of the compound can be varied over time.

An inhibitor disclosed herein can be administered in combination with one or more additional pharmaceutically active compounds/agents. The additional pharmaceutically active compounds/agents may be small molecules or can be macromolecules such as a proteins, antibodies, peptibodies, DNA, RNA or fragments of such macromolecules.

An inhibitor disclosed herein and other pharmaceutically active compounds, if desired, can be administered to a patient or subject by any suitable route, e.g. orally, rectally, parenterally, (for example, intravenously, intramuscularly, or subcutaneously) intracisternally, intravaginally, intraperitoneally, intravesically, or as a buccal, inhalation, or nasal spray. The administration can be to provide a systemic effect (e.g. enteral or parenteral). All methods that can be used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

An inhibitor described herein can be administered to a patient or subject at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that will be used can potentially depend on a number of factors, including the requirements of the patient or subject, the severity of the condition or disease being treated, and the pharmacological activity of the compound being administered. The determination of dosage ranges and optimal dosages for a particular patient or subject is within the ordinary skill in the art.

When a patient or subject is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Kits

Also provided herein are kits that include a pharmaceutical formulation comprising a compound of Formula (I) and/or Formula (II), as previously described herein, and instructions for administering the pharmaceutical formulation to a patient. In some embodiments the kit is provided with a device for administering the formulation to a patient. The kit may further include a variety of containers, e.g., vials, tubes, bottles, and the like. In some cases, the device of the kit is an aerosol dispensing device, wherein the formulation is prepackaged within the aerosol device. In various embodiments, the kit comprises a syringe and a needle, wherein the formulation is optionally prepackaged within the syringe.

EXAMPLES

The following examples are provided for illustration and are not intended to limit the scope of the invention.

Materials and Methods

Dual Luciferase Assay

Seed PC-3 prostate cancer cells (40,000 cells/well) were grown in 96-well plates in 10% FBS containing DMEM medium. Cells were transiently transfected with the Ga12QL activator of the Rho/MKL1 pathway, along with the SRE.L-firefly luciferase reporter construct for 6 hours. Additionally, cells were co-transfected with the TK-Renilla luciferase reporter as an indicator of non-specific compound effects. Various concentrations of the compounds disclosed herein were added to the 96-well plates. Plates were incubated for 19 hours at 37° C. and 5% C02 in 0.5% FBS containing DMEM medium. Cells were lysed with IX Passive Lysis Buffer (Promega). Plates were incubated for 30 minutes at room temperature. Luminescence counts were read with a Victor2 (Perkin-Elmer) plate reader.

WST1 Cell Viability Assay

One hour prior to cell lysis for the dual luciferase assay, 10 µl: per well of WST1 reagent (Roche) was added to the 96-well plates. Plates were incubated for 1 hour at 37° C. and 5% $CO_2$. Cell viability was measured by WST1 absorbance at 450 nm with a Victor2 (Perkin-Elmer) plate reader.

SRE.L-Luciferase Reporter Assay

Biological activity of the compounds disclosed herein were assessed in the SRE.L luciferase reporter assay. PC-3 prostate cancer cells were co-transfected with 2 ng of the Gα12Q231L expression plasmid along with 50 ng of the SRE.L and 7 ng of the pRL-TK luciferase reporter plasmids, as described in the Materials and Methods section. Cells were treated with 0 (vehicle, DMSO alone), 1, 3, 10, 30, and 100 µM of a compound disclosed herein for 19 hrs after transfection before lysis. Luminescence was determined as described in the Materials and Methods section. Just before cell lysis, the viability of the cells was measured using the WST-1 cell proliferation reagent as described in the Materials and Methods section. Data are expressed as percentage of inhibition (DMSO alone=0%). The experiments were performed three separate times to achieve n=3 in triplicate.

Results of SRE.L-Luciferase assay are shown in the Table, below.

| Example No. | SRE-Luciferase $IC_{50}$ (µM) | Structure/Name |
|---|---|---|
| E-001 | 7.3 | 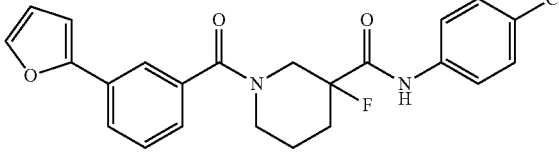<br>N-(4-chlorophenyl)-3-fluoro-1-(3-(furan-2-yl)benzoyl)piperidine-3-carboxamide |
| E-002 | 7.1 | 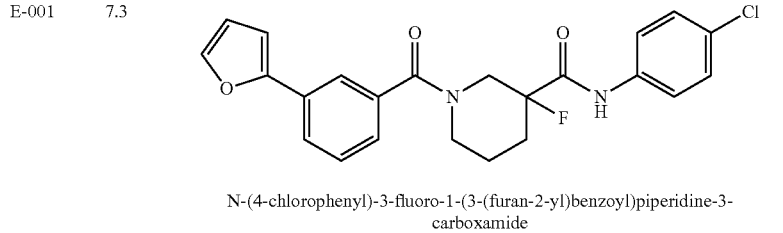<br>N-(4-chlorophenyl)-1-(3-(furan-2-yl)benzoyl)piperidine-3-carboxamide |

-continued
| Example No. | SRE-Luciferase IC$_{50}$ (μM) | Structure/Name |
|---|---|---|
| E-003 | 12 | 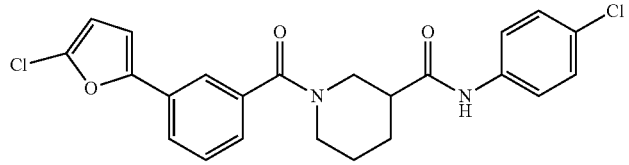 [SMILES: O=C(Nc1ccc(Cl)cc1)C1CCCN(C(=O)c2cccc(-c3ccc(Cl)o3)c2)C1] 1-(3-(5-chlorofuran-2-yl)benzoyl)-N-(4-chlorophenyl)piperidine-3-carboxamide |
| E-004 | 1.8 | 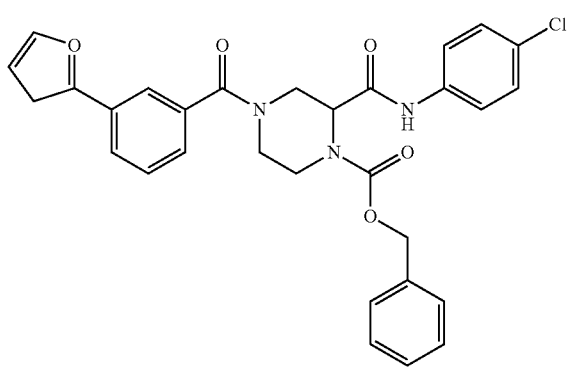 benzyl 2-((4-chlorophenyl)carbamoyl)-4-(3-(furan-2-yl)benzoyl)piperazine-1-carboxylate |
| E-005 | 19 | 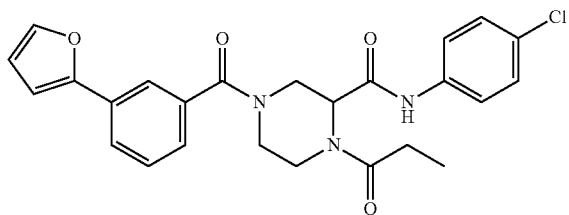 [SMILES: CCC(=O)N1CCN(C(=O)c2cccc(-c3ccco3)c2)CC1C(=O)Nc1ccc(Cl)cc1] N-(4-chlorophenyl)-4-(3-(furan-2-yl)benzoyl)-1-propionylpiperazine-2-carboxamide |
| E-006 | 12 | 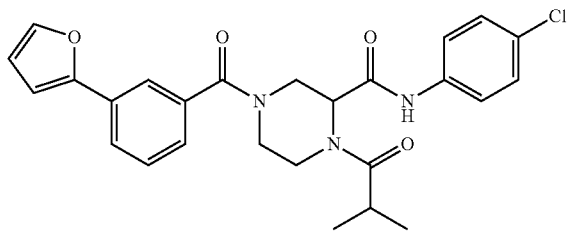 N-(4-chlorophen)-4-(3-(furan-2-yl)benzoyl)-1-isobutyrylpiperazine-2-carboxamide |

-continued

| Example No. | SRE-Luciferase IC$_{50}$ (μM) | Structure/Name |
|---|---|---|
| E-007 | 15 | 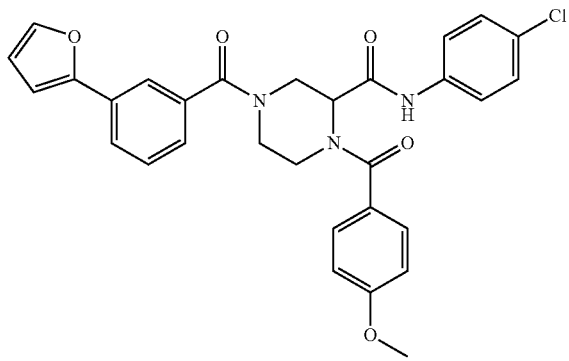 [SMILES: COc1ccc(C(=O)N2CCN(C(=O)c3cccc(-c4ccco4)c3)CC2C(=O)Nc2ccc(Cl)cc2)cc1]<br>N-(4-chlorophenyl)-4-(3-(furan-2-yl)benzoyl)-1-(4-methoxybenzoyl)piperazine-2-carboxamide |
| E-008 | 50 | 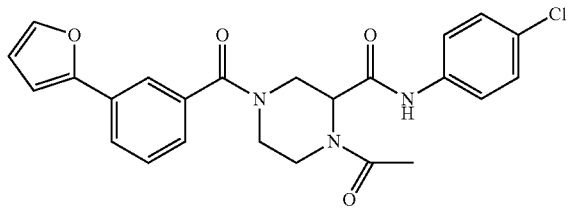 [SMILES: CC(=O)N1CCN(C(=O)c2cccc(-c3ccco3)c2)CC1C(=O)Nc1ccc(Cl)cc1]<br>1-acetyl-N-(4-chlorophenyl)-4-(3-(furan-2-yl)benzoyl)piperazine-2-carboxamide |
| E-009 | 18 | 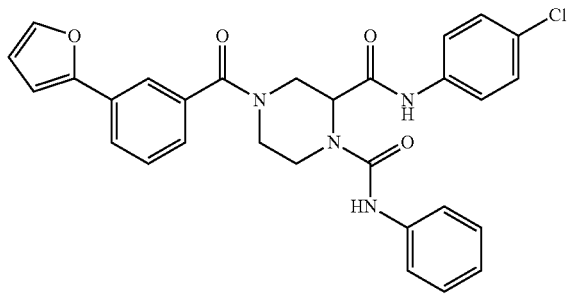<br>N2-(4-chlorophenyl)-4-(3-(furan-2-yl)benzoyl)-N1-phenylpiperazine-1,2-dicarboxamide |
| E-010 | 24 | 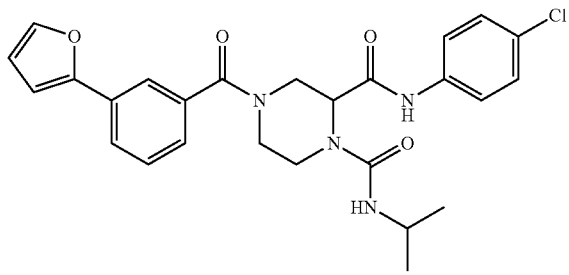<br>N2-(4-chlorophenyl)-4-(3-(furan-2-yl)benzoyl)-N1-isopropylpiperazine-1,2-dicarboxamide |

| Example No. | SRE-Luciferase IC$_{50}$ (μM) | Structure/Name |
|---|---|---|
| E-011 | 14 | 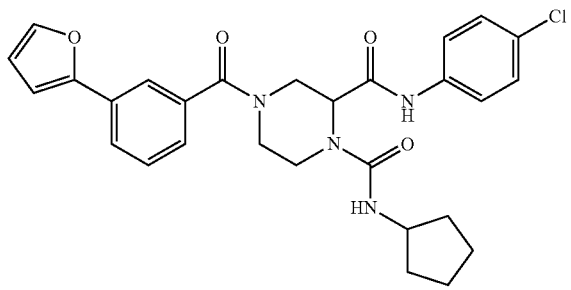 [SMILES: O=C(Nc1ccc(Cl)cc1)C1CN(C(=O)c2cccc(-c3ccco3)c2)CCN1C(=O)NC1CCCC1]<br>N2-(4-chlorophenyl)-N1-cyclopentyl-4-(3-(furan-2-yl)benzoyl)piperazine-1,2-dicarboxamide |
| E-012 | 25 | 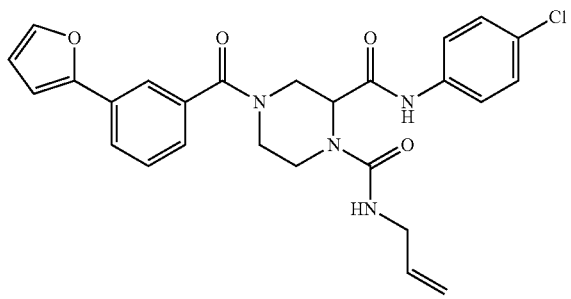 [SMILES: C=CCNC(=O)N1CCN(C(=O)c2cccc(-c3ccco3)c2)CC1C(=O)Nc1ccc(Cl)cc1]<br>N1-allyl-N2-(4-chlorophenyl)-4-(3-(furan-2-yl)benzoyl)piperazine-1,2-dicarboxamide |
| E-013 | 18 | 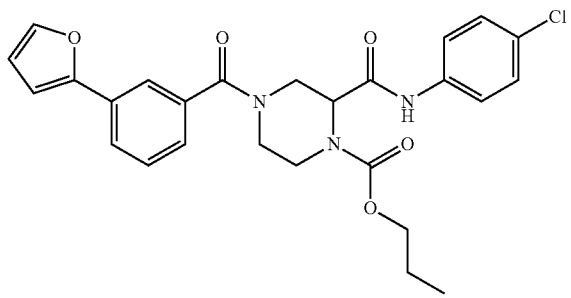 [SMILES: CCCOC(=O)N1CCN(C(=O)c2cccc(-c3ccco3)c2)CC1C(=O)Nc1ccc(Cl)cc1]<br>propyl 2((4-chlorophenyl)carbamoyl)-4-(3-(furan-2-yl)benzoyl)piperazine-1-carboxylate |
| E-014 | 16 | 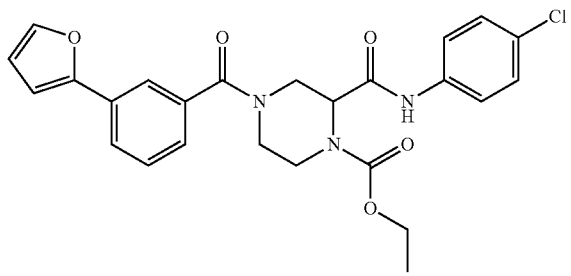 [SMILES: CCOC(=O)N1CCN(C(=O)c2cccc(-c3ccco3)c2)CC1C(=O)Nc1ccc(Cl)cc1]<br>ethyl 2((4-chlorophenyl)carbamoyl)-4-(3-(furan-2-yl)benzoyl)piperazine-1-carboxylate |

-continued

| Example No. | SRE-Luciferase IC$_{50}$ (μM) | Structure/Name |
|---|---|---|
| E-015 | 26 | 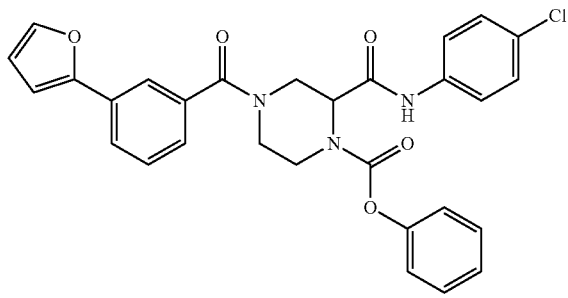<br>phenyl 2((4-chlorophenyl)carbamoyl)-4-(3-(furan-2-yl)benzoyl)piperazine-1-carboxylate |
| E-016 | 16 | 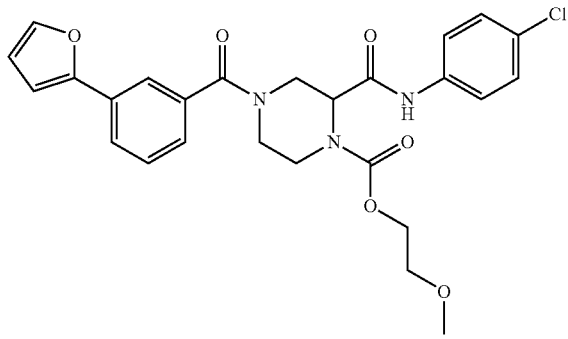 [SMILES: COCCOC(=O)N1CCN(C(=O)c2cccc(-c3ccco3)c2)CC1C(=O)Nc1ccc(Cl)cc1]<br>2-methoxyethyl 2((4-chlorophenyl)carbamoyl)-4-(3-(furan-2-yl)benzoyl)piperazine-1-carboxylate |
| E-017 | 16 | 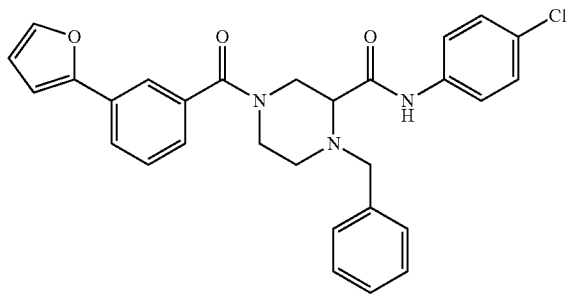 [SMILES: O=C(Nc1ccc(Cl)cc1)C1CN(C(=O)c2cccc(-c3ccco3)c2)CCN1Cc1ccccc1]<br>1-benzyl-N-(4-chlorophenyl)-4-(3-(furan-2-yl)benzoyl)piperazine-2-carboxamide |
| E-018 | 8.7 | 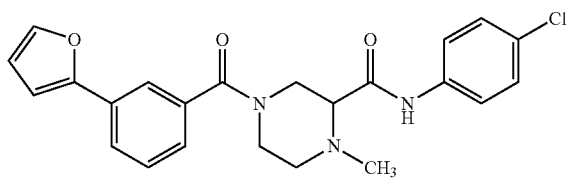 [SMILES: CN1CCN(C(=O)c2cccc(-c3ccco3)c2)CC1C(=O)Nc1ccc(Cl)cc1]<br>N-(4-chlorophenyl)-4-(3-(furan-2-yl)benzoyl)-1-methylpiperazine-2-carboxamide |

-continued

| Example No. | SRE-Luciferase IC$_{50}$ (μM) | Structure/Name |
|---|---|---|
| E-019 | 0.58 | 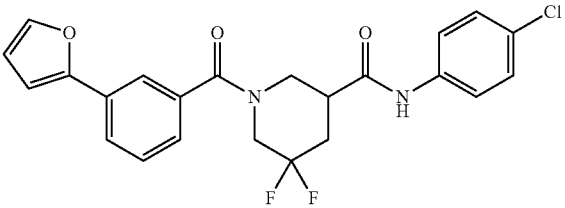<br>N-(4-chlorophenyl)-5,5-difluoro-1-(3-(furan-2-yl)benzoyl)piperidine-3-carboxamide |
| E-020 | 1.9 | 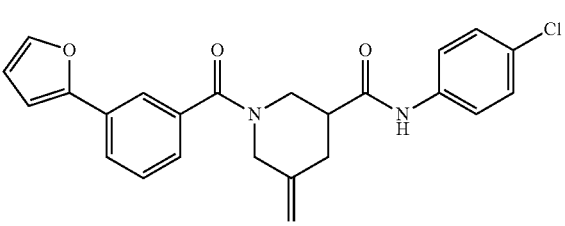 [SMILES: C=C1CC(C(=O)Nc2ccc(Cl)cc2)CN(C(=O)c2cccc(-c3ccco3)c2)C1]<br>N-(4-chlorophenyl)-1-(3-(furan-2-yl)benzoyl)-5-methylenepiperidine-3-carboxamide |
| E-021 | 4.4 | 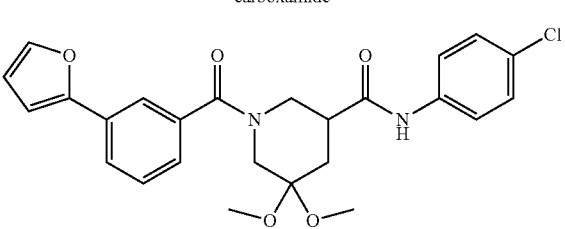<br>N-(4-chlorophenyl)-1-(3-(furan-2-yl)benzoyl)-5,5-dimethoxypiperidine-3-carboxamide |
| E-022 | 4.7 | 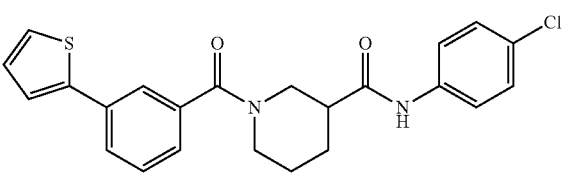<br>N-(4-chlorophenyl)-1-(3-(thiophen-2-yl)benzoyl)piperidine-3-carboxamide |
| E-023 | 4.9 | 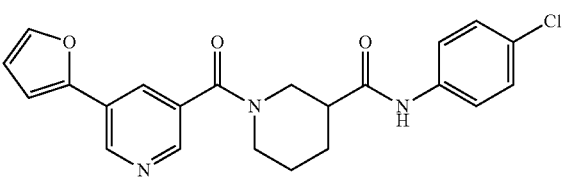 [SMILES: O=C(Nc1ccc(Cl)cc1)C1CCCN(C(=O)c2cncc(-c3ccco3)c2)C1]<br>N-(4-chlorophenyl)-1-(5-(furan-2-yl)nicotinoyl)piperidine-3-carboxamide |
| E-024 | 4.3 | 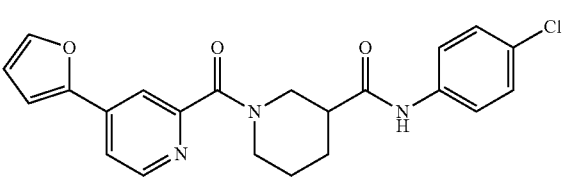<br>N-(4-chlorophenyl)-1-(4-(furan-2-yl)picolinoyl)piperidine-3-carboxamide |

| Example No. | SRE-Luciferase IC$_{50}$ (μM) | Structure/Name |
|---|---|---|
| E-025 | 0.81 | 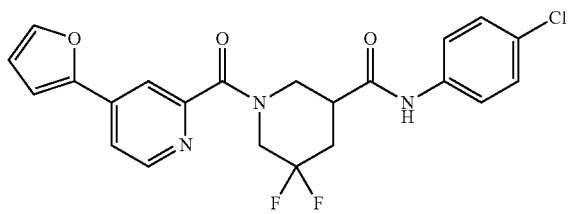 [SMILES: O=C(Nc1ccc(Cl)cc1)C1CN(C(=O)c2cc(-c3ccco3)ccn2)CC(F)(F)C1]<br>N-(4-chlorophenyl)-5,5-difluoro-1-{[4-(furan-2-yl)pyridin-2-yl]carbonyl}piperidine-3-carboxamide |
| E-026 | 5.3 | 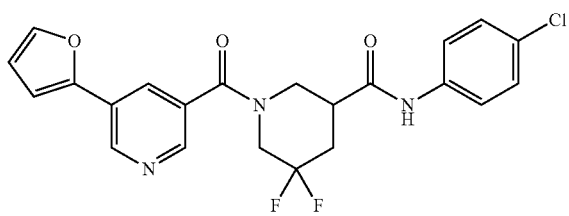<br>N-(4-chlorophenyl)-5,5-difluoro-1-{[5-(furan-2-yl)pyridin-3-yl]carbonyl}piperidine-3-carboxamide |
| E-027 | 12.5 | 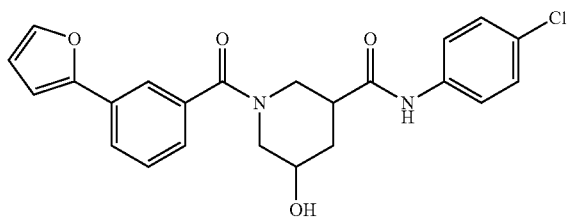 [SMILES: O=C(Nc1ccc(Cl)cc1)C1CC(O)CN(C(=O)c2cccc(-c3ccco3)c2)C1]<br>N-(4-chlorophenyl)-1-{[3-(furan-2-yl)phenyl]carbonyl}-5-hydroxypiperidine-3-carboxamide |
| E-028 | 5.0 | 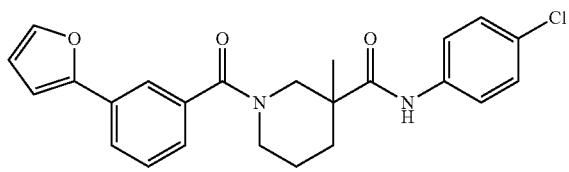 [SMILES: CC1(C(=O)Nc2ccc(Cl)cc2)CCCN(C(=O)c2cccc(-c3ccco3)c2)C1]<br>N-(4-chlorophenyl)-1-(3-(furan-2-yl)benzoyl)-3-methylpiperidine-3-carboxamide |
| E-029 | 3.1 | 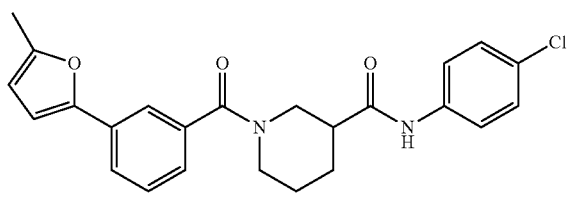 [SMILES: Cc1ccc(-c2cccc(C(=O)N3CCCC(C(=O)Nc4ccc(Cl)cc4)C3)c2)o1]<br>N-(4-chlorophenyl)-1-(3-(5-methylfuran-2-yl)benzoyl)piperidine-3-carboxamide |

| Example No. | SRE-Luciferase IC$_{50}$ (μM) | Structure/Name |
|---|---|---|
| E-030 | 6.1 | 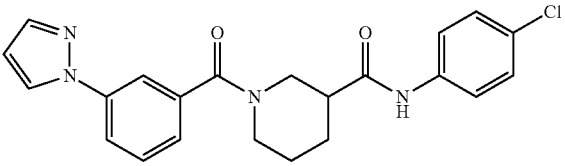 [SMILES: O=C(Nc1ccc(Cl)cc1)C1CCCN(C(=O)c2cccc(-n3cccn3)c2)C1]<br>1-(3-(1H-pyrazol-1-yl)benzoyl)-N-(4-chlorophenyl)piperidine-3-carboxamide |
| E-031 | 3.4 | 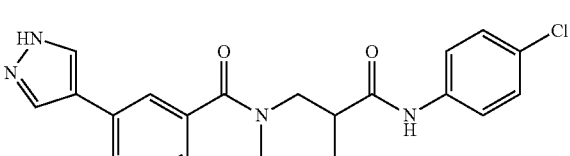<br>1-(3-(1H-pyrazol-4-yl)benzoyl)-N-(4-chlorophenyl)piperidine-3-carboxamide |
| E-032 | 3.2 | 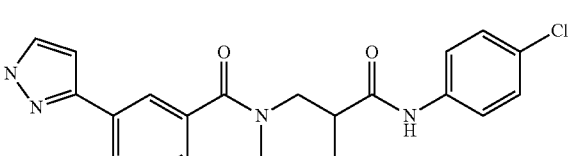<br>1-(3-(1H-pyrazol-3-yl)benzoyl)-N-(4-chlorophenyl)piperidine-3-carboxamide |
| E-033 | 2.7 | 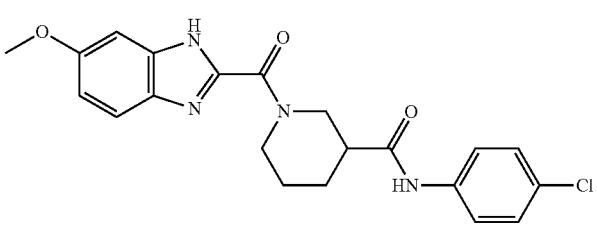 [SMILES: COc1ccc2nc(C(=O)N3CCCC(C(=O)Nc4ccc(Cl)cc4)C3)[nH]c2c1]<br>N-(4-chlorophenyl)-1-(6-methoxy-1H-benzo[d]imidazole-2-carbonyl)piperidine-3-carboxamide |
| E-034 | >100 | 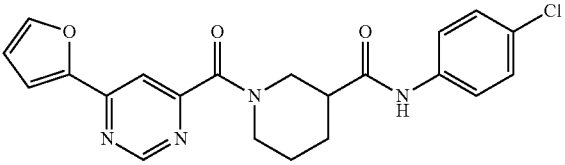<br>N-(4-chlorophenyl)-1-(6-(furan-2-yl)pyrimidine-4-carbonyl)piperidine-3-carboxamide |
| E-035 | 8.0 | 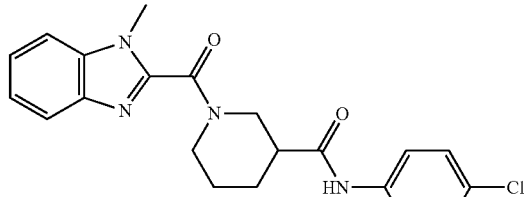<br>N-(4-chlorophenyl)-1-(1-methyl-1H-benzo[d]imidazole-2-carbonyl)piperidine-3-carboxamide |

-continued

| Example No. | SRE-Luciferase IC$_{50}$ (μM) | Structure/Name |
|---|---|---|
| E-036 | >100 | 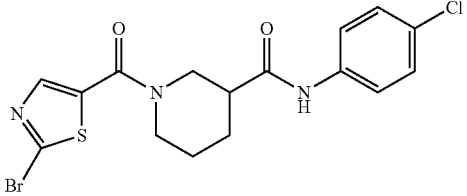 [SMILES: O=C(Nc1ccc(Cl)cc1)C1CCCN(C(=O)c2cnc(Br)s2)C1]<br>1-(2-bromothiazole-5-carbonyl)-N-(4-chlorophenyl)piperidine-3-carboxamide |
| E-037 | 18 | 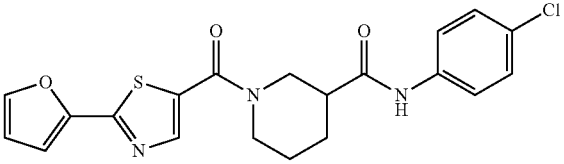 [SMILES: O=C(Nc1ccc(Cl)cc1)C1CCCN(C(=O)c2cnc(-c3ccco3)s2)C1]<br>N-(4-chlorophenyl)-1-(2-(furan-2-yl)thiazole-5-carbonyl)piperidine-3-carboxamide |
| E-038 | 6.5 | 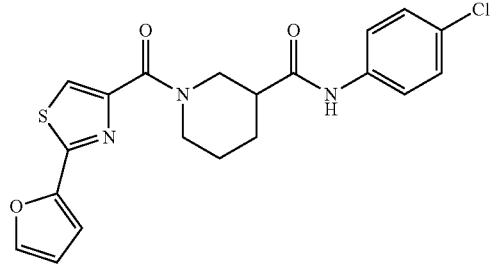 [SMILES: O=C(Nc1ccc(Cl)cc1)C1CCCN(C(=O)c2csc(-c3ccco3)n2)C1]<br>N-(4-chlorophenyl)-1-(2-(furan-2-yl)thiazole-4-carbonyl)piperidine-3-carboxamide |
| E-039 | 43 | 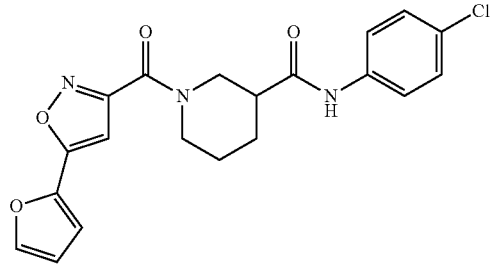 [SMILES: O=C(Nc1ccc(Cl)cc1)C1CCCN(C(=O)c2cc(-c3ccco3)on2)C1]<br>N-(4-chlorophenyl)-1-(5-(furan-2-yl)isoxazole-3-carbonyl)piperidine-3-carboxamide |
| E-040 | 8.1 | 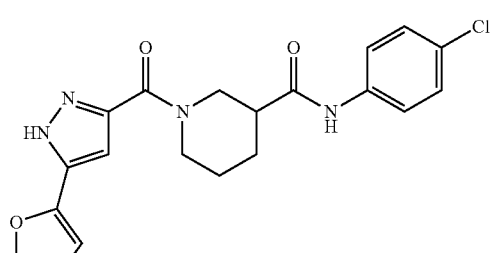<br>N-(4-chlorophenyl)-1-(5-(furan-2-yl)-1H-pyrazole-3-carbonyl)piperidine-3-carboxamide |

-continued

| Example No. | SRE-Luciferase IC$_{50}$ (μM) | Structure/Name |
|---|---|---|
| E-041 | 0.83 | 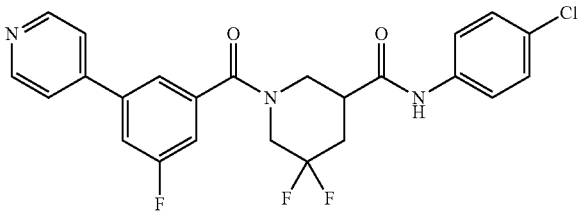 [SMILES: O=C(Nc1ccc(Cl)cc1)C1CN(C(=O)c2cc(F)cc(-c3ccncc3)c2)CC(F)(F)C1] N-(4-chlorophenyl)-5,5-difluoro-1-(3-fluoro-5-(pyridin-4-yl)benzoyl)piperidine-3-carboxamide |
| E-042 | 0.91 | 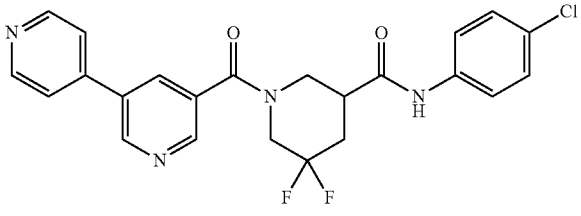 [SMILES: O=C(Nc1ccc(Cl)cc1)C1CN(C(=O)c2cncc(-c3ccncc3)c2)CC(F)(F)C1] 1-([3,4'-bipyridine]-5-carbonyl)-N-(4-chlorophenyl)-5,5-difluoropiperidine-3-carboxamide |
| E-043 | 5.0 | 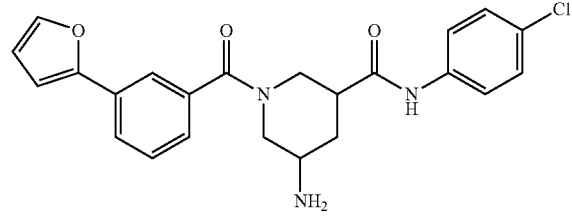 [SMILES: NC1CC(C(=O)Nc2ccc(Cl)cc2)CN(C(=O)c2cccc(-c3ccco3)c2)C1] 5-amino-N-(4-chlorophenyl)-1-(3-(furan-2-yl)benzoyl)piperidine-3-carboxamide |
| E-044 | 2.2 | 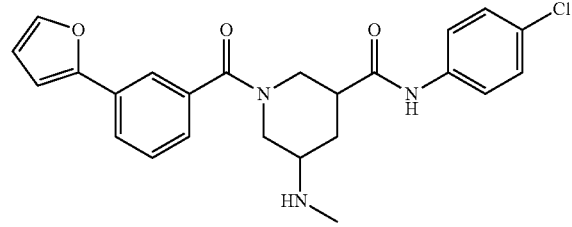 N-(4-chlorophenyl)-1-(3-(furan-2-yl)benzoyl)-5-(methylamino)piperidine-3-carboxamide |
| E-045 | 0.93 | 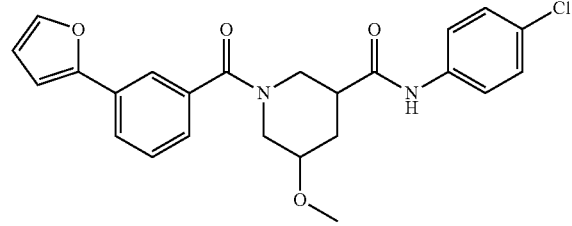 N-(4-chlorophenyl)-1-(3-(furan-2-yl)benzoyl)-5-methoxypiperidine-3-carboxamide-Diastereomer A |

| Example No. | SRE-Luciferase IC$_{50}$ (μM) | Structure/Name |
|---|---|---|
| E-046 | 2.3 | 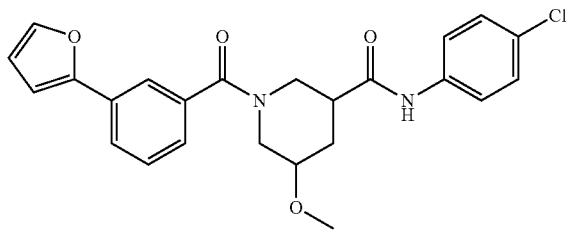 [SMILES: COC1CC(C(=O)Nc2ccc(Cl)cc2)CN(C(=O)c2cccc(-c3ccco3)c2)C1]<br>N-(4-chlorophenyl)-1-(3-(furan-2-yl)benzoyl)-5-methoxypiperidine-3-carboxamide-Diastereomer B |
| E-047 | 0.31 | 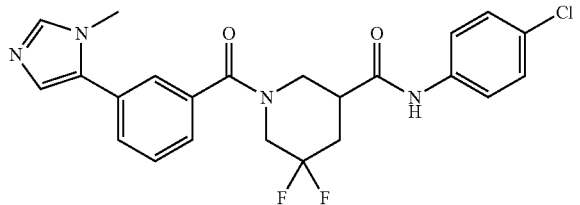 [SMILES: Cn1cncc1-c1cccc(C(=O)N2CC(C(=O)Nc3ccc(Cl)cc3)CC(F)(F)C2)c1]<br>N-(4-chlorophenyl)-5,5-difluoro-1-(3-(1-methyl-1H-imidazol-5-yl)benzoyl)piperidine-3-carboxamide |
| E-048 | 0.047 | 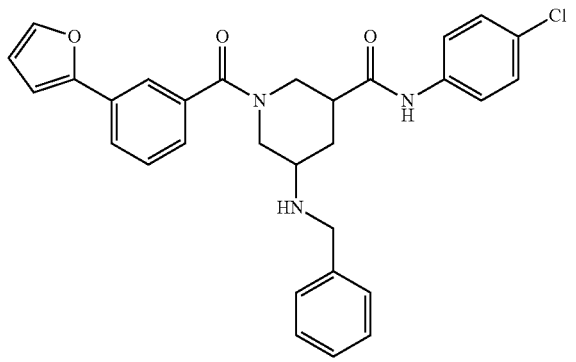 [SMILES: O=C(Nc1ccc(Cl)cc1)C1CC(NCc2ccccc2)CN(C(=O)c2cccc(-c3ccco3)c2)C1]<br>5-(benzylamino)-N-(4-chlorophenyl)-1-(3-(furan-2-yl)benzoyl)piperidine-3-carboxamide |
| E-049 | 6.3 | 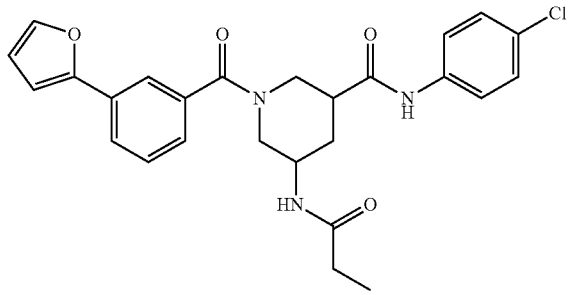 [SMILES: CCC(=O)NC1CC(C(=O)Nc2ccc(Cl)cc2)CN(C(=O)c2cccc(-c3ccco3)c2)C1]<br>N-(4-chlorophenyl)-1-(3-(furan-2-yl)benzoyl)-5-propionamidopiperidine-3-carboxamide |

-continued

| Example No. | SRE-Luciferase IC$_{50}$ (μM) | Structure/Name |
|---|---|---|
| E-050 | 1.1 | 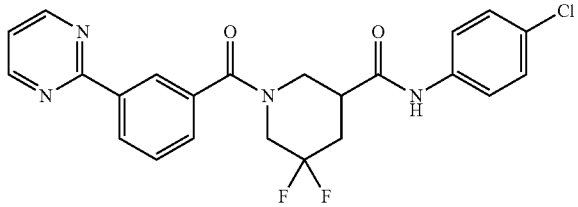 [SMILES: O=C(Nc1ccc(Cl)cc1)C1CN(C(=O)c2cccc(-c3ncccn3)c2)CC(F)(F)C1]<br>N-(4-chlorophenyl)-5,5-difluoro-1-(3-(pyrimidin-2-yl)benzoyl)piperidine-3-carboxamide |
| E-051 | 3.3 | 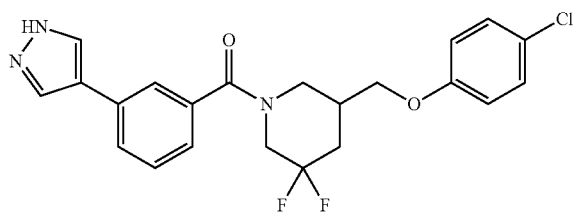 [SMILES: O=C(c1cccc(-c2cn[nH]c2)c1)N1CC(COc2ccc(Cl)cc2)CC(F)(F)C1]<br>(3-(1H-pyrazol-4-yl)phenyl)(5-((4-chlorophenoxy)methyl)-3,3-difluoropiperidin-1-yl)methanone |
| E-052 | 1.6 | 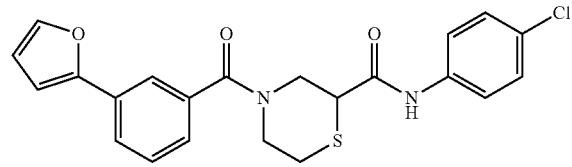<br>N-(4-chlorophenyl)-4-(3-(furan-2-yl)benzoyl)thiomorpholine-2-carboxamide |
| E-053 | 6.8 | 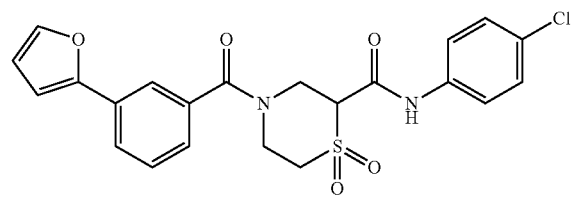 [SMILES: O=C(Nc1ccc(Cl)cc1)C1CN(C(=O)c2cccc(-c3ccco3)c2)CCS1(=O)=O]<br>N-(4-chlorophenyl)-4-(3-(furan-2-yl)benzoyl)thiomorpholine-2-carboxamide 1,1-dioxide |
| E-054 | 30 | 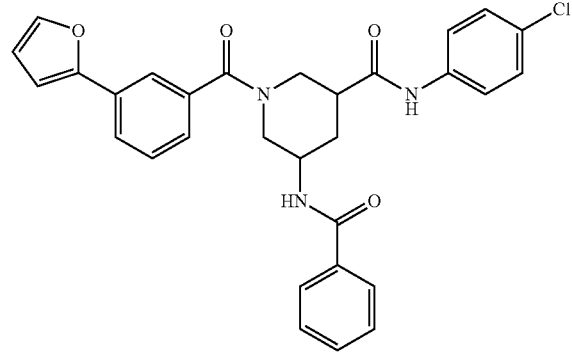 [SMILES: O=C(NC1CC(C(=O)Nc2ccc(Cl)cc2)CN(C(=O)c2cccc(-c3ccco3)c2)C1)c1ccccc1]<br>5-benzamido-N-(4-chlorophenyl)-1-(3-(furan-2-yl)benzoyl)piperidine-3-carboxamide Diastereomer A |

-continued

| Example No. | SRE-Luciferase IC$_{50}$ (μM) | Structure/Name |
|---|---|---|
| E-055 | 2.2 | 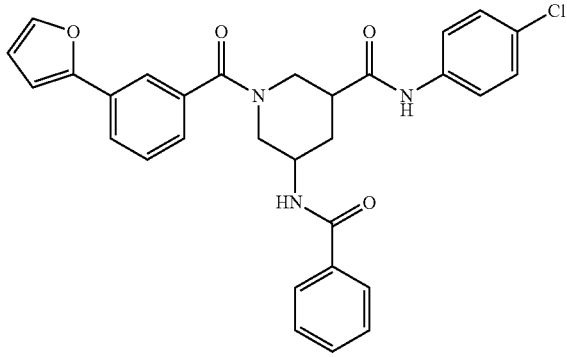 [SMILES: O=C(NC1CC(C(=O)Nc2ccc(Cl)cc2)CN(C(=O)c2cccc(-c3ccco3)c2)C1)c1ccccc1]<br>5-benzamido-N-(4-chlorophenyl)-1-(3-(furan-2-yl)benzoyl)piperidine-3-carboxamide Diastereomer B |
| E-056 | 38 | 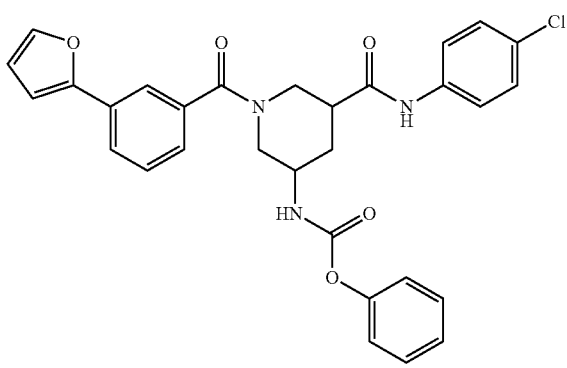 [SMILES: O=C(NC1CC(C(=O)Nc2ccc(Cl)cc2)CN(C(=O)c2cccc(-c3ccco3)c2)C1)Oc1ccccc1]<br>phenyl (5-((4-chlorophenyl)carbamoyl)-1-(3-(furan-2-yl)benzoyl)piperidin-3-yl)carbamate |
| E-057 | 22 | 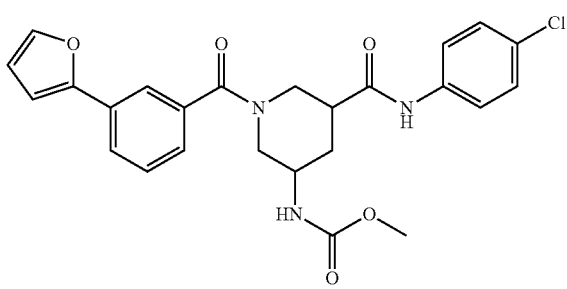 [SMILES: COC(=O)NC1CC(C(=O)Nc2ccc(Cl)cc2)CN(C(=O)c2cccc(-c3ccco3)c2)C1]<br>methyl (5-((4-chlorophenyl)carbamoyl)-1-(3-(furan-2-yl)benzoyl)piperidin-3-yl)carbamate |
| E-058 | 15 | 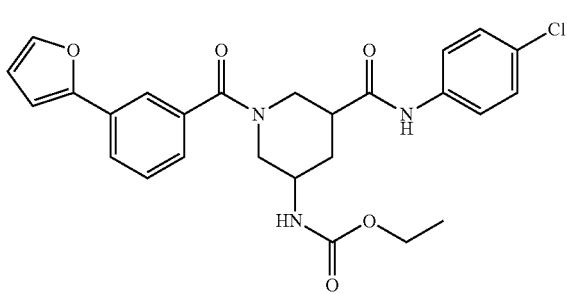<br>ethyl (5-((4-chlorophenyl)carbamoyl)-1-(3-(furan-2-yl)benzoyl)piperidin-3-yl)carbamate |

| Example No. | SRE-Luciferase IC$_{50}$ (μM) | Structure/Name |
|---|---|---|
| E-059 | 31 | (5-((4-chlorophenoxy)methyl)-3,3-difluoropiperidin-1-yl)(3-(furan-2-yl)phenyl)methanone |
| E-060 | 18 | 5-(benzyl(methyl)amino)-N-(4-chlorophenyl)-1-(3-(furan-2-yl)benzoyl)piperidine-3-carboxamide-Diastereomer A |
| E-061 | 1.9 | 5-(benzyl(methyl)amino)-N-(4-chlorophenyl)-1-(3-(furan-2-yl)benzoyl)piperidine-3-carboxamide-Diastereomer B |
| E-062 | 21 | 4-chloro-N-(1-(3-(furan-2-yl)benzoyl)piperidin-3-yl)benzenesulfonamide |
| E-063 | 15 | N-(4-chlorophenyl)-1-(3-(furan-2-yl)benzoyl)-5-oxopiperidine-3-carboxamide |

| Example No. | SRE-Luciferase IC$_{50}$ (μM) | Structure/Name |
|---|---|---|
| E-064 | 6.9 | 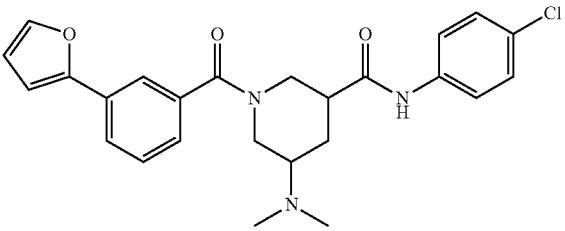<br>N-(4-chlorophenyl)-5-(dimethylamino)-1-(3-(furan-2-yl)benzoyl)piperidine-3-carboxamide |
| E-065 | 13 | 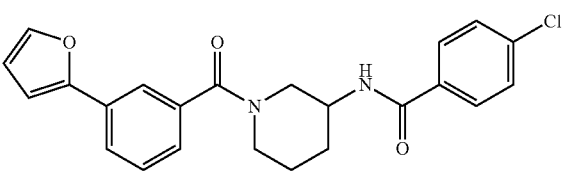 [SMILES: O=C(NC1CCCN(C(=O)c2cccc(-c3ccco3)c2)C1)c1ccc(Cl)cc1]<br>4-chloro-N-(1-(3-(furan-2-yl)benzoyl)piperidin-3-yl)benzamide |
| E-066 | 2.3 | 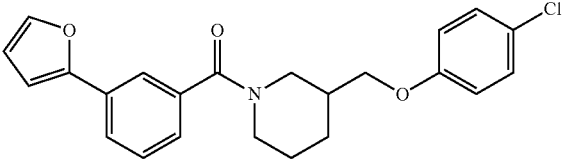 [SMILES: O=C(c1cccc(-c2ccco2)c1)N1CCCC(COc2ccc(Cl)cc2)C1]<br>(3-((4-chlorophenoxy)methyl)piperidin-1-yl)(3-(furan-2-yl)phenyl)methanone |
| E-067 | 7.0 | 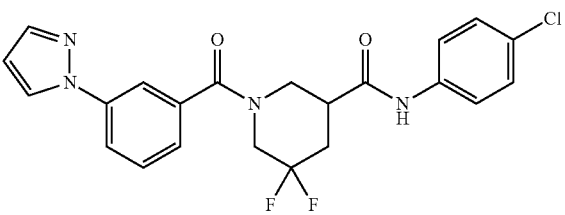<br>1-(3-(1H-pyrazol-1-yl)benzoyl)-N-(4-chlorophenyl)-5,5-difluoropiperidine-3-carboxamide |
| E-068 | 0.78 | 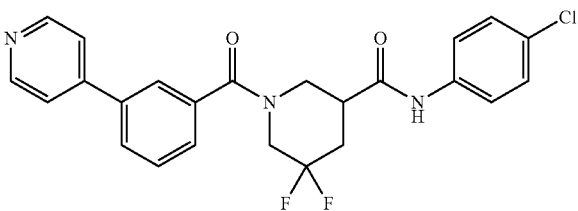 [SMILES: O=C(Nc1ccc(Cl)cc1)C1CN(C(=O)c2cccc(-c3ccncc3)c2)CC(F)(F)C1]<br>N-(4-chlorophenyl)-5,5-difluoro-1-(3-(pyridin-4-yl)benzoyl)piperidine-3-carboxamide |
| E-069 | 1.8 | 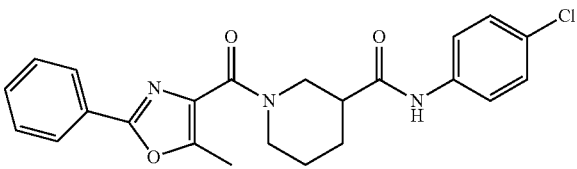 [SMILES: Cc1oc(-c2ccccc2)nc1C(=O)N1CCCC(C(=O)Nc2ccc(Cl)cc2)C1]<br>N-(4-chlorophenyl)-1-(5-methyl-2-phenyloxazole-4-carbonyl)piperidine-3-carboxamide |

-continued

| Example No. | SRE-Luciferase IC$_{50}$ (μM) | Structure/Name |
|---|---|---|
| E-070 | 9.1 | 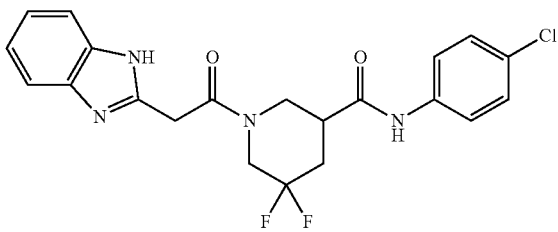 [SMILES: O=C(Nc1ccc(Cl)cc1)C1CN(C(=O)Cc2nc3ccccc3[nH]2)CC(F)(F)C1]<br>1-(2-(1H-benzo[d]imidazol-2-yl)acetyl)-N-(4-chlorophenyl)-5,5-difluoropiperidine-3-carboxamide |
| E-071 | 12 | 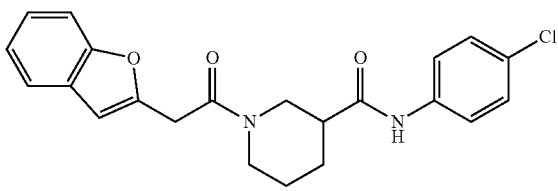 [SMILES: O=C(Nc1ccc(Cl)cc1)C1CCCN(C(=O)Cc2cc3ccccc3o2)C1]<br>1-(2-(benzofuran-2-yl)acetyl)-N-(4-chlorophenyl)piperidine-3-carboxamide |
| E-072 | 0.084 | 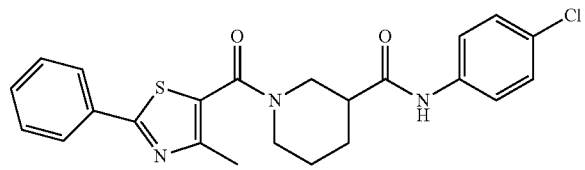 [SMILES: Cc1nc(-c2ccccc2)sc1C(=O)N1CCCC(C(=O)Nc2ccc(Cl)cc2)C1]<br>N-(4-chlorophenyl)-1-(4-methyl-2-phenylthiazole-5-carbonyl)piperidine-3-carboxamide |
| E-073 | 0.45 | 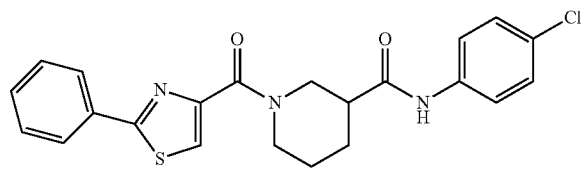 [SMILES: O=C(Nc1ccc(Cl)cc1)C1CCCN(C(=O)c2csc(-c3ccccc3)n2)C1]<br>N-(4-chlorophenyl)-1-(2-phenylthiazole-4-carbonyl)piperidine-3-carboxamide |
| E-074 | >100 | 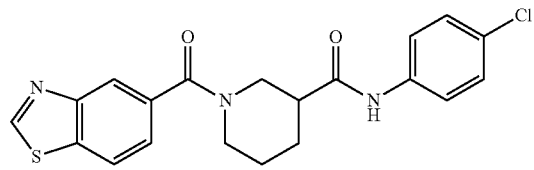 [SMILES: O=C(Nc1ccc(Cl)cc1)C1CCCN(C(=O)c2ccc3scnc3c2)C1]<br>1-(benzo[d]thiazole-5-carbonyl)-N-(4-chlorophenyl)piperidine-3-carboxamide |

-continued

| Example No. | SRE-Luciferase IC$_{50}$ (μM) | Structure/Name |
|---|---|---|
| E-075 | 0.68 | 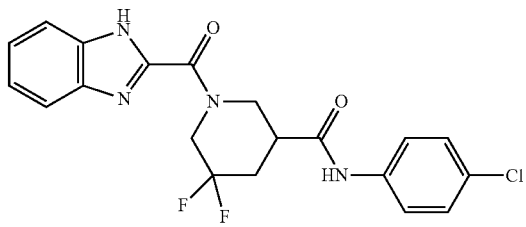 [SMILES: O=C(Nc1ccc(Cl)cc1)C1CN(C(=O)c2nc3ccccc3[nH]2)CC(F)(F)C1]<br>1-(1H-benzo[d]imidazole-2-carbonyl)-N-(4-chlorophenyl)-5,5-difluoropiperidine-3-carboxamide |
| E-076 | 1.6 | 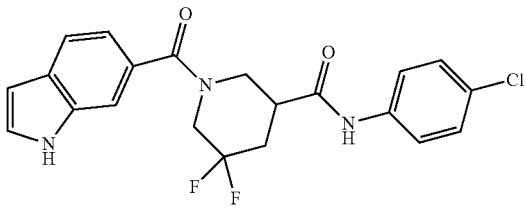 [SMILES: O=C(Nc1ccc(Cl)cc1)C1CN(C(=O)c2ccc3cc[nH]c3c2)CC(F)(F)C1]<br>N-(4-chlorophenyl)-5,5-difluoro-1-(1H-indole-6-carbonyl)piperidine-3-carboxamide |
| E-077 | 0.81 | 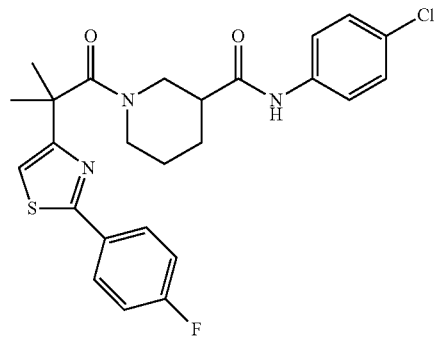 [SMILES: CC(C)(C(=O)N1CCCC(C(=O)Nc2ccc(Cl)cc2)C1)c1csc(-c2ccc(F)cc2)n1]<br>N-(4-chlorophenyl)-1-(2-(2-(4-fluorophenyl)thiazol-4-yl)-2-methylpropanoyl)piperidine-3-carboxamide |
| E-078 | 1.0 | 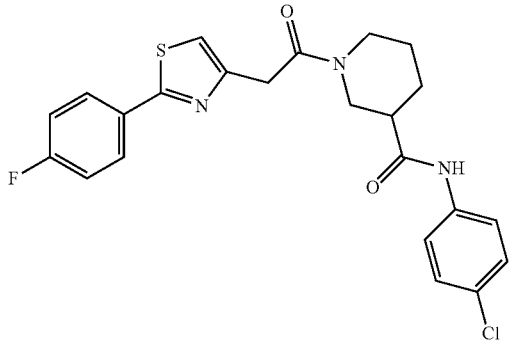 [SMILES: O=C(Nc1ccc(Cl)cc1)C1CCCN(C(=O)Cc2csc(-c3ccc(F)cc3)n2)C1]<br>N-(4-chlorophenyl)-1-(2-(2-(4-fluorophenyl)thiazol-4-yl)acetyl)piperidine-3-carboxamide |

| Example No. | SRE-Luciferase IC$_{50}$ (μM) | Structure/Name |
|---|---|---|
| E-079 | 0.92 | 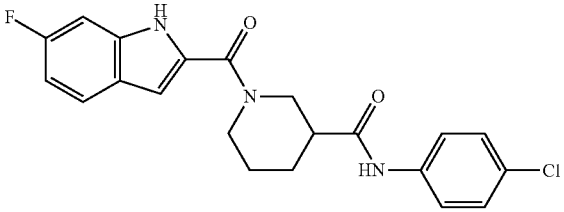 [SMILES: O=C(Nc1ccc(Cl)cc1)C1CCCN(C(=O)c2cc3ccc(F)cc3[nH]2)C1]<br>N-(4-chlorophenyl)-1-(6-fluoro-1H-indole-2-carbonyl)piperidine-3-carboxamide |
| E-080 | 0.31 | 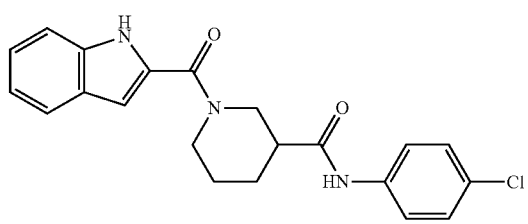 [SMILES: O=C(Nc1ccc(Cl)cc1)C1CCCN(C(=O)c2cc3ccccc3[nH]2)C1]<br>N-(4-chlorophenyl)-1-(1H-indole-2-carbonyl)piperidine-3-carboxamide |
| E-081 | 0.26 | 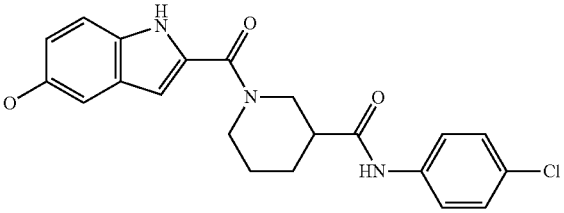 [SMILES: O=C(Nc1ccc(Cl)cc1)C1CCCN(C(=O)c2cc3cc(O)ccc3[nH]2)C1]<br>N-(4-chlorophenyl)-1-(5-methoxy-1H-indole-2-carbonyl)piperidine-3-carboxamide |
| E-082 | 0.37 | 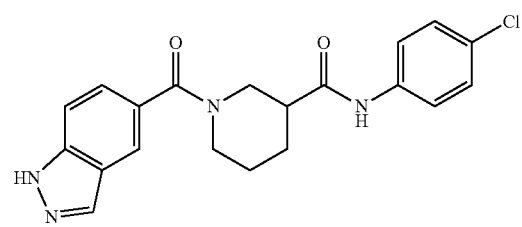 [SMILES: O=C(Nc1ccc(Cl)cc1)C1CCCN(C(=O)c2ccc3[nH]ncc3c2)C1]<br>N-(4-chlorophenyl)-1-(1H-indazole-5-carbonyl)piperidine-3-carboxamide |
| E-083 | 0.67 | 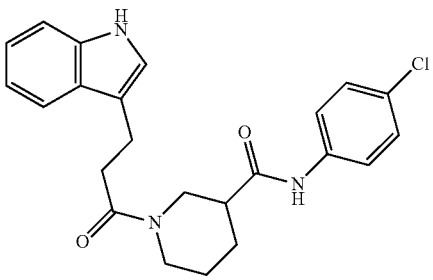 [SMILES: O=C(Nc1ccc(Cl)cc1)C1CCCN(C(=O)CCc2c[nH]c3ccccc23)C1]<br>1-(3-(1H-indol-3-yl)propanoyl)-N-(4-chlorophenyl)piperidine-3-carboxamide |

-continued
| Example No. | SRE-Luciferase IC$_{50}$ (μM) | Structure/Name |
|---|---|---|
| E-084 | 0.39 | 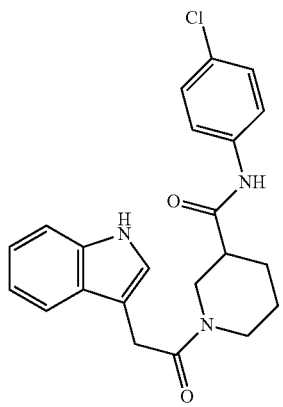 [SMILES: O=C(Nc1ccc(Cl)cc1)C1CCCN(C(=O)Cc2c[nH]c3ccccc23)C1]<br>1-(2-(1H-indol-3-yl)acetyl)-N-(4-chlorophenyl)piperidine-3-carboxamide |
| E-085 | 0.31 | 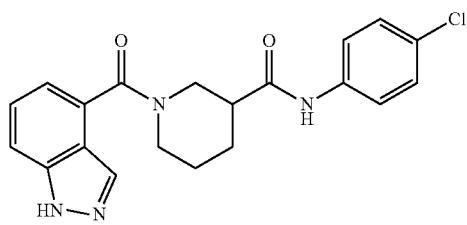 [SMILES: O=C(Nc1ccc(Cl)cc1)C1CCCN(C(=O)c2cccc3[nH]ncc23)C1]<br>N-(4-chlorophenyl)-1-(1H-indazole-4-carbonyl)piperidine-3-carboxamide |
| E-086 | 0.097 | 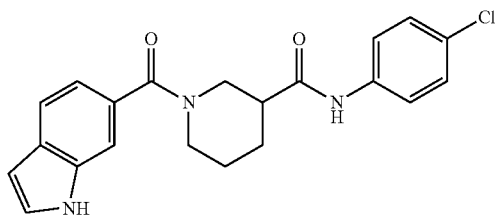 [SMILES: O=C(Nc1ccc(Cl)cc1)C1CCCN(C(=O)c2ccc3cc[nH]c3c2)C1]<br>N-(4-chlorophenyl)-1-(1H-indole-6-carbonyl)piperidine-3-carboxamide |
| E-087 | 0.13 | 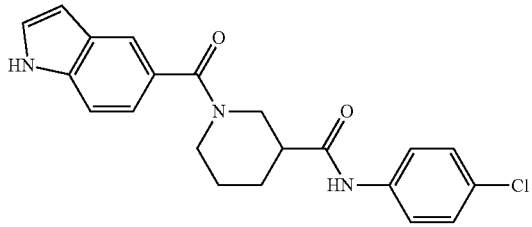 [SMILES: O=C(Nc1ccc(Cl)cc1)C1CCCN(C(=O)c2ccc3[nH]ccc3c2)C1]<br>N-(4-chlorophenyl)-1-(1H-indole-5-carbonyl)piperidine-3-carboxamide |

-continued

| Example No. | SRE-Luciferase IC$_{50}$ (μM) | Structure/Name |
|---|---|---|
| E-088 | 1.5 | 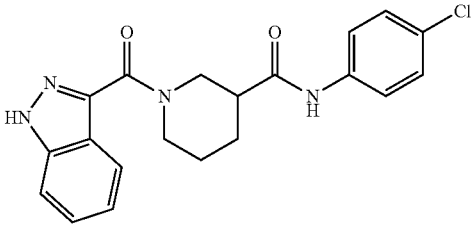 [SMILES: O=C(Nc1ccc(Cl)cc1)C1CCCN(C(=O)c2n[nH]c3ccccc23)C1]<br>N-(4-chlorophenyl)-1-(1H-indazole-3-carbonyl)piperidine-3-carboxamide |
| E-089 | 0.12 | 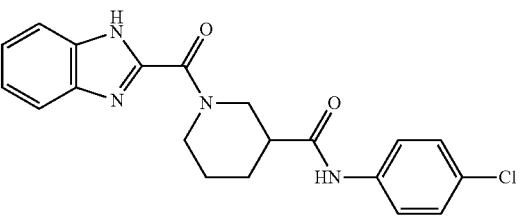 [SMILES: O=C(Nc1ccc(Cl)cc1)C1CCCN(C(=O)c2nc3ccccc3[nH]2)C1]<br>1-(1H-benzo[d]imidazole-2-carbonyl)-N-(4-chlorophenyl)piperidine-3-carboxamide |
| E-090 | 0.24 | 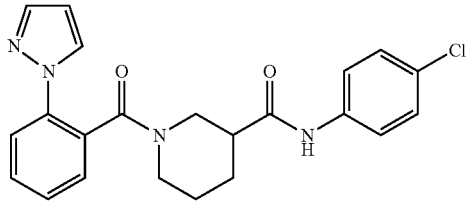 [SMILES: O=C(Nc1ccc(Cl)cc1)C1CCCN(C(=O)c2ccccc2-n2cccn2)C1]<br>1-(2-(1H-pyrazol-1-yl)benzoyl)-N-(4-chlorophenyl)piperidine-3-carboxamide |
| E-091 | 4.1 | 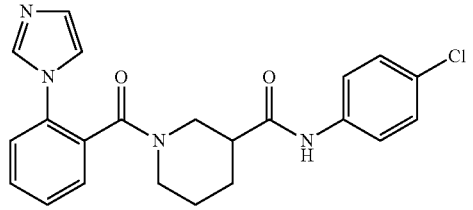 [SMILES: O=C(Nc1ccc(Cl)cc1)C1CCCN(C(=O)c2ccccc2-n2ccnc2)C1]<br>1-(2-(1H-imidazol-1-yl)benzoyl)-N-(4-chlorophenyl)piperidine-3-carboxamide |
| E-092 | 0.71 | 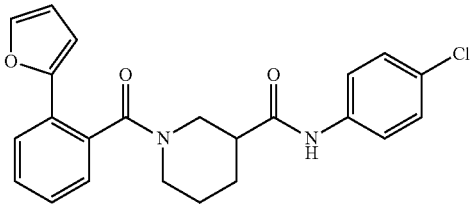 [SMILES: O=C(Nc1ccc(Cl)cc1)C1CCCN(C(=O)c2ccccc2-c2ccco2)C1]<br>N-(4-chlorophenyl)-1-(2-(furan-2-yl)benzoyl)piperidine-3-carboxamide |

-continued

| Example No. | SRE-Luciferase IC$_{50}$ (μM) | Structure/Name |
|---|---|---|
| E-093 | 0.49 | 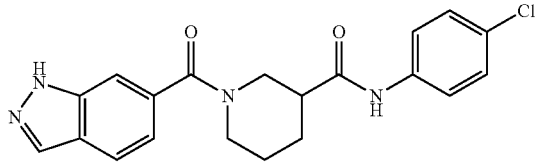 [SMILES: O=C(Nc1ccc(Cl)cc1)C1CCCN(C(=O)c2ccc3cn[nH]c3c2)C1]<br>N-(4-chlorophenyl)-1-(1H-indazole-6-carbonyl)piperidine-3-carboxamide |
| E-094 | 0.46 | 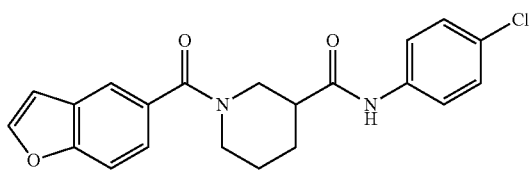 [SMILES: O=C(Nc1ccc(Cl)cc1)C1CCCN(C(=O)c2ccc3occc3c2)C1]<br>1-(benzofuran-5-carbonyl)-N-(4-chlorophenyl)piperidine-3-carboxamide |
| E-095 | 5.5 | 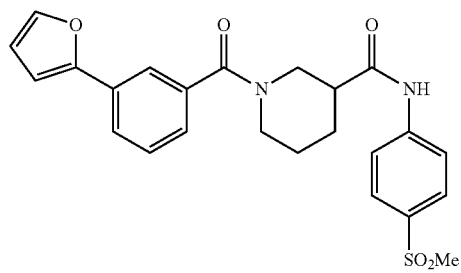 [SMILES: CS(=O)(=O)c1ccc(NC(=O)C2CCCN(C(=O)c3cccc(-c4ccco4)c3)C2)cc1]<br>1-(3-(furan-2-yl)benzoyl)-N-(4-(methylsulfonyl)phenyl)piperidine-3-carboxamide |
| E-096 | 1.1 | 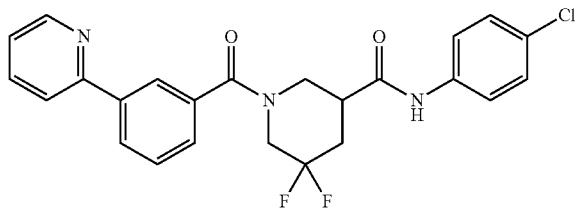 [SMILES: O=C(Nc1ccc(Cl)cc1)C1CN(C(=O)c2cccc(-c3ccccn3)c2)CC(F)(F)C1]<br>N-(4-chlorophenyl)-5,5-difluoro-1-(3-(pyridin-2-yl)benzoyl)piperidine-3-carboxamide |
| E-097 | 32 | 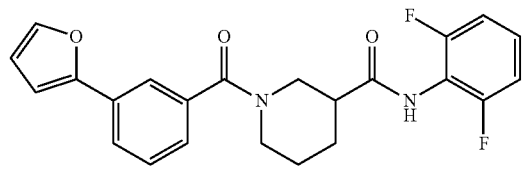 [SMILES: O=C(Nc1c(F)cccc1F)C1CCCN(C(=O)c2cccc(-c3ccco3)c2)C1]<br>N-(2,6-difluorophenyl)-1-(3-(furan-2-yl)benzoyl)piperidine-3-carboxamide |

| Example No. | SRE-Luciferase IC$_{50}$ (μM) | Structure/Name |
|---|---|---|
| E-098 | 10 | 1-(3-(1H-imidazol-2-yl)benzoyl)-N-(4-chlorophenyl)-5,5-difluoropiperidine-3-carboxamide |
| E-099 | 3.3 | N-(4-chlorophenyl)-5,5-difluoro-1-(3-(pyrimidin-5-yl)benzoyl)piperidine-3-carboxamide |
| E-100 | 0.91 | N-(4-chlorophenyl)-5,5-difluoro-1-(3-(pyridin-3-yl)benzoyl)piperidine-3-carboxamide |
| E-101 | 5.6 | N-(2-chlorophenyl)-1-(3-(furan-2-yl)benzoyl)piperidine-3-carboxamide |
| E-102 | 1.4 | 1-(1-(4-(1H-pyrazol-1-yl)phenyl)ethyl)-N-(4-chlorophenyl)piperidine-3-carboxamide - Diastereomer A |

-continued

| Example No. | SRE-Luciferase IC$_{50}$ (μM) | Structure/Name |
|---|---|---|
| E-103 | 2.2 | 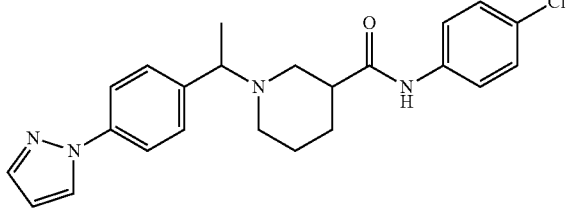<br>1-(1-(4-(1H-pyrazol-1-yl)phenyl)ethyl)-N-(4-chlorophenyl)piperidine-3-carboxamide - Diastereomer B |
| E-104 | 2.9 | 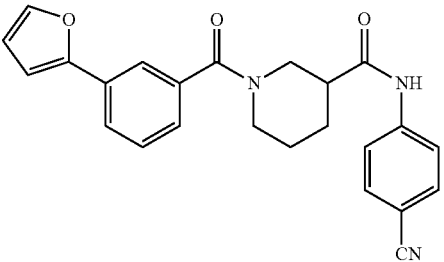 [SMILES: N#Cc1ccc(NC(=O)C2CCCN(C(=O)c3cccc(-c4ccco4)c3)C2)cc1]<br>N-(4-cyanophenyl)-1-(3-(furan-2-yl)benzoyl)piperidine-3-carboxamide |
| E-105 | 13 | 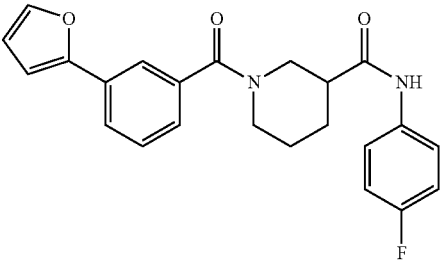<br>N-(4-fluorophenyl)-1-(3-(furan-2-yl)benzoyl)piperidine-3-carboxamide |
| E-106 | 15 | 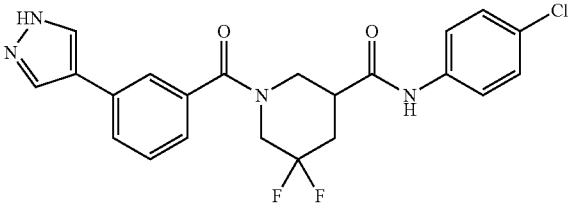 [SMILES: O=C(Nc1ccc(Cl)cc1)C1CN(C(=O)c2cccc(-c3cn[nH]c3)c2)CC(F)(F)C1]<br>1-(3-(1H-pyrazol-4-yl)benzoyl)-N-(4-chlorophenyl)-5,5-difluoropiperidine-3-carboxamide |
| E-107 | 14 | 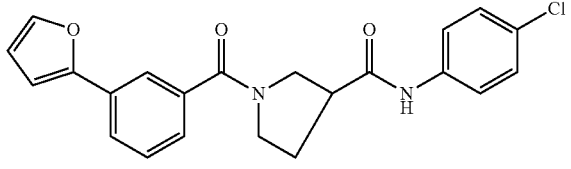 [SMILES: O=C(Nc1ccc(Cl)cc1)C1CCN(C(=O)c2cccc(-c3ccco3)c2)C1]<br>N-(4-chlorophenyl)-1-(3-(furan-2-yl)benzoyl)pyrrolidine-3-carboxamide |

-continued

| Example No. | SRE-Luciferase IC$_{50}$ (μM) | Structure/Name |
|---|---|---|
| E-108 | 12 | 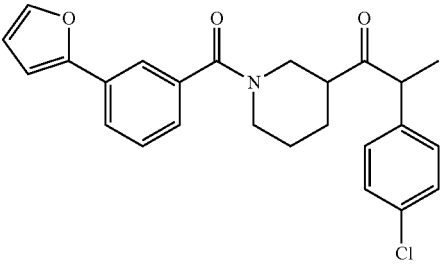 [SMILES: CC(C(=O)C1CCCN(C(=O)c2cccc(-c3ccco3)c2)C1)c1ccc(Cl)cc1]<br>N-(4-chlorophenyl)-1-(3-(furan-2-yl)benzoyl)-N-methylpiperidine-3-carboxamide |
| E-109 | 6.3 | 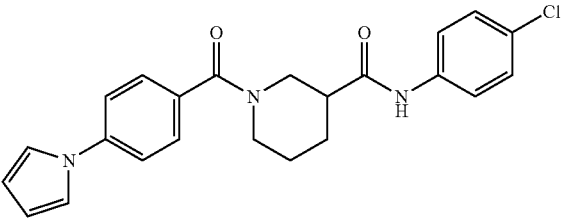 [SMILES: O=C(Nc1ccc(Cl)cc1)C1CCCN(C(=O)c2ccc(-n3cccc3)cc2)C1]<br>1-(4-(1H-pyrrol-1-yl)benzoyl)-N-(4-chlorophenyl)piperidine-3-carboxamide |
| E-110 | 2.9 | 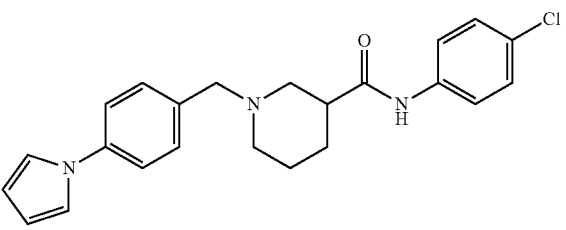 [SMILES: O=C(Nc1ccc(Cl)cc1)C1CCCN(Cc2ccc(-n3cccc3)cc2)C1]<br>1-(4-(1H-pyrrol-1-yl)benzyl)-N-(4-chlorophenyl)piperidine-3-carboxamide |
| E-111 | 15 | 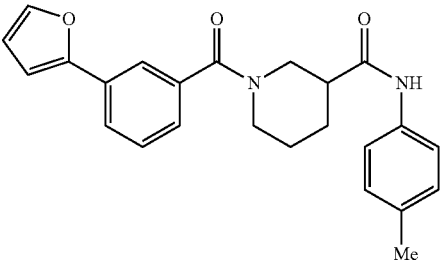<br>1-(3-(furan-2-yl)benzoyl)-N-(p-tolyl)piperidine-3-carboxamide |
| E-112 | 21 | 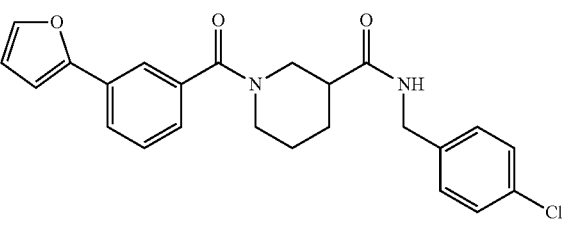 [SMILES: O=C(NCc1ccc(Cl)cc1)C1CCCN(C(=O)c2cccc(-c3ccco3)c2)C1]<br>N-(4-chlorobenzyl)-1-(3-(furan-2-yl)benzoyl)piperidine-3-carboxamide |

| Example No. | SRE-Luciferase IC$_{50}$ (μM) | Structure/Name |
|---|---|---|
| E-113 | 8.0 | N-(4-chlorophenyl)-1-(4-(ethylamino)benzyl)piperidine-3-carboxamide |
| E-114 | 1.6 | 1-(4-(1H-pyrazol-1-yl)benzyl)-N-(4-chlorophenyl)piperidine-3-carboxamide |
| E-115 | 5.2 | 1-(3-(1H-imidazol-1-yl)benzoyl)-N-(4-chlorophenyl)piperidine-3-carboxamide |

Assay for Inhibition of TGF-β Stimulated Expression of α-Smooth Muscle Actin (α-SMA)

Figure 2:
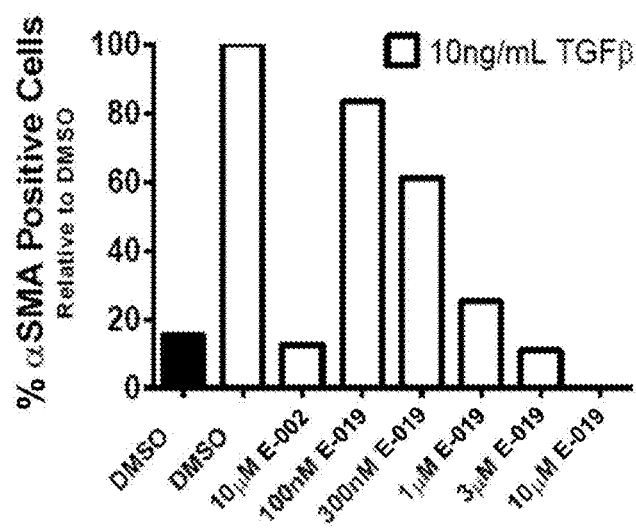
FIG. 2 depicts the % SMA positive cells in dermal fibroblasts that were treated with the indicated concentration of E-002 or E-019 in 0.1% DMSO, and with stimulation by 10 ng/mL of TGF β1.

Dermal fibroblasts from healthy human donors were treated for 72 hours with the indicated concentration of compound E-02 or E-019 (and 0.1% DMSO control), with or without stimulation by 10 ng/mL TGFβ1. Cells were then probed with primary antibody for α-SMA, then fluorophore-conjugated secondary antibody +DAPI. Cells were imaged using a fluorescent microscope at 40× magnification. For quantification, cells from three, random non-overlapping fields of view were scored as a-SMA positive or negative by an observer blinded to the treatment. See FIGS. 1 and 2.

Preparation 1: tert-butyl 3-((4-chlorophenyl)carbamoyl)-3-fluoropiperidine-1-carboxylate)

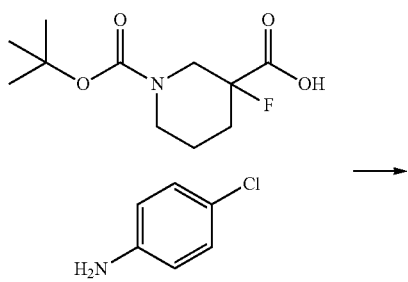

-continued

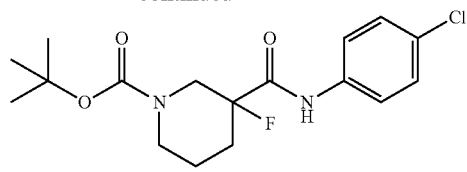

Oxalyl chloride (0.45 g, 3.56 mmol) was added dropwise to a stirred solution of 1-(tert-butoxycarbonyl)-3-fluoropiperidine-3-carboxylic acid (0.8 g, 3.24 mmol) in a mixture of THF (20 mL) and 1 drop of DMF under N$_2$ at 0-5° C. After an hour, the mixture was taken to dryness in vacuo and the residue redissolved in 15 mL of THF and stirred at room temperature under N$_2$. Diisopropylethylamine (0.50 g, 3.88 mmol) was added, followed by a solution of 4-chloroaniline (0.41 g, 3.24 mmol) in 4-5 mL of THF. After 18 hours the mixture was poured into 250 mL of water and stirred. After several hours the precipitate was filtered off, rinsed with water and dried to afford the product (1.10 g, 95%) as a white powder.

Preparation 2: N-(4-chlorophenyl)-3-fluoropiperidine-3-carboxamide trifluoroacetate

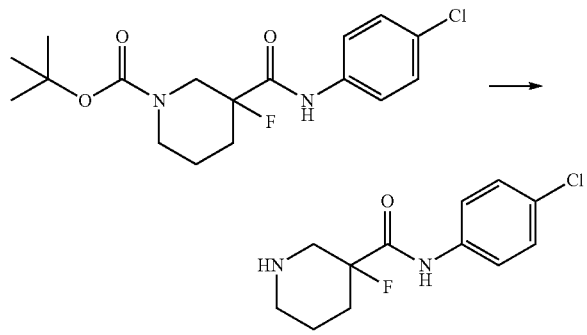

Trifluoroacetic acid (2.4 g, 21.0 mmol) was added to a stirred solution of tert-butyl 3-((4-chloro-phenyl)-carbamoyl)-3-fluoropiperidine-1-carboxylate (0.5 g, 1.04 mmol) in dichloromethane (9 mL) and stirred at room temperature. After 24 hours the mixture was stripped to dryness in vacuo. The residue was triturated in diethyl ether, filtered off, rinsed and dried to afford the product (0.5 g, 96%) as a white powder.

Example 1: N-(4-chlorophenyl)-3-fluoro-1-(3-(furan-2-yl)benzoyl)piperidine-3-carboxamide

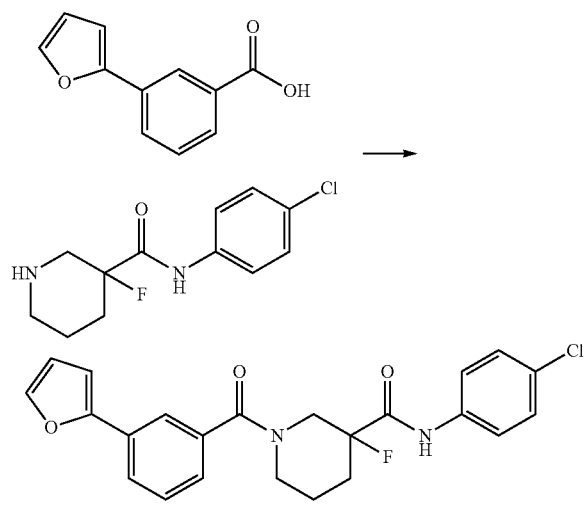

3-(Furan-2-yl)benzoic acid (0.115 g, 0.61 mmol) was added to a stirred solution of N-(4-chlorophenyl)-3-fluoropiperidine-3-carboxamide trifluoroacetate (0.25 g, 0.67 mmol), 1-ethyl-3-(3-dimethylaminopropyl)carbodiimide hydrochloride (0.141 g, 0.74 mmol), diisopropyl-ethylamine (0.198 g, 1.53 mmol), and 4-N,N-dimethylaminopyridine (0.030 g, 0.245 mmol) in dichloromethane (12 mL) under $N_2$ at room temperature. After 22 hours the mixture was diluted with 20 mL of dichloromethane and shaken with an equal volume of 1N HCl. The layers were separated and the organic layer washed with saturated aqueous $NaHCO_3$ then saturated brine and dried over $MgSO_4$. The solvent was removed under reduced pressure and the residue sonicated briefly in hexanes then the solid filtered off, rinsed with hexanes and dried to afford the crude product (0.16 g) as a white foam. Chromatography on a column of silica gel under pressure eluting with Hexanes/EtOAc/acetone 3:2:2 followed by crystallization from ethanol afforded the title compound as a white solid (98 mg, 38%). $^1$H NMR (400 MHz, DMSO-d6) δ 10.34, 10.16, 7.76, 7.67, 7.46-7.26, 7.04, 6.60, 4.72, 4.46, 3.8-3.7, 3.59, 3.33, 2.96, 2.1-2.0, 1.7-1.6.

Preparation 3: tert-butyl 3-((4-chlorophenyl)carbamoyl)piperidine-1-carboxylate

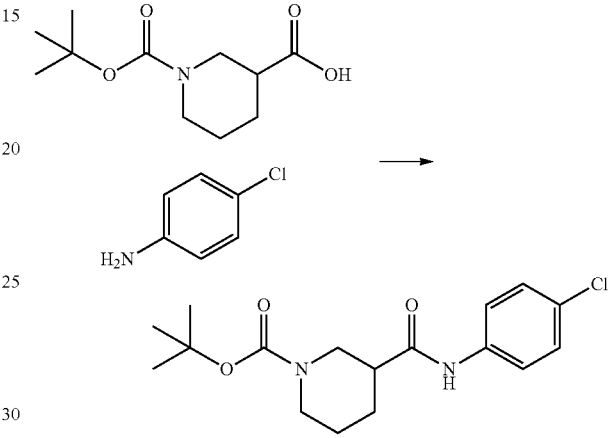

1-(tert-butoxycarbonyl)piperidine-3-carboxylic acid (4.0 g, 17.45 mmol) was added to a stirred solution of 4-chloroaniline (3.34 g, 26.2 mmol), 1-ethyl-3-(3-dimethylaminopropyl)carbodiimide hydrochloride (5.02 g, 26.2 mmol), diisopropylethylamine (3.61 g, 27.9 mmol), and 4-N,N-dimethylaminopyridine (0.32 g, 26.2 mmol) in dichloromethane (150 mL) under $N_2$ at room temperature. After 23 hours the mixture was diluted with 25 mL of dichloromethane and shaken with an equal volume of 1N HCl. The layers were separated and the organic layer washed with saturated aqueous $NaHCO_3$, then saturated brine, and dried over $MgSO_4$. The solvent was removed in vacuo to afford the product (4.4 g, 74%) as a cream-colored foam, sufficiently pure for the next step.

Preparation 4: N-(4-chlorophenyl)piperidine-3-carboxamide, trifluoroacetate

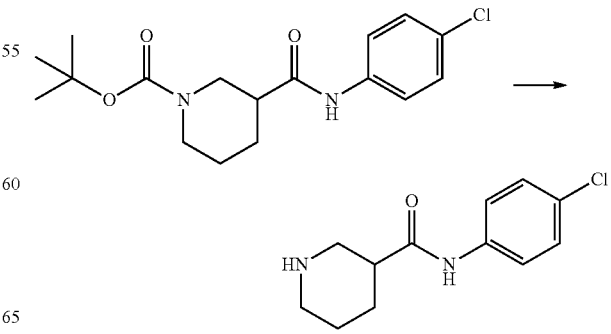

Trifluoroacetic acid (2.5 g, 22.1 mmol) was added to a stirred solution of tert-butyl 3-((4-chlorophenyl)carbamoyl)piperidine-1-carboxylate (0.5 g, 1.48 mmol) in dichloromethane (10 ml) at room temperature. After 20 hours the mixture was taken to dryness under reduced pressure leaving the product (5 g, 96%) as a clear dark amber syrup of sufficient purity for use in the next step.

Example 2: N-(4-chlorophenyl)-1-(3-(furan-2-yl)benzoyl)piperidine-3-carboxamide

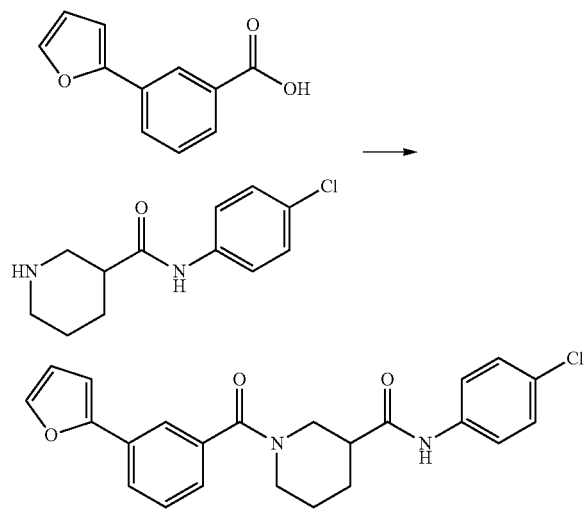

3-(Furan-2-yl)benzoic acid (0.24 g, 1.29 mmol) was added to a stirred solution of N-(4-chlorophenyl)-piperidine-3-carboxamide trifluoroacetate (0.5 g, 1.42 mmol), 1-ethyl-3-(3-dimethylaminopropyl)carbodiimide hydrochloride (0.30 g, 1.55 mmol), diisopropylethylamine (0.58 g, 4.51 mmol), and 4-N,N-dimethylaminopyridine (0.06 g, 0.52 mmol) in dichloromethane (12 mL) under N₂ at room temperature. After 18 hours the mixture was diluted with 30 mL of dichloromethane and shaken with an equal volume of 1N HCl. The layers were separated and the organic layer washed with saturated aqueous NaHCO₃, then saturated brine, and dried over MgSO₄. The solvent was removed in vacuo and the residue chromatographed on a column of silica gel under pressure, eluting with Hxa/EtOAc 1:1 to afford the product (0.3 g, 57%) as a white foam. $^1$H NMR (400 MHz, DMSO-d6) δ 10.22, 10.00, 7.78, 7.67, 7.36, 7.3-7.2, 7.04, 6.62, 4.54, 4.27, 3.7-3.5, 3.1-2.9, 2.6-2.5, 2.02, 1.7-1.6, 1.45.

Example 3: 1-(3-(5-chlorofuran-2-yl)benzoyl)-N-(4-chlorophenyl)piperidine-3-carboxamide

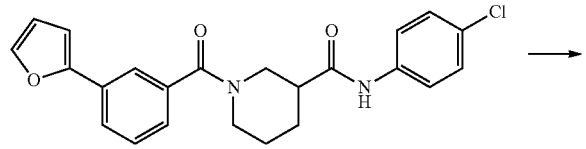

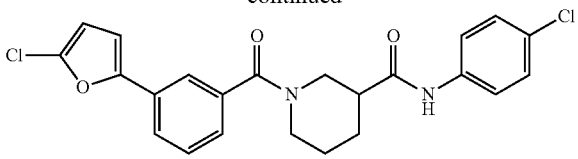

N-chlorosuccinimide (0.039 g, 293 mmol) was added to a stirred solution of N-(4-chlorophenyl)-1-(3-(furan-2-yl)benzoyl)piperidine-3-carboxamide (0.1 g, 245 mmol) in DMF (2 mL) under N₂ at room temperature. After 24 hours the mixture was heated to 60° C., and after another 24 hours to 85° C. for 2 hours, then allowed to cool. The mixture was diluted with 10 mL of water and stirred for 2 hours. The precipitate was filtered off, rinsed with water and dried, then dissolved in ethyl acetate/hexanes 1:1 and filtered through a short column of silica gel under pressure. The filtrate was stripped of solvent in vacuo to afford the product (0.044 g, 39%) as a white solid. $^1$H NMR (400 MHz, CDCl₃) δ 9.06, 7.66-7.62, 7.42, 7.29-7.26, 6.64, 6.25, 4.14, 4.0-3.9, 3.51, 2.75, 2.35, 1.93, 1.56.

Preparation 5: 1-benzyl 4-(tert-butyl) 2-((4-chlorophenyl)carbamoyl)piperazine-1,4-dicarboxylate

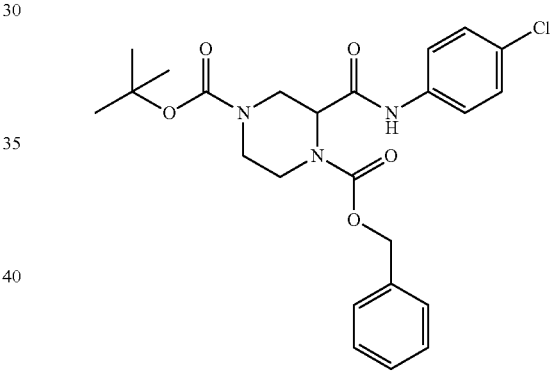

To a solution of 1-((benzyloxy)carbonyl)-4-(tert-butoxycarbonyl)piperazine-2-carboxylic acid (2.0 g, 5.5 mmol) in THF (30 mL) was added N-(3-dimethylaminopropyl)-N'-ethylcarbodiimide hydrochloride (1.1 g, 6.0 mmol), 4-chloroaniline (0.84 g, 6.6 mmol), catalytic 4-(dimethylamino)pyridine, and N,N-diisopropylethylamine (0.96 ml, 5.5 mmol). The resulting mixture was stirred overnight at room temperature. The reaction mixture was diluted with ethyl acetate and washed with saturated aqueous sodium bicarbonate solution, and brine. The organic layer was dried over magnesium sulfate, filtered, and concentrated. The crude residue was purified by column chromatography eluting with 10-30% ethyl acetate in hexanes to give the title compound (2.2 g, 85%). $^1$H NMR (400 MHz, CDCl₃) (Rotamers) δ 8.59-7.83, 7.37, 7.24, 5.20, 4.75, 4.56, 3.92, 3.23, 3.04, 1.44.

Preparation 6: Benzyl 2-((4-chlorophenyl)carbamoyl)piperazine-1-carboxylate

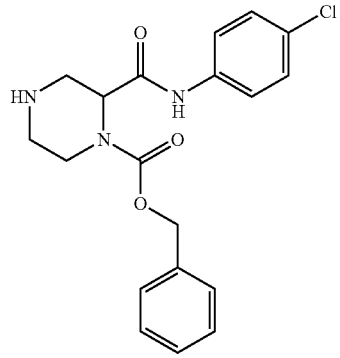 [SMILES: O=C(Nc1ccc(Cl)cc1)C1CNCCN1C(=O)OCc1ccccc1]

To a solution of 1-benzyl 4-(tert-butyl) 2-((4-chlorophenyl)carbamoyl)piperazine-1,4-dicarboxylate (2.2 g, 4.6 mmol) in dichloromethane (20 mL) was added trifluoroacetic acid (5 ml, 65 mmol). The reaction stirred overnight at room temperature. The reaction was concentrated and the resulting crude oil was dissolved in dichloromethane and washed with 1N aqueous NaOH, and brine. The organic layer was dried over magnesium sulfate, filtered, and concentrated to afford the title compound which was taken into the next step without purification (1.7 g, 100%).

Example 4: Benzyl 2-((4-chlorophenyl)carbamoyl)-4-(3-(furan-2-yl)benzoyl)piperazine-1-carboxylate

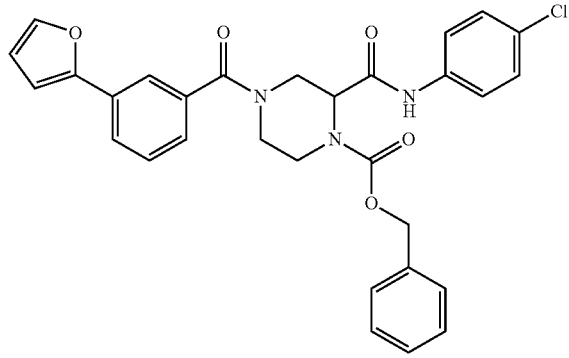 [SMILES: O=C(Nc1ccc(Cl)cc1)C1CN(C(=O)c2cccc(-c3ccco3)c2)CCN1C(=O)OCc1ccccc1]

To a solution of benzyl 2-((4-chlorophenyl)carbamoyl)piperazine-1-carboxylate (460 mg, 1.2 mmol) in THF (6 ml) was added 3-(furan-2-yl)benzoic acid (260 mg, 1.4 mmol) followed by N-(3-dimethylaminopropyl)-N'-ethylcarbodiimide hydrochloride (280 mg, 1.5 mmol), 4-(dimethylamino)pyridine (15 mg, 0.12 mmol), and N,N-diisopropylethylamine (0.32 ml, 1.8 mmol). The resulting mixture was stirred overnight at room temperature. The reaction was concentrated to remove THF, then diluted with dichloromethane and washed successively with 1N HCl, saturated aqueous sodium bicarbonate solution, and brine. The organic layer was dried over magnesium sulfate, filtered, and concentrated. The crude residue was purified by column chromatography eluting with 10-40% ethyl acetate in hexanes to give the title compound (660 mg, 98%). $^1$H NMR (400 MHz, CDCl$_3$) (Rotamers) δ 8.93, 8.08, 7.72, 7.52, 7.46, 7.36, 7.27, 6.67, 6.47, 5.23, 5.16-3.63, 3.52-2.98.

Preparation 7: N-(4-chlorophenyl)-4-(3-(furan-2-yl)benzoyl)piperazine-2-carboxamide

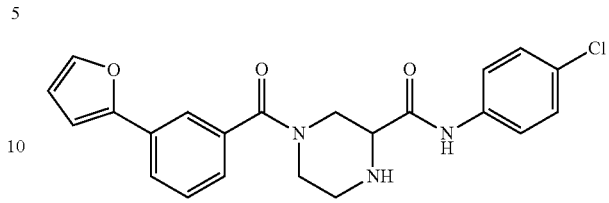

To a degassed solution of benzyl 2-((4-chlorophenyl)carbamoyl)-4-(3-(furan-2-yl)benzoyl)piperazine-1-carboxylate (330 mg, 0.61 mmol) in methanol (30 ml) was added a spatula tip full of 10% Pd on carbon. The reaction was placed under hydrogen at 49 psi and stirred overnight. The reaction was filtered through celite, and the filtrate was concentrated. The crude residue was purified by column chromatography on silica gel eluting with 80-100% ethyl acetate in hexanes to give the title compound as an amorphous solid (180 mg, 73%). $^1$H NMR (400 MHz, CDCl$_3$) (Rotamers) δ 9.02, 7.72, 7.55, 7.47, 7.43, 7.29, 6.70, 6.48, 4.33-3.50, 3.45, 3.25-2.76.

Example 5: N-(4-chlorophenyl)-4-(3-(furan-2-yl)benzoyl)-1-propionylpiperazine-2-carboxamide

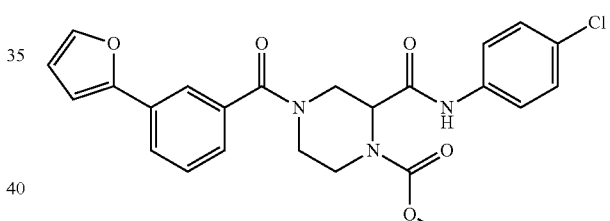

To a solution of N-(4-chlorophenyl)-4-(3-(furan-2-yl)benzoyl)piperazine-2-carboxamide (41 mg, 0.10 mmol) in THF (1 ml) was added propionic acid (0.011 ml, 0.15 mmol) followed by N-(3-dimethylaminopropyl)-N'-ethylcarbodiimide hydrochloride (29 mg, 0.15 mmol), N,N-diisopropylethylamine (0.026 ml, 0.15 mmol), and 4-(dimethylamino)pyridine (1.2 mg, 10 μmol). The reaction stirred at room temperature overnight. The reaction was poured into dichloromethane, and washed with saturated aqueous sodium bicarbonate and brine. The organic layer was dried over magnesium sulfate, filtered, and concentrated. The crude residue was purified by column chromatography eluting with 50-80% ethyl acetate in hexanes to give the title compound as a white solid (24 mg, 51%). $^1$H NMR (400 MHz, CDCl$_3$) (Rotamers) δ 9.68, 9.02, 8.51, 7.67, 7.53-7.11, 6.67, 6.47, 5.49-4.91, 4.72, 4.42, 4.29, 3.84, 3.60, 3.35, 2.62, 2.45, 1.19.

Example 6: N-(4-chlorophenyl)-4-(3-(furan-2-yl)benzoyl)-1-isobutyrylpiperazine-2-carboxamide

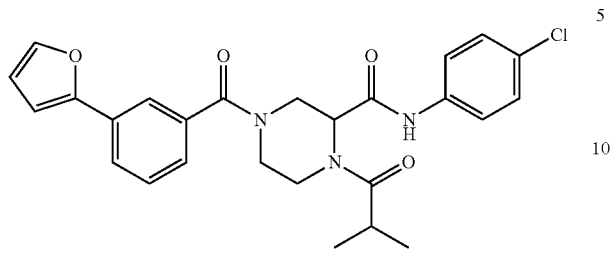

The above compound was prepared by following the general procedure for amide coupling described in Example 5. $^1$H NMR (400 MHz, CDCl$_3$)(Rotamers) δ 9.67, 8.92, 8.45, 7.85, 7.71, 7.46, 7.40, 7.22, 6.68, 6.47, 5.51-4.91, 4.79, 4.51, 4.31, 3.91, 3.65-3.15, 2.88, 1.28-1.11.

Example 7: N-(4-chlorophenyl)-4-(3-(furan-2-yl)benzoyl)-1-(4-methoxybenzoyl)piperazine-2-carboxamide

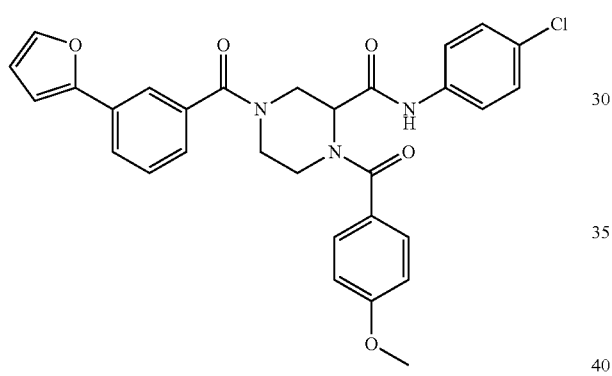

The above compound was prepared by following the general procedure for amide coupling described in Example 5. $^1$H NMR (400 MHz, CDCl$_3$) (Rotamers) δ 9.62-8.77, 7.90, 7.73, 7.47, 7.41, 7.27, 6.93, 6.69, 6.48, 5.59-4.25, 4.06-3.90, 3.84, 3.44, 3.23.

Example 8: 1-acetyl-N-(4-chlorophenyl)-4-(3-(furan-2-yl)benzoyl)piperazine-2-carboxamide

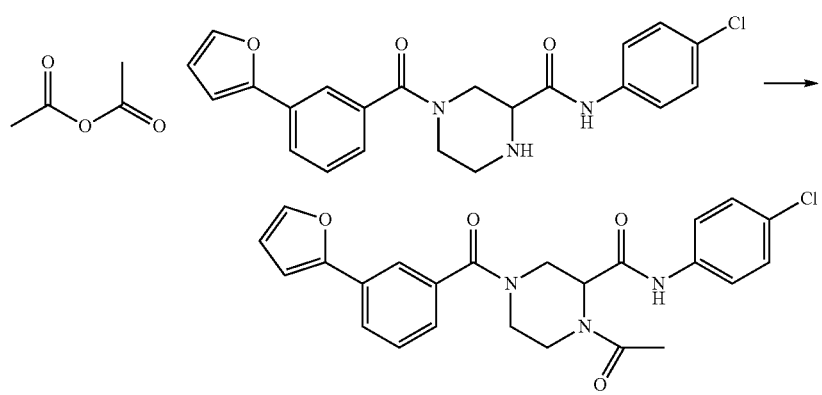

To a solution of N-(4-chlorophenyl)-4-(3-(furan-2-yl)benzoyl)piperazine-2-carboxamide (0.06 g, 0.15 mmol) in dry THF (2 mL) was added acetic anhydride (0.03 ml, 0.29 mmol) followed by catalytic 4-(dimethylamino)pyridine. The resulting mixture was stirred 18 hours at room temperature. Diluted with EtOAc and washed with saturated aqueous NaHCO₃, solution, then saturated aqueous NaCl. The organic layer was dried over magnesium sulfate, filtered and concentrated. The crude residue was purified by flash chromatography (EtOAc/hexane) to result in 1-acetyl-N-(4-chlorophenyl)-4-(3-(furan-2-yl)benzoyl)piperazine-2-carboxamide (0.03 g, 40.8%). $^1$H NMR (400 MHz, DMSO-d6) (Rotamers) δ 10.26, 9.92, 7.75-7.49, 6.74-7.48, 6.62, 4.85, 4.11-4.81, 2.21.

General Procedure for Ureas:

Example 9: N2-(4-chlorophenyl)-4-(3-(furan-2-yl)benzoyl)-N1-phenylpiperazine-1,2-dicarboxamide

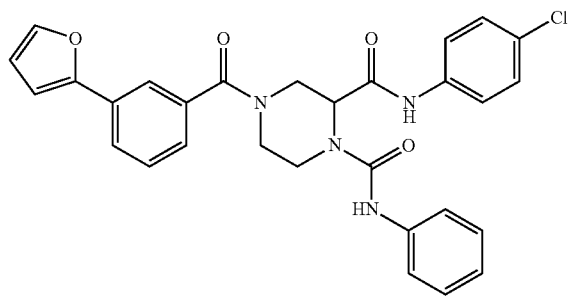 [SMILES: O=C(Nc1ccc(Cl)cc1)C1CN(C(=O)c2cccc(-c3ccco3)c2)CCN1C(=O)Nc1ccccc1]

To a solution of N-(4-chlorophenyl)-4-(3-(furan-2-yl)benzoyl)piperazine-2-carboxamide (53 mg, 0.13 mmol) in dichloromethane (1 ml) was added isocyanatobenzene (23 mg, 0.19 mmol) at room temperature. After 30 min, solid had precipitated out of solution. The solid was filtered off, washed with ether, and dried overnight to give the title compound as a white solid (46 mg, 67%). $^1$H NMR (400 MHz, DMSO-d6) (Rotamers) δ 10.29, 9.88, 8.68, 7.81-6.80, 6.54, 4.84, 4.65, 4.38, 4.04, 3.72, 3.08.

Example 10: N2-(4-chlorophenyl)-4-(3-(furan-2-yl)benzoyl)-N1-isopropylpiperazine-1,2-dicarboxamide

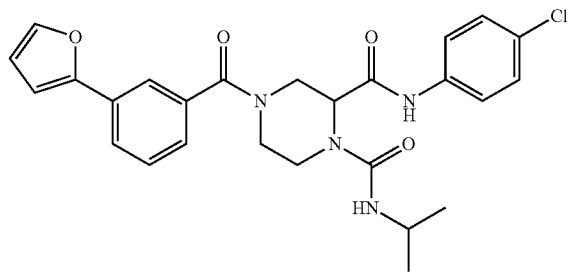 [SMILES: CC(C)NC(=O)N1CCN(C(=O)c2cccc(-c3ccco3)c2)CC1C(=O)Nc1ccc(Cl)cc1]

To a solution of N-(4-chlorophenyl)-4-(3-(furan-2-yl)benzoyl)piperazine-2-carboxamide (50 mg, 0.12 mmol) in dichloromethane (1 ml) was added 2-isocyanatopropane (0.018 ml, 0.18 mmol). The reaction was left in a shaker at room temperature overnight. The reaction was concentrated, then purified by flash chromatography eluting with 70-80% ethyl acetate in hexanes to give the title compound as a white solid (44 mg, 72%). $^1$H NMR (400 MHz, CDCl₃)(Rotamers) δ 9.69, 9.04, 7.87, 7.73, 7.62, 7.47, 7.42, 7.26, 6.69, 6.48, 5.51-4.68, 4.49, 4.29, 3.99, 3.80, 3.55, 3.45, 3.01, 1.22.

Example 11: N2-(4-chlorophenyl)-N1-cyclopentyl-4-(3-(furan-2-yl)benzoyl)piperazine-1,2-dicarboxamide

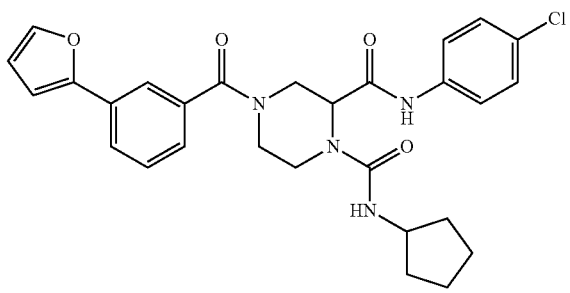 [SMILES: O=C(Nc1ccc(Cl)cc1)C1CN(C(=O)c2cccc(-c3ccco3)c2)CCN1C(=O)NC1CCCC1]

The above compound was prepared by following the general procedure for ureas described in Example 9. $^1$H NMR (400 MHz, DMSO-d6)(Rotamers) δ 10.21, 9.82, 7.82-6.74, 6.53, 6.41, 4.77, 4.55, 4.34, 3.97, 3.87, 3.76, 3.56, 2.98, 1.75, 1.60, 1.43.

Example 12: N1-allyl-N2-(4-chlorophenyl)-4-(3-(furan-2-yl)benzoyl)piperazine-1,2-dicarboxamide

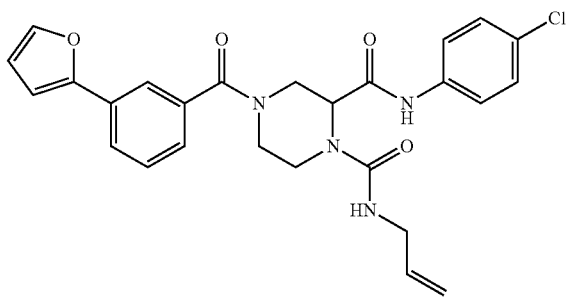 [SMILES: C=CCNC(=O)N1CCN(C(=O)c2cccc(-c3ccco3)c2)CC1C(=O)Nc1ccc(Cl)cc1]

The above compound was prepared by following the general procedure for ureas described in Example 9. The crude residue was purified by column chromatography. $^1$H NMR (400 MHz, CDCl₃)(Rotamers) δ 9.65, 9.01, 7.73, 7.60-7.07, 6.65, 6.46, 5.84, 5.45, 5.15, 4.87, 4.29, 3.81-3.07.

Example 13: propyl 2-((4-chlorophenyl)carbamoyl)-4-(3-(furan-2-yl)benzoyl)piperazine-1-carboxylate

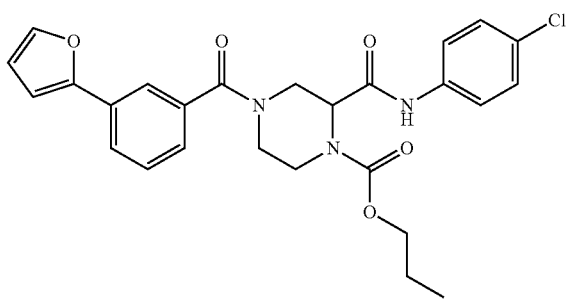 [SMILES: CCCOC(=O)N1CCN(C(=O)c2cccc(-c3ccco3)c2)CC1C(=O)Nc1ccc(Cl)cc1]

To a solution of N-(4-chlorophenyl)-4-(3-(furan-2-yl)benzoyl)piperazine-2-carboxamide (40 mg, 0.098 mmol) in dichloromethane (1 ml) was added triethylamine (0.034 ml, 0.24 mmol) followed by propyl carbonochloridate (0.027 ml, 0.24 mmol). The reaction was left at room temperature on a shaker for 30 min. The reaction mixture was poured into dichloromethane and washed with saturated aqueous sodium bicarbonate solution and brine. The organic layer was dried over magnesium sulfate, filtered and concentrated. The crude residue was purified by flash chromatography eluting with 40-60% ethyl acetate in hexanes to give the title compound as a white solid (44 mg, 72%). $^1$H NMR (400 MHz, CDCl$_3$)(Rotamers) δ 8.95, 8.06, 7.88-7.03, 6.68, 6.48, 5.25-4.29, 4.16, 4.08-3.62, 3.37, 1.70, 0.96.

General Procedure for Carbamates:

Example 14: ethyl 2-((4-chlorophenyl)carbamoyl)-4-(3-(furan-2-yl)benzoyl)piperazine-1-carboxylate

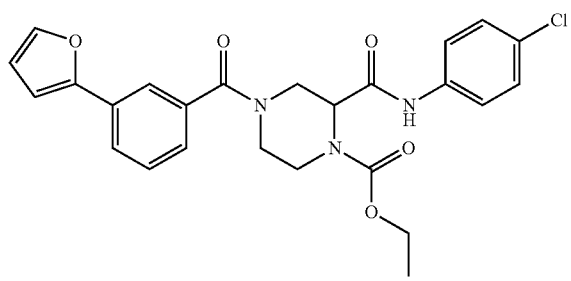 [SMILES: CCOC(=O)N1CCN(C(=O)c2cccc(-c3ccco3)c2)CC1C(=O)Nc1ccc(Cl)cc1]

To a solution of N-(4-chlorophenyl)-4-(3-(furan-2-yl)benzoyl)piperazine-2-carboxamide (50 mg, 0.12 mmol) in dichloromethane (1 ml) was added ethyl carbonochloridate (0.023 ml, 0.24 mmol). The reaction stirred at room temperature for 1 hour. The reaction was poured into dichloromethane, washed with saturated aqueous sodium bicarbonate solution, and brine. The organic layer was dried over magnesium sulfate, filtered, and concentrated. The crude residue was purified by column chromatography eluting with ethyl acetate and hexanes to afford the title compound (49 mg, 83%). $^1$H NMR (400 MHz, CDCl$_3$)(Rotamers) δ 8.93, 8.11, 7.90-7.22, 6.68, 6.48, 5.25-4.36, 4.25, 4.16-3.65, 3.49-2.96, 1.31.

Example 15: Phenyl 2-((4-chlorophenyl)carbamoyl)-4-(3-(furan-2-yl)benzoyl)piperazine-1-carboxylate

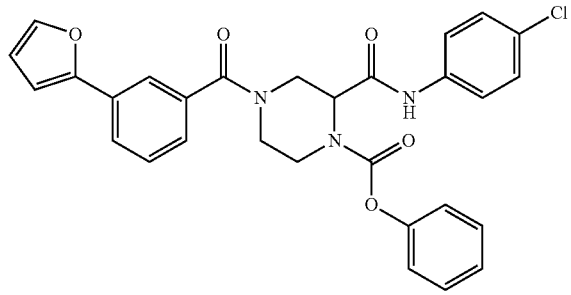 [SMILES: O=C(Nc1ccc(Cl)cc1)C1CN(C(=O)c2cccc(-c3ccco3)c2)CCN1C(=O)Oc1ccccc1]

The above compound was prepared by following the general procedure for carbamates described in Example 14. $^1$H NMR (400 MHz, CDCl$_3$)(Rotamers) δ 9.29, 8.98, 8.30, 7.71, 7.60-7.08, 6.65, 6.47, 5.28-3.02.

Example 16: 2-methoxyethyl 2-((4-chlorophenyl)carbamoyl)-4-(3-(furan-2-yl)benzoyl)piperazine-1-carboxylate

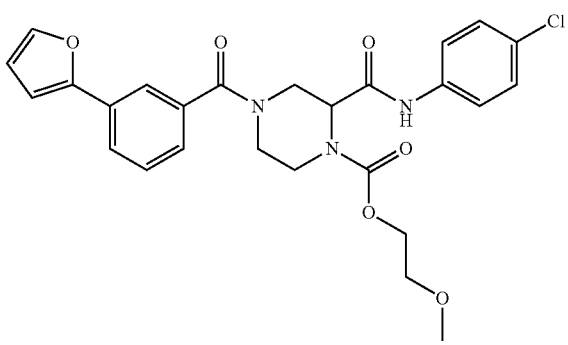 [SMILES: COCCOC(=O)N1CCN(C(=O)c2cccc(-c3ccco3)c2)CC1C(=O)Nc1ccc(Cl)cc1]

The above compound was prepared by following the general procedure for carbamates described in Example 14. $^1$H NMR (400 MHz, CDCl$_3$)(Rotamers) δ 8.95, 8.16, 7.82-7.16, 6.67, 6.47, 5.52-4.47, 4.34, 4.24-3.71, 3.63, 3.36, 3.33-3.01.

Example 17: 1-benzyl-N-(4-chlorophenyl)-4-(3-(furan-2-yl)benzoyl)piperazine-2-carboxamide

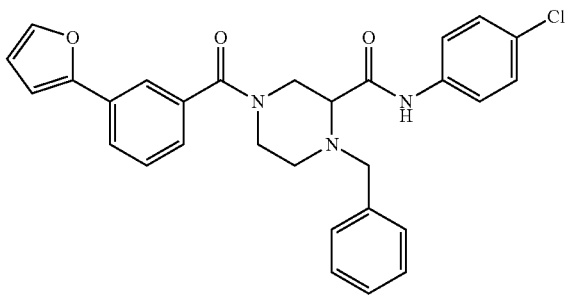 [SMILES: O=C(Nc1ccc(Cl)cc1)C1CN(C(=O)c2cccc(-c3ccco3)c2)CCN1Cc1ccccc1]

To a solution of N-(4-chlorophenyl)-4-(3-(furan-2-yl)benzoyl)piperazine-2-carboxamide (50 mg, 0.12 mmol) in dichloromethane (1 mL), was added sodium triacetoxyborohydride (39 mg, 0.18 mmol). The reaction stirred at room temperature for 2 h. To the reaction solution was added 1 drop of acetic acid, and the solution was left overnight. To the reaction mixture was added benzaldehyde (19 mg, 0.18 mmol) followed by additional sodium triacetoxyborohydride (39 mg, 0.18 mmol). The reaction stirred for 4 hrs. The reaction mixture was poured into dichloromethane and washed with saturated aqueous sodium bicarbonate solution followed by brine. The organic layer was dried over magnesium sulfate, filtered and concentrated. The crude residue was purified by flash chromatography eluting with 40-50% ethyl acetate in hexanes to give the title compound as a white solid (40 mg, 65%). $^1$H NMR (400 MHz, CDCl$_3$)(Rotamers) δ 8.90, 7.72, 7.54-7.26, 6.69, 6.48, 4.70, 4.25, 3.98, 3.57, 3.32, 3.19, 2.53.

Example 18: N-(4-chlorophenyl)-4-(3-(furan-2-yl)benzoyl)-1-methylpiperazine-2-carboxamide

Preparation 9: tert-butyl 3-((4-chlorophenyl)carbamoyl)-5-oxopiperidine-1-carboxylate

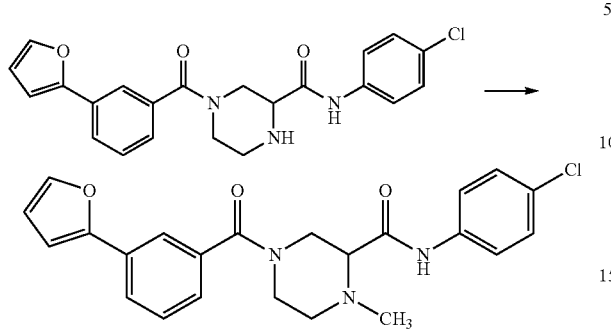

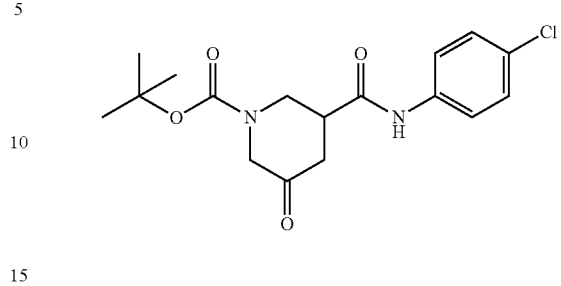

To a solution of N-(4-chlorophenyl)-4-(3-(furan-2-yl)benzoyl)piperazine-2-carboxamide (0.05 g, 0.12 mmol) in methanol (10 mL) was added the paraformaldehyde (3.7 mg, 0.122 mmol) in one portion. The resulting mixture was stirred 2 hours at room temperature. The solution became homogeneous. Sodium cyanoborohydride (0.06 g, 0.98 mmol) was added and the mixture was stirred overnight at room temperature. The reaction mixture was concentrated. The crude residue was purified by flash chromatography (MeOH/CH$_2$Cl$_2$) to result in N-(4-chlorophenyl)-4-(3-(furan-2-yl)benzoyl)-1-methylpiperazine-2-carboxamide (0.01 g, 25.1%). $^1$H NMR (400 MHz, DMSO-d6) (Rotamers) δ 10.53, 9.47, 7.25-7.78, 7.03, 6.62, 3.24-4.49, 2.74.

To a round bottom flask was added dichloromethane (30 ml) and oxalyl chloride (0.92 ml, 11 mmol). The resulting solution was cooled to −78° C. DMSO (1.5 mL, 21 mmol) was added dropwise. After 15 min, a solution of tert-butyl 3-((4-chlorophenyl)carbamoyl)-5-hydroxypiperidine-1-carboxylate (2.7 g, 7.5 mmol) in dichloromethane (15 mL) was added. After 15 min, triethylamine was added (4.6 mL, 33 mmol). The reaction stirred for 30 min and was warmed to room temperature over 30 min. The reaction was poured into saturated aqueous sodium bicarbonate solution and extracted 3× with dichloromethane. The combined organic layers were washed with brine, dried over magnesium sulfate, filtered, and concentrated. The crude residue was purified by column chromatography eluting with 50-70% ethyl acetate in hexanes to give the title compound as an amorphous solid (1.5 g, 58%).

Preparation 8: tert-butyl 3-((4-chlorophenyl)carbamoyl)-5-hydroxypiperidine-1-carboxylate

Preparation 10: tert-butyl 5-((4-chlorophenyl)carbamoyl)-3,3-difluoropiperidine-1-carboxylate

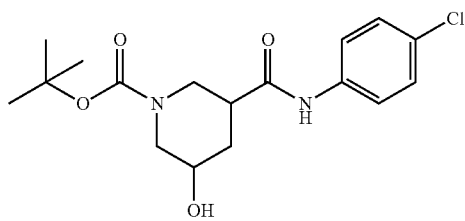 [SMILES: CC(C)(C)OC(=O)N1CC(O)CC(C(=O)Nc2ccc(Cl)cc2)C1]

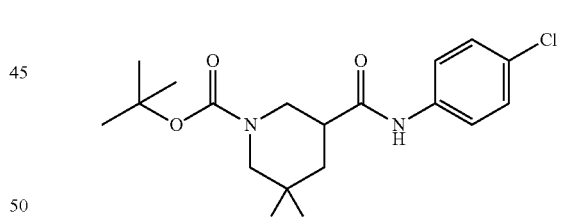

To a solution of 1-(tert-butoxycarbonyl)-5-hydroxypiperidine-3-carboxylic acid (5 g, 20 mmol) in DMF (50 ml) was added 4-chloroaniline (3.1 g, 24 mmol), N,N-diisopropylethylamine (11 ml, 61 mmol), and 1-[bis(dimethylamino)methylene]-1H-1,2,3-triazolo[4,5-b]pyridinium 3-oxid hexafluorophosphate (8.5 g, 22 mmol). The reaction stirred at room temperature overnight. The reaction mixture was poured into dichloromethane and washed with saturated aqueous sodium bicarbonate solution, and brine. The organic layer was dried over magnesium sulfate, filtered and concentrated. The crude residue was purified by column chromatography eluting with 50-70% ethyl acetate in hexanes to give the title compound as a white film (2.0 g, 28%).

To a solution of tert-butyl 3-((4-chlorophenyl)carbamoyl)-5-oxopiperidine-1-carboxylate (1.5 g, 4.2 mmol) in dichloromethane (20 ml) at −78° C. was added N,N-diethyl-1,1,1-trifluoro-14-sulfanamine (0.83 ml, 6.3 mmol). The reaction stirred for 30 min, and was warmed to room temperature. The reaction mixture was poured into dichloromethane and washed with saturated aqueous sodium bicarbonate solution and brine. The organic layer was dried over magnesium sulfate, filtered, and concentrated. The crude residue was purified by column chromatography eluting with 10-20% ethyl acetate in hexanes to give the title compound as an amorphous solid (450 mg, 29%).

Preparation 11: N-(4-chlorophenyl)-5,5-difluoropiperidine-3-carboxamide

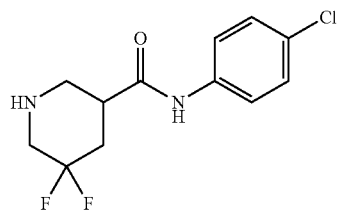 [SMILES: O=C(Nc1ccc(Cl)cc1)C1CNCC(F)(F)C1]

To a solution of tert-butyl 5-((4-chlorophenyl)carbamoyl)-3,3-difluoropiperidine-1-carboxylate (400 mg, 1.1 mmol) in dichloromethane (10 ml) was added trifluoroacetic acid (1.5 mL, 20 mmol). The reaction stirred at room temperature for 3 h, then was concentrated. The crude mixture was dissolved in dichloromethane and washed with saturated aqueous sodium bicarbonate solution and brine. The organic layer was dried over magnesium sulfate, filtered, and concentrated to give the title compound as a white solid (280 mg, 95%).

Example 19: N-(4-chlorophenyl)-5,5-difluoro-1-(3-(furan-2-yl)benzoyl)piperidine-3-carboxamide

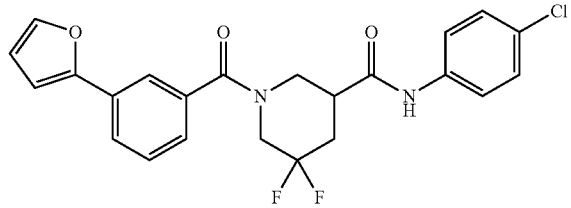 [SMILES: O=C(Nc1ccc(Cl)cc1)C1CN(C(=O)c2cccc(-c3ccco3)c2)CC(F)(F)C1]

To a solution of N-(4-chlorophenyl)-5,5-difluoropiperidine-3-carboxamide (280 mg, 1.0 mmol) in THF (15 ml) was added 3-(furan-2-yl)benzoic acid (230 mg, 1.2 mmol), 3-(((ethylimino)methylene)amino)-N,N-dimethylpropan-1-amine hydrochloride (290 mg, 1.5 mmol), N,N-diisopropylethylamine (0.55 ml, 3.5 mmol), and N,N-dimethylpyridin-4-amine (12 mg, 0.10 mmol). The reaction stirred at room temperature overnight. The reaction was poured into dichloromethane and washed with saturated aqueous sodium bicarbonate solution and brine. The organic layer was dried over magnesium sulfate, filtered, and concentrated. The crude residue was purified by column chromatography eluting with 10-30% ethyl acetate in hexanes to give the title compound as a white solid (420 mg, 94%). $^1$H NMR (400 MHz, CDCl$_3$) (Rotamers) δ 9.65, 8.64, 7.74, 7.44, 7.23, 7.19, 7.09, 6.68, 6.47, 5.03, 4.04, 3.41, 3.16, 2.96, 2.52-2.23.

Preparation 12: tert-butyl 3-((4-chlorophenyl)carbamoyl)-5-methylenepiperidine-1-carboxylate

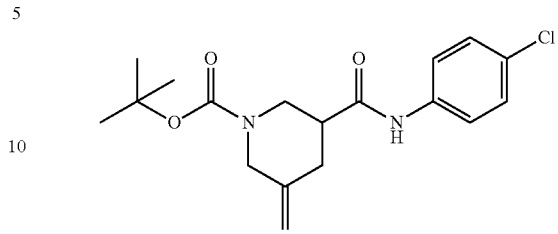

To a solution of methyltriphenylphosphonium bromide (250 mg, 0.71 mmol) in THF (2 ml) was added potassium tert-butoxide (80 mg, 0.71 mmol). After stirring at room temperature for 30 min, tert-butyl 3-((4-chlorophenyl)carbamoyl)-5-oxopiperidine-1-carboxylate (100 mg, 0.28 mmol) was added in one portion. The mixture stirred for 3 h. The reaction was poured into water and extracted with dichloromethane. The organic layer was washed with brine, dried over magnesium sulfate, filtered, and concentrated. The crude residue was purified by column chromatography eluting with 10-20% ethyl acetate in hexanes to give the title compound as a colorless oil which solidified upon standing (69 mg, 69%).

Preparation 13: N-(4-chlorophenyl)-5-methylenepiperidine-3-carboxamide trifluoroacetate

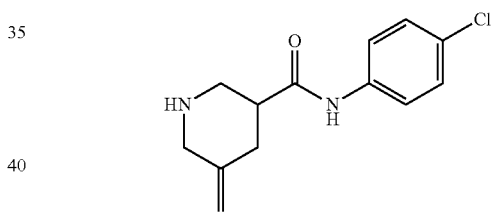

To a solution of tert-butyl 3-((4-chlorophenyl)carbamoyl)-5-methylenepiperidine-1-carboxylate (69 mg, 0.20 mmol) in dichloromethane (5 ml) was added trifluoroacetic acid (1 ml, 13 mmol). The reaction stirred at room temperature for 1 h. The reaction mixture was concentrated to give a colorless oil which was used in the next step without further purification (49 mg, 68%).

Example 20: N-(4-chlorophenyl)-1-(3-(furan-2-yl)benzoyl)-5-methylenepiperidine-3-carboxamide

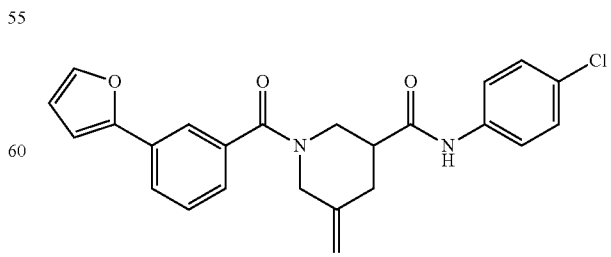

To a solution of N-(4-chlorophenyl)-5-methylenepiperidine-3-carboxamide trifluoroacetate (49 mg, 0.20 mmol) in THF (3 ml) was added 3-(furan-2-yl)benzoic acid (55 mg, 0.30 mmol), N,N-diisopropylethylamine (0.14 ml, 0.79 mmol), 3-(((ethylimino)methylene)amino)-N,N-dimethylpropan-1-amine hydrochloride (57 mg, 0.30 mmol), and N,N-dimethylpyridin-4-amine (2.4 mg, 0.020 mmol). The reaction stirred at room temperature for 3 h. The reaction was poured into ethyl acetate and washed with aqueous saturated sodium bicarbonate solution, followed by brine. The organic layer was dried over magnesium sulfate, filtered and concentrated. The crude residue was purified by column chromatography eluting with 20-40% ethyl acetate in hexanes to give the title compound as an amorphous solid (34 mg, 41%). $^1$H NMR (400 MHz, CDCl$_3$)(Rotamers) δ 9.47, 8.37, 7.72, 7.67, 7.57, 7.45, 7.40, 7.24, 7.08, 4.96, 4.77, 4.66, 4.48, 4.09, 3.92, 3.78, 3.62, 2.76, 2.62, 2.43.

Preparation 14: tert-butyl 5-((4-chlorophenyl)carbamoyl)-3,3-dimethoxypiperidine-1-carboxylate

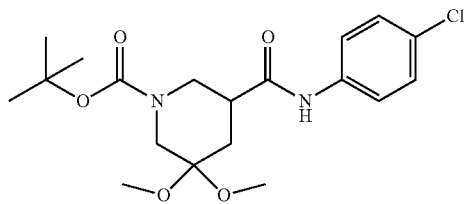 [SMILES: COC1(OC)CC(C(=O)Nc2ccc(Cl)cc2)CN(C(=O)OC(C)(C)C)C1]

To a solution of tert-butyl 3-((4-chlorophenyl)carbamoyl)-5-oxopiperidine-1-carboxylate (840 mg, 2.4 mmol) in methanol (15 ml) was added trimethyl orthoformate (3.9 ml, 36 mmol) followed by p-toluenesulfonic acid (380 mg, 2.2 mmol). The reaction stirred at room temperature for 3 h. The reaction was poured into dichloromethane and washed with aqueous sodium bicarbonate solution. The organic layer was washed with brine, dried over magnesium sulfate, filtered, and concentrated. The crude residue was purified by column chromatography eluting with 10-30% ethyl acetate in hexanes to afford the title compound (310 mg, 33%).

Preparation 15: N-(4-chlorophenyl)-5,5-dimethoxypiperidine-3-carboxamide

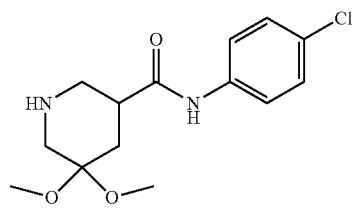 [SMILES: COC1(OC)CNCC(C(=O)Nc2ccc(Cl)cc2)C1]

To a solution of tert-butyl 5-((4-chlorophenyl)carbamoyl)-3,3-dimethoxypiperidine-1-carboxylate (310 mg, 0.78 mmol) in dichloromethane (6 ml) was added trifluoroacetic acid (1.0 ml, 13 mmol). The reaction stirred at room temperature for 3.5 h. The reaction was concentrated, dissolved in dichloromethane and washed with saturated sodium bicarbonate solution and brine. The organic layer was dried over magnesium sulfate, filtered, and concentrated. The product was introduced into subsequent reactions without purification (yield=120 mg, 53%).

Example 21: N-(4-chlorophenyl)-1-(3-(furan-2-yl)benzoyl)-5,5-dimethoxypiperidine-3-carboxamide

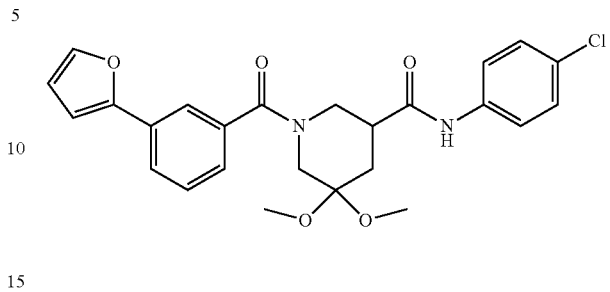

To a solution of N-(4-chlorophenyl)-5,5-dimethoxypiperidine-3-carboxamide (120 mg, 0.41 mmol) in THF (5 ml) was added 3-(furan-2-yl)benzoic acid (93 mg, 0.49 mmol), N,N-diisopropylethylamine (0.25 ml, 1.4 mmol), 3-(((ethylimino)methylene)amino)-N,N-dimethylpropan-1-amine hydrochloride (120 mg, 0.62 mmol), and N,N-dimethylpyridin-4-amine (5.0 mg, 0.041 mmol). The reaction stirred at room temperature overnight. The reaction mixture was poured into dichloromethane and washed with saturated aqueous sodium bicarbonate solution and brine. The organic layer was dried over magnesium sulfate, filtered, and concentrated. The crude residue was purified by column chromatography eluting with 30% ethyl acetate in hexanes to afford the title compound (50 mg, 26%). $^1$H NMR (400 MHz, CDCl$_3$) (Rotamers) δ 9.44, 8.47, 7.80, 7.75-7.62, 7.58, 7.47-7.35, 7.23, 7.13, 6.67, 6.47, 4.65, 4.40, 3.88, 3.75, 3.59, 3.26, 3.01, 2.94, 2.84, 2.49, 2.35-2.10.

Example 22: N-(4-chlorophenyl)-1-(3-(thiophen-2-yl)benzoyl)piperidine-3-carboxamide

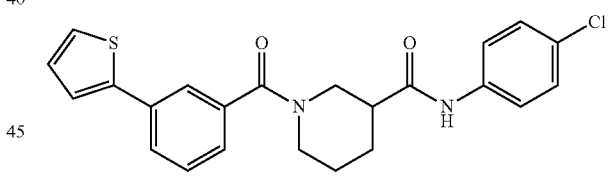

To a solution of N-(4-chlorophenyl)piperidine-3-carboxamide (57 mg, 0.24 mmol) in tetrahydrofuran (2 ml) was added 3-(thiophen-2-yl)benzoic acid (60 mg, 0.29 mmol) followed by N,N-diisopropylethylamine (0.064 ml, 0.37 mmol), 3-(((ethylimino)methylene)amino)-N,N-dimethylpropan-1-amine hydrochloride (70 mg, 0.37 mmol), and N,N-dimethylpyridin-4-amine (3.0 mg, 0.024 mmol). The reaction stirred at room temperature overnight. The reaction was poured into dichloromethane and washed with saturated aqueous sodium bicarbonate solution and brine. The organic layer was dried over magnesium sulfate, filtered, and concentrated. The crude residue was purified by column chromatography eluting with 40-60% ethyl acetate in hexanes to afford the title compound as an amorphous white solid (90 mg, 87%). $^1$H NMR (400 MHz, CDCl$_3$)(Rotamers) δ 9.25, 8.12, 7.64, 7.41, 7.24, 7.08, 4.60, 4.16, 3.95, 3.55, 3.43, 2.88, 2.68, 2.49, 2.23, 1.92, 1.60, 1.51.

Example 23: N-(4-chlorophenyl)-1-{[5-(furan-2-yl)pyridin-3-yl]carbonyl}piperidine-3-carboxamide

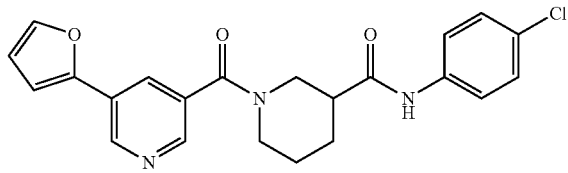 [SMILES: O=C(Nc1ccc(Cl)cc1)C1CCCN(C(=O)c2cncc(-c3ccco3)c2)C1]

To a solution of N-(4-chlorophenyl)piperidine-3-carboxamide trifluoroacetate (86 mg, 0.24 mmol) in THF (3 ml) was added 5-(furan-2-yl)nicotinic acid (46 mg, 0.24 mmol) followed by N,N-diisopropylethylamine (0.13 ml, 0.73 mmol), 3-(((ethylimino)methylene)amino)-N,N-dimethylpropan-1-amine hydrochloride (70 mg, 0.37 mmol), and N,N-dimethylpyridin-4-amine (3.0 mg, 0.024 mmol). The reaction stirred overnight at room temperature. The reaction was poured into ethyl acetate and washed with saturated sodium bicarbonate solution followed by brine. The organic layer was dried over magnesium sulfate, filtered, and concentrated. The crude residue was purified by column chromatography eluting with 0-100% ethyl acetate in hexanes to give the title compound as a clear film (51 mg, 51%). $^1$H NMR (400 MHz, DMSO-d6 at 50° C.) δ 9.96, 8.97, 8.47, 8.01, 7.82, 7.51, 7.27, 7.14, 6.63, 3.17, 3.14, 2.57, 2.00, 1.76, 1.50.

Example 24: N-(4-chlorophenyl)-1-{[4-(furan-2-yl)pyridin-2-yl]carbonyl}piperidine-3-carboxamide

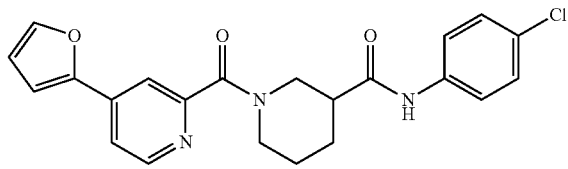

To 4-(furan-2-yl)picolinic acid (66 mg, 0.345 mmol) in THF (1 mL) was added a solution of N-(4-chlorophenyl)piperidine-3-carboxamide trifluoroacetate (150 mg, 0.42 mmol) in THF (2 mL). To this mixture was added N,N-diisopropylethylamine (0.18 ml, 1.0 mmol), 3-(((ethylimino)methylene)amino)-N,N-dimethylpropan-1-amine hydrochloride (100 mg, 0.52 mmol), and N,N-dimethylpyridin-4-amine (4.3 mg, 0.035 mmol). The reaction stirred at room temperature overnight. The reaction was poured into dichloromethane and washed with saturated aqueous sodium bicarbonate and brine. The organic layer was dried over magnesium sulfate, filtered, and concentrated. The crude residue was purified by column chromatography eluting with 60-80% ethyl acetate in hexanes to give the title compound as a white amorphous solid (26 mg, 18%). $^1$H NMR (400 MHz, CDCl$_3$) (Rotamers) δ 9.88, 9.25, 8.50, 7.94, 7.77, 7.54, 7.22, 6.90, 6.53, 4.40, 3.70, 3.40, 2.71, 2.35-1.60.

Example 25: N-(4-chlorophenyl)-5,5-difluoro-1-{[4-(furan-2-yl)pyridin-2-yl]carbonyl}piperidine-3-carboxamide

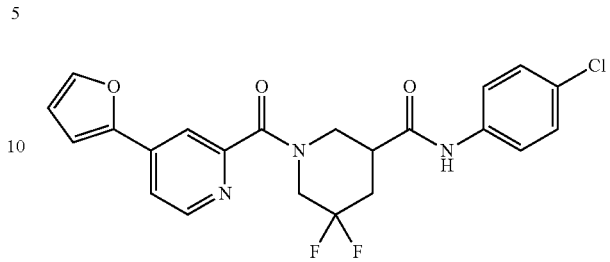

To a solution of N-(4-chlorophenyl)-5,5-difluoropiperidine-3-carboxamide (35 mg, 0.13 mmol) in tetrahydrofuran (2 ml) was added 4-(furan-2-yl)picolinic acid (29 mg, 0.15 mmol), N,N-diisopropylethylamine (0.045 ml, 0.25 mmol), 3-(((ethylimino)methylene)amino)-N,N-dimethylpropan-1-amine hydrochloride (37 mg, 0.19 mmol), and N,N-dimethylpyridin-4-amine (3.1 mg, 0.025 mmol). After stirring at room temperature for five hours, an additional 100 μL of N,N-diisopropylethylamine, 36 mg of 3-(((ethylimino)methylene)amino)-N,N-dimethylpropan-1-amine hydrochloride, and 28 mg of 4-(furan-2-yl)picolinic acid was added. The reaction mixture stirred overnight. The reaction mixture was diluted with dichloromethane and washed with saturated aqueous sodium bicarbonate solution and brine. The organic layer was dried over magnesium sulfate, filtered and concentrated. The crude residue was purified by column chromatography eluting with 40-70% ethyl acetate in hexanes to give 22 mg of the title compound. Dichloromethane was then added to the product, and the solid which precipitated out was dried under vacuum to give the title compound in greater purity (5.4 mg, 10%). $^1$H NMR (400 MHz, CDCl$_3$) δ 9.20, 8.73, 8.56, 8.00, 7.74-7.47, 7.30, 6.95, 6.56, 4.55, 4.32, 3.99, 3.77, 3.50, 3.05, 2.80-2.50, 2.39.

Example 26: N-(4-chlorophenyl)-5,5-difluoro-1-{[5-(furan-2-yl)pyridin-3-yl]carbonyl}piperidine-3-carboxamide

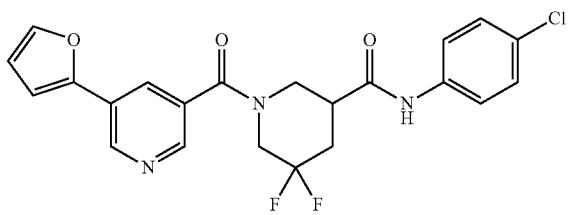 [SMILES: O=C(Nc1ccc(Cl)cc1)C1CN(C(=O)c2cncc(-c3ccco3)c2)CC(F)(F)C1]

To a solution of N-(4-chlorophenyl)-5,5-difluoropiperidine-3-carboxamide (35 mg, 0.13 mmol) in tetrahydrofuran (2 ml) was added 5-(furan-2-yl)nicotinic acid (29 mg, 0.15 mmol), N,N-diisopropylethylamine (0.045 ml, 0.25 mmol), 3-(((ethylimino)methylene)amino)-N,N-dimethylpropan-1-amine hydrochloride (37 mg, 0.19 mmol), and N,N-dimethylpyridin-4-amine (3.1 mg, 0.025 mmol). The reaction stirred at room temperature for 5 h. The reaction mixture was poured into dichloromethane and washed with saturated aqueous sodium bicarbonate solution and brine. The organic layer was dried over magnesium sulfate, filtered, and concentrated. The crude residue was purified by column chromatography eluting with 40-70% ethyl acetate in hexanes to afford the title compound as a white solid (48 mg, 84%). $^1$H NMR (400 MHz, CDCl$_3$) δ 9.21, 8.98, 8.53, 7.98, 7.52, 7.47, 7.23, 6.81, 6.51, 5.01, 4.81, 3.96, 3.48, 3.22, 2.98, 2.52, 2.41.

Preparation 16: 1-(tert-butoxycarbonyl)-5-((tert-butyldimethylsilyl)oxy)piperidine-3-carboxylic acid

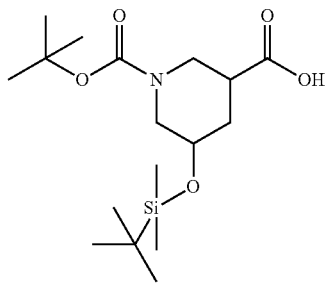 [SMILES: CC(C)(C)OC(=O)N1CC(O[Si](C)(C)C(C)(C)C)CC(C(=O)O)C1]

To a suspension of 1-(tert-butoxycarbonyl)-5-hydroxypiperidine-3-carboxylic acid (2.5 g, 10 mmol) in dichloromethane (50 ml) was added imidazole (1.5 g, 22 mmol) followed by tertbutyldimethylsilyl chloride (3.4 g, 22 mmol). The reaction stirred at room temperature overnight. The reaction was poured into dichloromethane and washed with 1N HCl and extracted with dichloromethane. The organic layer was dried over magnesium sulfate, filtered, and concentrated. The residue was dissolved in methanol (20 ml) and tetrahydrofuran (20 ml). 1M aqueous lithium hydroxide (10 ml, 10 mmol) was added. The reaction stirred at room temperature overnight. The reaction was poured into dichloromethane, and acidified with 1 N HCl. The organic layer was dried over magnesium sulfate, filtered and concentrated. The crude residue was purified by column chromatography eluting with 0-5% methanol in dichloromethane to afford the title compound as a white amorphous solid (2.6 g, 72%).

Preparation 17: tert-butyl 3-((tert-butyldimethylsilyl)oxy)-5-((4-chlorophenyl)carbamoyl)piperidine-1-carboxylate

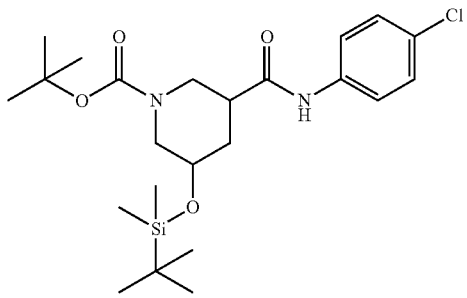 [SMILES: CC(C)(C)OC(=O)N1CC(O[Si](C)(C)C(C)(C)C)CC(C(=O)Nc2ccc(Cl)cc2)C1]

To a solution of 1-(tert-butoxycarbonyl)-5-((tert-butyldimethylsilyl)oxy)piperidine-3-carboxylic acid (1.0 g, 2.9 mmol) in tetrahydrofuran (14 ml) was added 4-chloroaniline (0.37 g, 2.9 mmol), N,N-diisopropylethylamine (1.5 ml, 8.8 mmol), 3-(((ethylimino)methylene)amino)-N,N-dimethylpropan-1-amine hydrochloride (0.84 g, 4.4 mmol) and N,N-dimethylpyridin-4-amine (0.071 g, 0.58 mmol). The reaction stirred at room temperature overnight. The reaction mixture was diluted with ethyl acetate and washed with 1N aqueous HCl, saturated sodium bicarbonate solution and brine. The organic layer was dried over magnesium sulfate, filtered and concentrated. The crude residue was purified by column chromatography eluting with 10-30% ethyl acetate in hexanes to afford the title compound as an amorphous solid (832 mg, 63%).

Preparation 18: 5-((tert-butyldimethylsilyl)oxy)-N-(4-chlorophenyl)piperidine-3-carboxamide

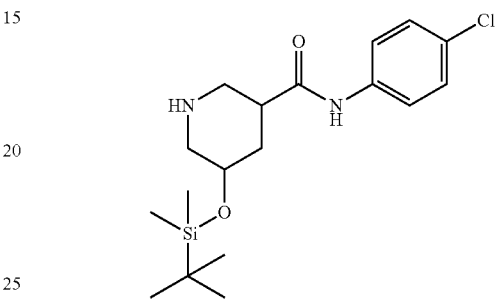

To a solution of tert-butyl 3-((tert-butyldimethylsilyl)oxy)-5-((4-chlorophenyl)carbamoyl)piperidine-1-carboxylate (33 mg, 0.070 mmol) in dichloromethane (1 ml) at 0° C. was added 2,6-lutidine (0.025 ml, 0.21 mmol) followed by trimethylsilyl trifluoromethanesulfonate (0.025 ml, 0.14 mmol). After 30 min, another 50 μL of trimethylsilyl trifluoromethanesulfonate was added. After 10 min, the reaction mixture was poured into dichloromethane and washed with saturated aqueous sodium bicarbonate and brine. The organic layer was dried over magnesium sulfate, filtered and concentrated. The crude residue was purified by column chromatography eluting with 5-10% methanol in dichloromethane to afford the title compound as a clear film (16 mg, 61%).

Preparation 19: 5-((tert-butyldimethylsilyl)oxy)-N-(4-chlorophenyl)-1-(3-(furan-2-yl)benzoyl)piperidine-3-carboxamide

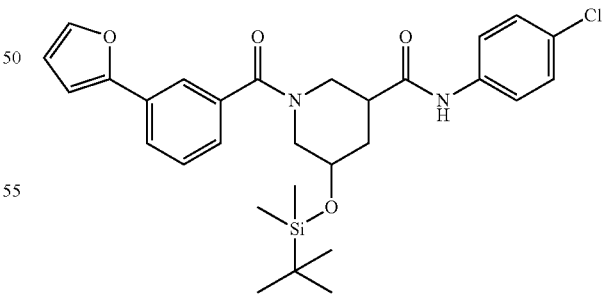

To a solution of 5-((tert-butyldimethylsilyl)oxy)-N-(4-chlorophenyl)piperidine-3-carboxamide (22 mg, 0.060 mmol) in tetrahydrofuran (1.5 ml) was added 3-(furan-2-yl) benzoic acid (13 mg, 0.072 mmol), N,N-diisopropylethylamine (0.021 ml, 0.12 mmol), 3-(((ethylimino)methylene) amino)-N,N-dimethylpropan-1-amine hydrochloride (17 mg, 0.089 mmol) and N,N-dimethylpyridin-4-amine (1.0 mg, 8.2 µmol). The reaction stirred at room temperature overnight. The reaction mixture was poured into water and extracted with dichloromethane. The organic layer was dried over magnesium sulfate, filtered, and concentrated. The crude residue was purified by column chromatography eluting with 10-30% ethyl acetate in hexanes to give the title compound (28 mg, 87%).

Example 27: N-(4-chlorophenyl)-1-(3-(furan-2-yl)benzoyl)-5-hydroxypiperidine-3-carboxamide

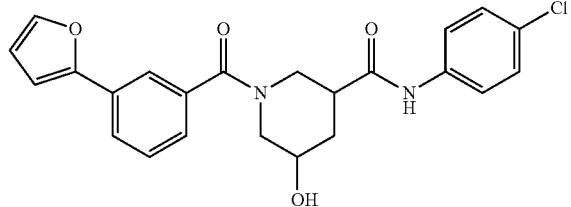 [SMILES: O=C(Nc1ccc(Cl)cc1)C1CC(O)CN(C(=O)c2cccc(-c3ccco3)c2)C1]

To a solution of 5-((tert-butyldimethylsilyl)oxy)-N-(4-chlorophenyl)-1-(3-(furan-2-yl)benzoyl)piperidine-3-carboxamide (28 mg, 0.052 mmol) in tetrahydrofuran (1 ml) was added tetrabutylammonium fluoride (1M in tetrahydrofuran) (0.078 ml, 0.078 mmol). The reaction stirred at room temperature for 1 h. The reaction was concentrated. The crude residue was purified by column chromatography eluting with 50-70% ethyl acetate in hexanes to afford the title compound as a mixture of diastereomers (19 mg, 85%). $^1$H NMR (400 MHz, CDCl$_3$) δ 9.20, 8.57, 7.75, 7.62, 7.44, 7.39, 7.34-7.20, 7.11, 6.64, 6.44, 4.83, 4.59, 4.26, 4.01, 3.82, 3.41, 3.28, 3.18, 3.00, 2.23, 2.10-1.93.

Preparation 20: t-Butyl 3-((4-chlorophenyl)carbamoyl)-3-methylpiperidine-1-carboxylate

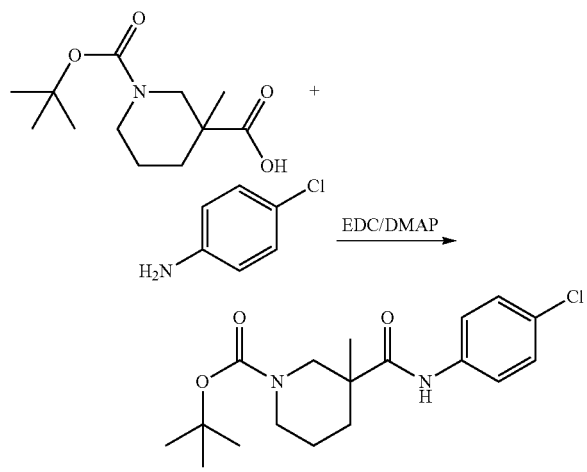

To the solution of carboxylic acid (0.5 g, 2.06 mmole), DMAP (25 mg, 0.20) and 4-chloroaniline (0.26 g) in DCM (20 mL) was added EDC (0.43 g). The reaction mixture was stirred under N$_2$ for 48 h. The reaction mixture was extracted with saturated NaHCO$_3$ (10 mL), 10% KHSO$_4$ (10 mL) and water (2×10 mL). The solution was dried (NaSO$_4$) and the solvent was removed under reduced pressure to give the product (0.61 g, 84%) in good purity for further transformation.

Preparation 21: N-(4-Chlorophenyl)-3-methylpiperidine-3-carboxamide

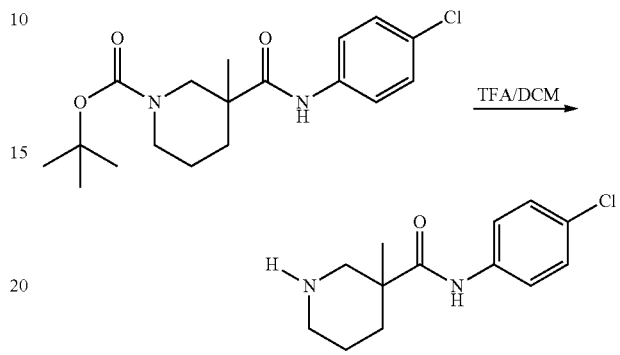

To a solution of the amide (0.52 g, 1.47 mmole) in DCM (10 mL) was added TFA (1 mL). The reaction mixture was stirred at the room temperature for 3 h. TLC indicated completion of reaction. The solvent was washed with H$_2$O (10 mL), 2M Na$_2$CO$_3$ (2×10 mL), H$_2$O (10 mL), dried (Na$_2$SO$_4$) and the solvent was removed under reduced pressure to give the free amine (0.2 g, 54%).

Example 28: N-(4-Chlorophenyl)-1-(3-(furan-2-yl)benzoyl)-3-methylpiperidine-3-carboxamide

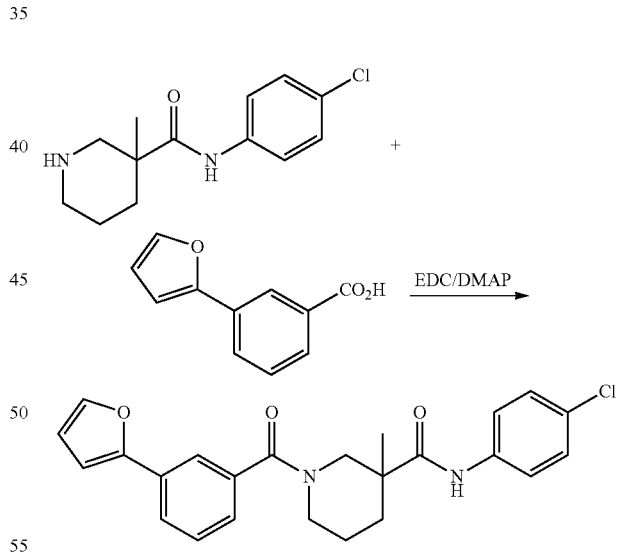

To the solution of carboxylic acid (0.045 g, 0.237 mmole), DMAP (6 mg, 0.047 mmole) and piperidine derivative (0.06 g, 0.237 mmole) in DCM (3 mL) was added EDC (0.05 g, 0.261 mmole). The reaction mixture was stirred at room temperature for 5 h. TLC indicated disappearance of the starting materials. The reaction mixture was extracted with saturated NaHCO$_3$ (2 mL), 10% KHSO$_4$ (1 mL) and H$_2$O (2×2 mL). The solution was dried (NaSO$_4$) and the solvent was removed under reduced pressure to give the crude product. The crude product was purified by column chromatography eluting with 20-45% EtOAc/hexanes over 350 mL. Fractions were pooled after checking TLC. The solvent was removed under reduced pressure to give the title compound (0.09 g, 90%). ¹H NMR (500 MHz, CDCl₃) δ 9.60, 7.82-7.71, 7.61, 7.51-7.46, 7.45-7.39, 7.35-7.28, 7.23-7.17, 6.65, 6.49, 5.12, 3.91-3.80, 3.24-3.11, 2.85, 2.73-2.62, 1.67-1.53 & 1.43-1.31.

Example 29: N-(4-Chlorophenyl)-1-(3-(5-methyl-furan-2-yl)benzoyl)piperidine-3-carboxamide

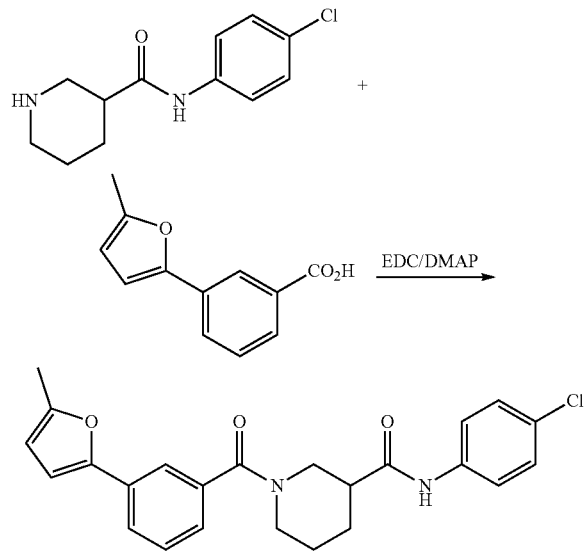

To a solution of carboxylic acid (0.085 g, 0.42 mmole), DMAP (10 mg, 0.084 mmole) and piperidine derivative (0.1 g, 0.42 mmole) in DCM (5 mL) was added EDC (0.088 g, 0.46 mmole). The reaction mixture was stirred under N₂ for 4 h. TLC indicated disappearance of the starting materials. The reaction mixture was extracted with saturated NaHCO₃ (2 mL), 10% KHSO₄ (1 mL) and water (2×2 mL). The separated organic portion was dried (NaSO₄) and the solvent was removed under reduced pressure to give the product. The crude compound was purified by column chromatography eluting with 40-65% EtOAc/hexanes over 350 mL. Fractions were pooled after checking TLC. The solvent was removed under reduced pressure to give the compound (0.14 g, 79%) in pure form. ¹H NMR (400 MHz, (CD₃)₂SO, 70° C.) δ 9.91, 7.67, 7.61-7.54, 7.43, 7.30, 7.23-7.19, 6.83, 6.19, 3.10-3.02, 2.65-2.50, 2.34, 2.05-1.97, 1.81-1.71 & 1.52-1.39.

Example 30: 1-(3-(1H-Pyrazol-1-yl)benzoyl)-N-(4-chlorophenyl)piperidine-3-carboxamide

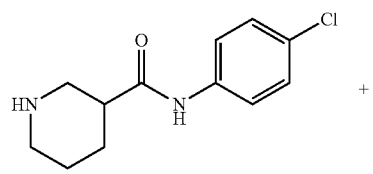

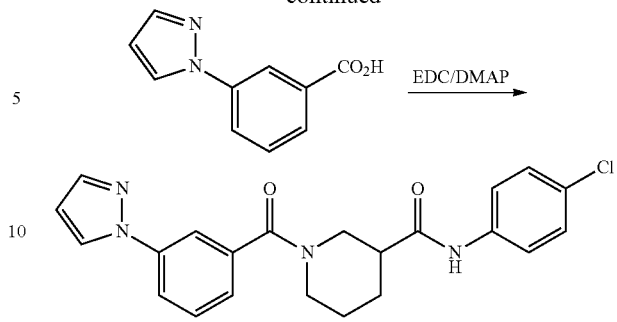

To a solution of carboxylic acid (0.079 g, 0.42 mmole), DMAP (10 mg, 0.084 mmole) and piperidine derivative (0.1 g, 0.42 mmole) in DCM (5 mL) was added EDC (0.088 g, 0.46 mmole). The reaction mixture was stirred under N₂ for 4 h. TLC indicated disappearance of the starting materials. The reaction mixture was extracted with saturated NaHCO₃ (2 mL), 10% KHSO₄ (1 mL) and water (2 mL). The separated organic portion was dried (NaSO₄) and the solvent was removed under reduced pressure to give the product. The crude compound was purified by column chromatography eluting with 50-80% EtOAc/hexanes over 400 mL. Fractions were pooled after checking TLC. The solvent was removed under reduced pressure to give the compound (0.145 g, 85%) in pure form. ¹H NMR (400 MHz, (CD₃)₂SO, 70° C.) δ 9.91, 8.47, 7.89, 7.84-7.81, 7.74, 7.61-7.50, 7.33-7.26, 6.53, 3.12-3.01, 4.47-3.49, 3.24-3.15, 2.63-2.53, 2.07-1.97, 1.83-1.71 & 1.55-1.42.

Example 31: 1-(3-(1H-Pyrazol-4-yl)benzoyl)-N-(4-chlorophenyl)piperidine-3-carboxamide

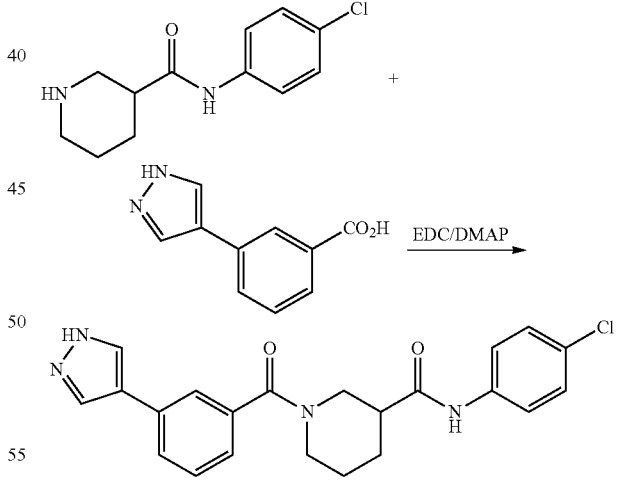

To a solution of carboxylic acid (0.047 g, 0.25 mmole), DMAP (6 mg, 0.05 mmole) and piperidine derivative (0.06 g, 0.25 mmole) in DCM (3 mL) was added EDC (0.053 g, 0.28 mmole). The reaction mixture was stirred under N₂ for 4 h. TLC indicated disappearance of the starting materials. The reaction mixture was extracted with saturated NaHCO₃ (2 mL), 10% KHSO₄ (1 mL) and water (2×2 mL). The solution was dried (NaSO₄) and the solvent was removed under reduced pressure to give the product. The crude compound was purified by column chromatography eluting with 60-100% EtOAc/hexanes over 500 mL. Fractions were pooled after checking TLC. The solvent was removed under reduced pressure to give the title compound (0.069 g, 67%) in pure form. $^1$H NMR (400 MHz, CDCl$_3$, 56° C.) δ 9.07, 7.82, 7.64-7.54, 7.49, 7.40, 7.27-7.19, 4.19-3.27, 2.68, 2.25, 1.95 & 1.71-1.43.

Example 32: 1-(3-(1H-Pyrazol-3-yl)benzoyl)-N-(4-chlorophenyl)piperidine-3-carboxamide To a solution of carboxylic acid (0.047 g, 0.25 mmole), DMAP (6 mg, 0.05 mmole) and piperidine derivative (0.06 g, 0.25 mmole) in DCM (3 mL) was added EDC (0.053 g, 0.28 mmole). The reaction mixture was stirred under N$_2$ for 4 h. TLC indicated disappearance of the starting materials. The reaction mixture was extracted with satd. NaHCO$_3$ (2 mL), 10% KHSO$_4$ (1 mL) and water (2×2 mL). The solution was dried (NaSO$_4$) and the solvent was removed under reduced pressure to give the product. The crude compound was purified by column chromatography eluting with 70-100% EtOAc/hexanes over 400 mL. Fractions were pooled after checking TLC. The solvent was removed under reduced pressure to give the title compound (0.078 g, 76%) in pure form. $^1$H NMR (400 MHz, CDCl$_3$, 55° C.) δ 9.17, 7.89, 7.79, 7.67-7.58, 7.46-7.28, 7.24-7.15, 6.60, 4.27-4.03, 3.69, 2.63, 2.27-2.04, 1.72-1.55, 1.95-1.85 & 1.48-1.40.
General Procedure for Amide Coupling to Piperidines

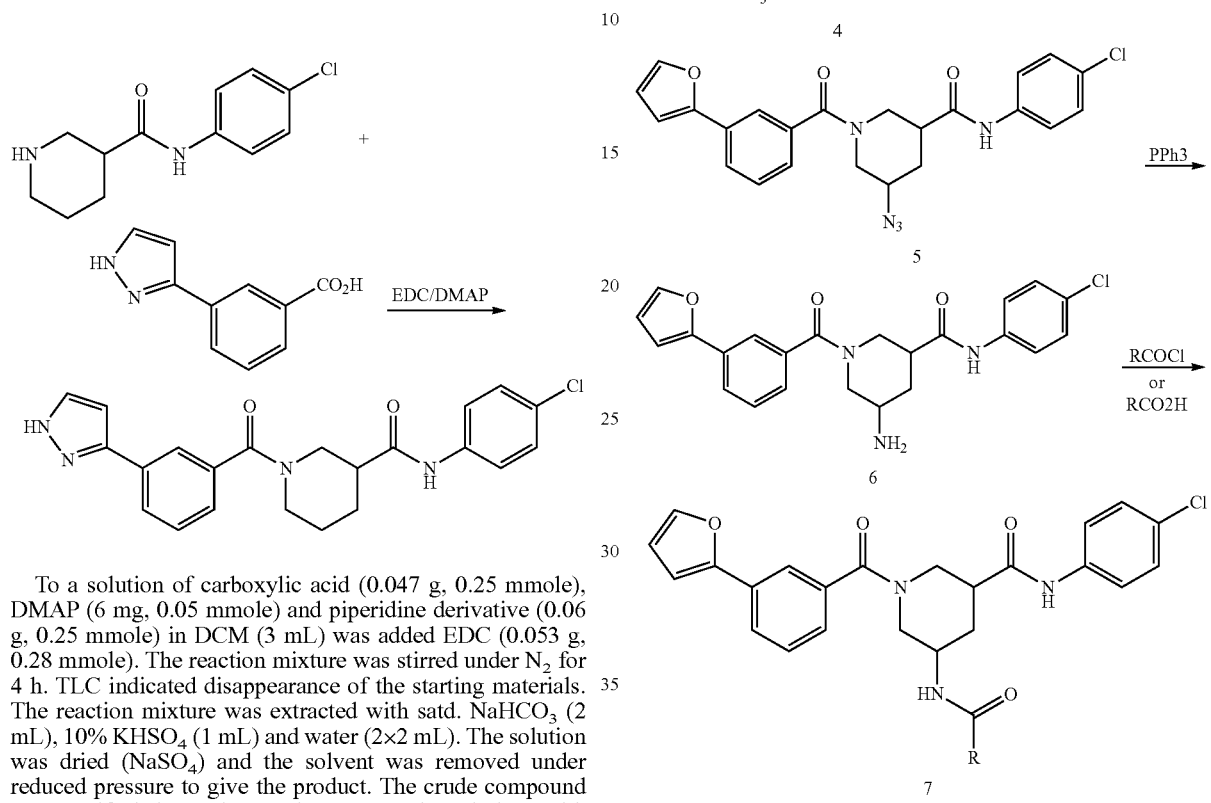

Example 33: N-(4-chlorophenyl)-1-(6-methoxy-1H-benzo[d]imidazole-2-carbonyl)piperidine-3-carboxamide

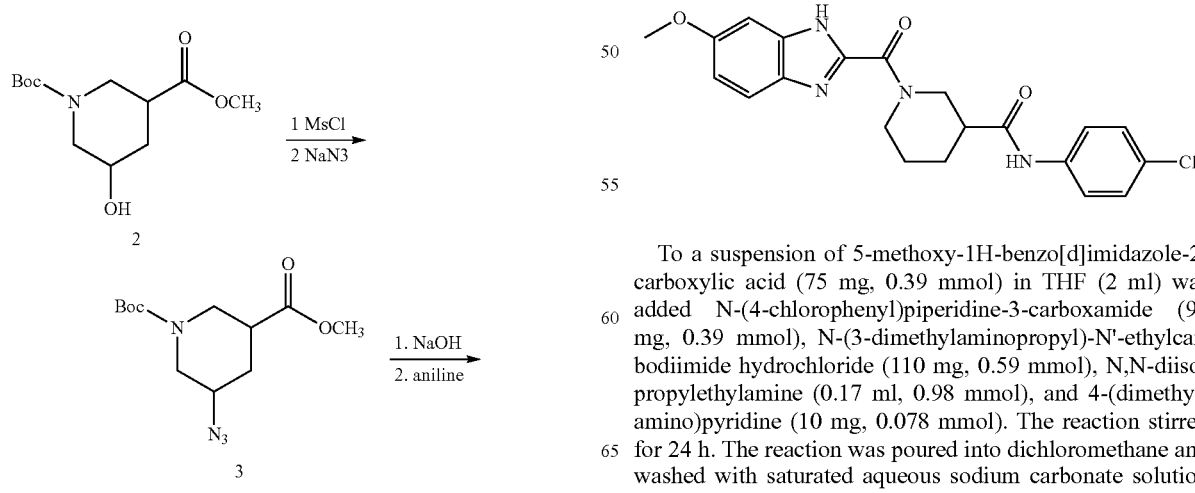

To a suspension of 5-methoxy-1H-benzo[d]imidazole-2-carboxylic acid (75 mg, 0.39 mmol) in THF (2 ml) was added N-(4-chlorophenyl)piperidine-3-carboxamide (93 mg, 0.39 mmol), N-(3-dimethylaminopropyl)-N'-ethylcarbodiimide hydrochloride (110 mg, 0.59 mmol), N,N-diisopropylethylamine (0.17 ml, 0.98 mmol), and 4-(dimethylamino)pyridine (10 mg, 0.078 mmol). The reaction stirred for 24 h. The reaction was poured into dichloromethane and washed with saturated aqueous sodium carbonate solution and brine. The organic layer was dried over magnesium sulfate, filtered and concentrated. The crude residue was purified by column chromatography eluting with 40-100% ethyl acetate in hexanes to afford the title compound as a white solid (38 mg, yield 23%). $^1$H NMR (400 MHz, DMSO-d6)(Rotamers) δ 12.95, 10.20, 10.14, 7.60, 7.34, 6.93, 5.56, 4.60, 4.38, 3.78, 3.76, 3.60, 3.27, 3.01, 2.61, 2.03, 1.85, 1.75, 1.53.

Example 34: N-(4-chlorophenyl)-1-(6-(furan-2-yl) pyrimidine-4-carbonyl)piperidine-3-carboxamide

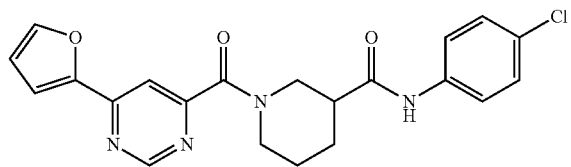

The above compound was prepared by following the general procedure for amide coupling described in Example 33 (23 mg, yield 22%). $^1$H NMR (400 MHz, DMSO-d6, 100° C.) δ 9.67, 9.11, 7.91, 7.75, 7.54, 7.40, 7.27, 6.71, 4.43 br, 3.82 br, 3.17, 2.64, 2.03, 1.81, 1.56.

Preparation 22: methyl 1-methyl-1H-benzo[d]imidazole-2-carboxylate

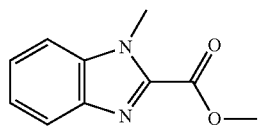

To a suspension of 1H-benzo[d]imidazole-2-carboxylic acid (240 mg, 1.5 mmol) in DMF (7 ml) was added sodium hydride (60% dispersion in mineral oil) (130 mg, 3.7 mmol). The reaction stirred at room temperature for 30 min. Methyl iodide (0.46 ml, 7.3 mmol) was added. After 4 h at room temperature, the reaction was quenched with saturated ammonium chloride. The aqueous layer was extracted with 50% ethyl acetate in hexanes. The organic layer was dried over magnesium sulfate, filtered, and concentrated. The crude residue was purified by column chromatography eluting with 20-100% ethyl acetate in hexanes to give the title compound as a white powder (109 mg, 39%).

Preparation 23: 1-methyl-1H-benzo[d]imidazole-2-carboxylic acid

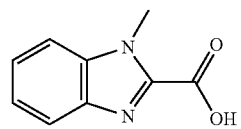

To methyl 1-methyl-1H-benzo[d]imidazole-2-carboxylate (110 mg, 0.56 mmol) in water (1.0 ml) and methanol (1 ml) was added sodium hydroxide (44 mg, 1.1 mmol). The reaction mixture was heated at 50° C. and stirred for 2 h. The reaction was concentrated to remove methanol, and 15 mL of water was added. The reaction mixture was acidified to pH 2, cooled over ice, and the resulting white solid was filtered. The filtrate was concentrated to approx 2 mL, and cooled again over ice. White solid was filtered. The combined solids were dried on vacuum overnight to give the title compound as of a white fluffy solid (48 mg, 49%).

Example 35: N-(4-chlorophenyl)-1-(1-methyl-1H-benzo[d]imidazole-2-carbonyl)piperidine-3-carboxamide

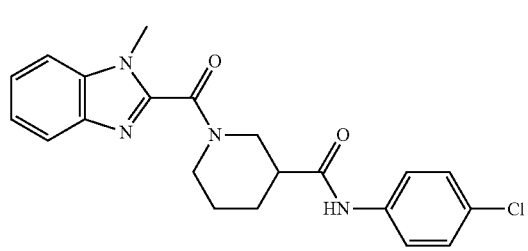 [SMILES: Cn1c(C(=O)N2CCCC(C(=O)Nc3ccc(Cl)cc3)C2)nc2ccccc21]

The above compound was prepared by following the general procedure for amide coupling described in Example 33 (6 mg, yield 6%). $^1$H NMR (400 MHz, CDCl$_3$) (rotamers) δ 10.39, 8.72, 7.69, 7.65, 7.43, 7.36, 7.24, 4.52, 4.02, 3.86, 3.65, 2.93, 2.45, 1.85, 1.78.

Example 36: 1-(2-bromothiazole-5-carbonyl)-N-(4-chlorophenyl)piperidine-3-carboxamide

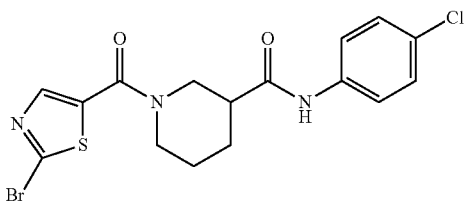 [SMILES: O=C(Nc1ccc(Cl)cc1)C1CCCN(C(=O)c2cnc(Br)s2)C1]

To a solution of N-(4-chlorophenyl)piperidine-3-carboxamide (110 mg, 0.44 mmol) in THF (3 ml) was added 4-bromothiazole-2-carboxylic acid (84 mg, 0.41 mmol), N-(3-dimethylaminopropyl)-N'-ethylcarbodiimide hydrochloride (120 mg, 0.61 mmol), N,N-diisopropylethylamine (0.18 ml, 1.0 mmol), and 4-(dimethylamino)pyridine (49 mg, 0.40 mmol). The reaction stirred at room temperature overnight. The reaction was poured into dichloromethane and washed with saturated aqueous sodium carbonate solution and brine. The organic layer was dried over magnesium sulfate, filtered, and concentrated. The crude reside was purified by column chromatography eluting with 50-100% ethyl acetate in hexanes to give the title compound as a white solid (80 mg, 46%). $^1$H NMR (400 MHz, DMSO-d6, 80° C.) δ 9.80, 8.02, 7.58, 7.30, 4.29, 4.07, 3.22, 3.09, 2.58, 2.02, 1.97, 1.78.

Example 37: N-(4-chlorophenyl)-1-(2-(furan-2-yl)thiazole-5-carbonyl)piperidine-3-carboxamide

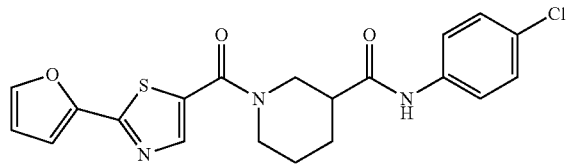 [SMILES: O=C(Nc1ccc(Cl)cc1)C1CCCN(C(=O)c2cnc(-c3ccco3)s2)C1]

To a solution 1-(2-bromothiazole-5-carbonyl)-N-(4-chlorophenyl)piperidine-3-carboxamide (48 mg, 0.11 mmol) in a mixture of 4:1 dioxane/water (3.7 mL) was added furan-2-ylboronic acid (14 mg, 0.12 mmol), cesium carbonate (160 mg, 0.50 mmol) followed by tetrakis(triphenylphosphine)palladium(0)(6.5 mg, 5.6 μmol). The reaction was heated to 80° C. and stirred for 48 h. The reaction was poured into water and extracted 3× with dichloromethane. The combined organic layers were dried over magnesium sulfate, filtered, and concentrated. The crude residue was purified by column chromatography eluting with 40-60% ethyl acetate in hexanes. Isolated the title compound as a white solid (37 mg, 62%). $^1$H NMR (400 MHz, DMSO-d6, 80° C.)(Rotamers) δ 9.79, 7.97, 7.81, 7.58, 7.30, 7.08, 6.66, 4.39, 4.18, 3.19, 3.09, 2.64, 2.04, 1.79, 1.54.

Example 38: N-(4-chlorophenyl)-1-(2-(furan-2-yl)thiazole-4-carbonyl)piperidine-3-carboxamide

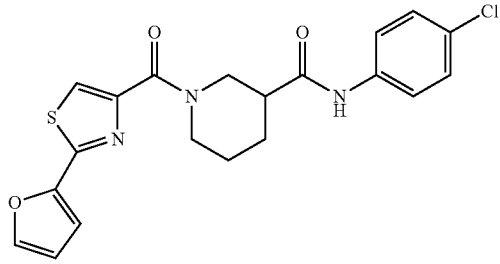 [SMILES: O=C(Nc1ccc(Cl)cc1)C1CCCN(C(=O)c2csc(-c3ccco3)n2)C1]

The above compound was prepared by following the general procedure for amide coupling described in Example 33 (72 mg, yield 82%). $^1$H NMR (400 MHz, DMSO-d6, 80° C.)(Rotamers) δ 9.80, 7.98, 7.81, 7.57, 7.30, 7.08, 6.66, 4.38, 4.17, 3.22, 3.08, 2.63, 2.02, 1.79, 1.53.

Example 39: N-(4-chlorophenyl)-1-(5-(furan-2-yl)isoxazole-3-carbonyl)piperidine-3-carboxamide

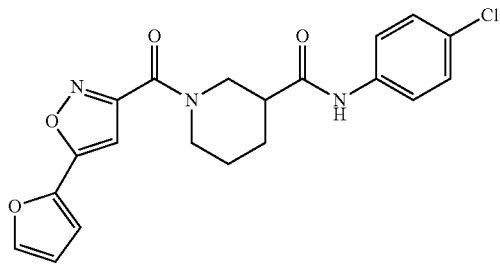 [SMILES: O=C(Nc1ccc(Cl)cc1)C1CCCN(C(=O)c2cc(-c3ccco3)on2)C1]

The above compound was prepared by following the general procedure for amide coupling described in Example 33 (46 mg, yield 59%). $^1$H NMR (400 MHz, DMSO-d6, 80° C.)(Rotamers) δ 9.80, 7.88, 7.57, 7.29, 7.13, 6.86, 6.70, 4.50, 4.16, 3.95, 3.50, 3.17, 2.61, 2.03, 1.81, 1.53.

Example 40: N-(4-chlorophenyl)-1-(5-(furan-2-yl)-1H-pyrazole-3-carbonyl)piperidine-3-carboxamide

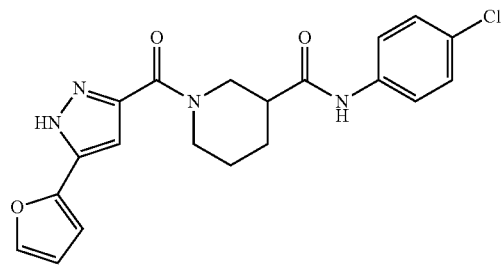 [SMILES: O=C(Nc1ccc(Cl)cc1)C1CCCN(C(=O)c2cc(-c3ccco3)[nH]n2)C1]

The above compound was prepared by following the general procedure for amide coupling described in Example 33 (45 mg, yield 49%). $^1$H NMR (400 MHz, DMSO-d6, 80° C.)(Rotamers) δ 13.39, 9.81, 7.68, 7.58, 7.30, 6.78, 6.73, 6.57, 4.50 br, 3.20, 2.59, 2.02, 1.79, 1.52.

Preparation 25: 3-fluoro-5-(pyridin-4-yl)benzoic acid

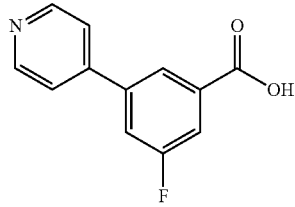 [SMILES: O=C(O)c1cc(F)cc(-c2ccncc2)c1]

To a solution of 3-bromo-5-fluorobenzoic acid (400 mg, 1.8 mmol) in ethanol (9 ml) was added pyridin-4-ylboronic acid (250 mg, 2.0 mmol) followed by potassium carbonate (760 mg, 5.5 mmol) and palladium(II) acetate (20 mg, 0.091 mmol). The reaction was degassed by bubbling a stream of nitrogen through it for 20 minutes. The reaction was heated at 80° C. for 8 h then cooled to room temperature. Acidified to pH 6 with 1N HCl, then washed 3× with dichloromethane. The aqueous layer was acidified again with 1N HCl until white solid crashed out. Solid was filtered and dried to give the title compound (186 mg, 47%).

Example 41: N-(4-chlorophenyl)-5,5-difluoro-1-(3-fluoro-5-(pyridin-4-yl)benzoyl)piperidine-3-carboxamide

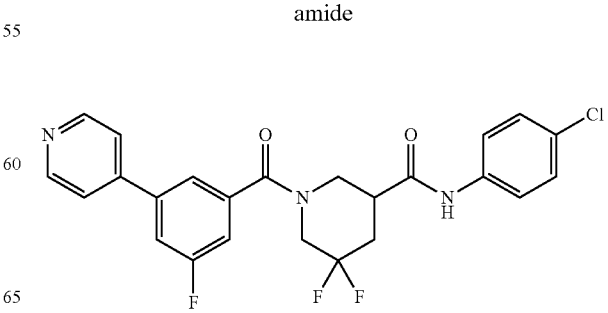

The above compound was prepared by following the general procedure for amide coupling described in Example 33 (60 mg, 46%). ¹H NMR (400 MHz, DMSO-d6, 80° C.)(Rotamers) δ 10.03, 8.66, 7.74, 7.71, 7.61, 7.57, 7.32, 4.23, 3.58, 3.26, 2.96, 2.33.

Preparation 26: 5-bromonicotinic acid

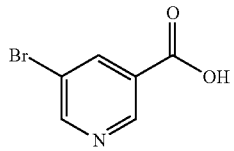

To a solution of methyl 5-bromonicotinate (500 mg, 2.3 mmol) in THF (5 ml) was added sodium hydroxide (1N aqueous solution) (5 ml, 2.3 mmol). The reaction stirred at room temperature for 10 min. The reaction was acidified to pH 6 with acetic acid, then extracted 3× with ethyl acetate. The combined organic layers were dried over magnesium sulfate, filtered, and concentrated to give the title compound as a white solid (153 mg, 33%).

Preparation 27: 1-(5-bromonicotinoyl)-N-(4-chlorophenyl)-5,5-difluoropiperidine-3-carboxamide

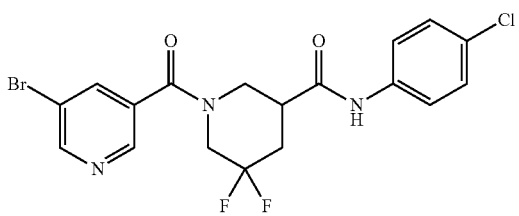 [SMILES: O=C(Nc1ccc(Cl)cc1)C1CN(C(=O)c2cncc(Br)c2)CC(F)(F)C1]

To a solution of N-(4-chlorophenyl)-5,5-difluoropiperidine-3-carboxamide (110 mg, 0.41 mmol) in THF (4 ml) was added 5-bromonicotinic acid (100 mg, 0.50 mmol), N-(3-dimethylaminopropyl)-N'-ethylcarbodiimide hydrochloride (120 mg, 0.62 mmol), N,N-diisopropylethylamine (0.14 ml, 0.83 mmol), and 4-(dimethylamino)pyridine (10 mg, 0.083 mmol). The reaction stirred at room temperature overnight. The reaction mixture was poured into ethyl acetate and washed with water. The organic layer was dried over magnesium sulfate, filtered, and concentrated. The crude residue was purified by column chromatography eluting with 20-50% ethyl acetate in hexanes to give the title compound as a clear film (168 mg, 89%).

Example 42: 1-([3,4'-bipyridine]-5-carbonyl)-N-(4-chlorophenyl)-5,5-difluoropiperidine-3-carboxamide

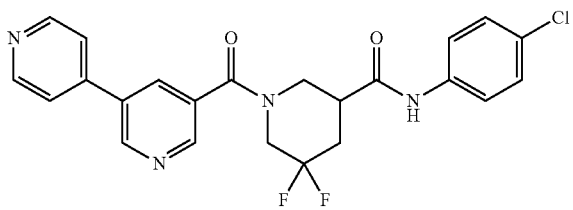 [SMILES: O=C(Nc1ccc(Cl)cc1)C1CN(C(=O)c2cncc(-c3ccncc3)c2)CC(F)(F)C1]

To a solution 1-(5-bromonicotinoyl)-N-(4-chlorophenyl)-5,5-difluoropiperidine-3-carboxamide (40 mg, 0.087 mmol) in a mixture of 4:1 dioxane/water (3.8 mL) was added pyridin-4-ylboronic (11 mg, 0.096 mmol) acid, and cesium carbonate (160 mg, 0.50 mmol) followed by tetrakis(triphenylphosphine)palladium(0) (5.0 mg, 4.4 mol). The reaction was heated to 80° C. and stirred for 3 h. The reaction was cooled to room temperature, then poured into water and extracted 3× with ethyl acetate. The combined organic layers were dried over magnesium sulfate, filtered, and concentrated. The crude residue was purified by column chromatography eluting with 80-100% ethyl acetate in hexanes to give the title compound as a white solid (29 mg, 72%). ¹H NMR (400 MHz, DMSO-d6, 80° C.)(Rotamers) δ 10.02, 9.07, 8.69, 8.17, 7.76, 7.57, 7.32, 4.24, 3.61, 3.31, 2.95, 2.35.

Preparation 28: 1-(tert-butyl) 3-methyl 5-((methylsulfonyl)oxy)piperidine-1,3-dicarboxylate

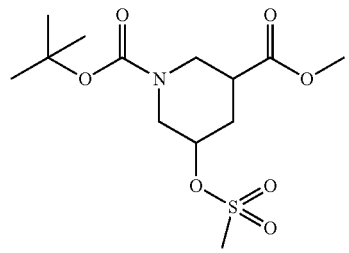 [SMILES: COC(=O)C1CC(OS(C)(=O)=O)CN(C(=O)OC(C)(C)C)C1]

To a solution of 1-(tert-butyl) 3-methyl 5-hydroxypiperidine-1,3-dicarboxylate (3.0 g, 11 mmol) in dichloromethane (45 ml) was added N,N-diisopropylethylamine (3.0 ml, 17 mmol) and methanesulfonyl chloride (1.1 ml, 14 mmol). The mixture stirred at room temperature for 2 h. An additional 300 uL methanesulfonyl chloride and 500 uL N,N-diisopropylethylamine were added and the reaction stirred for 12 h. The mixture was then poured into saturated aqueous sodium bicarbonate solution and extracted with dichloromethane. The organic layer was dried over magnesium sulfate, filtered and concentrated. Took into the next reaction without purification.

Preparation 29: 1-(tert-butyl) 3-methyl 5-azidopiperidine-1,3-dicarboxylate

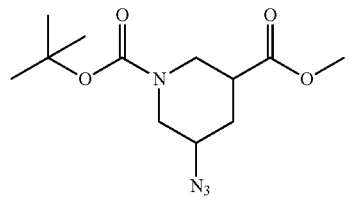 [SMILES: COC(=O)C1CC(N=[N+]=[N-])CN(C(=O)OC(C)(C)C)C1]

1-(tert-butyl) 3-methyl 5-((methylsulfonyl)oxy)piperidine-1,3-dicarboxylate (3.9 g, 11 mmol), was dissolved in DMF (60 ml). To this solution was added sodium azide (3.7 g, 58 mmol). The mixture was fitted with a blast shield, heated to 70° C. and stirred overnight. The reaction was cooled to room temperature, diluted with water, and extracted with dichloromethane. The organic layer was dried over magnesium sulfate, filtered, and concentrated. The crude residue was purified by column chromatography eluting with 25-45% ethyl acetate in hexanes. Isolated the title compound as a clear oil as a mixture of diastereomers (1.9 g, 53%).

Preparation 30: 5-azido-1-(tert-butoxycarbonyl)piperidine-3-carboxylic acid

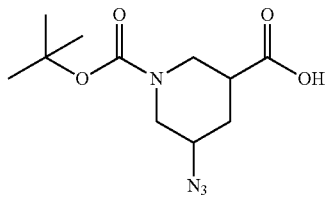 [SMILES: CC(C)(C)OC(=O)N1CC(N=[N+]=[N-])CC(C(=O)O)C1]

To a solution of 1-(tert-butyl) 3-methyl 5-azidopiperidine-1,3-dicarboxylate (1.9 g, 6.8 mmol) in methanol (15 ml) was added sodium hydroxide (15 ml of a 2M solution). The reaction stirred at room temperature for 6 h. The reaction was diluted with ethyl acetate and washed with 1N HCl and brine. The organic layer was dried over magnesium sulfate, filtered, and concentrated. The crude mixture was taken into the next step without further purification (1.5 g, yield 83%).

Preparation 31: tert-butyl 3-azido-5-((4-chlorophenyl)carbamoyl)piperidine-1-carboxylate

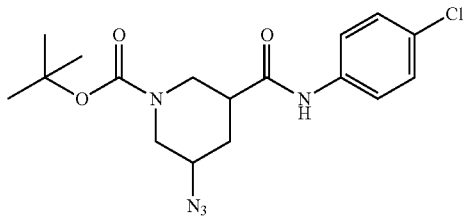 [SMILES: CC(C)(C)OC(=O)N1CC(N=[N+]=[N-])CC(C(=O)Nc2ccc(Cl)cc2)C1]

To a solution of 5-azido-1-(tert-butoxycarbonyl)piperidine-3-carboxylic acid (1.5 g, 5.6 mmol) in THF (30 mL) was added 4-chloroaniline (0.71 g, 5.6 mmol), N,N-diisopropylethylamine (1.9 ml, 11 mmol), N-(3-dimethylaminopropyl)-N'-ethylcarbodiimide hydrochloride (1.6 g, 8.3 mmol), and 4-(dimethylamino)pyridine (0.14 g, 1.1 mmol). The reaction stirred at room temperature overnight. The reaction was diluted with ethyl acetate and washed with saturated aqueous sodium bicarbonate solution and brine. The organic layer was dried over magnesium sulfate, filtered, and concentrated. The crude residue was purified by column chromatography eluting with 20-30% ethyl acetate in hexanes to give the title compound as an amorphous solid as a mixture of diastereomers (1.2 g, 56% yield).

Preparation 32: 5-azido-N-(4-chlorophenyl)piperidine-3-carboxamide

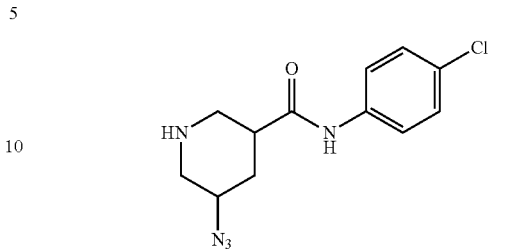

To a solution of tert-butyl 3-azido-5-((4-chlorophenyl)carbamoyl)piperidine-1-carboxylate (1.1 g, 2.9 mmol) in dichloromethane (12 ml) was added trifluoroacetic acid (1 mL, 13 mmol). The reaction stirred at room temperature overnight. An additional 1 mL of trifluoroacetic acid was added. The reaction stirred for 2 h. The reaction was concentrated, diluted with dichloromethane and washed with saturated aqueous sodium bicarbonate solution. The organic layer was dried over magnesium sulfate, filtered, and concentrated. Took into the next step without purification.

Preparation 33: 5-azido-N-(4-chlorophenyl)-1-(3-(furan-2-yl)benzoyl)piperidine-3-carboxamide

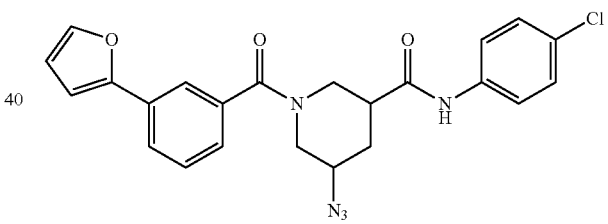

To a solution of 5-azido-N-(4-chlorophenyl)piperidine-3-carboxamide (1.0 g, 3.6 mmol) in THF (5 ml) was added N,N-diisopropylethylamine (1.2 ml, 7.1 mmol), 3-(furan-2-yl)benzoic acid (0.67 g, 3.6 mmol), N-(3-dimethylaminopropyl)-N'-ethylcarbodiimide hydrochloride (1.0 g, 5.4 mmol), and 4-(dimethylamino)pyridine (87 mg, 0.71 mmol). The reaction stirred at room temperature overnight. The reaction was poured into dichloromethane and washed with saturated aqueous sodium bicarbonate solution and brine. The organic layer was dried over magnesium sulfate, filtered, and concentrated. The crude residue was purified by column chromatography eluting with 30-50% ethyl acetate in hexanes to give the title compound as a mixture of diastereomers (1.2 g, 78%).

Example 43: 5-amino-N-(4-chlorophenyl)-1-(3-(furan-2-yl)benzoyl)piperidine-3-carboxamide

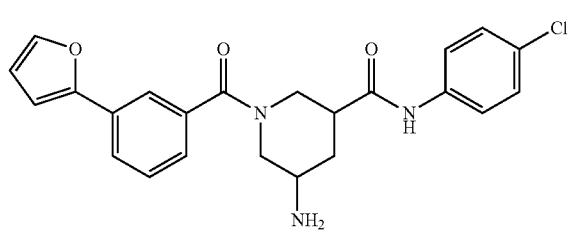 [SMILES: NC1CC(C(=O)Nc2ccc(Cl)cc2)CN(C(=O)c2cccc(-c3ccco3)c2)C1]

To a solution of 5-azido-N-(4-chlorophenyl)-1-(3-(furan-2-yl)benzoyl)piperidine-3-carboxamide (1.2 g, 2.8 mmol) in a mixture of THF (30 ml) and water (15.00 ml) was added triphenylphosphine (1.4 g, 5.6 mmol). The reaction was heated to 70° C. and stirred for 6 h. The reaction was stirred overnight at room temperature and then concentrated to dryness. The crude residue was purified by column chromatography eluting with 0-7% 7N methanolic ammonia in dichloromethane to give the title compound as a 1:1 mixture of diasteromers (1.1 g, 94% yield). $^1$H NMR (400 MHz, DMSO-d6, 80° C.) δ 9.92, 9.80, 7.75, 7.71, 7.65, 7.57, 7.48, 7.41, 7.29, 6.95, 6.90, 6.58, 4.23, 3.91, 3.47, 3.31, 3.20, 3.02, 2.94, 2.70, 2.62, 2.15, 1.99, 1.62.

Example 44: N-(4-chlorophenyl)-1-(3-(furan-2-yl)benzoyl)-5-(methylamino)piperidine-3-carboxamide

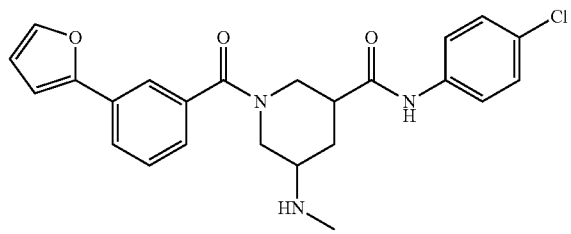

To a solution of 5-amino-N-(4-chlorophenyl)-1-(3-(furan-2-yl)benzoyl)piperidine-3-carboxamide (130 mg, 0.30 mmol) in dichloroethane (3 mL) was added formaldehyde (0.026 mL, 0.35 mmol) followed by 1 drop of acetic acid and sodium triacetoxyborohydride (130 mg, 0.59 mmol). The reaction stirred at room temperature for 4 h. An additional 26 uL of formaldehyde was added and the reaction stirred overnight. The crude residue was purified by column chromatography eluting with 0-5% methanol in dichloromethane with 1% 7N ammonia. Isolated the title compound as a mixture of diastereomers (11 mg, 8% yield). $^1$H NMR (400 MHz, CDCl$_3$, 50° C.)(Rotamers, 3:2 mixture of diastereomers) δ 11.56, 8.91, 7.69, 7.50, 7.45, 7.25, 6.62, 6.47, 4.30, 3.94, 3.81, 3.58, 3.01, 2.66, 2.33, 2.13, 1.93, 1.57.

Preparation 34: 1-(tert-butyl) 3-methyl 5-hydroxypiperidine-1,3-dicarboxylate

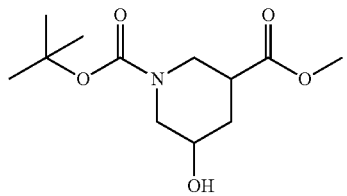 [SMILES: COC(=O)C1CC(O)CN(C(=O)OC(C)(C)C)C1]

To a solution of 1-(tert-butoxycarbonyl)-5-hydroxypiperidine-3-carboxylic acid (1.0 g, 4.1 mmol) in MeOH (4 ml) was added toluene (16 ml). The solution was then cooled to 0° C. and (trimethylsilyl)diazomethane (2M in hexanes) (2.5 ml, 4.9 mmol) was added dropwise. The reaction stirred at 0° C. for 1 h. Warmed to room temperature and stirred for 30 min. The reaction was quenched by the addition of a few drops of acetic acid. The reaction was poured into ethyl acetate and washed with saturated sodium bicarbonate solution. The organic layer was dried over magnesium sulfate, filtered and concentrated. The crude residue was purified by column chromatography eluting with 0-5% methanol in dichloromethane to give the title compound as a colorless oil (830 mg, 79% yield).

Preparation 35: 1-(tert-butoxycarbonyl)-5-methoxypiperidine-3-carboxylic acid

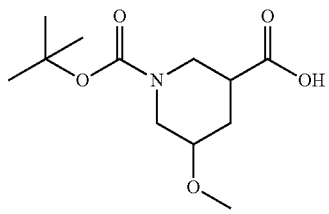 [SMILES: COC1CC(C(=O)O)CN(C(=O)OC(C)(C)C)C1]

To a solution of 1-(tert-butyl) 3-methyl 5-hydroxypiperidine-1,3-dicarboxylate (450 mg, 1.7 mmol) in THF (8 ml) at 0° C. was added sodium hydride (100 mg, 2.6 mmol). The reaction stirred for 15 min, then methyl iodide (0.16 ml, 2.6 mmol) was added. The reaction was allowed to warm to room temperature overnight. An additional 100 mg sodium hydride and 200 uL of methyl iodide was added. After 6 h, the reaction was quenched with the addition of ammonium chloride solution. The reaction mixture was poured into 1N HCl and extracted 3× with dichloromethane. The combined dichloromethane layers were dried over magnesium sulfate, filtered, and concentrated. The crude residue was purified by column chromatography eluting with 0-8% methanol in dichloromethane to give the title compound as a 2:1 mixture of diastereomers (393 mg, 65% yield).

Preparation 36: tert-butyl 3-((4-chlorophenyl)carbamoyl)-5-methoxypiperidine-1-carboxylate

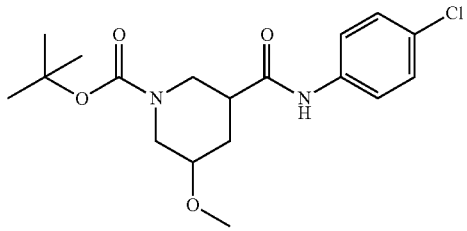 [SMILES: COC1CC(C(=O)Nc2ccc(Cl)cc2)CN(C(=O)OC(C)(C)C)C1]

To a solution of 1-(tert-butoxycarbonyl)-5-methoxypiperidine-3-carboxylic acid (290 mg, 1.1 mmol) in THF (4 ml) was added 4-chloroaniline (170 mg, 1.3 mmol), N-(3-dimethylaminopropyl)-N'-ethylcarbodiimide hydrochloride (330 mg, 1.7 mmol), N,N-diisopropylethylamine (0.30 ml, 1.7 mmol), and 4-(dimethylamino)pyridine (28 mg, 0.23 mmol). The reaction stirred at room temperature overnight. The reaction was poured into ethyl acetate and washed with saturated sodium bicarbonate solution and brine. The organic layer was dried over magnesium sulfate, filtered, and concentrated. The crude residue was purified by column chromatography eluting with 0-30% ethyl acetate in hexanes to give the title compound as a colorless oil (330 mg, 79% yield).

Preparation 37: N-(4-chlorophenyl)-5-methoxypiperidine-3-carboxamide

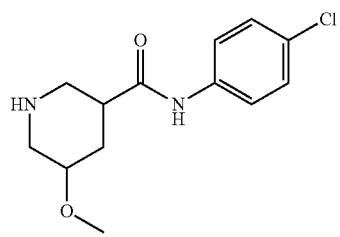 [SMILES: COC1CNCC(C(=O)Nc2ccc(Cl)cc2)C1]

To a solution of tert-butyl 3-((4-chlorophenyl)carbamoyl)-5-methoxypiperidine-1-carboxylate (330 mg, 0.89 mmol) in dichloromethane (8 ml) was added trifluoroacetic acid (2 ml, 26 mmol). The reaction was stirred at room temperature for 1.5 h. The reaction was concentrated to remove trifluoroacetic acid. The crude reaction mixture was diluted with dichloromethane and washed with saturated sodium carbonate solution. The organic layer was dried over magnesium sulfate, filtered, and concentrated to give the title compound which was used in the next step without purification (240 mg, yield 100%).

Example 45: N-(4-chlorophenyl)-1-(3-(furan-2-yl)benzoyl)-5-methoxypiperidine-3-carboxamide-Diastereomer A

Example 46: N-(4-chlorophenyl)-1-(3-(furan-2-yl)benzoyl)-5-methoxypiperidine-3-carboxamide-Diastereomer B

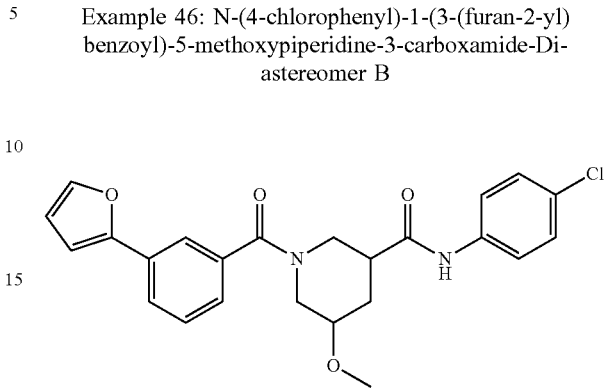

To a solution of N-(4-chlorophenyl)-5-methoxypiperidine-3-carboxamide (100 mg, 0.37 mmol) in THF (3 ml) was added 3-(furan-2-yl)benzoic acid (77 mg, 0.41 mmol), N,N-diisopropylethylamine (0.130 ml, 0.74 mmol), N-(3-dimethylaminopropyl)-N'-ethylcarbodiimide hydrochloride (110 mg, 0.56 mmol), and 4-(dimethylamino)pyridine (9.1 mg, 0.074 mmol). The reaction stirred overnight at room temperature. The reaction mixture was poured into water and extracted with dichloromethane. The organic layer was washed with brine, dried over magnesium sulfate, filtered, and concentrated. The crude residue was purified by column chromatography eluting with 40-60% ethyl acetate in hexanes to afford two separate diastereomers of the title compound.

Example 45

Diastereomer A (15 mg, 9% yield) $^1$H NMR (400 MHz, CDCl$_3$, 60° C.)(Rotamers) δ 8.46, 7.75, 7.71, 7.47, 7.41, 7.32, 7.24, 6.67, 6.47, 4.35, 3.76, 3.50, 3.36, 3.19, 2.95, 2.21, 2.09.

Example 46

Diastereomer B (51 mg, Yield 31%) $^1$H NMR (400 MHz, CDCl$_3$, 60° C.)(Rotamers) δ 9.17, 7.69, 7.56, 7.44, 7.39, 7.24, 6.61, 6.45, 4.25, 3.73, 3.63, 3.34, 3.21, 2.66, 2.43, 2.03.

Example 47: N-(4-chlorophenyl)-5,5-difluoro-1-(3-(1-methyl-1H-imidazol-5-yl)benzoyl)piperidine-3-carboxamide

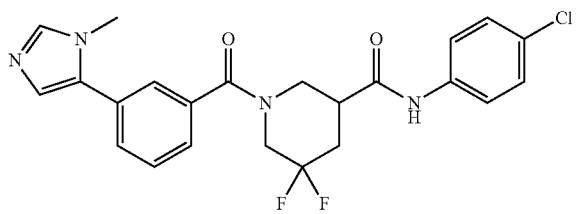 [SMILES: Cn1cncc1-c1cccc(C(=O)N2CC(C(=O)Nc3ccc(Cl)cc3)CC(F)(F)C2)c1]

To a solution of N-(4-chlorophenyl)-5,5-difluoropiperidine-3-carboxamide (50 mg, 0.18 mmol) in THF (2 ml) was added 3-(1-methyl-1H-imidazol-5-yl)benzoic acid (48 mg, 0.24 mmol) followed by N-(3-dimethylaminopropyl)-N'- ethylcarbodiimide hydrochloride (52 mg, 0.27 mmol), N,N-diisopropylethylamine (0.095 ml, 0.55 mmol) and 4-(dimethylamino)pyridine (4.4 mg, 0.036 mmol). The reaction stirred overnight at room temperature. The reaction mixture was poured into ethyl acetate and washed with saturated aqueous sodium bicarbonate solution and brine. The organic layer was dried over magnesium sulfate, filtered, and concentrated. The crude residue was purified by column chromatography eluting with 0-5% methanol in dichloromethane to afford the title compound as a white amorphous solid (80 mg, yield 96%). $^1$H NMR (400 MHz, DMSO-d6, 80° C.) δ 10.06, 7.66, 7.57, 7.55, 7.46, 7.39, 7.33, 7.08, 4.25, 3.67, 3.55, 3.22, 3.01, 2.94, 2.48, 2.29.

Example 48: 5-(benzylamino)-N-(4-chlorophenyl)-1-(3-(furan-2-yl)benzoyl)piperidine-3-carboxamide

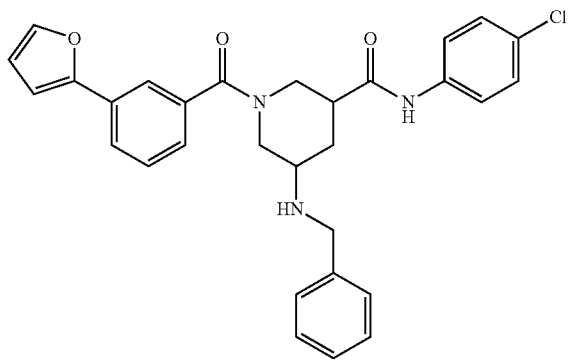 [SMILES: O=C(Nc1ccc(Cl)cc1)C1CC(NCc2ccccc2)CN(C(=O)c2cccc(-c3ccco3)c2)C1]

To a solution of 5-amino-N-(4-chlorophenyl)-1-(3-(furan-2-yl)benzoyl)piperidine-3-carboxamide (60 mg, 0.14 mmol) in dichloroethane (2 ml) was added benzaldehyde (0.022 ml, 0.21 mmol) followed by sodium triacetoxyborohydride (60 mg, 0.28 mmol). After 2 h, the reaction mixture was poured into dichloromethane, and washed with saturated aqueous sodium bicarbonate solution and brine. The organic layer was dried over magnesium sulfate, filtered, and concentrated. The crude residue was purified by column chromatography to give the title compound as a 3:1 mixture of diastereomers (10 mg, 13% yield). $^1$H NMR (400 MHz, DMSO-d6, 80° C.)(mixture of diastereomers) δ 9.87, 9.75, 7.76, 7.70, 7.67, 7.62, 7.56, 7.47, 7.41, 7.29, 7.20, 6.94, 6.86, 6.58, 4.28, 4.12, 3.68, 3.38, 3.08, 2.60, 2.48, 2.28, 2.00, 1.55.

Example 49: N-(4-chlorophenyl)-1-(3-(furan-2-yl)benzoyl)-5-propionamidopiperidine-3-carboxamide

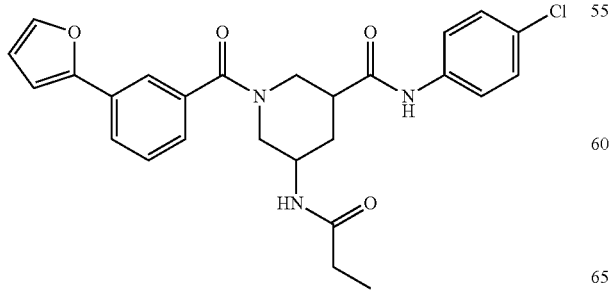

To a solution of 5-amino-N-(4-chlorophenyl)-1-(3-(furan-2-yl)benzoyl)piperidine-3-carboxamide (65 mg, 0.15 mmol) in dichloromethane (2 ml) was added triethylamine (0.043 ml, 0.31 mmol) followed by propionyl chloride (18 mg, 0.20 mmol). The reaction was stirred at room temperature overnight. The reaction was poured into dichloromethane and washed with saturated aqueous sodium bicarbonate solution and brine. The organic layer was dried over magnesium sulfate, filtered, and concentrated. The crude residue was purified by column chromatography eluting with 0-4% methanol in dichloromethane to give 2 separate diastereomers. Diastereomer B (most polar in 4% methanol in dichloromethane) was isolated as an 87:5 mixture of diastereomers (36 mg, yield 49%). $^1$H NMR (400 MHz, DMSO-d6, 80° C.) δ 9.91, 7.75, 7.70, 7.68, 7.57, 7.47, 7.31, 7.29, 6.97, 6.58, 4.15, 3.76, 3.00, 2.73, 2.18, 2.04, 1.69, 0.97.

Example 50: N-(4-chlorophenyl)-5,5-difluoro-1-(3-(pyrimidin-2-yl)benzoyl)piperidine-3-carboxamide

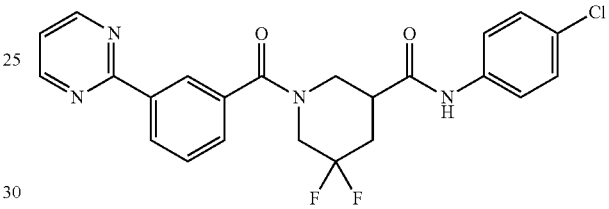

To a solution of N-(4-chlorophenyl)-5,5-difluoropiperidine-3-carboxamide (50 mg, 0.18 mmol) in THF (2 ml) was added 3-(pyrimidin-2-yl)benzoic acid (44 mg, 0.22 mmol) followed by N-(3-dimethylaminopropyl)-N'-ethylcarbodiimide hydrochloride (52 mg, 0.27 mmol), N,N-diisopropylethylamine (0.095 ml, 0.55 mmol), and 4-(dimethylamino)pyridine (4.4 mg, 0.036 mmol). The reaction stirred overnight at room temperature. The reaction mixture was poured into ethyl acetate and washed with saturated aqueous sodium bicarbonate solution and brine. The organic layer was dried over magnesium sulfate, filtered, and concentrated. The crude residue was purified by column chromatography eluting with 40-60% ethyl acetate in hexanes to give the title compound (75 mg, 90%). $^1$H NMR (400 MHz, DMSO-d6, 80° C.) δ 10.04, 8.90, 8.49, 8.43, 7.63, 7.56, 7.44, 7.32, 4.33, 4.20, 3.57, 3.25, 3.00, 2.96, 2.46, 2.30.

Preparation 38: 1-(tert-butyl) 3-methyl 5-oxopiperidine-1,3-dicarboxylate

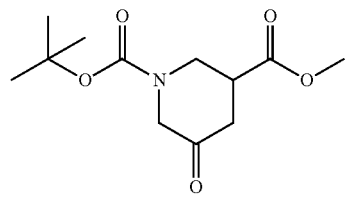 [SMILES: COC(=O)C1CC(=O)CN(C(=O)OC(C)(C)C)C1]

To a solution of oxalyl chloride (0.49 ml, 5.6 mmol) in dichloromethane (20 ml) at −78° C. was added dimethyl sulfoxide (0.79 ml, 11 mmol). The reaction stirred at −78° C. for 15 min and a solution of 1-(tert-butyl) 3-methyl 5-hydroxypiperidine-1,3-dicarboxylate (1.0 g, 4.0 mmol) in 3 mL of dichloromethane was added. 15 min later, triethylamine (2.4 ml, 17 mmol) was added. The reaction stirred at −78° C. for 30 min, and then was warmed to room temperature. After 2 h, the reaction was poured into dichloromethane and washed with aqueous saturated sodium bicarbonate solution and brine. The organic layer was dried over magnesium sulfate, filtered, and concentrated. The crude residue was purified by column chromatography eluting with 0-5% methanol in dichloromethane to afford the title compound as an orange oil (890 mg, 87% yield).

Preparation 39: 1-(tert-butyl) 3-methyl 5,5-difluoropiperidine-1,3-dicarboxylate

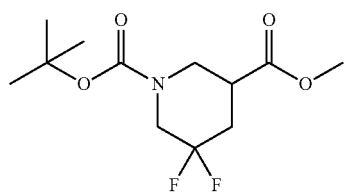 [SMILES: COC(=O)C1CN(C(=O)OC(C)(C)C)CC(F)(F)C1]

To a solution of 1-(tert-butyl) 3-methyl 5-oxopiperidine-1,3-dicarboxylate (440 mg, 1.7 mmol) in dichloromethane (6 ml) at −78° C. was added diethylaminosulfur trifluoride (0.45 ml, 3.4 mmol). The reaction stirred at −78° C. for 1 h, then was warmed to room temperature over 2 h. The reaction was poured into dichloromethane and washed with saturated sodium bicarbonate solution and brine. The organic layer was dried over magnesium sulfate, filtered, and concentrated. Purified by column chromatography (staining with potassium permanganate solution) eluting with 10-15% ethyl acetate in hexanes to afford the title compound as a colorless oil (240 mg, yield 50%).

Preparation 40: tert-butyl 3,3-difluoro-5-(hydroxymethyl)piperidine-1-carboxylate

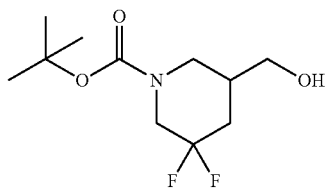 [SMILES: CC(C)(C)OC(=O)N1CC(CO)CC(F)(F)C1]

To a solution of 1-(tert-butyl) 3-methyl 5,5-difluoropiperidine-1,3-dicarboxylate (240 mg, 0.86 mmol) in methanol (5 ml) at room temperature was added sodium borohydride (65 mg, 1.7 mmol). Stirred at room temperature for 4 days. The reaction was quenched with the addition of saturated aqueous ammonium chloride solution. Extracted 3× with dichloromethane. The combined organic extracts were dried over magnesium sulfate, filtered and concentrated. The crude residue was purified by column chromatography eluting with 15-35% ethyl acetate in hexanes to give the title compound as a colorless film (170 mg, yield 79%).

Preparation 41: tert-butyl 3,3-difluoro-5-(((methylsulfonyl)oxy)methyl)piperidine-1-carboxylate

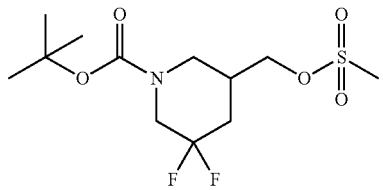 [SMILES: CC(C)(C)OC(=O)N1CC(COS(C)(=O)=O)CC(F)(F)C1]

To a solution of tert-butyl 3,3-difluoro-5-(hydroxymethyl)piperidine-1-carboxylate (170 mg, 0.68 mmol) in dichloromethane (5 ml) was added triethylamine (0.19 ml, 1.3 mmol) followed by methanesulfonyl chloride (0.079 ml, 1.0 mmol). After stirring for 1 h, the reaction mixture was poured into dichloromethane and washed with saturated aqueous sodium bicarbonate solution and brine. The organic layer was dried over magnesium sulfate, filtered, and concentrated. The crude mixture was used in the next step without purification (222 mg, 100%).

Preparation 42: tert-butyl 5-((4-chlorophenoxy)methyl)-3,3-difluoropiperidine-1-carboxylate

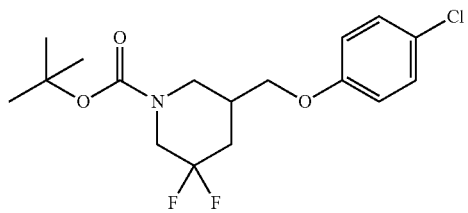 [SMILES: CC(C)(C)OC(=O)N1CC(COc2ccc(Cl)cc2)CC(F)(F)C1]

To a solution of tert-butyl 3,3-difluoro-5-(((methylsulfonyl)oxy)methyl)piperidine-1-carboxylate (220 mg, 0.67 mmol) in DMF (4 ml) was added cesium carbonate (550 mg, 1.7 mmol) and 4-chlorophenyl (170 mg, 1.3 mmol). The reaction was heated to 75° C. and stirred for 5 h. Left for 48 h at room temperature. The reaction was poured into saturated aqueous sodium carbonate solution and brine. The organic layer was dried over magnesium sulfate, filtered, and concentrated. The crude residue was purified by column chromatography eluting with 10-30% ethyl acetate in hexanes to afford the title compound as a colorless oil (257 mg).

Preparation 43: 5-((4-chlorophenoxy)methyl)-3,3-difluoropiperidine

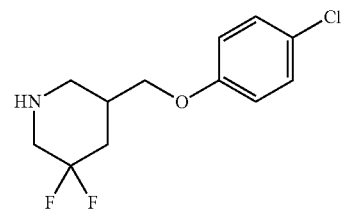 [SMILES: FC1(F)CNCC(COc2ccc(Cl)cc2)C1]

To a solution of tert-butyl 5-((4-chlorophenoxy)methyl)-3,3-difluoropiperidine-1-carboxylate (250 mg, 0.71 mmol) in dichloromethane (5 ml) was added trifluoroacetic acid (1 ml, 13 mmol). The reaction stirred at room temperature for 5 h. The reaction was concentrated to remove trifluoroacetic acid, then diluted with dichloromethane and washed with aqueous sodium carbonate solution and brine. The organic layer was dried over magnesium sulfate, filtered, and concentrated. The crude residue was purified by column chromatography eluting with 0-4% methanol in dichloromethane to give the title compound (90 mg, yield 2 steps 51%).

Example 51: (3-(1H-pyrazol-4-yl)phenyl)(5-((4-chlorophenoxy)methyl)-3,3-difluoropiperidin-1-yl)methanone

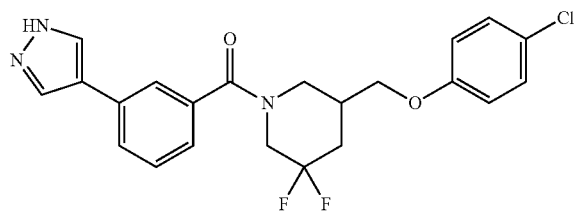 [SMILES: O=C(c1cccc(-c2cn[nH]c2)c1)N1CC(COc2ccc(Cl)cc2)CC(F)(F)C1]

To a solution of 5-((4-chlorophenoxy)methyl)-3,3-difluoropiperidine (48 mg, 0.18 mmol) in THF (2 ml) was added 3-(1H-pyrazol-4-yl)benzoic acid (34 mg, 0.18 mmol), N-(3-dimethylaminopropyl)-N'-ethylcarbodiimide hydrochloride (53 mg, 0.28 mmol), N,N-diisopropylethylamine (0.096 ml, 0.55 mmol), and 4-(dimethylamino)pyridine (4.5 mg, 0.037 mmol). The reaction stirred at room temperature overnight. The reaction was diluted with ethyl acetate and washed with saturated sodium carbonate solution and brine. The organic layer was dried over magnesium sulfate, filtered, and concentrated. The crude residue was purified by column chromatography eluting with 0-5% methanol in dichloromethane to afford the title compound as a white amorphous solid (12 mg, yield 15%). $^1$H NMR (400 MHz, CDCl$_3$, 55° C.) δ 10.39, 7.84, 7.56, 7.41, 7.27, 7.22, 7.67, 4.38, 4.25, 3.91, 3.40, 3.08, 2.45, 2.35, 1.99.

Preparation 44: tert-butyl 2-((4-chlorophenyl)carbamoyl)thiomorpholine-4-carboxylate

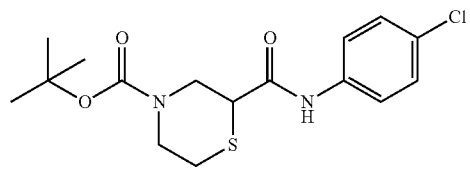 [SMILES: CC(C)(C)OC(=O)N1CCSC(C(=O)Nc2ccc(Cl)cc2)C1]

To a solution of 4-(tert-butoxycarbonyl)thiomorpholine-2-carboxylic acid (300 mg, 1.2 mmol) in THF (6 ml) was added 4-chloroaniline (170 mg, 1.3 mmol), N-(3-dimethylaminopropyl)-N'-ethylcarbodiimide hydrochloride (350 mg, 1.8 mmol), N,N-diisopropylethylamine (0.64 ml, 3.6 mmol), and 4 N,N-diisopropylethylamine (29 mg, 0.24 mmol). The reaction stirred overnight at room temperature. The reaction was poured into ethyl acetate, and washed with 1N HCl, saturated sodium bicarbonate solution and brine. The organic layer was dried over magnesium sulfate, filtered, and concentrated. The crude residue was purified by column chromatography eluting with 10-30% ethyl acetate in hexanes to give the title compound as a colorless gum (296 mg, yield 68%).

Preparation 45: N-(4-chlorophenyl)thiomorpholine-2-carboxamide

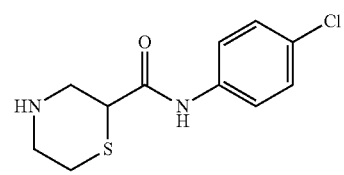 [SMILES: O=C(Nc1ccc(Cl)cc1)C1CNCCS1]

To a solution of N-(4-chlorophenyl)thiomorpholine-2-carboxamide (120 mg, 0.49 mmol) in dichloromethane (4 ml) was added trifluoroacetic acid (1 ml, 13 mmol). The reaction stirred at room temperature for 4 h. The reaction mixture was concentrated to remove trifluoroacetic acid, then diluted with dichloromethane and washed with saturated aqueous sodium carbonate solution and brine. The organic layer was dried over magnesium sulfate, filtered, and concentrated to a colorless oil which solidified upon standing, to give the title compound (125 mg, yield 89%).

Example 52: N-(4-chlorophenyl)-4-(3-(furan-2-yl)benzoyl)thiomorpholine-2-carboxamide

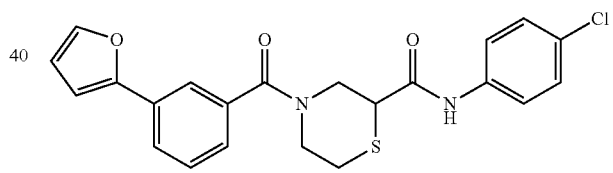

To a solution of N-(4-chlorophenyl)thiomorpholine-2-carboxamide (130 mg, 0.49 mmol) in THF (3 ml) was added 3-(furan-2-yl)benzoic acid (100 mg, 0.54 mmol), N-(3-dimethylaminopropyl)-N'-ethylcarbodiimide hydrochloride (140 mg, 0.73 mmol), N,N-diisopropylethylamine (0.17 ml, 0.97 mmol), and 4-(dimethylamino)pyridine (12 mg, 0.097 mmol). The reaction stirred overnight at room temperature. The reaction was poured into ethyl acetate and washed with saturated aqueous sodium carbonate and brine. The organic layer was dried over magnesium sulfate, filtered, and concentrated. The crude residue was purified by column chromatography eluting with 60% ethyl acetate in hexanes to afford the title compound as a white amorphous solid (194 mg, 94%). $^1$H NMR (400 MHz, CDCl$_3$, 50° C.) δ 8.61, 7.73, 7.69, 7.50, 7.47, 7.42, 7.30, 7.27, 7.26, 6.67, 6.48, 4.54, 4.15, 3.97, 3.70, 3.51, 2.90, 2.65.

Example 53: N-(4-chlorophenyl)-4-(3-(furan-2-yl)benzoyl)thiomorpholine-2-carboxamide 1,1-dioxide

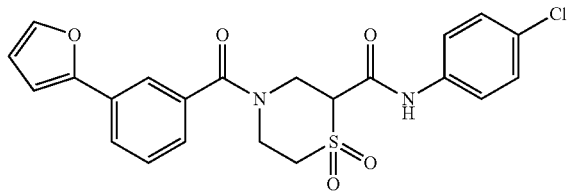 [SMILES: O=C(Nc1ccc(Cl)cc1)C1CN(C(=O)c2cccc(-c3ccco3)c2)CCS1(=O)=O]

To a solution of N-(4-chlorophenyl)-4-(3-(furan-2-yl)benzoyl)thiomorpholine-2-carboxamide (48 mg, 0.11 mmol) in dichloromethane (2 ml) at 0° C. was added 3-chloroperoxybenzoic acid (19 mg, 0.11 mmol). The reaction stirred at 0° C. overnight. The reaction mixture was diluted with dichloromethane and washed with saturated aqueous sodium bicarbonate solution and brine. The organic layer was dried over magnesium sulfate, filtered, and concentrated. The crude residue was purified by column chromatography eluting with 50-70% ethyl acetate in hexanes to afford the title compound as a white solid (20 mg, yield 39%). $^1$H NMR (400 MHz, DMSO-d6, 80° C.) δ 10.14, 7.69, 7.50, 7.42, 7.31, 6.88, 6.56, 4.42, 4.30, 4.10, 4.03, 3.67, 3.28, 3.20.

Example 54: 5-benzamido-N-(4-chlorophenyl)-1-(3-(furan-2-yl)benzoyl)piperidine-3-carboxamide Diastereomer A

Example 55: 5-benzamido-N-(4-chlorophenyl)-1-(3-(furan-2-yl)benzoyl)piperidine-3-carboxamide Diastereomer B

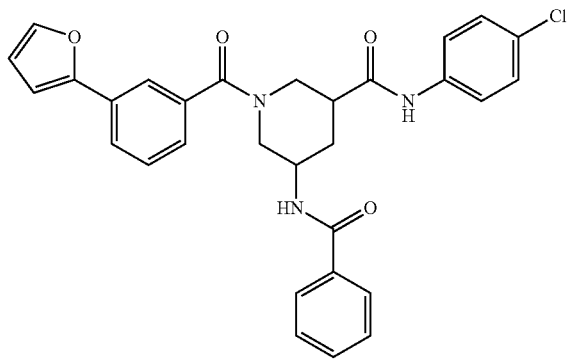 [SMILES: O=C(NC1CC(C(=O)Nc2ccc(Cl)cc2)CN(C(=O)c2cccc(-c3ccco3)c2)C1)c1ccccc1]

To a solution of 5-amino-N-(4-chlorophenyl)-1-(3-(furan-2-yl)benzoyl)piperidine-3-carboxamide (33 mg, 0.078 mmol) in dichloromethane (1 ml) was added triethylamine (0.022 ml, 0.16 mmol) followed by benzoyl chloride (11 µl, 0.093 mmol). The reaction stirred at room temperature for 1 h. The reaction mixture was poured into dichloromethane, and washed with saturated aqueous sodium bicarbonate solution and brine. The organic layer was dried over magnesium sulfate, filtered, and concentrated. The crude residue was purified by column chromatography eluting with 60-80% ethyl acetate in hexanes to afford two isolated diastereomers.

Example 54

Diastereomer A (least polar): (17 mg, 42% yield) (232480). $^1$H NMR (400 MHz, DMSO-d6, 80° C.) δ 9.78, 7.92, 7.80, 7.66, 7.62, 7.51, 7.43, 7.30, 7.20, 6.79, 6.51, 4.33, 3.91, 3.72, 3.61, 3.18, 3.03, 2.10.

Example 55

Diastereomer B (more polar) (16 mg, 39% yield) (232481). $^1$H NMR (400 MHz, DMSO-d6, 80° C.) δ 9.97, 8.28, 7.80, 7.74, 7.69, 7.57, 7.43, 7.31, 6.96, 6.57, 4.17, 4.04, 3.14, 3.01, 2.77, 2.48, 2.28, 1.91.

Example 56: phenyl (5-((4-chlorophenyl)carbamoyl)-1-(3-(furan-2-yl)benzoyl)piperidin-3-yl)carbamate

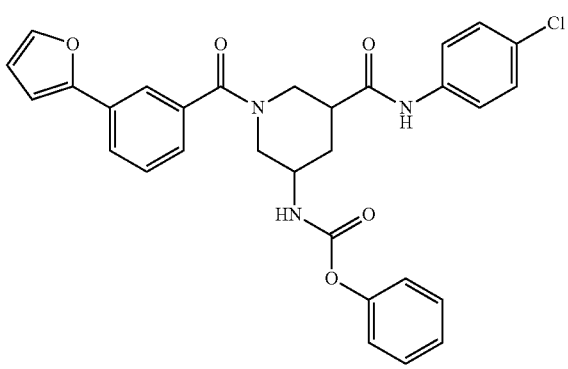 [SMILES: O=C(NC1CC(C(=O)Nc2ccc(Cl)cc2)CN(C(=O)c2cccc(-c3ccco3)c2)C1)Oc1ccccc1]

To a solution of 5-amino-N-(4-chlorophenyl)-1-(3-(furan-2-yl)benzoyl)piperidine-3-carboxamide (30 mg, 0.071 mmol) in dichloromethane (1 ml) was added triethylamine (0.020 ml, 0.14 mmol) followed by phenyl chloroformate (0.013 ml, 0.11 mmol). The reaction stirred at room temperature for 2 h. The reaction was poured into dichloromethane and washed with saturated aqueous sodium bicarbonate solution and brine. The organic layer was dried over magnesium sulfate, filtered, and concentrated. The crude residue was purified by chromatography eluting with 50-70% ethyl acetate in hexanes to afford 33 mg of a white solid. The solid was dissolved in chloroform, and the solid which precipitated out was filtered and dried to give the title compound as a mixture of diastereomers. A white solid was isolated (14 mg, yield 37%). $^1$H NMR (400 MHz, DMSO-d6, 80° C.)(diastereomers) δ 9.96, 9.70, 7.74, 7.70, 7.57, 7.47, 7.33, 7.17, 7.05, 6.97, 6.89, 6.57, 6.55, 4.20, 4.00, 3.61, 3.08, 3.04, 2.91, 2.74, 2.30, 2.13, 1.99, 1.81.

Example 57: methyl (5-((4-chlorophenyl)carbamoyl)-1-(3-(furan-2-yl)benzoyl)piperidin-3-yl)carbamate

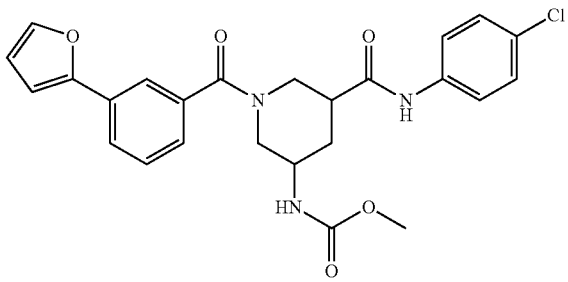 [SMILES: COC(=O)NC1CC(C(=O)Nc2ccc(Cl)cc2)CN(C(=O)c2cccc(-c3ccco3)c2)C1]

To a solution of 5-amino-N-(4-chlorophenyl)-1-(3-(furan-2-yl)benzoyl)piperidine-3-carboxamide (30 mg, 0.071 mmol) in dichloromethane (1 ml) was added triethylamine (0.020 ml, 0.14 mmol) followed by methyl chloroformate (8.2 µl, 0.11 mmol). The reaction stirred at room temperature for 2 h. The reaction was poured into dichloromethane and washed with saturated aqueous sodium bicarbonate solution and brine. The organic layer was dried over magnesium sulfate, filtered, and concentrated. The crude residue was purified by chromatography eluting with 50-70% ethyl acetate in hexanes to give the title compound as a mixture of diastereomers. A white amorphous solid was isolated (26 mg, yield 76%). $^1$H NMR (400 MHz, DMSO-d6, 80° C.)(diastereomers) δ 9.91, 9.65, 7.73, 7.66, 7.61, 7.54, 7.46, 7.36, 7.27, 7.20, 7.00, 6.94, 6.86, 6.74, 6.55, 4.19, 4.05, 3.84, 3.47, 3.43, 3.01, 2.88, 2.71, 2.17, 2.02, 1.87, 1.69.

Example 58: ethyl (5-((4-chlorophenyl)carbamoyl)-1-(3-(furan-2-yl)benzoyl)piperidin-3-yl)carbamate To a solution of 5-((4-chlorophenoxy)methyl)-3,3-difluoropiperidine (45 mg, 0.17 mmol) in THF (1 ml) was added 3-(furan-2-yl)benzoic acid (32 mg, 0.17 mmol), N-(3-dimethylaminopropyl)-N'-ethylcarbodiimide hydrochloride (49 mg, 0.26 mmol), N,N-diisopropylethylamine (0.090 ml, 0.52 mmol), and 4-(dimethylamino)pyridine (4.2 mg, 0.034 mmol). The reaction stirred at room temperature overnight. The reaction was diluted with ethyl acetate and washed with saturated sodium carbonate solution and brine. The organic layer was dried over magnesium sulfate, filtered, and concentrated. The crude residue was purified by column chromatography eluting with 0-30% ethyl acetate in hexanes to afford the title compound as an amorphous solid (61 mg, yield 82%). $^1$H NMR (400 MHz, CDCl$_3$, 50° C.)(rotamers) δ 7.75, 7.72, 7.29, 7.27, 7.21, 6.77, 6.68, 6.48, 4.26, 3.90, 3.39, 3.08, 2.45, 2.34, 2.00.

Preparation 46: tert-butyl 3-(benzyl(methyl)amino)-5-((4-chlorophenyl)carbamoyl)piperidine-1-carboxylate

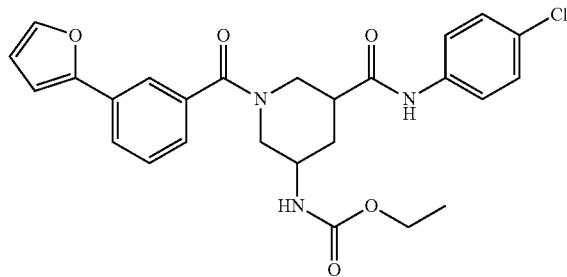 [SMILES: CCOC(=O)NC1CC(C(=O)Nc2ccc(Cl)cc2)CN(C(=O)c2cccc(-c3ccco3)c2)C1]

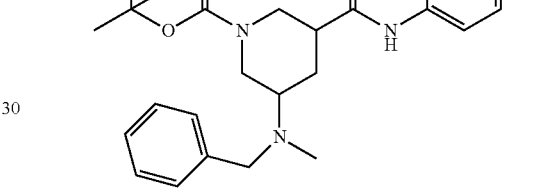

To a solution of 5-amino-N-(4-chlorophenyl)-1-(3-(furan-2-yl)benzoyl)piperidine-3-carboxamide (30 mg, 0.071 mmol) in dichloromethane (1 ml) was added triethylamine (0.020 ml, 0.14 mmol) followed by ethyl chloroformate (10 µl, 0.11 mmol). The reaction stirred at room temperature for 2 h. The reaction was poured into dichloromethane and washed with saturated aqueous sodium bicarbonate solution and brine. The organic layer was dried over magnesium sulfate, filtered, and concentrated. The crude residue was purified by chromatography eluting with 50-70% ethyl acetate in hexanes to give the title compound as a 1:1 mixture of diastereomers. A white solid was isolated (31 mg, yield 88%). $^1$H NMR (400 MHz, DMSO-d6, 80° C.)(diastereomers) δ 9.92, 9.65, 7.75, 7.69, 7.64, 7.56, 7.48, 7.39, 7.31, 7.23, 6.97, 6.89, 6.67, 6.59, 4.21, 4.06, 3.94, 3.51, 3.02, 2.90, 2.78, 2.69, 2.49, 2.19, 2.04, 1.90, 1.71, 1.11.

Example 59: (5-((4-chlorophenoxy)methyl)-3,3-difluoropiperidin-1-yl)(3-(furan-2-yl)phenyl)methanone To a solution of tert-butyl 3-((4-chlorophenyl)carbamoyl)-5-oxopiperidine-1-carboxylate (550 mg, 1.6 mmol) in dichloroethane (7 ml) was added N-methyl-1-phenylmethanamine (380 mg, 3.1 mmol), sodium triacetoxyborohydride (990 mg, 4.6 mmol), and acetic acid (1 drop). The reaction stirred at room temperature overnight. The reaction was poured into dichloromethane and washed with saturated sodium carbonate solution. The organic layer was dried over magnesium sulfate, filtered and concentrated. The crude residue was purified by column chromatography eluting with 0-7% methanol in dichloromethane to give the title compound as an amorphous solid (540 mg, yield 76%).

Preparation 47: 5-(benzyl(methyl)amino)-N-(4-chlorophenyl)piperidine-3-carboxamide

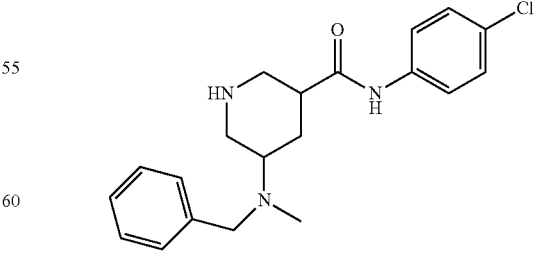

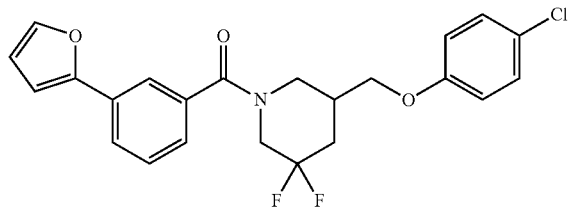 [SMILES: O=C(c1cccc(-c2ccco2)c1)N1CC(COc2ccc(Cl)cc2)CC(F)(F)C1]

To a solution of tert-butyl 3-(benzyl(methyl)amino)-5-((4-chlorophenyl)carbamoyl)piperidine-1-carboxylate (540 mg, 1.2 mmol) in dichloromethane (6 ml) was added trifluoroacetic acid (1 ml, 13 mmol). The reaction stirred at

143 room temperature for 4 h. The reaction was concentrated, dissolved in dichloromethane and washed with aqueous sodium carbonate and brine. The organic layer was dried over magnesium sulfate, filtered, and concentrated. The title compound was taken into the next step without purification (348 mg, yield 82%).

Example 60: 5-(benzyl(methyl)amino)-N-(4-chlorophenyl)-1-(3-(furan-2-yl)benzoyl)piperidine-3-carboxamide-Diastereomer A Example 61: 5-(benzyl(methyl)amino)-N-(4-chlorophenyl)-1-(3-(furan-2-yl)benzoyl)piperidine-3-carboxamide-Diastereomer B

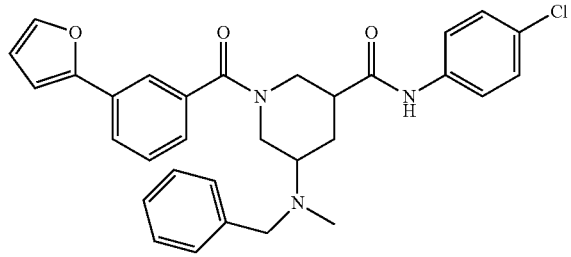 [SMILES: CN(Cc1ccccc1)C1CC(C(=O)Nc2ccc(Cl)cc2)CN(C(=O)c2cccc(-c3ccco3)c2)C1]

To a solution of 5-(benzyl(methyl)amino)-N-(4-chlorophenyl)piperidine-3-carboxamide (350 mg, 0.97 mmol) in THF (7 ml) was added 3-(furan-2-yl)benzoic acid (180 mg, 0.97 mmol) followed by diisopropylethylamine (0.34 ml, 1.9 mmol), N-(3-dimethylaminopropyl)-N'-ethylcarbodiimide dihydrochloride (280 mg, 1.4 mmol), and 4-(dimethylamino)pyridine (24 mg, 0.19 mmol). The reaction stirred at room temperature overnight. The reaction was poured into dichloromethane and washed with saturated aqueous sodium carbonate. The organic layer was dried over magnesium sulfate, filtered, and concentrated. The crude residue was purified by column chromatography eluting with 50-90% ethyl acetate in hexanes to afford the title compound as 2 separate diastereomers.

Example 60

Diastereomer A. White amorphous solid (302 mg, yield 58%) (rotamers)$^1$H NMR (400 MHz, CDCl$_3$) δ 9.14, 8.64, 7.73, 7.68, 7.54, 7.45, 7.39, 7.22, 7.10, 7.65, 6.47, 4.83, 4.74, 3.91, 3.63, 3.45, 3.08, 2.95, 2.59, 2.36, 2.23, 2.13.

Example 61

Diastereomer B. White amorphous solid (123 mg, yield 23%) (rotamers)$^1$H NMR (400 MHz, CDCl$_3$) δ 9.49, 7.72, 7.63, 7.45, 7.26, 7.16, 6.62, 6.47, 4.76, 3.81, 3.53, 3.40, 3.29, 3.01, 2.71, 2.56, 2.04, 1.89.

Preparation 48: tert-butyl 3-((4-chlorophenyl)sulfonamido)piperidine-1-carboxylate

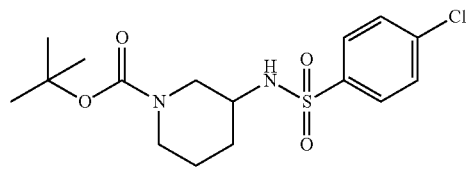 [SMILES: CC(C)(C)OC(=O)N1CCCC(NS(=O)(=O)c2ccc(Cl)cc2)C1]

144

To a solution of tert-butyl 3-aminopiperidine-1-carboxylate (300 mg, 1.5 mmol) in dichloromethane (7 ml) at room temperature was added triethylamine (0.31 ml, 2.2 mmol) followed by 4-chlorobenzenesulfonyl chloride (380 mg, 1.8 mmol). The reaction stirred at room temperature over night. The reaction was diluted with dichloromethane, washed with saturated sodium carbonate solution, and brine. The organic layer was dried over magnesium sulfate, filtered and concentrated. The crude residue was purified by column chromatography eluting with 20-60% ethyl acetate in hexanes to give the title compound as a white, amorphous solid (469 mg, yield 84%).

Preparation 49: 4-chloro-N-(piperidin-3-yl)benzenesulfonamide

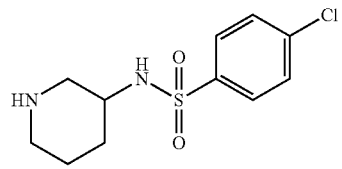 [SMILES: O=S(=O)(NC1CCCNC1)c1ccc(Cl)cc1]

To a solution of tert-butyl 3-((4-chlorophenyl)sulfonamido)piperidine-1-carboxylate (340 mg, 0.91 mmol) in dichloromethane (6 ml) was added trifluoroacetic acid (1 ml, 13 mmol). The reaction stirred at room temperature for 4 h. The reaction was concentrated, diluted with dichloromethane and washed with saturated aqueous sodium carbonate and brine. The organic layer was dried over magnesium sulfate, filtered and concentrated. The crude residue was used in the next reaction without purification.

Example 62: 4-chloro-N-(1-(3-(furan-2-yl)benzoyl)piperidin-3-yl)benzenesulfonamide

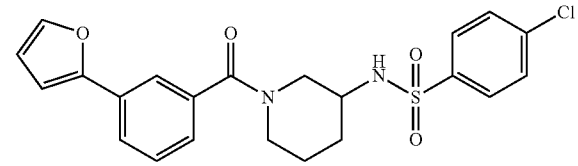 [SMILES: O=C(c1cccc(-c2ccco2)c1)N1CCCC(NS(=O)(=O)c2ccc(Cl)cc2)C1]

To a solution of 4-chloro-N-(piperidin-3-yl)benzenesulfonamide (92 mg, 0.34 mmol) in THF (3 ml) was added 3-(furan-2-yl)benzoic acid (63.0 mg, 0.33 mmol), N-(3-dimethylaminopropyl)-N'-ethylcarbodiimide hydrochloride (96 mg, 0.50 mmol), diisopropylethylamine (0.12 ml, 0.67 mmol), and 4-(dimethylamino)pyridine (8.2 mg, 0.067 mmol). The reaction stirred at room temperature overnight. The reaction was poured into dichloromethane, and washed with saturated sodium bicarbonate solution and brine. The organic layer was dried over magnesium sulfate, filtered, and concentrated. The crude residue was purified by column chromatography eluting with 50-90% ethyl acetate in hexanes to afford the title compound as a white amorphous solid (133 mg, yield 89%). $^1$H NMR (400 MHz, CDCl$_3$) (rotamers) δ 7.85, 7.70, 7.60, 7.47, 7.36, 7.15, 6.70, 6.47, 6.00, 4.04, 3.86, 3.51, 3.34, 3.21, 3.08, 2.88, 2.06, 1.80, 1.68, 1.41.

Preparation 50: N-(4-chlorophenyl)-5-oxopiperidine-3-carboxamide

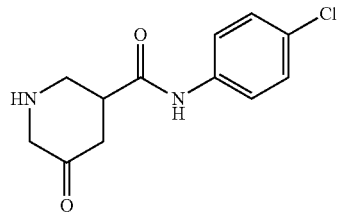 [SMILES: O=C1CNCC(C(=O)Nc2ccc(Cl)cc2)C1]

To a solution of tert-butyl 3-((4-chlorophenyl)carbamoyl)-5-oxopiperidine-1-carboxylate (300 mg, 0.85 mmol) in dioxane (4 mL) was added HCl (4N in dioxane) (1 ml, 4.0 mmol). The reaction stirred at room temperature for 4 h. Added additional HCl (4N in dioxane) (1 ml, 4.00 mmol). After 1.5 h the reaction was concentrated and rotovapped twice from ethyl acetate. Took into the next reaction as the HCl salt without further purification.

Example 63: N-(4-chlorophenyl)-1-(3-(furan-2-yl)benzoyl)-5-oxopiperidine-3-carboxamide

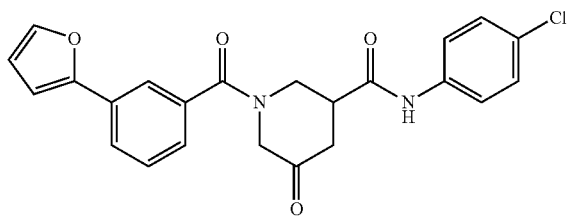 [SMILES: O=C1CC(C(=O)Nc2ccc(Cl)cc2)CN(C(=O)c2cccc(-c3ccco3)c2)C1]

To a solution of N-(4-chlorophenyl)-5-oxopiperidine-3-carboxamide.HCl (250 mg, 0.85 mmol) in THF (3 ml) was added 3-(furan-2-yl)benzoic acid (160 mg, 0.85 mmol) followed by diisopropylethylamine (0.45 ml, 2.6 mmol), N-(3-dimethylaminopropyl)-N'-ethylcarbodiimide hydrochloride (240 mg, 1.3 mmol), and 4-(dimethylamino)pyridine (21 mg, 0.17 mmol). The reaction was left overnight. The reaction was poured into dichloromethane and washed with saturated aqueous sodium bicarbonate solution and brine. The organic layer was dried over magnesium sulfate, filtered, and concentrated. The crude residue was purified by column chromatography eluting with 50-70% ethyl acetate in hexanes to give the title compound as a solid (35 mg, yield 10%). $^1$H NMR (400 MHz, DMSO-d6, 80° C.) 9.95, 7.71, 7.66, 7.57, 7.54, 7.38, 7.29, 7.18, 6.84, 6.56, 4.26, 4.10, 3.96, 3.87, 3.19, 2.68.

Preparation 51: tert-butyl 3-((4-chlorophenyl)carbamoyl)-5-(dimethylamino)piperidine-1-carboxylate

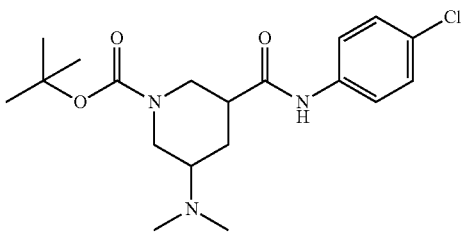 [SMILES: CN(C)C1CC(C(=O)Nc2ccc(Cl)cc2)CN(C(=O)OC(C)(C)C)C1]

To a solution of tert-butyl 3-((4-chlorophenyl)carbamoyl)-5-oxopiperidine-1-carboxylate (260 mg, 0.74 mmol) in dichloroethane (4 ml) was added dimethylamine (2M in THF) (0.74 ml, 1.4 mmol), sodium triacetoxyborohydride (235 mg, 1.1 mmol), and acetic acid (42 µl, 0.74 mmol).

The reaction stirred at room temperature for 4 h. The reaction was diluted with dichloromethane and washed with saturated aqueous sodium bicarbonate solution and brine. The organic layer was dried over magnesium sulfate, filtered, and concentrated. The crude residue was purified by column chromatography eluting with 3-5% methanol in dichloromethane to afford the title compound as a white amorphous solid (276 mg, yield 98%).

Preparation 52: N-(4-chlorophenyl)-5-(dimethylamino)piperidine-3-carboxamide

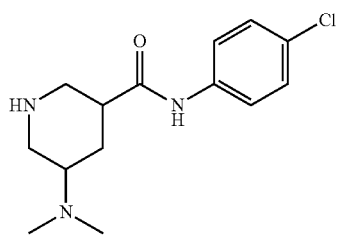 [SMILES: CN(C)C1CNCC(C(=O)Nc2ccc(Cl)cc2)C1]

To a solution of tert-butyl 3-((4-chlorophenyl)carbamoyl)-5-(dimethylamino)piperidine-1-carboxylate (280 mg, 0.72 mmol) in dichloromethane (5 ml) was added trifluoroacetic acid (1 ml, 13 mmol). The reaction stirred at room temperature for 4 h. The reaction was concentrated, diluted with dichloromethane, and washed with saturated aqueous sodium carbonate solution. The organic layer was dried over magnesium sulfate, filtered and concentrated. Used in the next reaction without purification.

Example 64: N-(4-chlorophenyl)-5-(dimethylamino)-1-(3-(furan-2-yl)benzoyl)piperidine-3-carboxamide

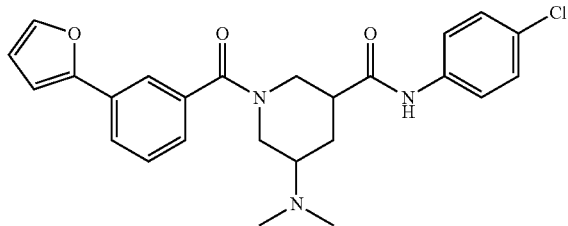 [SMILES: CN(C)C1CC(C(=O)Nc2ccc(Cl)cc2)CN(C(=O)c2cccc(-c3ccco3)c2)C1]

The above compound was prepared by following the general procedure for amide coupling described in Example 33 (30 mg, yield 2 steps 25%)(mixture of diastereomers) $^1$H NMR (400 MHz, CDCl$_3$) δ 10.36, 9.50, 9.03, 7.69, 7.42, 7.24, 6.67, 6.48, 4.81, 4.70, 3.93, 3.83, 3.67, 3.46, 3.24, 2.99, 2.58, 2.45, 2.20, 2.11, 1.94, 1.78.

Preparation 53: tert-butyl 3-(4-chlorobenzamido)piperidine-1-carboxylate

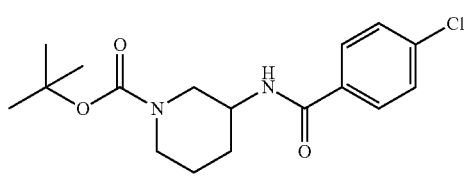 [SMILES: CC(C)(C)OC(=O)N1CCCC(NC(=O)c2ccc(Cl)cc2)C1]

To a solution of tert-butyl 3-aminopiperidine-1-carboxylate (500 mg, 2.5 mmol) in THF (12 mL) was added 4-chlorobenzoic acid (470 mg, 3.0 mmol) followed by diisopropylethylamine (870 μl, 5.0 mmol), 3-(((ethylimino)methylene)amino)-N,N-dimethylpropan-1-amine hydrochloride (720 mg, 3.7 mmol), and N,N-dimethylpyridin-4-amine (61.0 mg, 0.50 mmol). The reaction stirred at room temperature overnight. The crude residue was purified by column chromatography eluting with 30-50% ethyl acetate in hexanes to afford the title compound as an amorphous solid (702 mg, 83%).

Preparation 54: 4-chloro-N-(piperidin-3-yl)benzamide

To a solution of tert-butyl 3-(4-chlorobenzamido)piperidine-1-carboxylate (700 mg, 2.1 mmol) in dichloromethane (10 ml) was added trifluoroacetic acid (2 ml, 26 mmol). The reaction stirred at room temperature for 5 h. The reaction was concentrated, diluted with dichloromethane, and washed with saturated aqueous sodium carbonate solution. The organic layer was dried over magnesium sulfate, filtered and concentrated. The crude reaction mixture was used in the next reaction without purification.

Example 65: 4-chloro-N-(1-(3-(furan-2-yl)benzoyl)piperidin-3-yl)benzamide

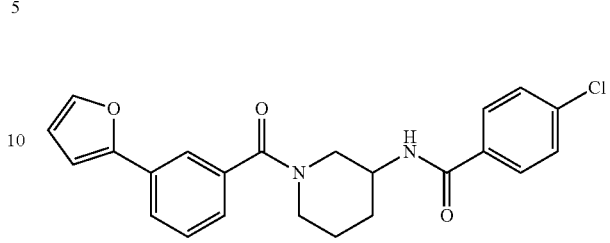

To a solution of 4-chloro-N-(piperidin-3-yl)benzamide (100 mg, 0.42 mmol) in tetrahydrofuran (4 ml) was added 3-(furan-2-yl)benzoic acid (79 mg, 0.42 mmol), 3-(((ethylimino)methylene)amino)-N,N-dimethylpropan-1-amine hydrochloride (120 mg, 0.63 mmol), diisopropylethylamine (110 mg, 0.84 mmol), and N,N-dimethylpyridin-4-amine (10 mg, 0.084 mmol). The reaction stirred at room temperature overnight. The reaction was poured into dichloromethane and washed with saturated aqueous sodium bicarbonate solution and brine. The organic layer was dried over magnesium sulfate, filtered, and concentrated. The crude residue was purified by column chromatography eluting with 50-60% ethyl acetate in hexanes to afford the title compound as a white amorphous solid (149 mg, yield 87%)(rotamers) $^1$H NMR (400 MHz, CDCl$_3$, 50° C.) δ 7.67, 7.42, 7.36, 7.31, 7.24, 6.62, 6.44, 4.14, 3.79, 3.58, 3.47, 2.15, 1.97, 1.71, 1.59.

Preparation 55: tert-butyl 3-(((methylsulfonyl)oxy)methyl)piperidine-1-carboxylate

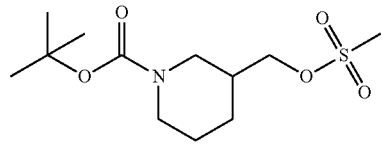 [SMILES: CC(C)(C)OC(=O)N1CCCC(COS(C)(=O)=O)C1]

To a solution of tert-butyl 3-(hydroxymethyl)piperidine-1-carboxylate (1 g, 4.6 mmol) in dichloromethane (20 ml) at 0° C. was added triethylamine (0.97 ml, 7.0 mmol) followed by methanesulfonyl chloride (0.43 ml, 5.6 mmol). The reaction was warmed to room temperature and stirred overnight. The reaction was poured into dichloromethane and washed with saturated sodium bicarbonate solution and brine. The organic layer was dried over magnesium sulfate, filtered, and concentrated to afford the title compound as a viscous oil (1.49 g, yield quantitative) Took into the next reaction without purification.

Preparation 56: tert-butyl 3-((4-chlorophenoxy)methyl)piperidine-1-carboxylate

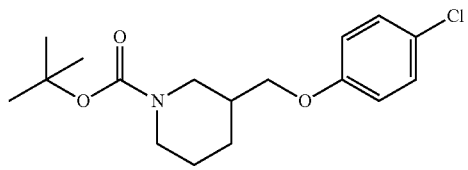 [SMILES: CC(C)(C)OC(=O)N1CCCC(COc2ccc(Cl)cc2)C1]

To a solution of tert-butyl 3-(((methylsulfonyl)oxy)methyl)piperidine-1-carboxylate (510 mg, 1.7 mmol) in dimethylformamide (8 ml) was added 4-chlorophenyl (330 mg, 2.6 mmol) followed by cesium carbonate (1.7 g, 5.2 mmol). The reaction was heated to 75° C. After 3 h, the reaction was cooled to room temperature and left at room temperature for 36 h. The reaction mixture was poured into water and extracted with 30% ethyl acetate in hexanes. The organic layer was dried over magnesium sulfate, filtered, and concentrated. Purified by column chromatography eluting with 0-10% ethyl acetate in hexanes to give the title compound as a colorless oil (367 mg, yield 65%).

Preparation 57:
3-((4-chlorophenoxy)methyl)piperidine

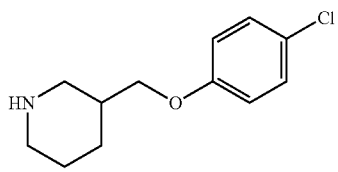 [SMILES: Clc1ccc(OCC2CCCNC2)cc1]

To a solution of tert-butyl 3-((4-chlorophenoxy)methyl)piperidine-1-carboxylate (370 mg, 1.1 mmol) in dichloromethane (6 ml) was added trifluoroacetic acid (1 ml, 13 mmol). The reaction stirred at room temperature overnight. The reaction was concentrated, and taken into the next reaction without purification.

Example 66: (3-((4-chlorophenoxy)methyl)piperidin-1-yl)(3-(furan-2-yl)phenyl)methanone

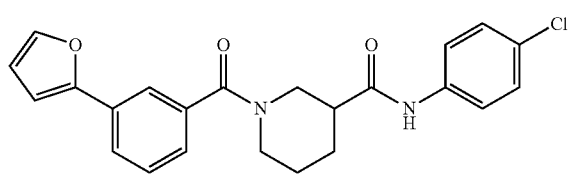 [SMILES: O=C(Nc1ccc(Cl)cc1)C1CCCN(C(=O)c2cccc(-c3ccco3)c2)C1]

To 3-((4-chlorophenoxy)methyl)piperidine (120 mg, 0.53 mmol) and 3-(furan-2-yl)benzoic acid (100 mg, 0.53 mmol) in THF (2 ml) was added diisopropylethylamine (0.19 ml, 1.1 mmol), N-(3-dimethylaminopropyl)-N'-ethylcarbodiimide hydrochloride (150 mg, 0.80 mmol), and 4-(dimethylamino)pyridine (13 mg, 0.11 mmol). The reaction stirred at room temperature overnight. The reaction was poured into dichloromethane and washed with saturated aqueous sodium bicarbonate solution and brine. The organic layer was dried over magnesium sulfate, filtered, and concentrated. The crude residue was purified by column chromatography eluting with 30-50% ethyl acetate in hexanes to afford the title compound as a clear gum (162 mg, yield 77%). $^1$H NMR (400 MHz, CDCl$_3$, 50° C.) δ 7.69, 7.67, 7.44, 7.36, 7.22, 7.10, 6.82, 6.64, 6.56, 6.45, 4.71, 4.33, 3.83, 3.72, 3.03, 2.08, 1.92, 1.80, 1.65, 1.45.

Example 67: 1-(3-(1H-pyrazol-1-yl)benzoyl)-N-(4-chlorophenyl)-5,5-difluoropiperidine-3-carboxamide

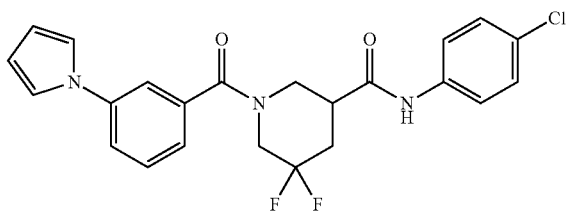 [SMILES: O=C(Nc1ccc(Cl)cc1)C1CN(C(=O)c2cccc(-n3cccc3)c2)CC(F)(F)C1]

The above compound was prepared by following the general procedure for amide coupling described in Example 33 (77 mg, 79%). $^1$H NMR (400 MHz, CDCl$_3$, 50° C.) (rotamers) δ 9.44, 9.06, 7.90, 7.81, 7.71, 7.51, 7.43, 7.31, 7.18, 6.47, 5.01, 4.82, 3.99, 3.42, 3.16, 2.96, 2.82, 2.37.

Example 68: N-(4-chlorophenyl)-5,5-difluoro-1-(3-(pyridin-4-yl)benzoyl)piperidine-3-carboxamide

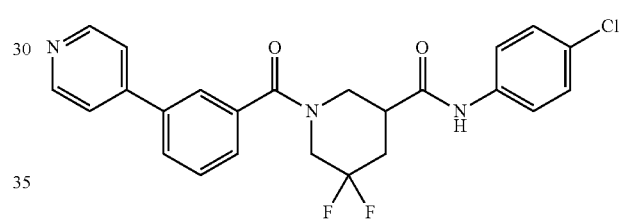

The above compound was prepared by following the general procedure for amide coupling described in Example 33 (78 mg, 94%). $^1$H NMR (400 MHz, DMSO-d6, 80° C.) δ 10.04, 8.65, 7.88, 7.76, 7.68, 7.62, 7.58, 7.50, 7.32, 4.31, 4.19, 3.57, 3.24, 3.00, 2.50, 2.31.

Example 69: N-(4-Chlorophenyl)-1-(5-methyl-2-phenyloxazole-4-carbonyl)piperidine-3-carboxamide

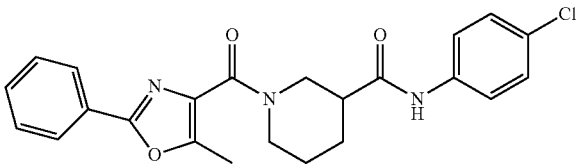 [SMILES: Cc1oc(-c2ccccc2)nc1C(=O)N1CCCC(C(=O)Nc2ccc(Cl)cc2)C1]

The above compound was prepared following the general procedure for amide coupling described in Example 33. (34 mg, 96%). 1H NMR (400 MHz, DMSO-d6, 80° C.) δ 9.93, 7.97-7.91, 7.63-7.57, 7.54-7.47, 7.34-7.28, 4.52, 4.35, 3.11, 2.64, 2.53, 2.08-1.99, 1.88-1.74, 1.55.

Example 70: 1-(2-(1H-Benzo[d]imidazol-2-yl)acetyl)-N-(4-chlorophenyl)-5,5-difluoropiperidine-3-carboxamide

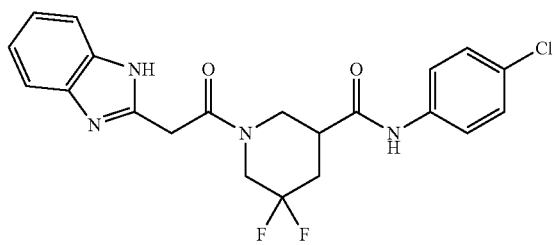 [SMILES: O=C(Nc1ccc(Cl)cc1)C1CN(C(=O)Cc2nc3ccccc3[nH]2)CC(F)(F)C1]

The above compound was prepared following the general procedure for amide coupling described in Example 33. (14 mg, 44%). $^1$H NMR (400 MHz, DMSO-d6, 80° C.) δ 12.13, 10.13, 7.66-7.59, 7.49, 7.39-7.30, 7.17-7.09, 4.65-4.33, 4.27-4.05, 3.48-3.26, 2.93, 2.47-2.19.

Example 71: 1-(2-(Benzofuran-2-yl)acetyl)-N-(4-chlorophenyl)piperidine-3-carboxamide

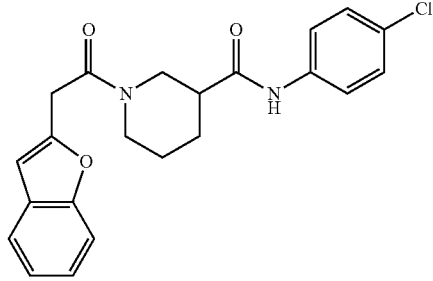 [SMILES: O=C(Nc1ccc(Cl)cc1)C1CCCN(C(=O)Cc2cc3ccccc3o2)C1]

The above compound was prepared following the general procedure for amide coupling described in Example 33. (30 mg, 90%). $^1$H NMR (400 MHz, DMSO-d6, 80° C.) δ 9.87, 7.63-7.54, 7.47, 7.35-7.30, 7.26-7.18, 6.69, 4.01, 3.08, 2.84, 2.51, 1.98, 1.79-1.68, 1.47-1.37.

Example 72: N-(4-Chlorophenyl)-1-(4-methyl-2-phenylthiazole-5-carbonyl)piperidine-3-carboxamide

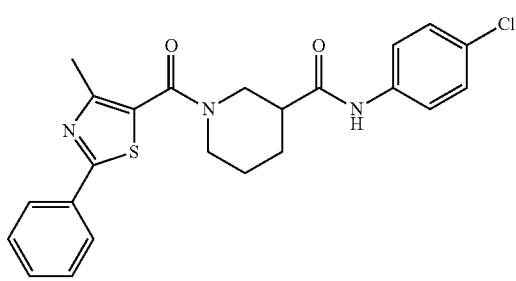 [SMILES: Cc1nc(-c2ccccc2)sc1C(=O)N1CCCC(C(=O)Nc2ccc(Cl)cc2)C1]

The above compound was prepared following the general procedure for amide coupling described in Example 33. (35 mg, 95%). $^1$H NMR (400 MHz, DMSO-d6, 80° C.) δ 9.91, 7.93-7.86, 7.62-7.57, 7.52-7.47, 7.34-7.29, 4.15, 3.86, 3.35-3.18, 2.60, 2.44-2.40, 2.02, 1.80, 1.56-1.42.

Example 73: N-(4-Chlorophenyl)-1-(2-phenylthiazole-4-carbonyl)piperidine-3-carboxamide

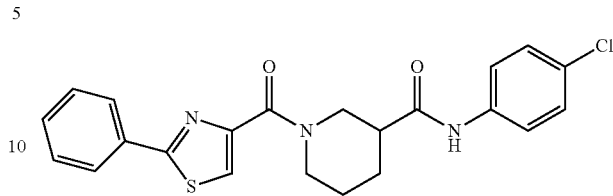

The above compound was prepared following the general procedure for amide coupling described in Example 33. (30 mg, 84%). $^1$H NMR (400 MHz, DMSO-d6, 80° C.) δ 9.95, 8.08, 7.99-7.92, 7.60, 7.49, 7.37-7.28, 4.50, 4.29, 3.14-3.04, 2.69, 2.05, 1.87-1.72, 1.64-1.49.

Example 74: 1-(Benzo[d]thiazole-5-carbonyl)-N-(4-chlorophenyl)piperidine-3-carboxamide

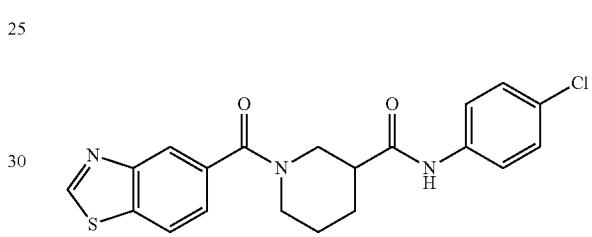

The above compound was prepared following the general procedure for amide coupling described in Example 33. (25 mg, 75%). $^1$H NMR (400 MHz, DMSO-d6, 80° C.) δ 9.90, 9.43, 8.21, 8.07, 7.58, 7.49, 7.35-7.27, 4.43-3.66, 3.31-3.18, 3.15-3.10, 2.67-2.57, 2.09-1.99, 1.84-1.73, 1.57-1.46.

Example 75: 1-(1H-Benzo[d]imidazole-2-carbonyl)-N-(4-chlorophenyl)-5,5-difluoropiperidine-3-carboxamide

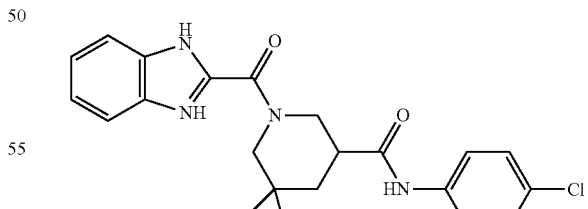

The above compound was prepared following the general procedure for amide coupling described in Example 33. (32 mg, 84%). $^1$H NMR (400 MHz, DMSO-d6, 80° C.) δ 13.03, 10.17, 7.71-7.59, 7.38-7.28, 3.99-3.41, 4.77, 2.50-2.33, 3.04-2.93.

Example 76: N-(4-Chlorophenyl)-5,5-difluoro-1-(1H-indole-6-carbonyl)piperidine-3-carboxamide

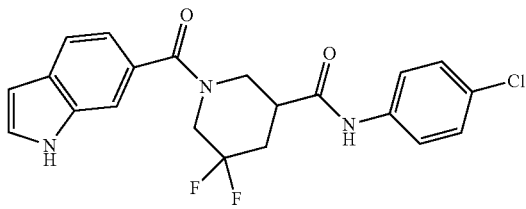 [SMILES: O=C(Nc1ccc(Cl)cc1)C1CN(C(=O)c2ccc3cc[nH]c3c2)CC(F)(F)C1]

The above compound was prepared following the general procedure for amide coupling described in Example 33. (45 mg, 99%). $^1$H NMR (500 MHz, DMSO-d6, 50° C.) δ 11.24, 10.25, 7.61, 7.50, 7.47, 7.38-7.33, 7.09-7.05, 4.53-4.11, 6.53-6.48, 3.70-3.45, 3.20-3.12, 3.00-2.90, 2.36-2.21, 2.48-2.43.

Example 77: N-(4-Chlorophenyl)-1-(2-(2-(4-fluorophenyl)thiazol-4-yl)-2-methylpropanoyl)-piperidine-3-carboxamide

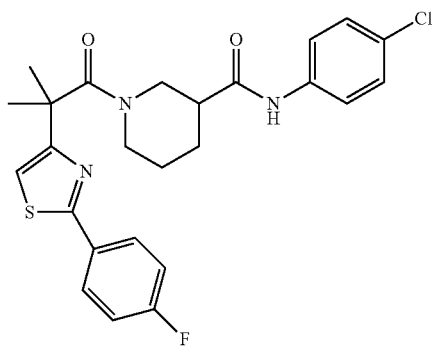 [SMILES: CC(C)(C(=O)N1CCCC(C(=O)Nc2ccc(Cl)cc2)C1)c1csc(-c2ccc(F)cc2)n1]

The above compound was prepared following the general procedure for amide coupling described in Example 33. (53 mg, 87%). $^1$H NMR (400 MHz, DMSO-d6, 80° C.) δ 9.76, 7.95-7.89, 7.55, 7.44, 7.32-7.23, 4.24, 3.90-3.77, 2.82, 2.70-2.62, 2.34-2.24, 1.85, 1.56, 1.53-1.41, 1.08.

Example 78: N-(4-Chlorophenyl)-1-(2-(2-(4-fluorophenyl)thiazol-4-yl)acetyl)piperidine-3-carboxamide

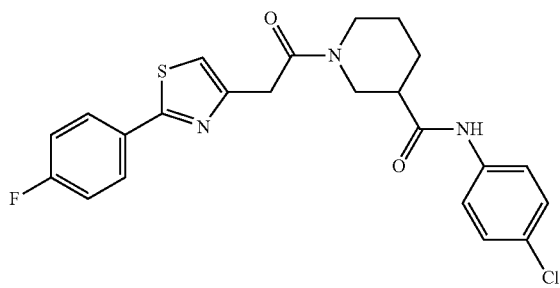 [SMILES: O=C(Nc1ccc(Cl)cc1)C1CCCN(C(=O)Cc2csc(-c3ccc(F)cc3)n2)C1]

The above compound was prepared following the general procedure for amide coupling described in Example 33. (55 mg, 96%). $^1$H NMR (400 MHz, DMSO-d6, 80° C.) δ 9.85, 7.87-8.03, 7.55-7.65, 7.42, 7.19-7.37, 4.03-4.55, 3.87-4.01, 3.14-3.43, 2.66-2.96, 2.40-2.48, 1.92-2.06, 1.65-1.81, 1.32-1.49.

Example 79: N-(4-Chlorophenyl)-1-(6-fluoro-1H-indole-2-carbonyl)piperidine-3-carboxamide

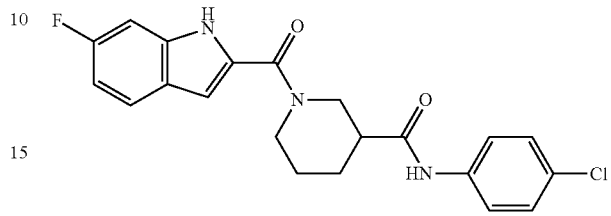

The above compound was prepared following the general procedure for amide coupling described in Example 33. (37 mg, 74%). $^1$H NMR (400 MHz, DMSO-d6, 80° C.) δ 11.42, 9.91, 7.74-7.53, 7.42-7.27, 7.20-7.12, 6.98-6.79, 4.58-4.43, 4.40-4.25, 3.40-3.26, 2.67-2.59, 2.17-2.02, 1.95-1.76, 1.69-1.48.

Example 80: N-(4-Chlorophenyl)-1-(1H-indole-2-carbonyl)piperidine-3-carboxamide

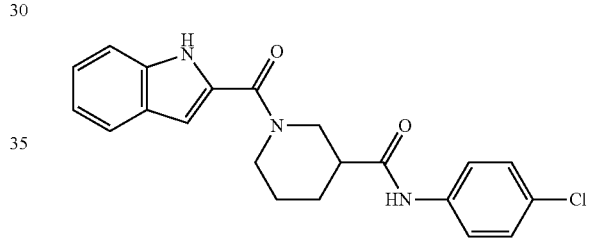

The above compound was prepared following the general procedure for amide coupling described in Example 33. (43 mg, 90%). $^1$H NMR (400 MHz, DMSO-d6, 80° C.) δ 11.32, 9.92, 7.70-7.56, 7.44, 7.39-7.29, 7.18, 7.04, 6.78, 4.64-4.46, 4.45-4.22, 3.36-3.16, 2.71-2.59, 2.14-2.02, 1.94-1.76, 1.66-1.49.

Example 81: N-(4-Chlorophenyl)-1-(5-methoxy-1H-indole-2-carbonyl)piperidine-3-carboxamide

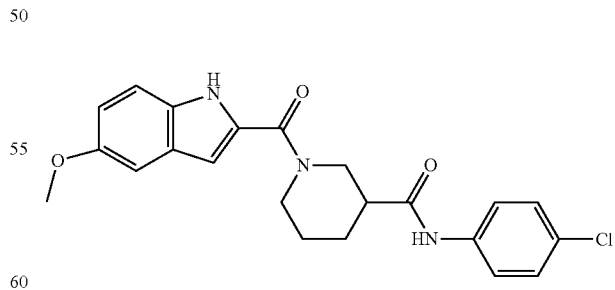

The above compound was prepared following the general procedure for amide coupling described in Example 33. (38 mg, 93%). $^1$H NMR (400 MHz, DMSO-d6, 80° C.) δ 11.17, 9.92, 7.67-7.57, 7.40-7.29, 7.07, 6.85, 6.74-6.67, 4.60-4.44, 4.40-4.28, 3.77, 3.42-3.22, 2.67-2.59, 2.12-2.02, 1.90-1.76, 1.62-1.49.

Example 82: N-(4-Chlorophenyl)-1-(1H-indazole-5-carbonyl)piperidine-3-carboxamide

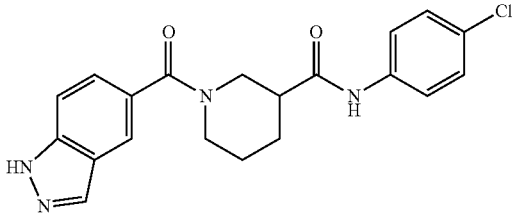 [SMILES: O=C(Nc1ccc(Cl)cc1)C1CCCN(C(=O)c2ccc3[nH]ncc3c2)C1]

The above compound was prepared following the general procedure for amide coupling described in Example 33. (16 mg, 33%). $^1$H NMR (400 MHz, DMSO-d6, 80° C.) δ 13.08, 9.92, 8.13, 7.91-7.84, 7.68-7.58, 7.46-7.32, 4.31-4.16, 4.03-3.89, 3.28-3.20, 3.17-3.12, 2.69-2.60, 2.11-2.02, 1.88-1.75, 1.60-1.47.

Example 83: 1-(3-(1H-Indol-3-yl)propanoyl)-N-(4-chlorophenyl)piperidine-3-carboxamide

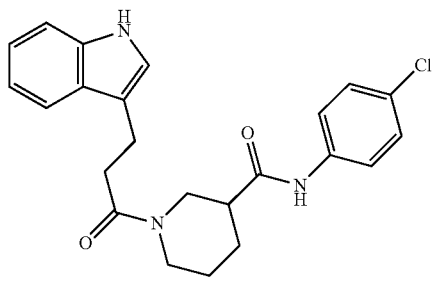 [SMILES: O=C(Nc1ccc(Cl)cc1)C1CCCN(C(=O)CCc2c[nH]c3ccccc23)C1]

The above compound was prepared following the general procedure for amide coupling described in Example 33. (43 mg, 83%). $^1$H NMR (400 MHz, DMSO-d6, 80° C.) δ 10.58, 9.89, 7.68-7.58, 7.57-7.49, 7.40-7.29, 7.17-6.93, 4.62-3.71, 3.10, 3.07-2.88, 2.79-2.71, 2.50, 2.05-1.92, 1.81-1.67, 1.46-1.31.

Example 84: 1-(2-(1H-Indol-3-yl)acetyl)-N-(4-chlorophenyl)piperidine-3-carboxamide

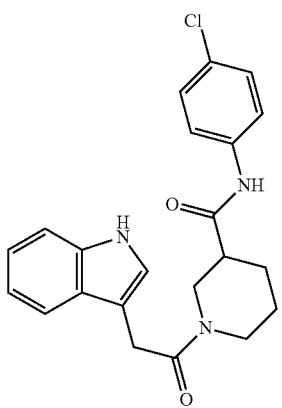 [SMILES: O=C(Nc1ccc(Cl)cc1)C1CCCN(C(=O)Cc2c[nH]c3ccccc23)C1]

The above compound was prepared following the general procedure for amide coupling described in Example 33. (36 mg, 72%). $^1$H NMR (400 MHz, DMSO-d6, 80° C.) δ 10.72, 9.85, 7.68-7.54, 7.42-7.29, 7.19, 7.10, 6.99, 4.64-3.94, 3.91-3.75, 3.07-2.63, 2.47-2.38, 2.02-1.89, 1.76-1.63, 1.37-1.22.

Example 85: N-(4-Chlorophenyl)-1-(1H-indazole-4-carbonyl)piperidine-3-carboxamide

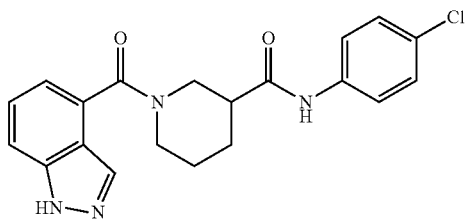 [SMILES: O=C(Nc1ccc(Cl)cc1)C1CCCN(C(=O)c2cccc3[nH]ncc23)C1]

The above compound was prepared following the general procedure for amide coupling described in Example 33. (36 mg, 75%). $^1$H NMR (400 MHz, DMSO-d6, 80° C.) δ 13.13, 9.92, 8.04, 7.70-7.58, 7.44-7.39, 7.38-7.33, 7.14, 4.38-4.07, 3.97-3.75, 3.32-3.26, 3.15-3.08, 2.69-2.60, 2.11-2.02, 1.85-1.75, 1.54-1.44.

Example 86: N-(4-Chlorophenyl)-1-(1H-indole-6-carbonyl)piperidine-3-carboxamide

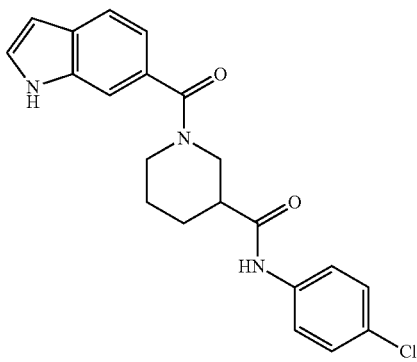 [SMILES: O=C(Nc1ccc(Cl)cc1)C1CCCN(C(=O)c2ccc3cc[nH]c3c2)C1]

The above compound was prepared following the general procedure for amide coupling described in Example 33. (39 mg, 81%). $^1$H NMR (400 MHz, DMSO-d6, 80° C.) δ 11.10, 9.92, 7.65-7.55, 7.51-7.40, 7.38-7.29, 7.10-7.03, 6.53-6.41, 4.34-4.15, 4.07-3.89, 3.26-3.15, 3.11-3.03, 2.67-2.57, 2.12-1.97, 1.86-1.70, 1.59-1.43.

Example 87: N-(4-Chlorophenyl)-1-(1H-indole-5-carbonyl)piperidine-3-carboxamide

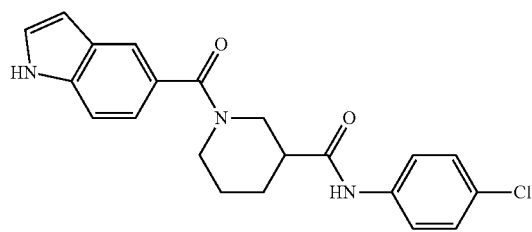 [SMILES: O=C(Nc1ccc(Cl)cc1)C1CCCN(C(=O)c2ccc3[nH]ccc3c2)C1]

The above compound was prepared following the general procedure for amide coupling described in Example 33. (39 mg, 81%). ¹H NMR (400 MHz, DMSO-d6, 80° C.) δ 11.12, 9.93, 7.68-7.58, 7.48-7.43, 7.41, 7.38-7.31, 7.20-7.15, 6.56-6.48, 4.33-4.19, 4.10-3.95, 3.24-3.16, 3.12-3.03, 2.68-2.58, 2.11-2.01, 1.87-1.74, 1.58-1.46.

Example 88: N-(4-Chlorophenyl)-1-(1H-indazole-3-carbonyl)piperidine-3-carboxamide

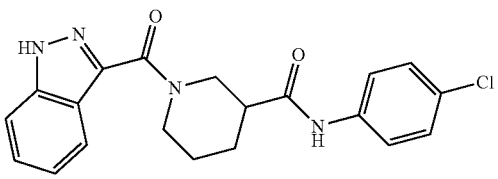 [SMILES: O=C(Nc1ccc(Cl)cc1)C1CCCN(C(=O)c2n[nH]c3ccccc23)C1]

The above compound was prepared following the general procedure for amide coupling described in Example 33. (38 mg, 79%). ¹H NMR (400 MHz, DMSO-d6, 80° C.) δ 13.31, 9.94, 8.04-7.97, 7.70-7.54, 7.48-7.39, 7.39-7.29, 7.28-7.19, 4.85-4.73, 4.65-4.56, 3.43-3.14, 2.73-2.61, 2.15-2.04, 1.92-1.75, 1.65-1.47.

Example 89: 1-(1H-Benzo[d]imidazole-2-carbonyl)-N-(4-chlorophenyl)piperidine-3-carboxamide

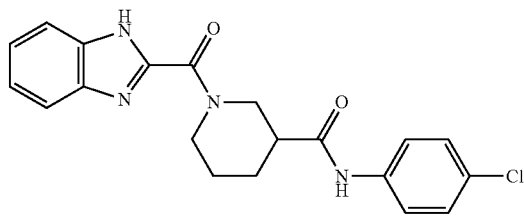 [SMILES: O=C(Nc1ccc(Cl)cc1)C1CCCN(C(=O)c2nc3ccccc3[nH]2)C1]

The above compound was prepared following the general procedure for amide coupling described in Example 33. (29 mg, 60%). ¹H NMR (400 MHz, DMSO-d6, 80° C.) δ 13.07-12.71, 9.97, 7.86-7.51, 7.42-7.19, 5.56-5.17, 4.81-4.25, 3.90-3.22, 2.77-2.63, 2.18-2.04, 1.98-1.79, 1.69-1.55.

Example 90: 1-(2-(1H-Pyrazol-1-yl)benzoyl)-N-(4-chlorophenyl)piperidine-3-carboxamide

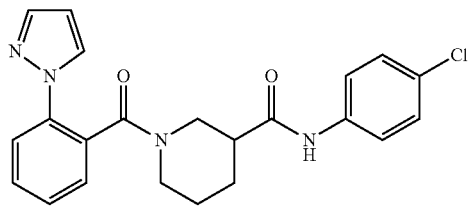 [SMILES: O=C(Nc1ccc(Cl)cc1)C1CCCN(C(=O)c2ccccc2-n2cccn2)C1]

The above compound was prepared following the general procedure for amide coupling described in Example 33. (57 mg, 67%). ¹H NMR (400 MHz, DMSO-d6, 80° C.) δ 9.82, 7.99-7.88, 7.67-7.59, 7.59-7.32, 7.31-7.14, 6.41, 4.40, 3.30-3.07, 2.96-2.54, 1.97-1.65, 1.58-1.37.

Example 91: 1-(2-(1H-Imidazol-1-yl)benzoyl)-N-(4-chlorophenyl)piperidine-3-carboxamide

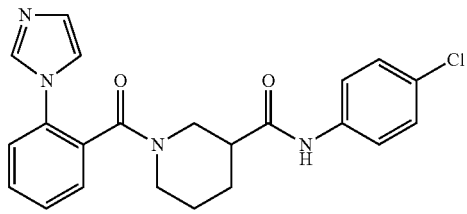 [SMILES: O=C(Nc1ccc(Cl)cc1)C1CCCN(C(=O)c2ccccc2-n2ccnc2)C1]

The above compound was prepared following the general procedure for amide coupling described in Example 33. (56 mg, 65%). ¹H NMR (400 MHz, DMSO-d6, 80° C.) δ 9.91, 7.78, 7.60-7.53, 7.49, 7.43-7.38, 7.35-7.24, 7.07, 4.51-4.37, 3.32-3.02, 2.99-2.69, 2.00-1.69, 1.62-1.46.

Example 92: N-(4-Chlorophenyl)-1-(2-(furan-2-yl)benzoyl)piperidine-3-carboxamide

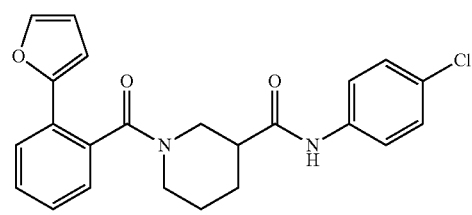 [SMILES: O=C(Nc1ccc(Cl)cc1)C1CCCN(C(=O)c2ccccc2-c2ccco2)C1]

The above compound was prepared following the general procedure for amide coupling described in Example 33. (48 mg, 56%). ¹H NMR (400 MHz, DMSO-d6, 80° C.) δ 9.96, 7.81-7.68, 7.65-7.45, 7.42-7.31, 7.26, 6.81-6.50, 4.71-4.49, 3.37-3.10, 3.08-2.80, 2.77-2.53, 2.12-1.82, 1.75-1.62, 1.59-1.24.

Example 93: N-(4-Chlorophenyl)-1-(1H-indazole-6-carbonyl)piperidine-3-carboxamide

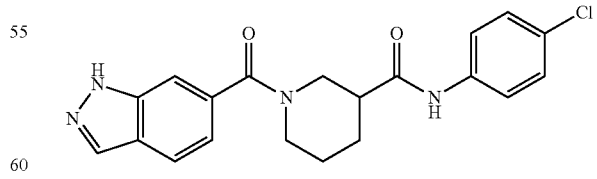

The above compound was prepared following the general procedure for amide coupling described in Example 33. (62 mg, 77%). ¹H NMR (500 MHz, DMSO-d6, 50° C.) δ 13.13, 10.02, 8.11, 7.81, 7.59, 7.54, 7.35-7.30, 7.10, 4.50-3.41, 3.17-2.97, 2.06-1.99, 1.80-1.70, 1.47, 1.25.

Example 94: 1-(Benzofuran-5-carbonyl)-N-(4-chlorophenyl)piperidine-3-carboxamide

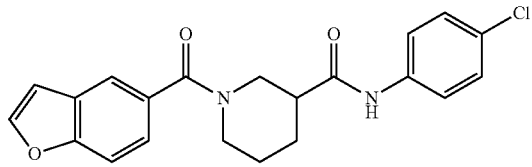 [SMILES: O=C(Nc1ccc(Cl)cc1)C1CCCN(C(=O)c2ccc3occc3c2)C1]

The above compound was prepared following the general procedure for amide coupling described in Example 33. (76 mg, 95%). $^1$H NMR (500 MHz, Chloroform-d, 50° C.) δ 9.08, 7.71-7.54, 7.51, 7.32, 7.25-7.23, 6.80-6.75, 4.22, 3.93-3.88, 3.51, 2.70, 2.30, 1.93, 1.64-1.48.

Preparation 1: Methyl 1-(3-(furan-2-yl)benzoyl)piperidine-3-carboxylate

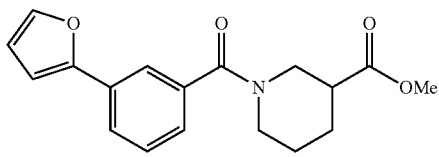 [SMILES: COC(=O)C1CCCN(C(=O)c2cccc(-c3ccco3)c2)C1]

To the solution of 3-(furan-2-yl)benzoic acid (0.21 g, 1.12 mmole), DMAP (20 mg, 0.16 mmole) and piperidine carboxylate (0.184 g, 1.28 mmole) in DCM (7 mL) was added EDC (0.24 g, 1.23 mmole). The reaction mixture was stirred at RT for 6 h. TLC indicated formation of product, however, the reaction was allowed to proceed at RT for overnight. The reaction mixture was extracted with satd. NaHCO$_3$ (10 mL), 10% KHSO$_4$ (10 mL) and brine (10 mL). The solution was dried (NaSO$_4$) and the solvent was removed under reduced pressure to yield the crude compound. The crude compound was applied on a filled column of silicagel (25 g) and eluted with 10-20% EtOAc/hexanes over 400 mL followed by up to 45% EtOAc/hexanes over 150 mL. Fractions were pooled after checking TLC. Yield: 0.17 g (49%).

Preparation 2: 1-(3-(Furan-2-yl)benzoyl)piperidine-3-carboxylic acid

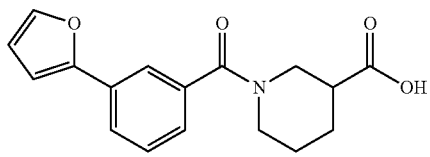 [SMILES: O=C(O)C1CCCN(C(=O)c2cccc(-c3ccco3)c2)C1]

To the solution of methyl 1-(3-(furan-2-yl)benzoyl)piperidine-3-carboxylate (0.17 g, 0.54 mmole) in THF (2 mL) and H$_2$O (5 mL) was added LiOH (0.104 g, 4.43 mmole). The reaction mixture was stirred at RT for 2 h. TLC indicated completion of reaction. The reaction mixture was diluted with H$_2$O (3 mL) and acidified with 2N HCl to pHl. The solution was extracted with EtOAc (2×10 mL), the combined organic layer was washed with brine (2×10 mL), dried (NaSO$_4$). The solvent was removed under reduced pressure to yield the product. Yield: 160 mg 99%)

Example 95: 1-(3-(Furan-2-yl)benzoyl)-N-(4-(methylsulfonyl)phenyl)piperidine-3-carboxamide

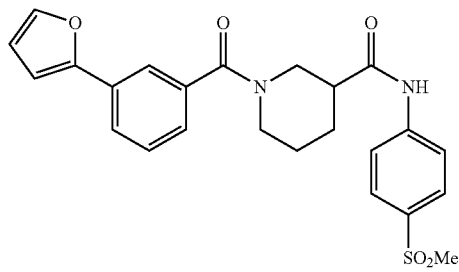 [SMILES: CS(=O)(=O)c1ccc(NC(=O)C2CCCN(C(=O)c3cccc(-c4ccco4)c3)C2)cc1]

To the solution of piperidine carboxylic acid derivative (0.044 g, 0.147 mmole), DMAP (7 mg, 0.057 mmole) and the aniline derivative (0.025 g, 0.147 mmole) in DMF (1.4 mL) was added HATU (0.061 g, 0.162 mmole). The reaction mixture was stirred at RT for 4 h. TLC indicated still the presence of starting materials. The reaction was allowed to stir at RT for 20 h. TLC indicated some formation of product but still there was appreciable starting materials left in the reaction mixture. The reaction mixture was allowed to stir at RT for 65 h. The reaction was worked up by pouring on ice water. The precipitate became sticky, it was extracted with EtOAc (2×7 mL), washed with water (5 mL) and brine (5 mL). The solution was dried (NaSO$_4$) and the solvent was removed under reduced pressure to give the crude product. The crude compound was applied on flash column of silicagel (4 g) and eluted with 50-80% EtOAc/hexanes over 300 mL at 12 mL/minute. Fractions were pooled after checking TLC. Yield: 13 mg (20%). $^1$H NMR (500 MHz, Chloroform-d, 50° C.) δ 9.48, 7.91-7.85, 7.77-7.67, 7.47-7.46, 7.42, 7.24, 6.66, 6.48-6.47, 4.38, 3.88-3.80, 3.64-3.37, 3.02, 2.83-2.72, 2.47-2.29, 1.99-1.87, 1.61-1.52.

Example 96: N-(4-Chlorophenyl)-5,5-difluoro-1-(3-(pyridin-2-yl)benzoyl)piperidine-3-carboxamide

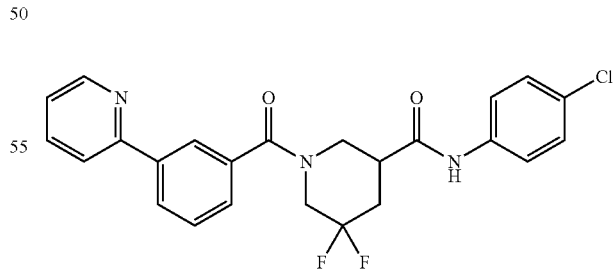

The above compound was prepared following the general procedure for amide coupling described in Example 33. (47 mg, 94%). $^1$H NMR (500 MHz, DMSO-d6, 50° C.) δ 10.24, 8.71-8.67, 8.21-8.17, 8.15-8.12, 8.01-7.97, 7.93-7.88, 7.67-7.54, 7.48, 7.41-7.31, 4.84-3.48, 3.21, 3.01-2.89, 2.52-2.43, 2.39-2.22.

Example 97: N-(2,6-Difluorophenyl)-1-(3-(furan-2-yl)benzoyl)piperidine-3-carboxamide

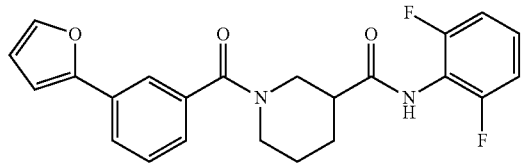 [SMILES: O=C(Nc1c(F)cccc1F)C1CCCN(C(=O)c2cccc(-c3ccco3)c2)C1]

To the solution of 1-(3-(furan-2-yl)benzoyl)piperidine-3-carboxylic acid (0.052 g, 0.167 mmole) and CDI (33 mg, 0.2 mmole) in THF (3 mL) was stirred at RT for 1 h. Then the aniline derivative (26 mg, 0.2 mmole) was added. The reaction mixture was stirred at Reflux for 24 h.

Then the reaction mixture was allowed to cool to RT. Water was added and extracted with EtOAc (2×7 mL). The combined organic layer was washed with water (5 mL), dried (NaSO$_4$) and the solvent was removed under reduced pressure to give the crude product. The crude compound was applied on flash column of silicagel (4 g) and eluted with 20-50% EtOAc/hexanes over 350 mL. Fractions collected were pooled after checking TLC. Yield: 15 mg (22%). $^1$H NMR (500 MHz, Chloroform-d, 50° C.) δ 8.27, 7.73-7.67, 7.48-7.45, 7.42-7.38, 7.29-7.26, 7.20-7.13, 6.90, 6.69-6.64, 6.49-6.45, 4.18-3.92, 3.67-3.21, 2.83-2.63, 2.31-2.12, 2.04-1.93, 1.73-1.63, 1.59-1.49.

Example 98: 1-(3-(1H-Imidazol-2-yl)benzoyl)-N-(4-chlorophenyl)-5,5-difluoropiperidine-3-carboxamide

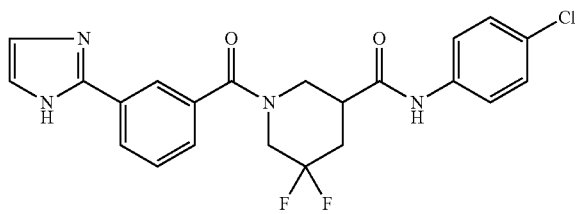 [SMILES: O=C(Nc1ccc(Cl)cc1)C1CN(C(=O)c2cccc(-c3ncc[nH]3)c2)CC(F)(F)C1]

The above compound was prepared following the general procedure for amide coupling described in Example 33. (56 mg, 69%). $^1$H NMR (400 MHz, DMSO-d6, 75° C.) δ 12.43, 10.10, 8.04-8.01, 7.99-7.97, 4.48-3.99, 7.58, 7.52, 7.36-7.31, 7.18-7.06, 3.63-3.45, 3.30-3.17, 2.96-2.89, 2.42-2.18.

Example 99: N-(4-Chlorophenyl)-5,5-difluoro-1-(3-(pyrimidin-5-yl)benzoyl)piperidine-3-carboxamide

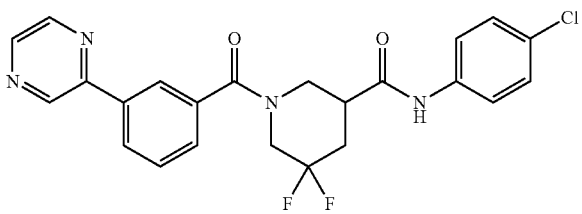 [SMILES: O=C(Nc1ccc(Cl)cc1)C1CN(C(=O)c2cccc(-c3cnccn3)c2)CC(F)(F)C1]

The above compound was prepared following the general procedure for amide coupling described in Example 33. (42 mg, 84%). $^1$H NMR (400 MHz, DMSO-d6, 75° C.) δ 10.09, 9.17, 9.13-9.08, 7.89-7.86, 7.78-7.75, 7.64-7.60, 7.58-7.53, 7.50-7.46, 7.33-7.28, 4.49-3.95, 3.65-3.46, 3.30-3.15, 2.98-2.88, 2.42-2.13.

Example 100: N-(4-Chlorophenyl)-5,5-difluoro-1-(3-(pyridin-3-yl)benzoyl)piperidine-3-carboxamide

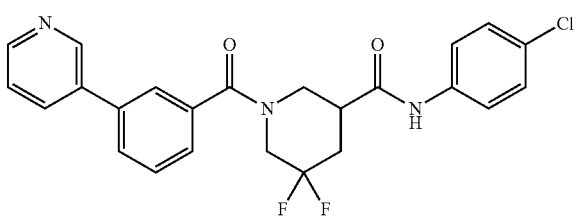 [SMILES: O=C(Nc1ccc(Cl)cc1)C1CN(C(=O)c2cccc(-c3cccnc3)c2)CC(F)(F)C1]

The above compound was prepared following the general procedure for amide coupling described in Example 33. (24 mg, 48%). $^1$H NMR (400 MHz, DMSO-d6, 75° C.) δ 10.13, 8.92-8.87, 8.62-8.56, 8.09-8.03, 7.86-7.80, 7.70, 7.63-7.56, 7.50-7.44, 7.35-7.31, 4.53, 3.67-3.47, 3.30-3.14, 3.09, 3.00-2.89, 2.44-2.19.

Example 101: N-(2-Chlorophenyl)-1-(3-(furan-2-yl)benzoyl)piperidine-3-carboxamide

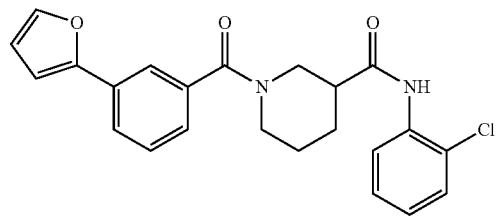 [SMILES: O=C(Nc1ccccc1Cl)C1CCCN(C(=O)c2cccc(-c3ccco3)c2)C1]

The above compound was prepared following the procedure for amide coupling described in Example 95. (6 mg, 16%). $^1$H NMR (500 MHz, Chloroform-d, 50° C.) δ 8.30-8.22, 7.76-7.67, 7.47-7.45, 7.41, 7.35, 7.30-7.27, 7.27-7.22, 7.08-6.99, 6.70-6.65, 6.50-6.43, 4.66, 3.37-3.26, 3.20-2.97, 2.58, 2.18-2.10, 2.02-1.91, 1.89-1.75, 1.67-1.52.

Preparation 3: 1-((4-(1H-Pyrazol-1-yl)phenyl)(butoxy)methyl)-N-(4-chlorophenyl)-piperidine-3-carboxamide

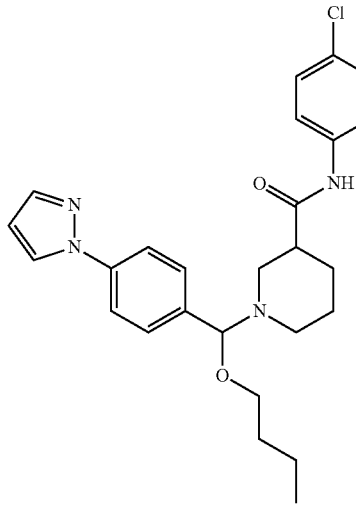

Mixture of 4-(1H-pyrazol-1-yl)benzaldehyde (51 mg, 0.297 mmole), N-(4-chlorophenyl)piperidine-3-carboxamide (85 mg, 0.356 mmole), $K_2CO_3$ (41 mg, 0.297 mmole) and n-BuOH (0.5 mL, 5.46 mmole) was heated at 75° C. for 24 h. DCM was added and the mixture was filtered with the aid of celite. The solvent was removed under reduced pressure at 80° C. The residue was used as such without purification in the below reaction. Yield: 0.11 g (79%).

Example 102: 1-(1-(4-(1H-Pyrazol-1-yl)phenyl)ethyl)-N-(4-chlorophenyl)piperidine-3-carboxamide (Diastereomer B)

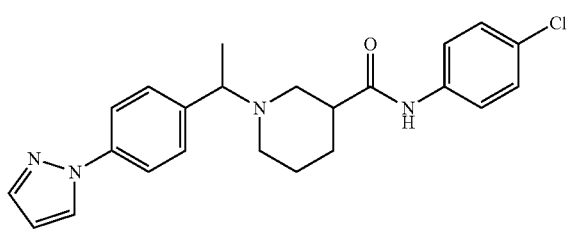 [SMILES: CC(c1ccc(-n2cccn2)cc1)N1CCCC(C(=O)Nc2ccc(Cl)cc2)C1]

To a solution of the compound (0.11 g, 0.236 mmole) in ether (7 mL) was added slowly MeMgBr (3M in ether, 0.2 mL, 0.471 mmole). The reaction mixture was stirred at RT for 24 h. Then it was quenched with ice cold saturated ammonium chloride solution and the solution was basified with 10% NaOH solution. It was extracted with EtOAc (2×15 mL). The combined organic portion was washed with water (10 mL), dried ($Na_2SO_4$) and the solvent was removed under reduced pressure. The crude compound was applied on a 10 g biotage column and first eluted with 50% EtOAc/hexanes over 150 mL. Followed by up 80% (1% 2N NH3-EtOAc/hexanes). The fractions were pooled after checking TLC. Yield: 22 mg (23%). $^1$H NMR (500 MHz, Chloroform-d) δ 10.40, 7.92-7.88, 7.73-7.65, 7.52-7.47, 7.38-7.35, 7.30-7.26, 6.48-6.44, 3.63, 3.31-3.19, 2.95-2.87, 2.67-2.61, 2.42-2.34, 2.09-2.01, 1.79-1.68, 1.62-1.55, 1.51.

Example 103: 1-(1-(4-(1H-Pyrazol-1-yl)phenyl)ethyl)-N-(4-chlorophenyl)piperidine-3-carboxamide (Diastereomer A)

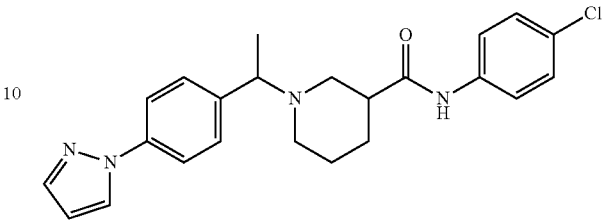

The above compound was prepared following the procedure of Example 102. (6 mg, 6%). $^1$H NMR (500 MHz, Chloroform-d, 50° C.) δ 10.58, 8.05-7.97, 7.92-7.89, 7.75-7.70, 7.68-7.62, 7.56-7.49, 7.36-7.28, 6.55-6.44, 3.68, 3.11-3.03, 2.68-2.56, 2.33-2.11, 2.07-1.97, 1.83-1.73, 1.68-1.48.

Example 104: N-(4-Cyanophenyl)-1-(3-(furan-2-yl)benzoyl)piperidine-3-carboxamide

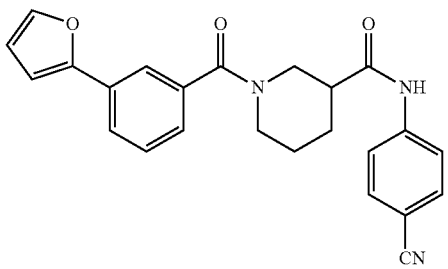 [SMILES: N#Cc1ccc(NC(=O)C2CCCN(C(=O)c3cccc(-c4ccco4)c3)C2)cc1]

The above compound was prepared following the procedure for amide coupling described in Example 95. (14 mg, 32%). $^1$H NMR (500 MHz, Chloroform-d) δ 9.76, 7.82, 7.73, 7.68, 7.58, 7.47, 7.45-7.41, 7.24, 6.67, 6.49, 4.17-3.93, 3.62-3.44, 2.78-2.68, 2.34-2.20, 1.95-1.85, 1.66-1.50.

Example 105: N-(4-Fluorophenyl)-1-(3-(furan-2-yl)benzoyl)piperidine-3-carboxamide

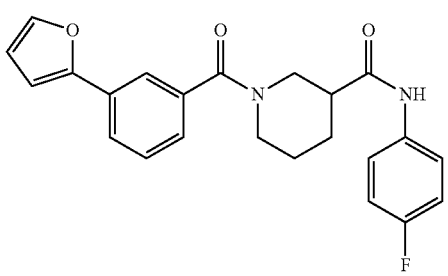 [SMILES: O=C(Nc1ccc(F)cc1)C1CCCN(C(=O)c2cccc(-c3ccco3)c2)C1]

The above compound was prepared following the procedure for amide coupling described in Example 33. (9 mg, 21%). $^1$H NMR (500 MHz, Chloroform-d) δ 9.01, 7.77-7.59, 7.49-7.38, 7.26-7.22, 7.07-6.95, 6.70-6.63, 6.51-6.44, 4.25-4.09, 4.04-3.93, 3.61-3.28, 2.73, 2.39-2.25, 1.95-1.85, 1.65-1.45.

Example 106: 1-(3-(1H-Pyrazol-4-yl)benzoyl)-N-(4-chlorophenyl)-5,5-difluoropiperidine-3-carboxamide

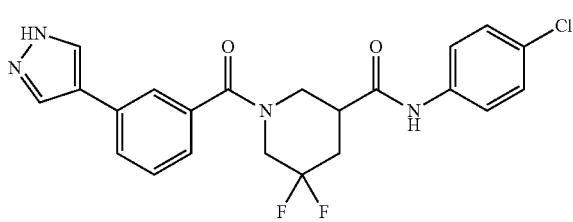 [SMILES: O=C(Nc1ccc(Cl)cc1)C1CN(C(=O)c2cccc(-c3cn[nH]c3)c2)CC(F)(F)C1]

The above compound was prepared following the procedure for amide coupling described in Example 33. (28 mg, 64%). ¹H NMR (500 MHz, Chloroform-d) δ 10.89, 9.24, 7.86, 7.63, 7.61-7.55, 7.53, 7.46, 7.33-7.27, 4.86-4.64, 4.10-3.91, 3.56-3.41, 3.40-3.31, 2.98-2.87, 2.61-2.44, 2.40-2.28.

Example 107: N-(4-Chlorophenyl)-1-(3-(furan-2-yl)benzoyl)pyrrolidine-3-carboxamide

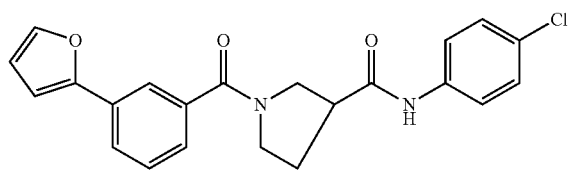 [SMILES: O=C(Nc1ccc(Cl)cc1)C1CCN(C(=O)c2cccc(-c3ccco3)c2)C1]

The above compound was prepared following the procedure for amide coupling described in Example 33. (81 mg, 92%). ¹H NMR (400 MHz, DMSO-d6, 80° C.) δ 9.96, 7.79-7.75, 7.73, 7.63-7.57, 7.49, 7.44-7.39, 7.36-7.29, 6.98, 6.59, 3.71-3.46, 2.23-2.18, 2.19-2.06.

Example 108: N-(4-Chlorophenyl)-1-(3-(furan-2-yl)benzoyl)-N-methylpiperidine-3-carboxamide

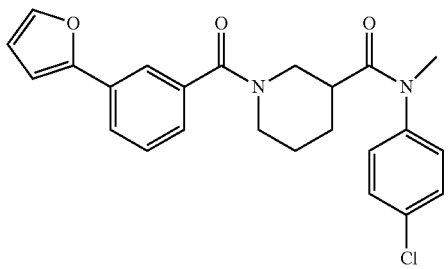 [SMILES: CN(C(=O)C1CCCN(C(=O)c2cccc(-c3ccco3)c2)C1)c1ccc(Cl)cc1]

The above compound was prepared following the procedure for amide coupling described in Example 33. (29 mg, 54%). ¹H NMR (400 MHz, Chloroform-d) δ 7.85-7.33, 7.15, 6.82, 6.69, 6.51, 4.62, 3.83-2.65, 2.38, 1.84, 1.38.

Example 109: 1-(4-(1H-Pyrrol-1-yl)benzoyl)-N-(4-chlorophenyl)piperidine-3-carboxamide

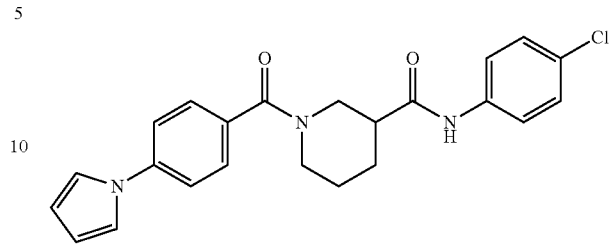

To the solution of 4-(1H-pyrrol-1-yl)benzaldehyde (0.022 g, 0.129 mmole) and N-(4-chlorophenyl)piperidine-3-carboxamide (0.04 g, 0.168 mmole) in dry MeCN (1.5 mL) was added t-BuOOH (0.04 mL, 5 M in decane, 0.168 mmole). The reaction mixture was stirred at reflux for 5 h. TLC indicated some presence of the starting materials. More of the TBHP (0.05 mL) was added and the reaction was refluxed for further 5 h. Then it was quenched with water (5 mL) and the organic portion was extracted with DCM (5 mL), washed with H₂O (3 mL) and the separated organic layer was dried (Na₂SO₄). The solvent was removed under reduced pressure.

The crude compound was applied on a filled column of silicagel (10 g) and eluted with 30-50% EtOAc/hexanes over 350 mL followed by up to 80% EtOAc/hexanes over 150 mL. Fractions were pooled after checking TLC. Yield: 0.11 g (21%). ¹H NMR (500 MHz, Chloroform-d) δ 9.13, 7.66, 7.48, 7.43, 7.29, 7.11, 6.38, 5.30, 4.25, 3.91, 3.56, 2.76, 2.41, 1.92, 1.68.

Example 110: 1-(4-(1H-Pyrrol-1-yl)benzyl)-N-(4-chlorophenyl)piperidine-3-carboxamide

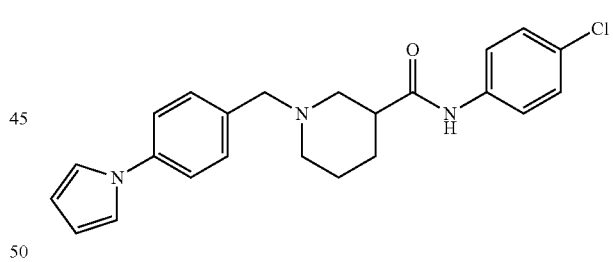

To the solution of 4-(1H-pyrrol-1-yl)benzaldehyde (0.029 g, 0.168 mmloe), AcOH (0.01 mL, 0.168 mmole) and N-(4-chlorophenyl)piperidine-3-carboxamide (0.04 g, 0.168 mmole) in THF (1 mL) was added NaBH(OAc)₃ (0.071 g, 0.335 mmole). The reaction mixture was stirred at RT for 6 h. TLC indicated some presence of the starting materials. The reaction was stirred at RT for further 18 h. The reaction was quenched with MeOH (2 mL) and water (10 mL). The organic portion was extracted with EtOAc, washed with 1N NaOH (2 mL), Brine (2 mL), and the separated organic layer was dried (Na₂SO₄). The solvent was removed under reduced pressure. The crude compound was applied on a filled column of silicagel (4 g) and eluted with 40-80% EtOAc/hexanes over 250 mL and then up to 100% EtOAc. Fractions were pooled after checking TLC. Yield: 0.04 g (61%). ¹H NMR (500 MHz, Chloroform-d) δ 10.43, 7.49-

7.45, 7.39-7.34, 7.28, 7.27, 7.07, 6.35, 3.59, 3.55, 3.14, 2.68-2.62, 2.35, 2.17, 2.07, 1.81-1.73, 1.66-1.59.

Example 111: 1-(3-(Furan-2-yl)benzoyl)-N-(p-tolyl)piperidine-3-carboxamide

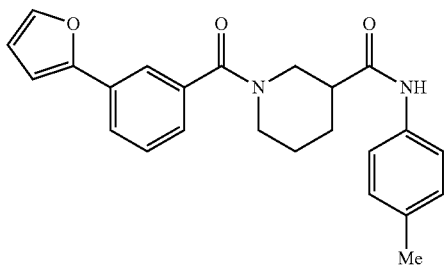

The above compound was prepared following the procedure for amide coupling described in Example 33. (44 mg, 81%). ¹H NMR (500 MHz, Chloroform-d) δ 8.63, 7.74-7.67, 7.51, 7.42, 7.26, 7.13, 6.67, 6.48, 4.06, 3.49, 2.70, 2.32, 1.94, 1.81-1.46.

Example 112: N-(4-Chlorobenzyl)-1-(3-(furan-2-yl)benzoyl)piperidine-3-carboxamide

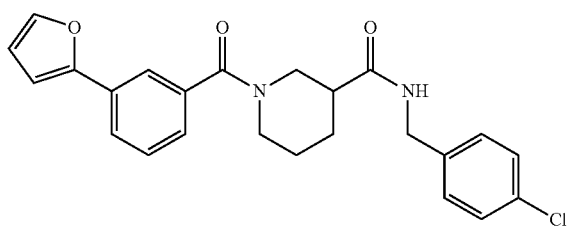 [SMILES: O=C(NCc1ccc(Cl)cc1)C1CCCN(C(=O)c2cccc(-c3ccco3)c2)C1]

The above compound was prepared following the procedure for amide coupling described in Example 33. (46 mg, 78%). ¹H NMR (500 MHz, Chloroform-d) δ 7.72-7.69, 7.59, 7.49, 7.39, 7.29, 7.25, 7.21-7.17, 7.08-7.04, 6.69-6.64, 6.51-6.46, 4.56, 4.37-4.29, 3.95, 3.44, 2.57, 2.24, 1.89, 1.55-1.49.

Example 113: N-(4-Chlorophenyl)-1-(4-(ethylamino)benzyl)piperidine-3-carboxamide

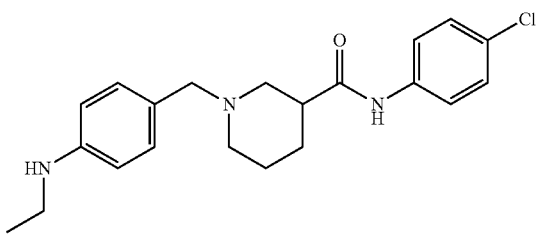 [SMILES: CCNc1ccc(CN2CCCC(C(=O)Nc3ccc(Cl)cc3)C2)cc1]

The above compound was prepared following the procedure for reductive amination described in Example 110. (32 mg, 51%). ¹H NMR (500 MHz, Chloroform-d, 50° C.) δ 10.55, 7.48-7.43, 7.26-7.23, 7.11-7.07, 6.58-6.53, 3.46, 3.37, 3.15, 3.01, 2.60, 2.23, 2.08, 1.78-1.67), 1.64-1.55, 1.25.

Example 114: 1-(4-(1H-Pyrazol-1-yl)benzyl)-N-(4-chlorophenyl)piperidine-3-carboxamide

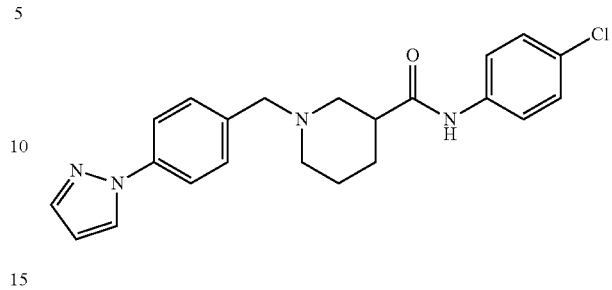

The above compound was prepared following the procedure for reductive amination described in Example 110. (33 mg, 50%). ¹H NMR (500 MHz, Chloroform-d, 50° C.) δ 10.47, 7.96-7.91, 7.77-7.66, 7.53-7.38, 7.32-7.26, 6.61-6., 3.68-3.52, 3.23-2.95, 2.72-2.60, 2.45-2.32, 2.24-2.03, 1.80-1.60.

Example 115: 1-(3-(1H-Imidazol-1-yl)benzoyl)-N-(4-chlorophenyl)piperidine-3-carboxamide

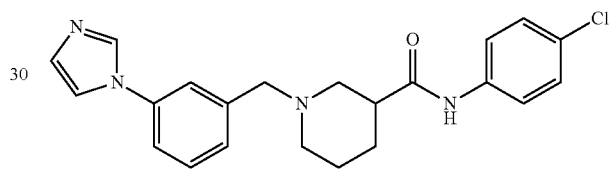

The above compound was prepared following the procedure for amide coupling described in Example 33. (53 mg, 62%). ¹H NMR (400 MHz, DMSO-d6, 80° C.) δ 9.89, 8.22, 7.71-7.67, 7.62-7.61, 7.60-7.54, 7.35-7.31, 7.29, 7.10, 3.30-3.14, 3.14-3.11, 3.08-3.04, 2.64-2.53, 2.04-1.98, 1.80-1.72, 1.53-1.44.

Aspects of the Disclosure

In one aspect, provided herein is a compound of Formula (I), or a pharmaceutically acceptable salt thereof:

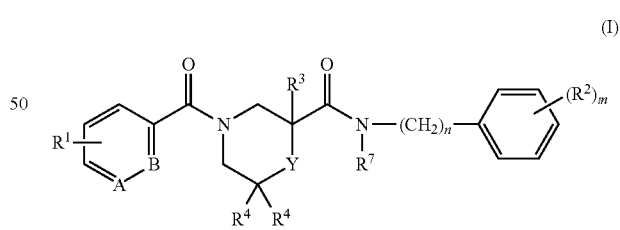

wherein:

m is 0, 1, or 2;

n is 0, 1, or 2;

one of A and B is $CR^6$ and the other is $CR^6$ or N;

Y is $CH_2$, C=O, CHOH, CHF, $CF_2$, $NR^5$, $NCONHR^5$, $NCOR^5$, $NCO_2R^5$, or $NSO_2R^5$;

$R^1$ is heteroaryl;

each $R^2$ independently is halo, $C_{1-6}$ alkyl, $OC_1$-$C_6$ alkyl, $OC_{0-6}$ alkylene-aryl, $OC_{0-6}$ alkylene-heteroaryl, or $SO_2NR^5{}_2$;

$R^3$ is H, halo, OH, $C_{1-3}$ alkyl, or $OC_{1-3}$ alkyl;

each $R^4$ independently is H, F, $C_{1-3}$ alkyl, $OR^5$, $NR^5_2$, $NR^5CONHR^5$, $NR^5COR^5$, $NR^5CO_2R^5$, $NR^5SO_2R^5$, or both $R^4$ together with the carbon to which they are attached form C=O, C=CH$_2$, or $C_{3-7}$ cycloalkyl;

each $R^5$ independently is H, $C_{1-6}$ alkyl, $C_{3-7}$ cycloalkyl, $C_{2-6}$ alkenyl, $C_{3-6}$ alkylene-ether, $C_{0-6}$ alkylene-aryl, $C_{0-6}$ alkylene-heteroaryl, or two $R^5$ together with a nitrogen to which they are attached form a 3-7 atom heterocyclic ring;

each $R^6$ independently is H, halo, $C_{1-3}$ haloalkyl, or $OC_{1-3}$ haloalkyl; and $R^7$ is H or $C_{1-3}$ alkyl;

with the proviso that when n is 0, m is 1, A and B are each CH, $R^2$ is chloro, each $R^4$ is H, and Y is CH$_2$, then $R^1$ is other than furanyl, thiophenyl, thiazolyl, oxazolyl, or oxadiazolyl.

The compound of paragraph [00316], wherein the compound comprises Formula (IA):

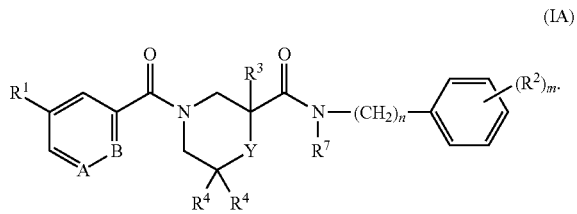

(IA)

The compound of paragraph [00316] or [00317], wherein n is 0.

The compound of any one of paragraphs [00316] to [00318], wherein A and B are each CH.

The compound of any one of paragraphs [00316] to [00318], wherein one of A or B is CH and the other is N.

The compound of any one of paragraphs [00316] to [00320], wherein Y is CH$_2$, $NR^5$, $NCONHR^5$, $NCOR^5$, or $NCO_2R^5$; and $R^5$ is $C_{1-6}$ alkyl, $C_{3-7}$ cycloalkyl, $C_{2-6}$ alkenyl, $C_{3-6}$ alkylene-ether, or $C_{0-6}$ alkylene-aryl.

The compound of paragraph [00321], wherein Y is CH$_2$, NMe, NCH$_2$Ph, NCONHiPr, NCONHPh, NCONH-cyclopentyl, NCONHCH$_2$CH=CH$_2$, NCOMe, NCOEt, NCOiPr, NCO(para-methoxyphenyl), NCO$_2$Et, NCO$_2$Pr, NCO$_2$Ph, NCO$_2$CH$_2$Ph, or NCO$_2$CH$_2$CH$_2$OMe.

The compound of paragraph [00322] wherein Y is CH$_2$.

The compound of any one of paragraphs [00316] to [00323], wherein $R^1$ is pyrrolyl, pyrazolyl, imidazolyl, triazolyl, furanyl, thiophenyl, oxazolyl, isooxazolyl, oxadiazolyl, thiazolyl, pyridinyl, pyridazinyl, pyrimidinyl, or pyrazinyl.

The compound of paragraph [00324], wherein $R^1$ is pyrrolyl, pyrazolyl, imidazolyl, furanyl, thiophenyl, oxazolyl, isooxazolyl, oxadiazolyl, or thiazolyl.

The compound of any one of paragraphs [00316] to [00325], wherein m is 1 and $R^2$ is halo.

The compound of any one of paragraphs [00316] to [00325], wherein at least one $R^2$ is halo.

The compound of paragraph [00326] or [00327], wherein $R^2$ is Cl.

The compound of paragraph [00329], wherein the compound comprises Formula (IB):

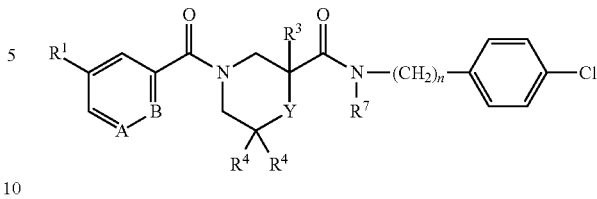

(IB)

The compound of any one of paragraphs [00316] to [00329], wherein $R^3$ is H, F or Me.

The compound of paragraph [00330], wherein $R^3$ is H.

The compound of any one of paragraphs [00316] to [00331], wherein each $R^4$ is H.

The compound of any one of paragraphs [00316] to [00331], wherein one $R^4$ is OH or OMe, and the other is H, OH, or OMe, or both $R^4$ together with the carbon to which they are attached form C=O or C=CH$_2$.

The compound of any one of paragraphs [00316] to [00331], wherein each $R^4$ is F.

The compound of any one of paragraphs [00316] to [00334], wherein $R^7$ is $C_{1-3}$ alkyl.

The compound of any one of paragraphs [00316] to [00334], wherein $R^7$ is H.

The compound of paragraph [00334] to [00336], wherein the compound comprises Formula (ID):

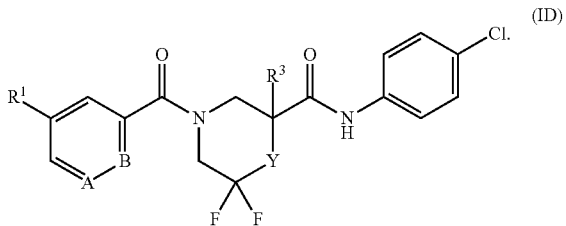

(ID)

A compound selected from the group consisting of E-001 and E-003 to E-032

A pharmaceutical formulation comprising a compound of any one of paragraphs [00316] to [00338] and a pharmaceutically acceptable excipient.

A kit comprising the pharmaceutical formulation of paragraph [00339] and instructions for administering the pharmaceutical formulation to a patient.

A method of inhibiting MRTF/SRF-mediated gene transcription in a cell, comprising contacting the cell with a compound of any one of paragraphs [00316] to [00338] in an amount to inhibit the gene transcription.

The method of paragraph [00341], wherein the contacting occurs in vivo.

The method of paragraph [00341] or [00342], wherein the contacting comprises administering to a patient in need thereof.

The method of paragraph [00343], wherein the patient suffers from a disease associated with dysfunction of MRTF/SRF-mediated gene transcription.

A method of treating a disease associated with dysfunction of MRTF/SRF-mediated gene transcription in a patient comprising administering to the patient a therapeutically effective amount of the pharmaceutical formulation of paragraph [00339].

The method of paragraph [00344] to [00345], wherein the disease is selected from the group consisting of cancer, fibrotic disease, diabetes, insulin sensitivity, hyperactive platelets, metabolic disease, inflammation, inflammatory disease, pulmonary arterial hypertension, axon regeneration following nerve damage, Raynaud's phenomenon, cerebral vascular disease, cardiovascular disease, erectile dysfunction, and combinations thereof.

The method of paragraph [00346], wherein the cancer is selected from the group consisting of fibrosarcoma, myxosarcoma, liposarcoma, chondrosarcoma, osteogenic sarcoma, chordoma, angiosarcoma, endotheliosarcoma, lymphangiosarcoma, Ewing's tumor, lymphangioendotheliosarcoma, synovioma, mesothelioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, glioblastoma, leukemia, megakaryoblastic leukemia, polycythemia vera, lymphoma, multiple myeloma, Waldenstrom's macroglobulinemia, heavy chain disease, and combinations thereof.

The method of paragraph [00347], wherein the cancer is megakaryoblastic leukemia, melanoma, breast cancer, prostate cancer, glioblastoma, or combinations thereof.

The method of paragraph [00346], wherein the fibrotic disease is systemic sclerosis, pulmonary fibrosis, cardiac fibrosis, liver fibrosis, liver cirrhosis, renal fibrosis, chronic renal failure, lung fibrosis, nephrogenic systemic fibrosis, graft versus host disease, Dupuytren's contracture, inflammatory bowel disease, Crohn's disease, ocular fibrosis, diabetic retinopathy, age-related macular degeneration, postoperative adhesions, reactive fibrosis, chronic heart failure, or combinations thereof.

The method of paragraph [00349], wherein the fibrotic disease is systemic sclerosis or idiopathic pulmonary fibrosis.

The method of paragraph [00346], wherein the metabolic disease is obesity, diabetes, insulin resistance, or combinations thereof.

The method of paragraph [00351], wherein the diabetes is type II diabetes.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

We claim:

1. A compound of Formula (II), or a pharmaceutically acceptable salt thereof:

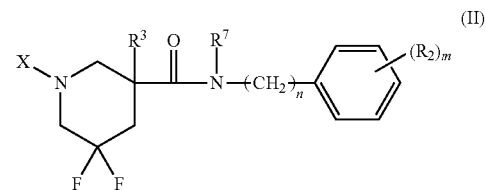

wherein:

X is

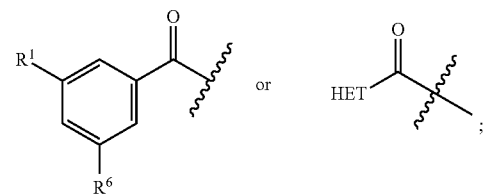

HET is 3-pyridyl, benzoimidazolyl, indolyl, or indazolyl;

m is 1 or 2;

n is 0, 1, or 2;

$R^1$ is pyrrolyl, furanyl, thiophenyl, pyridyl, or pyrimidinyl;

each $R^2$ independently is halo, $C_{1-6}$ alkyl, $OC_{1-6}$ alkyl, $OC_{0-6}$ alkylene-aryl, $OC_{0-6}$ alkylene-heteroaryl, $SO_2NR^5{}_2$, CN, or $SO_2C_{1-3}$alkyl;

$R^3$ is H, halo, OH, $C_{1-3}$ alkyl, or $OC_{1-3}$ alkyl;

each $R^5$ independently is H, $C_{1-6}$ alkyl, $C_{3-7}$ cycloalkyl, $C_{2-6}$ alkenyl, $C_{3-6}$ alkylene-ether, $C_{0-6}$ alkylene-aryl, $C_{0-6}$ alkylene-heteroaryl, or two $R^5$ together with a nitrogen to which they are attached form a 3-7 atom heterocyclic ring; and $R^6$ is H, halo, $C_{1-3}$ haloalkyl, or $OC_{1-3}$ haloalky $R^7$ is H or $C_{1-3}$ alkyl.

2. The compound of claim 1, wherein X is
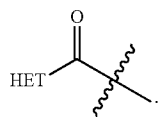
3. The compound of claim 2, wherein HET is:
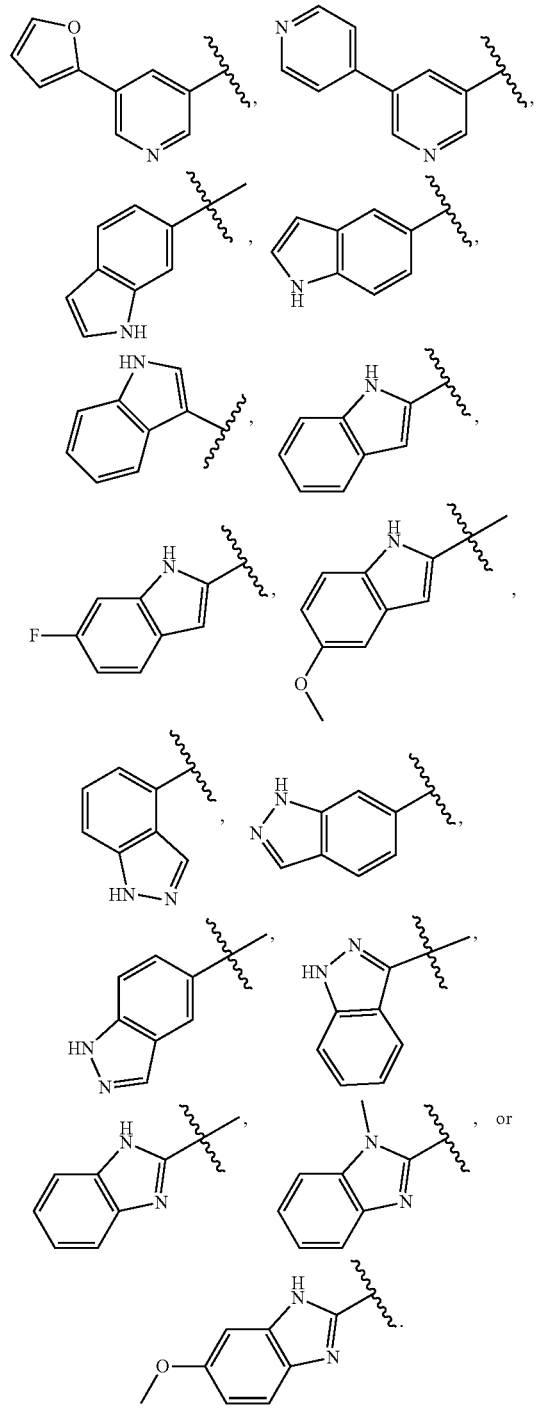
4. The compound of claim 1, wherein X is
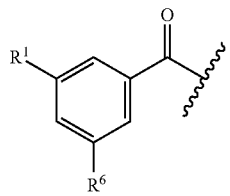
5. The compound of claim 1, wherein X is selected from the group consisting of:
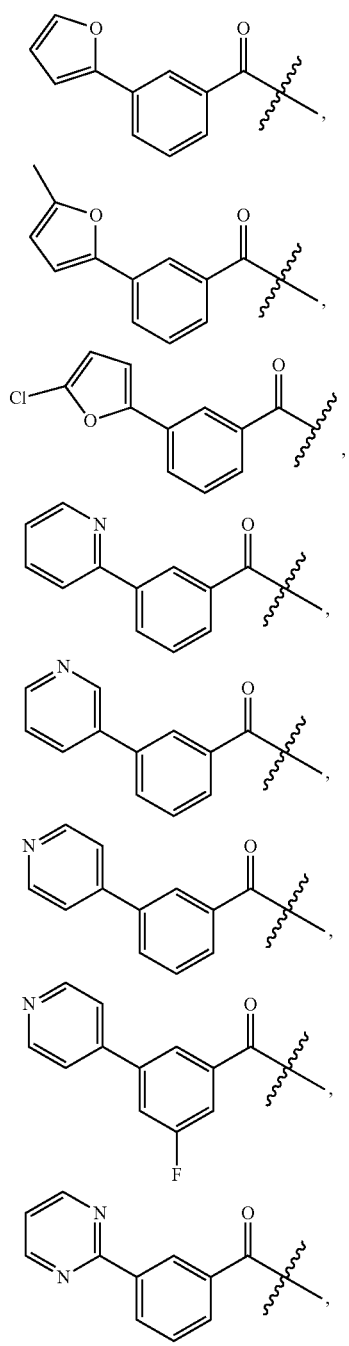

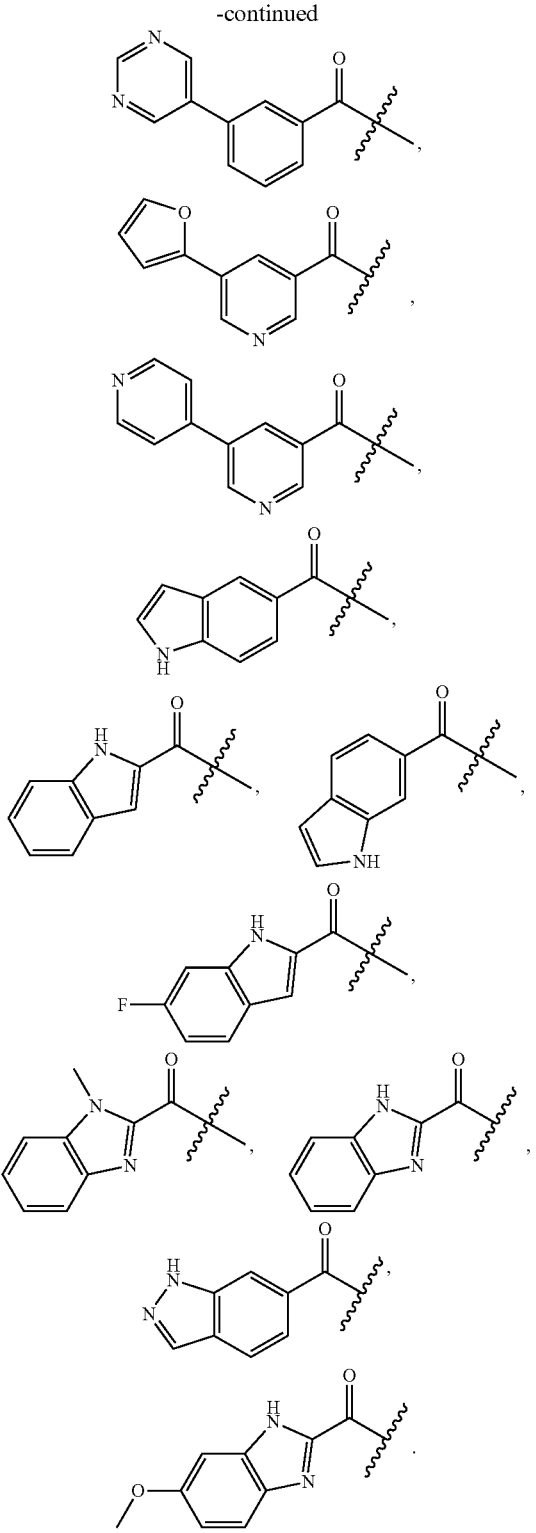
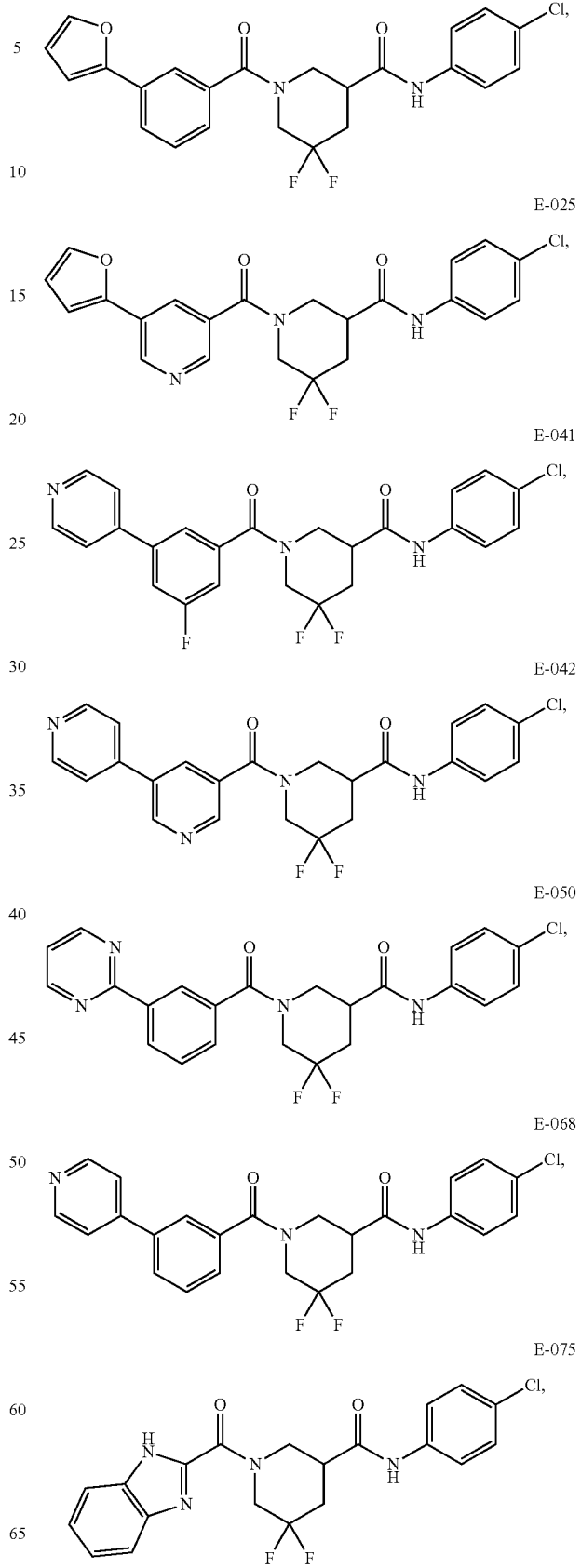
6. The compound of claim 1, wherein R³ is H or Me.
7. The compound of claim 1: wherein
(a) m is 1 and R² is Cl; or
(b) at least one R² is F, CN, SO₂Me, or Me.
8. The compound of claim 1 selected from the group consisting of:

-continued

E-076
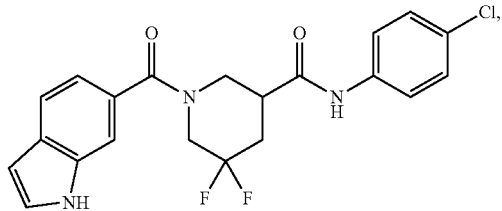

E-096
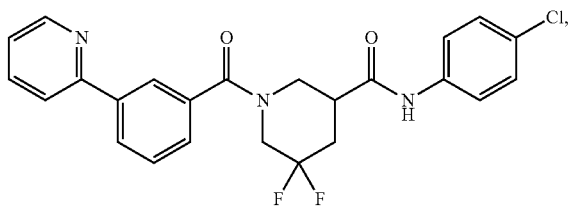

E-099
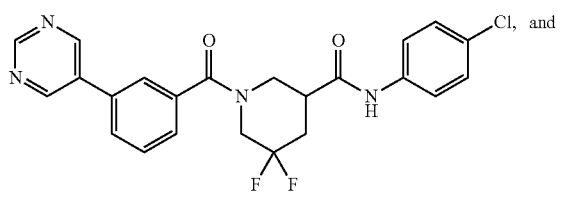

-continued

E-100
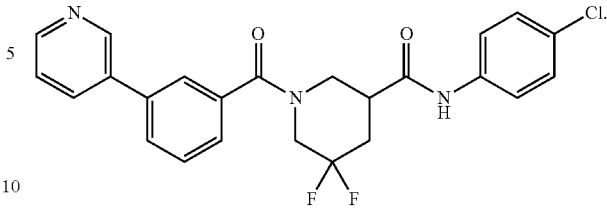

9. A pharmaceutical formulation comprising a compound of claim 1 and a pharmaceutically acceptable excipient.

10. A method of inhibiting MRTF/SRF-mediated gene transcription in a cell, comprising contacting the cell with a compound of claim 1, or a pharmaceutically acceptable salt thereof, in an amount to inhibit the gene transcription.

11. The method of claim 10, wherein the contacting comprises administering to a patient suffering from a disease associated with dysfunction of MRTF/SRF-mediated gene transcription.

12. The compound of claim 8 selected from the group consisting of E-019, E-041, E-068, and E-096, or a pharmaceutically acceptable salt thereof.

* * * * *